(12) United States Patent
Londesbrough et al.

(10) Patent No.: US 11,851,451 B2
(45) Date of Patent: *Dec. 26, 2023

(54) PREPARATION OF PSILOCYBIN, DIFFERENT POLYMORPHIC FORMS, INTERMEDIATES, FORMULATIONS AND THEIR USE

(71) Applicant: COMPASS PATHFINDER LIMITED, Altrincham (GB)

(72) Inventors: Derek John Londesbrough, Hartlepool (GB); Christopher Brown, Gateshead (GB); Julian Scott Northen, South Shields (GB); Gillian Moore, Sedgefield (GB); Hemant Kashinath Patil, Surrey (GB); David E. Nichols, Chapel Hill, NC (US)

(73) Assignee: COMPASS PATHFINDER LIMITED, Altrincham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,979

(22) Filed: Nov. 21, 2022

(65) Prior Publication Data
US 2023/0119714 A1 Apr. 20, 2023

Related U.S. Application Data

(63) Continuation of application No. 16/679,009, filed on Nov. 8, 2019, now Pat. No. 11,505,564, which is a continuation of application No. 16/155,386, filed on Oct. 9, 2018, now Pat. No. 10,519,175.

(30) Foreign Application Priority Data

Oct. 9, 2017 (GB) ...................................... 1716505
Jun. 28, 2018 (GB) ...................................... 1810588
Oct. 9, 2018 (GB) ...................................... 1816438

(51) Int. Cl.
| | | |
|---|---|---|
| C07D 209/16 | (2006.01) | |
| C07F 9/572 | (2006.01) | |
| A61K 9/20 | (2006.01) | |
| A61K 9/00 | (2006.01) | |
| A61K 47/36 | (2006.01) | |
| A61K 47/38 | (2006.01) | |

(52) U.S. Cl.
CPC .......... *C07F 9/5728* (2013.01); *A61K 9/0053* (2013.01); *A61K 9/2054* (2013.01); *A61K 47/36* (2013.01); *A61K 47/38* (2013.01); *C07D 209/16* (2013.01); *C07B 2200/13* (2013.01)

(58) Field of Classification Search
CPC ............................ C07F 9/5728; C07D 209/16
See application file for complete search history.

(56) References Cited

U.S. PATENT DOCUMENTS

| | | |
|---|---|---|
| 3,075,992 A | 1/1963 | Albert et al. |
| 3,183,172 A | 5/1965 | Roger et al. |
| 3,192,111 A | 6/1965 | Albert et al. |
| 4,499,096 A | 2/1985 | Lotsof |
| 4,587,243 A | 5/1986 | Lotsof |
| 4,721,612 A | 1/1988 | Janoff et al. |
| 5,145,677 A | 9/1992 | Von Eichborn et al. |
| 5,264,443 A | 11/1993 | Jarreau et al. |
| 5,468,486 A | 11/1995 | Reddick et al. |
| 5,482,706 A | 1/1996 | Igari et al. |
| 5,545,617 A | 8/1996 | Dartt et al. |
| 5,573,776 A | 11/1996 | Harrison et al. |
| 5,626,863 A | 5/1997 | Hubbell et al. |
| 5,629,307 A | 5/1997 | Olney |
| 5,643,586 A | 7/1997 | Perricone |
| 5,696,125 A | 12/1997 | Altura et al. |
| 5,725,871 A | 3/1998 | Illum |
| 5,736,161 A | 4/1998 | Garces et al. |
| 5,785,989 A | 7/1998 | Stanley et al. |
| 5,804,592 A | 9/1998 | Volicer |
| 5,827,819 A | 10/1998 | Yatvin et al. |
| 5,871,710 A | 2/1999 | Bogdanov et al. |
| 5,874,477 A | 2/1999 | McConnell et al. |
| 5,879,690 A | 3/1999 | Perricone |
| 5,902,815 A | 5/1999 | Olney et al. |
| 5,914,129 A | 6/1999 | Mauskop |
| 5,922,341 A | 7/1999 | Smith et al. |
| 5,925,634 A | 7/1999 | Olney |
| 5,935,925 A | 8/1999 | Weinshank et al. |
| 5,942,241 A | 8/1999 | Chasin et al. |

(Continued)

FOREIGN PATENT DOCUMENTS

| | | |
|---|---|---|
| AU | 2016208412 A1 | 8/2016 |
| AU | 2018203524 A1 | 6/2018 |

(Continued)

OTHER PUBLICATIONS

Aaron, M. (2017) "Open Your Mind: Merging Psychedelic Therapy with Sex Therapy" Psychology Today [online]. Retrieved from: https://www.psychologytoday.com/us/blog/standard-deviations/201710/open-your-mind-merging-psychedelic-therapy-sex-therapy, retrieved Oct. 24, 2017, 4 pages.

(Continued)

*Primary Examiner* — Rebecca L Anderson
(74) *Attorney, Agent, or Firm* — COOLEY LLP

(57) ABSTRACT

This invention relates to the large-scale production of psilocybin for use in medicine. More particularly, it relates to a method of obtaining high purity crystalline psilocybin, particularly, in the form of Polymorph A. It further relates to a method for the manufacture of psilocybin and intermediates in the production thereof and formulations containing psilocybin.

30 Claims, 29 Drawing Sheets

(56) References Cited

U.S. PATENT DOCUMENTS

| | | |
|---|---|---|
| 5,942,503 A | 8/1999 | Jung et al. |
| 5,958,919 A | 9/1999 | Olney et al. |
| 6,037,346 A | 3/2000 | Doherty, Jr. et al. |
| 6,121,264 A | 9/2000 | Sakamoto et al. |
| 6,126,924 A | 10/2000 | Scales-Medeiros et al. |
| 6,204,245 B1 | 3/2001 | Siegel et al. |
| 6,217,904 B1 | 4/2001 | Midha et al. |
| 6,228,864 B1 | 5/2001 | Smith et al. |
| 6,294,550 B1 | 9/2001 | Place et al. |
| 6,323,236 B2 | 11/2001 | McElroy |
| 6,348,456 B1 | 2/2002 | Mash et al. |
| 6,380,176 B2 | 4/2002 | Takahashi et al. |
| 6,383,471 B1 | 5/2002 | Chen et al. |
| 6,444,665 B1 | 9/2002 | Helton et al. |
| 6,479,074 B2 | 11/2002 | Murdock et al. |
| 6,489,341 B1 | 12/2002 | Jerussi |
| 6,495,154 B1 | 12/2002 | Tam et al. |
| 6,495,498 B2 | 12/2002 | Niemiec et al. |
| 6,500,459 B1 | 12/2002 | Chhabra et al. |
| 6,541,043 B2 | 4/2003 | Lang |
| 6,544,998 B2 | 4/2003 | Mylari |
| 6,592,901 B2 | 7/2003 | Durig et al. |
| 6,604,698 B2 | 8/2003 | Verhoff et al. |
| 6,635,279 B2 | 10/2003 | Kolter et al. |
| 6,693,135 B2 | 2/2004 | Yeager et al. |
| 6,720,348 B2 | 4/2004 | Mylari |
| 6,814,976 B1 | 11/2004 | Hille et al. |
| 6,893,662 B2 | 5/2005 | Dittmar et al. |
| 6,913,768 B2 | 7/2005 | Couch et al. |
| 6,962,717 B1 | 11/2005 | Huber et al. |
| 6,977,070 B2 | 12/2005 | Dugger, III |
| 6,979,447 B2 | 12/2005 | Jameson et al. |
| 7,045,543 B2 | 5/2006 | Yatvin et al. |
| 7,084,156 B2 | 8/2006 | DeVita et al. |
| 7,220,737 B1 | 5/2007 | Mash |
| 7,229,784 B2 | 6/2007 | Holtzman et al. |
| 7,241,797 B2 | 7/2007 | Horseman |
| 7,294,649 B2 | 11/2007 | Hui et al. |
| 7,384,651 B2 | 6/2008 | Hille et al. |
| 7,517,900 B2 | 4/2009 | Pendri et al. |
| 7,638,651 B2 | 12/2009 | Gant et al. |
| 7,666,877 B2 | 2/2010 | Baenteli et al. |
| 7,670,627 B2 | 3/2010 | Shefer et al. |
| 7,671,030 B2 | 3/2010 | Mickle et al. |
| 7,678,770 B2 | 3/2010 | Mickle et al. |
| 7,754,710 B2 | 7/2010 | Mash |
| 7,772,222 B2 | 8/2010 | Mickle |
| 7,799,337 B2 | 9/2010 | Levin |
| 7,833,546 B2 | 11/2010 | Petereit et al. |
| 7,838,034 B2 | 11/2010 | Kugelmann et al. |
| 7,981,441 B2 | 7/2011 | Pantelidis et al. |
| 8,008,285 B2 | 8/2011 | Roberts et al. |
| 8,067,028 B2 | 11/2011 | Bennett |
| 8,101,661 B2 | 1/2012 | Mickle |
| 8,263,561 B2 | 9/2012 | Saeed |
| 8,318,210 B2 | 11/2012 | Tengler et al. |
| 8,318,813 B2 | 11/2012 | Sanfilippo |
| 8,329,663 B2 | 12/2012 | Griffin |
| 8,362,007 B1 | 1/2013 | Mash et al. |
| 8,445,016 B2 | 5/2013 | Santerre et al. |
| 8,512,751 B2 | 8/2013 | Rariy et al. |
| 8,574,604 B2 | 11/2013 | Esfand et al. |
| 8,617,607 B2 | 12/2013 | Moses et al. |
| 8,673,351 B2 | 3/2014 | Andr Sek et al. |
| 8,742,096 B2 | 6/2014 | Moriarty et al. |
| 8,747,832 B2 | 6/2014 | Uhrich et al. |
| 8,754,119 B2 | 6/2014 | Scheller et al. |
| 8,784,835 B2 | 7/2014 | Austin |
| 8,785,500 B2 | 7/2014 | Charney et al. |
| 8,846,100 B2 | 9/2014 | Shojaei et al. |
| 8,852,638 B2 | 10/2014 | Luk et al. |
| 8,859,579 B2 | 10/2014 | Sewell |
| 8,859,622 B1 | 10/2014 | Bristol et al. |
| 8,906,413 B2 | 12/2014 | Chang et al. |
| 8,906,847 B2 | 12/2014 | Cleemann et al. |
| 8,921,393 B2 | 12/2014 | Weiner et al. |
| 8,962,697 B2 | 2/2015 | Laronde et al. |
| 8,980,308 B2 | 3/2015 | Horstmann et al. |
| 8,980,880 B1 | 3/2015 | King et al. |
| 9,737,759 B2 | 8/2017 | Mrowka et al. |
| 9,878,138 B2 | 1/2018 | Altschul et al. |
| 10,058,253 B2 | 8/2018 | Parton et al. |
| 10,058,584 B2 | 8/2018 | Young et al. |
| 10,064,856 B2 | 9/2018 | Bosse et al. |
| 10,085,994 B2 | 10/2018 | Lozinsky et al. |
| 10,148,534 B2 | 12/2018 | Lazarescu et al. |
| 10,183,001 B1 | 1/2019 | King et al. |
| 10,231,651 B2 | 3/2019 | Deng et al. |
| 10,254,298 B1 | 4/2019 | Koh |
| 10,519,175 B2 | 12/2019 | Londesbrough et al. |
| 10,596,378 B2 | 3/2020 | Rustick |
| 10,729,706 B2 | 8/2020 | Kucuksen et al. |
| 10,738,268 B2 | 8/2020 | Leo |
| 10,947,257 B2 | 3/2021 | Londesbrough et al. |
| 10,954,259 B1 | 3/2021 | Londesbrough et al. |
| 11,149,044 B2 | 10/2021 | Londesbrough et al. |
| 11,180,517 B2 | 11/2021 | Londesbrough et al. |
| 11,447,510 B2 | 9/2022 | Londesbrough et al. |
| 11,505,564 B2 | 11/2022 | Derek et al. |
| 11,564,935 B2 | 1/2023 | Londesbrough et al. |
| 11,629,159 B2 | 4/2023 | Londesbrough et al. |
| 2001/0004644 A1 | 6/2001 | Levin |
| 2002/0015730 A1 | 2/2002 | Hoffmann et al. |
| 2002/0019421 A1 | 2/2002 | Biberman |
| 2002/0044962 A1 | 4/2002 | Cherukuri et al. |
| 2002/0137785 A1 | 9/2002 | Kindness et al. |
| 2003/0013689 A1 | 1/2003 | Helton et al. |
| 2003/0049308 A1 | 3/2003 | Theobald et al. |
| 2003/0051728 A1 | 3/2003 | Lloyd et al. |
| 2003/0082225 A1 | 5/2003 | Mason |
| 2003/0096831 A1 | 5/2003 | Stone et al. |
| 2003/0099711 A1 | 5/2003 | Meadows et al. |
| 2003/0114512 A1 | 6/2003 | Collier, Jr. et al. |
| 2003/0119884 A1 | 6/2003 | Epstein et al. |
| 2003/0135202 A1 | 7/2003 | Harper et al. |
| 2003/0144220 A1 | 7/2003 | Obach |
| 2003/0153552 A1 | 8/2003 | Mash et al. |
| 2003/0171435 A1 | 9/2003 | Pouletty et al. |
| 2003/0180357 A1 | 9/2003 | Martino et al. |
| 2003/0203912 A1 | 10/2003 | May et al. |
| 2003/0224057 A1 | 12/2003 | Martin-Letellier et al. |
| 2003/0235617 A1 | 12/2003 | Martino et al. |
| 2004/0006043 A1 | 1/2004 | Margalit et al. |
| 2004/0023952 A1 | 2/2004 | Leventhal |
| 2004/0024038 A1 | 2/2004 | Ebert et al. |
| 2004/0029860 A1 | 2/2004 | Gil-Ad et al. |
| 2004/0077540 A1 | 4/2004 | Quay |
| 2004/0132780 A1 | 7/2004 | Allen et al. |
| 2004/0186155 A1 | 9/2004 | Dayno et al. |
| 2004/0214215 A1 | 10/2004 | Yu et al. |
| 2004/0224942 A1 | 11/2004 | Weiner et al. |
| 2005/0009815 A1 | 1/2005 | DeVita et al. |
| 2005/0014786 A1 | 1/2005 | Sun et al. |
| 2005/0026842 A1 | 2/2005 | Simon |
| 2005/0070501 A1 | 3/2005 | Neurath et al. |
| 2005/0096396 A1 | 5/2005 | Davis et al. |
| 2005/0106220 A1 | 5/2005 | Inagawa et al. |
| 2005/0148673 A1 | 7/2005 | Harbut et al. |
| 2005/0176790 A1 | 8/2005 | Bartholomaus et al. |
| 2005/0203011 A1 | 9/2005 | Ron |
| 2005/0209218 A1 | 9/2005 | Meyerson et al. |
| 2005/0215521 A1 | 9/2005 | Lalji et al. |
| 2005/0215571 A1 | 9/2005 | Romano |
| 2005/0222270 A1 | 10/2005 | Olney et al. |
| 2005/0233010 A1 | 10/2005 | Satow |
| 2005/0245460 A1 | 11/2005 | Meyerson et al. |
| 2005/0245617 A1 | 11/2005 | Meyerson et al. |
| 2005/0255091 A1 | 11/2005 | Loomis |
| 2005/0260258 A1 | 11/2005 | Ficht et al. |
| 2005/0261278 A1 | 11/2005 | Weiner et al. |
| 2005/0265955 A1 | 12/2005 | Raman et al. |
| 2005/0288375 A1 | 12/2005 | Hobden et al. |
| 2006/0019963 A1 | 1/2006 | Barnette et al. |
| 2006/0025387 A1 | 2/2006 | Hochman |

(56) References Cited

U.S. PATENT DOCUMENTS

| | | |
|---|---|---|
| 2006/0030625 A1 | 2/2006 | Hart et al. |
| 2006/0034872 A1 | 2/2006 | Woolf |
| 2006/0045865 A1 | 3/2006 | Jacob et al. |
| 2006/0051408 A1 | 3/2006 | Parente Duena et al. |
| 2006/0067937 A1 | 3/2006 | Karumanchi et al. |
| 2006/0093679 A1 | 5/2006 | Mayer et al. |
| 2006/0110327 A1 | 5/2006 | Emigh et al. |
| 2006/0135403 A1 | 6/2006 | Gervais et al. |
| 2006/0183744 A1 | 8/2006 | Rohrer et al. |
| 2006/0229293 A1 | 10/2006 | Lotsof |
| 2006/0240014 A1 | 10/2006 | Sukhatme |
| 2006/0240043 A1 | 10/2006 | Meyerson et al. |
| 2006/0241172 A1 | 10/2006 | Zhou et al. |
| 2006/0264508 A1 | 11/2006 | Stone |
| 2006/0270592 A1 | 11/2006 | Ousler, III et al. |
| 2007/0053954 A1 | 3/2007 | Rowe et al. |
| 2007/0059367 A1 | 3/2007 | Cherukuri |
| 2007/0065463 A1 | 3/2007 | Aung-Din |
| 2007/0066996 A1 | 3/2007 | Katzman et al. |
| 2007/0092586 A1 | 4/2007 | Cutler |
| 2007/0099977 A1 | 5/2007 | Nudelman et al. |
| 2007/0100000 A1 | 5/2007 | Epstein et al. |
| 2007/0190130 A1 | 8/2007 | Mark et al. |
| 2007/0190142 A1 | 8/2007 | Breitenbach et al. |
| 2007/0203216 A1 | 8/2007 | Ebert et al. |
| 2007/0207222 A1 | 9/2007 | Yu et al. |
| 2007/0213394 A1 | 9/2007 | Beguin et al. |
| 2008/0015181 A1 | 1/2008 | Roberts et al. |
| 2008/0026014 A1 | 1/2008 | Michel |
| 2008/0026189 A1 | 1/2008 | Lin et al. |
| 2008/0066741 A1 | 3/2008 | LeMahieu et al. |
| 2008/0075789 A1 | 3/2008 | Vawter et al. |
| 2008/0103127 A1 | 5/2008 | Haas |
| 2008/0103165 A1 | 5/2008 | Barlow et al. |
| 2008/0103179 A1 | 5/2008 | Tam et al. |
| 2008/0103199 A1 | 5/2008 | Haas |
| 2008/0193540 A1 | 8/2008 | Soula et al. |
| 2008/0207600 A1 | 8/2008 | Goldstein et al. |
| 2008/0226715 A1 | 9/2008 | Cha et al. |
| 2008/0233201 A1 | 9/2008 | Royere et al. |
| 2008/0241255 A1 | 10/2008 | Rose et al. |
| 2008/0255096 A1 | 10/2008 | Knipper-Breer et al. |
| 2008/0260844 A1 | 10/2008 | Soula et al. |
| 2009/0036468 A1 | 2/2009 | Samoriski et al. |
| 2009/0041838 A1 | 2/2009 | Guimberteau et al. |
| 2009/0069308 A1 | 3/2009 | Deregnaucourt et al. |
| 2009/0105222 A1 | 4/2009 | Kranzler et al. |
| 2009/0143435 A1 | 6/2009 | Ebert et al. |
| 2009/0156581 A1 | 6/2009 | Dillon et al. |
| 2009/0169566 A1 | 7/2009 | Rawlin et al. |
| 2009/0176792 A1 | 7/2009 | Gant et al. |
| 2009/0186099 A1 | 7/2009 | Dugger, III |
| 2009/0198145 A1 | 8/2009 | Chow |
| 2009/0232898 A1 | 9/2009 | Pettersson et al. |
| 2009/0252786 A1 | 10/2009 | Hanz |
| 2009/0259039 A1 | 10/2009 | Bristol et al. |
| 2009/0285916 A1 | 11/2009 | Haritou |
| 2009/0291137 A1 | 11/2009 | Guimberteau et al. |
| 2009/0298814 A1 | 12/2009 | Nudelman et al. |
| 2010/0016280 A1 | 1/2010 | Nichols et al. |
| 2010/0098722 A1 | 4/2010 | Bachmann et al. |
| 2010/0152108 A1 | 6/2010 | Hung et al. |
| 2010/0166889 A1 | 7/2010 | Sanfilippo |
| 2010/0179221 A1 | 7/2010 | Nagel et al. |
| 2010/0189818 A1 | 7/2010 | Tsai |
| 2010/0216964 A1 | 8/2010 | Zech et al. |
| 2010/0255094 A1 | 10/2010 | Jackson et al. |
| 2010/0266701 A1 | 10/2010 | Guimberteau et al. |
| 2010/0303903 A1 | 12/2010 | Hackett |
| 2011/0038915 A1 | 2/2011 | Gonzalez |
| 2011/0053859 A1 | 3/2011 | Deadwyler et al. |
| 2011/0077239 A1 | 3/2011 | Knipper et al. |
| 2011/0091508 A1 | 4/2011 | Esfand et al. |
| 2011/0111029 A1 | 5/2011 | Schmitz et al. |
| 2011/0118189 A1 | 5/2011 | Farr et al. |
| 2011/0144209 A1 | 6/2011 | Zachar |
| 2011/0207718 A1 | 8/2011 | Bird |
| 2011/0217289 A1 | 9/2011 | Kolter et al. |
| 2011/0245261 A1 | 10/2011 | Lagarde et al. |
| 2011/0274634 A1 | 11/2011 | Rieth et al. |
| 2011/0306596 A1 | 12/2011 | Rao et al. |
| 2012/0058125 A1 | 3/2012 | Strittmatter et al. |
| 2012/0059066 A1 | 3/2012 | Bartholomaus et al. |
| 2012/0108510 A1 | 5/2012 | Young et al. |
| 2012/0129834 A1 | 5/2012 | Hughes et al. |
| 2012/0135960 A2 | 5/2012 | Mouthon et al. |
| 2012/0159656 A1 | 6/2012 | Gerber et al. |
| 2012/0282255 A1 | 11/2012 | Plucinski |
| 2012/0302590 A1 | 11/2012 | Bhide et al. |
| 2012/0302592 A1 | 11/2012 | Johnson et al. |
| 2013/0045979 A1 | 2/2013 | Sanfilippo |
| 2013/0116215 A1 | 5/2013 | Coma et al. |
| 2013/0276799 A1 | 10/2013 | Davidson et al. |
| 2013/0281401 A1 | 10/2013 | Turner |
| 2013/0295170 A1 | 11/2013 | Dordunoo |
| 2014/0093577 A1 | 4/2014 | Tengler et al. |
| 2014/0099336 A1 | 4/2014 | Woiwode et al. |
| 2014/0100282 A1 | 4/2014 | Wong |
| 2014/0148491 A1 | 5/2014 | Valia et al. |
| 2014/0178480 A1 | 6/2014 | King et al. |
| 2014/0187655 A1 | 7/2014 | Mash et al. |
| 2014/0220150 A1 | 8/2014 | Stamets |
| 2014/0255522 A1 | 9/2014 | Lozinsky et al. |
| 2014/0288056 A1 | 9/2014 | Friedhoff |
| 2014/0294923 A1 | 10/2014 | Cartt et al. |
| 2014/0315837 A1 | 10/2014 | Mash et al. |
| 2014/0356428 A1 | 12/2014 | Barnscheid et al. |
| 2014/0364367 A1 | 12/2014 | Cotter |
| 2015/0011644 A1 | 1/2015 | Leech |
| 2015/0094466 A1 | 4/2015 | Moriarty |
| 2015/0099741 A1 | 4/2015 | Li et al. |
| 2015/0118301 A1 | 4/2015 | Haswani et al. |
| 2015/0118327 A1 | 4/2015 | Sewell |
| 2015/0196533 A1 | 7/2015 | Mao et al. |
| 2015/0216799 A1 | 8/2015 | Farber |
| 2015/0231300 A1 | 8/2015 | Lozinsky et al. |
| 2015/0258114 A1 | 9/2015 | Friedhoff |
| 2016/0051476 A1 | 2/2016 | Pilgaonkar et al. |
| 2016/0331725 A1 | 11/2016 | Gillessen et al. |
| 2016/0338945 A1 | 11/2016 | Knight |
| 2016/0340334 A1 | 11/2016 | Knight |
| 2017/0086727 A1 | 3/2017 | Dagum |
| 2017/0258382 A1 | 9/2017 | Dagum |
| 2017/0258383 A1 | 9/2017 | Dagum |
| 2017/0276676 A1 | 9/2017 | Slotman |
| 2017/0287348 A1 | 10/2017 | Mosher et al. |
| 2017/0348303 A1 | 12/2017 | Bosse et al. |
| 2018/0021326 A1 | 1/2018 | Stamets |
| 2018/0036303 A1 | 2/2018 | Raz |
| 2018/0104490 A1 | 4/2018 | Rustick |
| 2018/0147142 A1 | 5/2018 | Knight |
| 2018/0221396 A1 | 8/2018 | Chadeayne |
| 2018/0343812 A1 | 12/2018 | Leo |
| 2018/0344743 A1 | 12/2018 | Lozinsky et al. |
| 2018/0353434 A1 | 12/2018 | Hatanaka et al. |
| 2018/0354995 A1 | 12/2018 | Gudkov et al. |
| 2019/0105313 A1 | 4/2019 | Stamets |
| 2019/0142851 A1 | 5/2019 | Chadeayne |
| 2019/0187163 A1 | 6/2019 | Koh |
| 2019/0192498 A1 | 6/2019 | Stamets |
| 2019/0246591 A1 | 8/2019 | Leo |
| 2020/0078368 A1 | 3/2020 | Lehmann et al. |
| 2020/0093416 A1 | 3/2020 | Rogers et al. |
| 2020/0101041 A1 | 4/2020 | Kleidon |
| 2020/0147038 A1 | 5/2020 | Russ et al. |
| 2020/0215297 A1 | 7/2020 | Rabin et al. |
| 2020/0375967 A1 | 12/2020 | Stamets |
| 2021/0015833 A1 | 1/2021 | LaRosa et al. |
| 2021/0267966 A1 | 9/2021 | Petcavich |
| 2022/0088041 A1 | 3/2022 | Londesbrough et al. |
| 2022/0169668 A1 | 6/2022 | Londesbrough et al. |
| 2022/0402949 A1 | 12/2022 | Londesbrough et al. |

(56) References Cited

U.S. PATENT DOCUMENTS

| | | | |
|---|---|---|---|
| 2023/0000883 A1 | 1/2023 | Londesbrough et al. | |
| 2023/0023092 A1 | 1/2023 | Londesbrough et al. | |
| 2023/0124137 A1 | 4/2023 | Londesbrough et al. | |

FOREIGN PATENT DOCUMENTS

| | | |
|---|---|---|
| CA | 672478 A | 10/1963 |
| CA | 2338326 A1 | 2/2000 |
| CA | 2416650 A1 | 1/2002 |
| CA | 2422730 A1 | 3/2002 |
| CA | 2492823 A1 | 3/2003 |
| CA | 2492826 A1 | 3/2003 |
| CA | 2487849 A1 | 1/2004 |
| CA | 2489410 A1 | 1/2004 |
| CA | 2498938 A1 | 4/2004 |
| CA | 2517675 A1 | 10/2004 |
| CA | 2541090 A1 | 5/2005 |
| CA | 2594451 A1 | 6/2007 |
| CA | 3050679 A1 | 7/2018 |
| CN | 103535561 A | 1/2014 |
| CN | 103549133 A | 2/2014 |
| CN | 103751943 A | 4/2014 |
| CN | 103773056 A | 5/2014 |
| CN | 107252080 A | 10/2017 |
| CN | 108619214 A | 10/2018 |
| EP | 0152379 A2 | 8/1985 |
| EP | 0218479 A2 | 4/1987 |
| EP | 0493380 B1 | 10/1997 |
| EP | 0628042 B1 | 8/2001 |
| EP | 0554352 B1 | 3/2003 |
| EP | 0932416 B1 | 6/2005 |
| EP | 1944017 A2 | 7/2008 |
| EP | 2106799 A1 | 10/2009 |
| EP | 1774968 B1 | 12/2011 |
| EP | 2142185 B1 | 8/2012 |
| EP | 2525226 A1 | 11/2012 |
| EP | 2649989 A1 | 10/2013 |
| EP | 2053919 B1 | 12/2013 |
| EP | 2183227 B1 | 9/2014 |
| EP | 2023900 B1 | 12/2014 |
| EP | 2818177 A1 | 12/2014 |
| EP | 2481740 B1 | 11/2015 |
| EP | 3151906 B1 | 12/2019 |
| ES | 2693502 T3 | 12/2018 |
| FI | 20176142 A1 | 6/2019 |
| FI | 20185254 A1 | 9/2019 |
| GB | 911946 A | 12/1962 |
| GB | 912714 A | 12/1962 |
| HR | P20050421 A2 | 12/2005 |
| IE | 24138 L | 8/1959 |
| JP | S5576859 A | 6/1980 |
| JP | S5728046 A | 2/1982 |
| JP | 4174016 B2 | 10/2008 |
| JP | 2013233437 A | 11/2013 |
| MX | 2014005372 A | 7/2014 |
| TW | 201605856 A | 2/2016 |
| WO | WO-9728798 A1 | 8/1997 |
| WO | WO-9728799 A1 | 8/1997 |
| WO | WO-9728800 A1 | 8/1997 |
| WO | WO-9729121 A1 | 8/1997 |
| WO | WO-9747285 A1 | 12/1997 |
| WO | WO-9850027 A1 | 11/1998 |
| WO | WO-9859234 A1 | 12/1998 |
| WO | WO-9903458 A1 | 1/1999 |
| WO | WO-9909828 A1 | 3/1999 |
| WO | WO-9948501 A1 | 9/1999 |
| WO | WO-9966909 A2 | 12/1999 |
| WO | WO-0003679 A2 | 1/2000 |
| WO | WO-0003701 A1 | 1/2000 |
| WO | WO-0003746 A2 | 1/2000 |
| WO | WO-0006139 A2 | 2/2000 |
| WO | WO-0056403 A1 | 9/2000 |
| WO | WO-0113935 A2 | 3/2001 |
| WO | WO-0126642 A2 | 4/2001 |
| WO | WO-0152832 A1 | 7/2001 |
| WO | WO-0167890 A2 | 9/2001 |
| WO | WO-0172839 A2 | 10/2001 |
| WO | WO-0182915 A2 | 11/2001 |
| WO | WO-0205851 A2 | 1/2002 |
| WO | WO-0224865 A2 | 3/2002 |
| WO | WO-03016903 A2 | 2/2003 |
| WO | WO-03024480 A2 | 3/2003 |
| WO | WO-03024481 A2 | 3/2003 |
| WO | WO-03026564 A2 | 4/2003 |
| WO | WO-03041645 A2 | 5/2003 |
| WO | WO-03045353 A1 | 6/2003 |
| WO | WO-03047551 A1 | 6/2003 |
| WO | WO-03066030 A2 | 8/2003 |
| WO | WO-2004000275 A1 | 12/2003 |
| WO | WO-2004007538 A2 | 1/2004 |
| WO | WO-2004009116 A2 | 1/2004 |
| WO | WO-2004014429 A1 | 2/2004 |
| WO | WO-2004025268 A2 | 3/2004 |
| WO | WO-2004032900 A1 | 4/2004 |
| WO | WO-2004071431 A2 | 8/2004 |
| WO | WO-2004084940 A1 | 10/2004 |
| WO | WO-2004111185 A2 | 12/2004 |
| WO | WO-2005039502 A2 | 5/2005 |
| WO | WO-2005039546 A2 | 5/2005 |
| WO | WO-2005058319 A1 | 6/2005 |
| WO | WO-2005067930 A2 | 7/2005 |
| WO | WO-2005102390 A2 | 11/2005 |
| WO | WO-2006006858 A1 | 1/2006 |
| WO | WO-2006047032 A2 | 5/2006 |
| WO | WO-2006079999 A2 | 8/2006 |
| WO | WO-2006121552 A2 | 11/2006 |
| WO | WO-2006127418 A1 | 11/2006 |
| WO | WO-2007050697 A2 | 5/2007 |
| WO | WO-2007066240 A2 | 6/2007 |
| WO | WO-2007067519 A2 | 6/2007 |
| WO | WO-2007085898 A2 | 8/2007 |
| WO | WO-2007092043 A2 | 8/2007 |
| WO | WO-2007101884 A1 | 9/2007 |
| WO | WO-2008009125 A1 | 1/2008 |
| WO | WO-2008010223 A2 | 1/2008 |
| WO | WO-2008023261 A1 | 2/2008 |
| WO | WO-2008026046 A1 | 3/2008 |
| WO | WO-2008038291 A1 | 4/2008 |
| WO | WO-2008039179 A1 | 4/2008 |
| WO | WO-2008119097 A1 | 10/2008 |
| WO | WO-2008122990 A1 | 10/2008 |
| WO | WO-2008130638 A2 | 10/2008 |
| WO | WO-2009018338 A2 | 2/2009 |
| WO | WO-2009021055 A1 | 2/2009 |
| WO | WO-2009050354 A1 | 4/2009 |
| WO | WO-2009055001 A2 | 4/2009 |
| WO | WO-2009061436 A1 | 5/2009 |
| WO | WO-2009079765 A1 | 7/2009 |
| WO | WO-2009091605 A2 | 7/2009 |
| WO | WO-2009097596 A1 | 8/2009 |
| WO | WO-2009102805 A1 | 8/2009 |
| WO | WO-2009109428 A2 | 9/2009 |
| WO | WO-2009118179 A1 | 10/2009 |
| WO | WO-2009118763 A1 | 10/2009 |
| WO | WO-2009149252 A1 | 12/2009 |
| WO | WO-2010099522 A1 | 9/2010 |
| WO | WO-2010123577 A2 | 10/2010 |
| WO | WO-2010124089 A2 | 10/2010 |
| WO | WO-2011027060 A2 | 3/2011 |
| WO | WO-2011028875 A1 | 3/2011 |
| WO | WO-2011045443 A1 | 4/2011 |
| WO | WO-2011045769 A1 | 4/2011 |
| WO | WO-2011048494 A2 | 4/2011 |
| WO | WO-2011072398 A1 | 6/2011 |
| WO | WO-2011097269 A1 | 8/2011 |
| WO | WO-2011109809 A2 | 9/2011 |
| WO | WO-2011116189 A1 | 9/2011 |
| WO | WO-2011138142 A1 | 11/2011 |
| WO | WO-2011143254 A2 | 11/2011 |
| WO | WO-2011158964 A1 | 12/2011 |
| WO | WO-2012012764 A1 | 1/2012 |
| WO | WO-2012022928 A2 | 2/2012 |
| WO | WO-2012031125 A2 | 3/2012 |
| WO | WO-2012039660 A1 | 3/2012 |

(56) References Cited

FOREIGN PATENT DOCUMENTS

| | | |
|---|---|---|
| WO | WO-2012045118 A1 | 4/2012 |
| WO | WO-2012054815 A1 | 4/2012 |
| WO | WO-2012063257 A2 | 5/2012 |
| WO | WO-2012066537 A2 | 5/2012 |
| WO | WO-2012074588 A2 | 6/2012 |
| WO | WO-2012077110 A2 | 6/2012 |
| WO | WO-2012085919 A2 | 6/2012 |
| WO | WO-2012110537 A1 | 8/2012 |
| WO | WO-2012134436 A1 | 10/2012 |
| WO | WO-2012137971 A1 | 10/2012 |
| WO | WO-2012158892 A2 | 11/2012 |
| WO | WO-2012177962 A1 | 12/2012 |
| WO | WO-2013004999 A1 | 1/2013 |
| WO | WO-2013040471 A2 | 3/2013 |
| WO | WO-2013068949 A1 | 5/2013 |
| WO | WO-2013083710 A1 | 6/2013 |
| WO | WO-2013085849 A2 | 6/2013 |
| WO | WO-2013085850 A2 | 6/2013 |
| WO | WO-2013085922 A1 | 6/2013 |
| WO | WO-2013091900 A1 | 6/2013 |
| WO | WO-2013097947 A1 | 7/2013 |
| WO | WO-2013112163 A1 | 8/2013 |
| WO | WO-2013112757 A1 | 8/2013 |
| WO | WO-2013169355 A1 | 11/2013 |
| WO | WO-2014015993 A1 | 1/2014 |
| WO | WO-2014031958 A1 | 2/2014 |
| WO | WO-2014035473 A1 | 3/2014 |
| WO | WO-2014064703 A1 | 5/2014 |
| WO | WO-2014078857 A1 | 5/2014 |
| WO | WO-2014093277 A1 | 6/2014 |
| WO | WO-2014098877 A1 | 6/2014 |
| WO | WO-2014117089 A1 | 7/2014 |
| WO | WO-2014140925 A2 | 9/2014 |
| WO | WO-2014143085 A1 | 9/2014 |
| WO | WO-2014145126 A2 | 9/2014 |
| WO | WO-2014146082 A1 | 9/2014 |
| WO | WO-2014153099 A2 | 9/2014 |
| WO | WO-2014176556 A1 | 10/2014 |
| WO | WO-2014186623 A2 | 11/2014 |
| WO | WO-2014190440 A1 | 12/2014 |
| WO | WO-2014195872 A1 | 12/2014 |
| WO | WO-2015004245 A1 | 1/2015 |
| WO | WO-2015006315 A1 | 1/2015 |
| WO | WO-2015034846 A1 | 3/2015 |
| WO | WO-2015061125 A1 | 4/2015 |
| WO | WO-2015065546 A2 | 5/2015 |
| WO | WO-2015066344 A1 | 5/2015 |
| WO | WO-2015134405 A1 | 9/2015 |
| WO | WO-2015112168 A2 | 11/2015 |
| WO | WO-2015187289 A1 | 12/2015 |
| WO | WO-2016161138 A1 | 10/2016 |
| WO | WO-2016176177 A1 | 11/2016 |
| WO | WO-2016178053 A1 | 11/2016 |
| WO | WO-2017023679 A1 | 2/2017 |
| WO | WO-2018035477 A1 | 2/2018 |
| WO | WO-2018135943 A1 | 7/2018 |
| WO | WO-2018141063 A1 | 8/2018 |
| WO | WO-2018145219 A1 | 8/2018 |
| WO | WO-2018148605 A1 | 8/2018 |
| WO | WO-2018184206 A1 | 10/2018 |
| WO | WO-2018195455 A1 | 10/2018 |
| WO | WO-2018223044 A1 | 12/2018 |
| WO | WO-2019073379 A1 | 4/2019 |
| WO | WO-2019079742 A1 | 4/2019 |
| WO | WO-2019081764 A1 | 5/2019 |
| WO | WO-2019099745 A1 | 5/2019 |
| WO | WO-2019109124 A1 | 6/2019 |
| WO | WO-2019122525 A1 | 6/2019 |
| WO | WO-2019144140 A1 | 7/2019 |
| WO | WO-2019161050 A1 | 8/2019 |
| WO | WO-2019173797 A1 | 9/2019 |
| WO | WO-2019180309 A1 | 9/2019 |
| WO | WO-2019213551 A1 | 11/2019 |
| WO | WO-2019246532 A1 | 12/2019 |
| WO | WO-2020024060 A1 | 2/2020 |
| WO | WO-2020041329 A1 | 2/2020 |
| WO | WO-2020053196 A1 | 3/2020 |
| WO | WO-2020142259 A1 | 7/2020 |
| WO | WO-2020157569 A1 | 8/2020 |
| WO | WO-2020212948 A1 | 10/2020 |
| WO | WO-2020212951 A1 | 10/2020 |
| WO | WO-2020212952 A1 | 10/2020 |
| WO | WO-2022207746 | 10/2022 |

OTHER PUBLICATIONS

Abramovitch, A. et al. (Jul./Aug. 2015). Comorbidity Between Attention Deficit/Hyperactivity Disorder and Obsessive-Compulsive Disorder Across the Lifespan: A Systematic and Critical Review. Harvard Review of Psychiatry, 23(4):245-262.

Adams, K.S. and Breden Crouse, E.L. (2014). Melatonin agonists in the management of sleep disorders: A focus on ramelteon and tasimelteon. Ment Health Clin, 4:59-64. https://doi.org/10.9740/mhc.n190087.

Adams, T.G. et al. (Apr. 2017). Intranasal ketamine and cognitive-behavioral therapy for treatment-refractory obsessive-compulsive disorder. Journal of Clinical Psychopharmacology, 37(2):269-271. HHS Public Access Author Manuscript; available in PMC Apr. 1, 2018, 4 pages.

Adelow, C. et al. (2012). Hospitalization for psychiatric disorders before and after onset of unprovoked seizures/epilepsy. Neurology, 78(6), 396-401. https://doi.org/10.1212/WNL.0b013e318245f461.

Advokat, C. and M. Scheithauer (May 2013). Attention-deficit hyperactivity disorder (ADHD) stimulant medications as cognitive enhancers. Front Neurosci, 7:Article 92, 8 pages.

Agin-Liebes, G.I. et al. (2020). Long-term follow-up of psilocybin-assisted psychotherapy for psychiatric and existential distress in patients with life-threatening cancer. J Psychopharmacol [online]; retrieved from: https://doi.org/10.1177/0269881119897615, 12 pages.

Aguglia, A., Signorelli, M. S., Albert, U., & Maina, G. (2018). The impact of general medical conditions in obsessive-compulsive disorder. Psychiatry Investigation, 15(3):246-253. https://doi.org/10.30773/pi.2017.06.17.2.

Alayadhi, L.Y. et al. (2016). High-resolution SNP genotyping platform identified recurrent and novel CNVs in autism multiplex families. Neuroscience, 339:561-570.

Albelda, N., & Joel, D. (2012). Current animal models of obsessive compulsive disorder: An update. Neuroscience, 211:83-106. https://doi.org/10.1016/j.neuroscience.2011.08.070.

Alcaro, A., and J. Panksepp (2011). The Seeking mind: Primal neuro-affective substrates for appetitive incentive states and their pathological dynamics in addictions and depression. Neurosci Biobehav Rev, 35:1805-1820. https://doi.org/10.1016/j.neubiorev.2011.03.002.

Alderson, R.M. et al. (2013) Attention-deficit/hyperactivity disorder (ADHD) and working memory in adults: A meta-analytic review. Neuropsychology, 27(3):287-302.

Allam, J.S., Collop, N., 2018. Central Sleep Apnea Syndrome (Idiopathic CSA, Cheyne-Stokes Respiration, CSA due to a drug or substance, High-altitude Periodic breathing, CSA due to a medical condition other than Cheyne-Stokes). Pulmonology Advisor (2018): pp. 1-14. Retrieved from: https://www.pulmonologyadvisor.com/home/decision-support-in-medicine/pulmonary-medicine/central-sleep-apnea-syndrome-idiopathic-csa-cheyne-stokes-respiration-csa-due-to-a-drug-or-substance-high-altitude-periodic-breathing-csa-due-to-a-medical-condition-ot (accessed Jul. 30, 2020).

Allen, G. and E. Courchesne (Jan. 1, 2001). Attention function and dysfunction in autism. Frontiers in Bioscience, 6:d105-119.

Alonso, P., López-Solà, C., Real, E., Segalàs, C., & Menchón, J. M. (2015). Animal models of obsessive-compulsive disorder: Utility and limitations. In Neuropsychiatric Disease and Treatment, 11:1939-1955. https://doi.org/10.2147/NDT.S62785.

Alvarez, A.J. et al. (2009) "Polymorph Screening: Comparing a Semi-Automated Approach with a High Throughput Method" Crystal Growth and Design, 9:4181-4188.

Alzheimer's Association (2019). Alzheimer's Disease Facts and Figures. Alzheimers Dement, 15(3):321-387, with Appendices, 90 total pages.

(56) References Cited

OTHER PUBLICATIONS

Alzheimer's Association (2019). FDA-approved treatments for Alzheimer's. TS-0087. 5 pages.
American Parkinson Disease Association. (2019). Medications for Parkinson's. Retrieved from https://www.apdaparkinson.org/what-is-parkinsons/treatment-medication/medication/; retrieved on Jul. 30, 2020, 18 pages.
American Psychiatric Association (2013) Binge-eating disorder. In: Diagnostic and Statistical Manual of Mental Disorders. 5th ed. Arlington, VA: American Psychiatric Association; p. 350-353.
American Psychiatric Association (2013). Diagnostic and statistical manual of mental disorders (5th ed.). American Journal of Psychiatry. https://doi.org/10.1176/appi.books.9780890425596.744053, 970 pages.
American Psychiatric Association (2013). Sleep-Wake Disorders. In: Diagnostic and Statistical Manual of Mental Disorders. 5th Edition. [online]. Retrieved from: https://doi.org/10.1176/appi.books.9780890425596.dsm12, 2 pages.
Amiri, S. et al. (2008) Modafinil as a treatment for Attention-Deficit/Hyperactivity Disorder in children and adolescents: A double blind, randomized clinical trial. Prog Neuro-Psychopharmacol Biol Psychiatry. 32(1):145-149.
Amodeo, D.A. et al. (2012). Differences in BTBR T+ tf/J and C57BL/6J mice on probabilistic reversal learning and stereotyped behaviors. Behavioural Brain Research,227(1):64-72. NIH Public Access Author Manuscript, available Mar. 1, 2012, 19 pages.
Andermann, F. (1987). Migraine-epilepsy relationships. Epilepsy Research, 1(4):213-226. https://doi.org/10.1016/0920-1211(87)90028-3.
Andersson, M. et al. (2017) Psychoactive substances as a last resort—a qualitative study of self-treatment of migraine and cluster headaches. Harm Reduction Journal, 14:60, DOI:10.1186/s12954-017-0186-6, 11 pages.
Andrés-Pepiñá, S. et al. (2019). Long-term outcome and psychiatric comorbidity of adolescent-onset anorexia nervosa. Clinical Child Psychology and Psychiatry [online]. Retrieved from: https://doi.org/10.1177/1359104519827629, 12 pages.
Angst, J., Gamma, A., Endrass, J., Goodwin, R., Ajdacic, V., Eich, D., & Rössler, W. (2004). Obsessive-compulsive severity spectrum in the community: Prevalence, comorbidity, and course. European Archives of Psychiatry and Clinical Neuroscience, 254(3):156-164. https://doi.org/10.1007/s00406-004-0459-4.
Anwar, M.A. et al. (2013). Negative regulatory approaches to the attenuation of Toll-like receptor signaling. Experimental & Molecular Medicine, 45(2):e11, 14 pages. https://doi.org/10.1038/emm.2013.28.
Ara, A. et al. (2016). Sleep disturbances and substance use disorders: A bi-directional relationship. Psychiatr Ann, 46(7):408-412.
Arcelus, J., Mitchell, A. J., Wales, J., & Nielsen, S. (Jul. 2011). Mortality rates in patients with anorexia nervosa and other eating disorders. A meta-analysis of 36 studies. Archives of General Psychiatry, 68(7):724-731. https://doi.org/10.1001/archgenpsychiatry.2011.74.
Armstrong, M.J. and M.S. Okun (2020). Diagnosis and Treatment of Parkinson Disease. A Review. JAMA, 323(6):548-560.
Arzt, E. et al. (1991). Serotonin inhibition of tumor necrosis factor-α synthesis by human monocytes. Life Sciences, 48(26):2557-2562.
Asnis, G.M. et al. (2016). Pharmacotherapy treatment options for insomnia: A primer for clinicians. Int J Mol Sci, 17:50, 11 pages. https://doi.org/10.3390/ijms17010050.
Attia, E., Kaplan, A. S., Walsh, B. T., Gershkovich, M., Yilmaz, Z., Musante, D., & Wang, Y. (2011). Olanzapine versus placebo for out-patients with anorexia nervosa. Psychological Medicine, 41(10):2177-2182. https://doi.org/10.1017/S0033291711000390.
Auger, R.R. et al. (2005). Risks of high-dose stimulants in the treatment of disorders of excessive somnolence: A case-control study. Sleep, 28(6):667-672.
Avidan, A.Y. (2012). Comorbidities of central nervous system hypersomnia. Sleep Med Clin, 7:291-302.

Ayaz, G. et al. (2017). Evaluation of 5-HT7 Receptor Trafficking on In Vivo and In Vitro Model of Lipopolysaccharide (LPS)-Induced Inflammatory Cell Injury in Rats and LPS-Treated A549 Cells. Biochemical Genetics, 55(1):34-47.
Babu, C.S. et al. (2009). Co-morbidities in people living with epilepsy: Hospital based case-control study from a resource-poor setting. Epilepsy Research, 86(2-3):146-152.
Baglioni, C. et al. (2016). Sleep and mental disorders: A meta-analysis of polysomnographic research. Psychol Bull, 142:969-990. HHS Public Access Author Manuscript, available Sep. 1, 2017, 56 pages.
Bai, D. et al. (Jul. 17, 2019). Association of Genetic and Environmental Factors With Autism in a 5-Country Cohort. JAMA Psychiatry, 76(10):1035-1043.
Baio, J. (Mar. 30, 2012). Prevalence of autism spectrum disorders—Autism and developmental disabilities monitoring network, 14 sites, United States, 2008. Morbidity and Mortality Weekly Report (MMWR), 61(3):1-24.
Baker, L.A. et al. (2006) Behavioral Genetics: The Science of Antisocial Behavior. Law Contemp Probl, 69(1-2):7-46. NIH Public Access Author Manuscript, 37 pages.
Bandeen-Roche, K. et al. (2009). Measuring Systemic Inflammatory Regulation in Older Adults: Evidence and Utility. Rejuvenation Research, 12(6):403-410.
Bandelow, B. and S. Michaelis (2015). Epidemiology of anxiety disorders in the 21st century. Dialogues Clin Neurosci, 17:327-335.
Banks, W.A. et al. (1994). Penetration of interleukin-6 across the murine blood-brain barrier. Neuroscience Letters, 179(1-2):53-56.
Barnes, D.T. (1970). The uses and abuses of L.S.D. and other hallucinogenic drugs. The Australian and New Zealand Journal of Psychiatry, 4(4):170-173.
Barnes, P. J. (2006). How corticosteroids control inflammation: Quintiles Prize Lecture 2005. British Journal of Pharmacology, 148(3):245-254.
Barnes, T.R.E. (1989) A Rating Scale for Drug-Induced Akathisia. Br J Psychiatry, 154:672-676.
Baron-Cohen, S. et al. (2000) The amygdala theory of autism. Neurosci Biobehav Rev, 24(3):355-364.
Barrett, F.S. et al. (Nov. 2015) Validation of the revised Mystical Experience Questionnaire in experimental sessions with psilocybin. Journal of Psychopharmacology. 29:1182-1190. HHS Public Access Author Manuscript, 20 pages.
Barrett, F.S. et al. (Dec. 2016) The Challenging Experience Questionnaire: Characterization of challenging experiences with psilocybin mushrooms. Journal of Psychopharmacology, 30(12):1279-1295. HHS Public Access Author Manuscript, 42 pages.
Barrett, F.S. et al. (Nov. 2018) Serotonin 2A Receptor Signaling Underlies LSD-Induced Alteration of the Neural Response to Dynamic Changes in Music. Cerebral Cortex, 28:3939-3950.
Bassetti, C. and M.S. Aldrich (1997). Idiopathic hypersomnia. A series of 42 patients. Brain, 120:1423-1435.
Bateman, R.J. et al. (Aug. 30, 2012). Clinical and biomarker changes in dominantly inherited Alzheimer's disease. The New England Journal of Medicine, 367(9):795-804.
Bech, P. et al. (1978) The mania rating scale: scale construction and inter-observer agreement. Neuropharmacology. 17(6):430-431.
Becker, D. and Grilo, C. (2015). Comorbidity of mood and substance use disorders in patients with binge-eating disorder: Associations with personality disorder and eating disorder pathology. Journal of Psychosomatic Research, 79(2), pp. 159-164.
Becker, P.M. (2006). Insomnia: Prevalence, Impact, Pathogenesis, Differential Diagnosis, and Evaluation. Psychiatr Clin North Am, 26:855-870.
Bell, R.F. and E.A. Kalso (2018) Ketamine for pain management. Pain Reports, 3:e674, 8 pages.
Belli, H. et al. (2012). Dissociative symptoms and dissociative disorder comorbidity in patients with obsessive-compulsive disorder. Comprehensive Psychiatry, 53(7):975-980.
Bello, N. and Yeomans, B. (2018). Safety of pharmacotherapy options for bulimia nervosa and binge eating disorder. Expert Opinion on Drug Safety, 17(1), pp. 17-23.

(56) References Cited

OTHER PUBLICATIONS

Belzeaux, R. et al. (Feb. 2018). Focusing on the Opioid System for Addiction Biomarker Discovery. Trends in Molecular Medicine, 24(2), pp. 206-220.

Benzon, H.T. et al. (2013) Preface. Practical Management of Pain, 5th Edition. Philadelphia, PA: Elsevier Mosby; 13 total pages.

Berg, A.T. (Jan. 2011). Epilepsy, cognition, and behavior: The clinical picture. Epilepsia, 52(Suppl 1):7-12. NIH Public Access Author Manuscript, available Jan. 1, 2012, 8 pages.

Berg, A.T. et al. (2008). Residual cognitive effects of uncomplicated idiopathic and cryptogenic epilepsy. Epilepsy & Behavior, 13(4):614-619.

Berg, D. et al. (Nov. 12, 2015). MDS research criteria for prodromal Parkinson's disease. Movement Disorders, 30(12):1600-1609.

Berlin, H.A. et al. (2011). Double-blind, placebo-controlled trial of topiramate augmentation in treatment-resistant obsessive-compulsive disorder. Journal of Clinical Psychiatry, 72(5):716-721. https://doi.org/10.4088/JCP.09m05266gre.

Berthold-Losleben, M. & H. Himmerich (2008). The TNF-alpha System: Functional Aspects in Depression, Narcolepsy and Psychopharmacology. Current Neuropharmacology, 6(3):193-202.

Besnard, J. et al. (Dec. 13, 2012) Automated design of ligands to polypharmacological profiles. Nature, 492(7428):215-220. https://doi.org/10.1038/nature11691.

Bhidayasiri, R. & P. Martinez-Martin (2017). Clinical Assessments in Parkinson's Disease: Scales and Monitoring. 132:129-182.

Billiard, M. & Bentley, A. (2004). Is insomnia best categorized as a symptom or a disease? Sleep Med. 5(Suppl 1):S35-S40. https://doi.org/10.1016/S1389-9457(04)90006-8.

Billiard, M. (2008). Narcolepsy: Current treatment options and future approaches. Neuropsychiatr Dis Treat, 4(3):557-566.

Binukumar, B.K. et al. (2015). Peptide TFP5/TP5 derived from Cdk5 activator P35 provides neuroprotection in the MPTP model of Parkinson's disease. Molecular Biology of the Cell, 26(24):4478-4491. https://doi.org/10.1091/mbc.E15-06-0415.

Bird, A.D. & Cuntz, H. (Jun. 4, 2019). Dissecting Sholl Analysis into Its Functional Components. Cell Reports, 27(10):3081-3096.

Bison, S. et al. (2009). Differential behavioral, physiological, and hormonal sensitivity to LPS challenge in rats. International Journal of Interferon, Cytokine and Mediator Research, 1:1-13. https://doi.org/10.2147/IJICMR.S4273.

Black, D.W. (2015) The Natural History of Antisocial Personality Disorder. The Canadian Journal of Psychiatry. 60(7):309-314.

Blair, J.B. et al. (2000) Effect of Ring Fluorination on the Pharmacology of Hallucinogenic Tryptamines. J Med Chem, 43(24):4701-4710. https://doi.org/10.1021/jm000339w.

Blasio, A. et al. (2014). Opioid system in the medial prefrontal cortex mediates binge-like eating. Addiction Biology, 19(4), pp. 652-662.

Blum, A. (2014). HMG-CoA reductase inhibitors (statins), inflammation, and endothelial progenitor cells—New mechanistic insights of atherosclerosis. BioFactors, 40(3), 295-302. https://doi.org/10.1002/biof.1157.

Bonnet, M.H. et al. (1990). The effect of triazolam on arousal and respiration in central sleep apnea patients. Sleep, 13:31-41.

Borovcanin, M.M. et al. (Nov. 6, 2017). Interleukin-6 in Schizophrenia—Is There a Therapeutic Relevance? Frontiers in Psychiatry, 8:Article 221, 10 pages. https://doi.org/10.3389/fpsyt.2017.00221.

Bortolato, B. et al. (2015). The Involvement of TNF-alpha in Cognitive Dysfunction Associated with Major Depressive Disorder: An Opportunity for Domain Specific Treatments. Current Neuropharmacology, 13(5):558-576.

Bosanac, P. et al. (2005). Serotonergic and dopaminergic systems in anorexia nervosa: a role for atypical antipsychotics? Australian and New Zealand Journal of Psychiatry, 39(3):146-153.

Bossers, K. et al. (2009). Analysis of gene expression in Parkinson's disease: possible involvement of neurotrophic support and axon guidance in dopaminergic cell death. Brain Pathology, 19(1):91-107.

Braak, H. et al. (2003). Staging of brain pathology related to sporadic Parkinson's disease. Neurobiology of Aging, 24(2):197-211.

Bradley, T.D. and Phillipson, E.A. (1992). Central sleep apnea. Clin. Chest Med, 13(3):493-505 (abstract).

Bradley, T.D. et al. (1986). Clinical and physiologic heterogeneity of the central sleep apnea syndrome. Am. Rev. Respir. Dis., 134:217-221.

Braga, R.J. et al. (2013). Anxiety comorbidity in schizophrenia. Psychiatry Res, 210:1-7.

Brakoulias, V. et al. (2017). Comorbidity, age of onset and suicidality in obsessive-compulsive disorder (OCD): An international collaboration. Comprehensive Psychiatry, 76:79-86.

Brandt, C. & Mula, M. (2016). Anxiety disorders in people with epilepsy. Epilepsy Behav., 59:87-91. https://doi.org/10.1016/j.yebeh.2016.03.020.

Brandt, R.B. et al. (2020) Pharmacotherapy for Cluster Headache. CNS Drugs, 34:171-184, doi.org/10.1007/s40263-019-00696-2.

Brasure, M. et al. (2015). Management of Insomnia Disorder. Comparative Effectiveness Review No. 159. (Prepared by the Minnesota Evidence-based Practice Center under Contract No. 290-2012-00016-I). AHRQ Publication No. 15(16)-EHC027-EF. Rockville, MD: Agency for Healthcare Research and Quality. Dec. 2015 [online]. Retrieved from: www.effectivehealthcare.ahrq.gov/reports/final.cfm, 288 pages.

Bratland-Sanda, S. et al. (2019). Defining compulsive exercise in eating disorders: Acknowledging the exercise paradox and exercise obsessions. Journal of Eating Disorders, 7(1):8, https://doi.org/10.1186/s40337-019-0238-2, 3 pages.

Brawman-Mintzer, O. et al. (1993). Psychiatric comorbidity in patients with generalized anxiety disorder. Am. J. Psychiatry, 150:1216-1218.

Brockmeyer, T. et al. (2017) Advances in the treatment of anorexia nervosa: A review of established and emerging interventions. Psychological Medicine, 48(8):1228-1256. Cambridge University Press. https://doi.org/10.1017/S0033291717002604.

Brown, C. M., & Stokes, M.A. (2020). Intersection of Eating Disorders and the Female Profile of Autism. Child and Adolescent Psychiatric Clinics of North America, 29:409-417.

Brown, R.T. et al. (2017). Pharmacokinetics of Escalating Doses of Oral Psilocybin in Healthy Adults. Clinical Pharmacokinetics, 56(12):1543-1554. https://doi.org/10.1007/s40262-017-0540-6.

Brown, T.A. et al. (2001). Current and Lifetime Comorbidity of the DSM-IV Anxiety and Mood Disorders in a Large Clinical Sample. J. Abnorm. Psychol., 110:585-599.

Brownley, K. et al. (2016). Binge-Eating Disorder in Adults. Annals of Internal Medicine, 165(6):409-420.

Bruce, S.E. et al. (2005). Influence of psychiatric comorbidity on recovery and recurrence in generalized anxiety disorder, social phobia, and panic disorder: A 12-year prospective study. Am. J. Psychiatry, 162:1179-1187. NIH Public Access Author Manuscript, available in PMC Feb. 6, 2012, 16 pages.

Böszörményi, Z. (1961) Psilocybin and diethyltryptamine: Two tryptamine hallucinogens. In: Rothlin E (ed) neuropsychopharmacology, vol. II. Elsevier, Amsterdam, pp. 226-229.

Buescher, A.V. S. et al. (2014). Costs of autism spectrum disorders in the United Kingdom and the United States. JAMA Pediatrics, 168(8):721-728.

Bulik, C.M. et al. (1997). Eating disorders and antecedent anxiety disorders: a controlled study. Acta Psychiatr. Scand. 96, 101-107. https://doi.org/10.1111/j.1600-0447.1997.tb09913.x.

Burgess, E. et al. (2016). Effects of transcranial direct current stimulation (tDCS) on binge-eating disorder. International Journal of Eating Disorders, 49(10), pp. 930-936.

Burt, D.R. et al. (1976). Binding interactions of lysergic acid diethylamide and related agents with dopamine receptors in the brain. Molecular Pharmacology, 12(4):631-638.

Buscemi, N. et al. (Jun. 2005). Manifestations and management of chronic insomnia in adults: summary. In: AHRQ Evidence Report Summaries. Rockville (MD): Agency for Healthcare Research and Quality (US); 1998-2005. 125. https://doi.org/10.1037/e439752005-001, 11 pages.

(56) References Cited

OTHER PUBLICATIONS

Buxbaum, J.D., & Hof, P.R. (2013). Introduction. In the Neuroscience of Autism Spectrum Disorders. Elsevier, 7 pages. https://doi.org/10.1016/C2011-0-04170-4.
Buysse, D.J. et al. (1989). The Pittsburgh Sleep Quality Index: A New Instrument for Psychiatric Practice and Research. Psychiatry Res, 28:193-213.
Cabarkapa S. et al. (Aug. 13, 2019) Co-morbid obsessive-compulsive disorder and attention deficit hyperactivity disorder: Neurobiological commonalities and treatment implications. Front Psychiatry, 10:Article 557, 4 pages.
Cahill, C.M., & Rogers, J.T. (Sep. 19, 2008). Interleukin (IL) 1β Induction of IL-6 Is Mediated by a Novel Phosphatidylinositol 3-Kinase-dependent AKT/IκB Kinase α Pathway Targeting Activator Protein-1. Journal of Biological Chemistry, 283(38):25900-25912.
Caira, "Crystalline Polymorphism of Organic Compounds," Topics in Current Chemistry, Jan. 1, 1998, 198, 163-208.
Callahan, P. M., & Appel, J.B. (1988). Differences in the stimulus properties of 3,4-methylenedioxyamphetamine and 3,4-methylenedioxymethamphetamine in animals trained to discriminate hallucinogens from saline. J Pharmacol Exp Ther, 246(3):866-870.
Calvin, A.D. et al. (2010). Advanced heart failure and nocturnal hypoxaemia due to central sleep apnoea are associated with increased serum erythropoietin. Eur. J. Heart Fail., 12:354-359. https://doi.org/10.1093/eurjhf/hfq005.
Campolongo, M. et al. (2018) Sociability deficits after prenatal exposure to valproic acid are rescued by early social enrichment. Molecular Autism, 9:36, https://doi.org/10.1186/s13229-018-0221-9, 17 pages.
Canellas, F. et al. (2014). Dual cases of type 1 narcolepsy with schizophrenia and other psychotic disorders. J. Clin. Sleep Med., 10(9):1011-1018. https://doi.org/10.5664/jcsm.4040.
Carhart-Harris et al., "Psilocybin for treatment-resistant depression: fMRI-measured brain mechanisms," Scientific Reports, 2017, 7:13187, 11 pages.
Carhart-Harris, R. et al. (2012). Implications for psychedelic-assisted psychotherapy: functional magnetic resonance imaging study with psilocybin. British Journal of Psychiatry, 200(3):238-244.
Carhart-Harris, R.L. et al. (May 17, 2016) "Psilocybin with psychological support for treatment-resistant depression: an open-label feasibility study" Lancet Psychiatry, 3:619-627.
Carhart-Harris, R.L. et al. (2018) "Psilocybin with psychological support for treatment-resistant depression: six-month follow-up" Psychopharmacology, 235:399-408.
Carlsson, T. et al. (2011). Systemic administration of neuregulin-1β1 protects dopaminergic neurons in a mouse model of Parkinson's disease. Journal of Neurochemistry, 117(6), 1066-1074. https://doi.org/10.1111/j.1471-4159.2011.07284.x.
Carosi, J. M., & Sargeant, T. J. (2019). Rapamycin and Alzheimer disease: a double-edged sword? Autophagy, 15(8):1460-1462. https://doi.org/10.1080/15548627.2019.1615823.
Carter, O.L. (2005) Using psilocybin to investigate the relationship between attention, working memory, and the serotonin 1A and 2A receptors. J Cogn Neurosci., 17(10):1497-1508.
Cashman, J.N. (1996). The mechanisms of action of NSAIDs in analgesia. Drugs, 52(SUPPL. 5):13-23. https://doi.org/10.2165/00003495-199600525-00004.
Cassano, G.B. et al. (2002). Psychopharmacology of anxiety disorders. Dialogues Clin. Neurosci., 4(3):271-285.
Cavalli, E et al. (2019). The neuropathic pain: An overview of the current treatment and future therapeutic approaches. Intl J Immunopathol Pharmacol, 33:1-10; DOI: 10.1177/2058738419838383.
Cecil Textbook of Medicine, 20th edition (1996), vol. 2, pp. 1992-1996.
Cecil Textbook of Medicine, 20th edition (1996), vol. 2, pp. 2050-2057.
Chang, A. et al. (Jun. 3, 2020). Capsaicin. StatPearls. NCBI Bookshelf [online]. Retrieved from: https://www.ncbi.nlm.nih.gov/books/NBK459168/?report=printable; retrieved on Jul. 30, 2020, 4 pages.
Chang, S. et al. (2015). Disease monitoring in inflammatory bowel disease. World Journal of Gastroenterology, 21(40):11246-11259.
Chang, T.-T. and Yen, Y.-C. (2010). Cytokines and Major Psychiatric Disorders. Taiwanese Journal of Psychiatry, 24(4):257-268.
Chang, Y.C. et al. (2017). Behavioral phenotyping for autism spectrum disorders in mice. Current Protocols in Toxicology. 72:11.22.1-11.22.21, doi: 10.1002/cptx.19.
Charles, P. et al. (1999). Regulation of Cytokines, Cytokine Inhibitors, and Acute-Phase Proteins Following Anti-TNF-α Therapy in Rheumatoid Arthritis. The Journal of Immunology, 163(3):1521-1528. http://www.jimmunol.org/content/163/3/1521.
Chelminski, P.R. et al. (Jan. 2005) A primary care, multidisciplinary disease management program for opioid-treated patients with chronic non-cancer pain and a high burden of psychiatric comorbidity. BMC Health Serv Res, 5:3, doi:10.1186/1472-6963-5-3, 13 pages.
Cheng, Z. et al. (2019). Ethnic differences in eating disorder prevalence, risk factors, and predictive effects of risk factors among young women. Eating Behaviors, 32, pp. 23-30.
Chieffi, S. et al. (2017). Orexin system: The key for a healthy life. Front. Physiol., 8:357, doi: 10.3389/fphys.2017.00357, 9 pages.
Choi, G.B. et al. (2016). The maternal interleukin-17a pathway in mice promotes autism-like phenotypes in offspring. Science, 351(6276):933-939.
Chrem, Mendez, P. et al. (2019). Biomarkers for Alzheimer's disease. Where we stand and where we are headed. Medicina (Buenos Aires), 79:546-551.
Citrome, L. (2014). Suvorexant for insomnia: A systematic review of the efficacy and safety profile for this newly approved hypnotic—What is the number needed to treat, number needed to harm and likelihood to be helped or harmed? Int. J. Clin. Pract., 68(12):1429-1441. https://doi.org/10.1111/ijcp.12568.
Citrome, L. (2019). Binge eating disorder revisited: what's new, what's different, what's next. CNS Spectrums, 24, pp. 4-12.
Clark, B. (1968). Some early observations on the use of psilocybin in psychiatric patients. Brit. J. Soc. Psychiatry, 2:21-25.
Clemmensen, C. et al. (2012). The microtubule-associated protein 1A (MAP1A) is an early molecular target of soluble Aβ-peptide. Cellular and Molecular Neurobiology, 32(4):561-566.
ClinicalTrials.gov, "Effects of Psilocybin in Major Depressive Disorder", NCT03181529, First posted Jun. 8, 2017.
Cloëz-Tayarani, I. et al. (2003). Differential effect of serotonin on cytokine production in lipopolysaccharide-stimulated human peripheral blood mononuclear cells: Involvement of 5-hydroxytryptamine$_{2a}$ receptors. International Immunology, 15(2), 233-240. https://doi.org/10.1093/intimm/dxg027.
Coley, A.A., & Gao, W.J. (2019). PSD-95 deficiency disrupts PFC-associated function and behavior during neurodevelopment. Scientific Reports, 9:9486, https://doi.org/10.1038/s41598-019-45971-w, 13 pages.
Collins, K.L. et al. (2018). A review of current theories and treatments for phantom limb pain. J Clin Invest, 128(6):2168-2176. https://doi.org/10.1172/JCI94003.
Colloca, L. et al. (2017) Neuropathic pain. Nat Rev Dis Primers, 3:17002, doi:10.1038/nrdp.2017.2, 45 pages.
Connolly, J. et al. (Sep. 2015). ADHD & Pharmacotherapy: Past, Present and Future. Ther Innoc Regul Sci., 49(5):632-642. HHS Public Access, available in PMC Sep. 1, 2016, 19 pages.
Cooper, C.M. et al. (2015) Tianeptine in an experimental medicine model of antidepressant action. Journal of Psychopharmacology, 29(5):582-590.
Co-pending U.S. Appl. No. 17/604,610, inventors Londesbrough; Derek John et al., filed Oct. 18, 2021.
Coric, V. et al. (2005). Riluzole augmentation in treatment-resistant obsessive-compulsive disorder: An open-label trial. Biological Psychiatry, 58(5):424-428. https://doi.org/10.1016/j.biopsych.2005.04.043.
Cornillie, F. et al. (2001) Infliximab induces potent anti-inflammatory and local immunomodulatory activity but no systemic

(56) References Cited

OTHER PUBLICATIONS immune suppression in patients with Crohn's disease. Alimentary Pharmacology and Therapeutics, 15(4), 463-473. https://doi.org/10.1046/j.1365-2036.2001.00956.x.
Cossrow, N. et al. (2016). Estimating the Prevalence of Binge Eating Disorder in a Community Sample From the United States: Comparing DSM-IV-TR and DSM-5 Criteria. The Journal of Clinical Psychiatry, 77(8), pp. e968-e974.
Costa-Mattioli, M., & Monteggia, L.M. (2013). mTOR complexes in neurodevelopmental and neuropsychiatric disorders. Nature Neuroscience, 16(11):1537-1543.
Cowie, M.R. et al. (2015) Adaptive servo-ventilation for central sleep apnea in systolic heart failure. N. Engl. J. Med., 373:1095-1105. doi.org/10.1056/NEJMoa1506459.
Croall, I.D. et al. (2020). Cognitive Deficit and White Matter Changes in Persons with Celiac Disease: a Population-Based Study. Gastroenterology. 158:2112-2122.
Crow, S.J. et al. (2009). Increased mortality in bulimia nervosa and other eating disorders. American Journal of Psychiatry, 166(12):1342-1346.
Crowson, C. S. et al. (2009). Which Measure of Inflammation to Use? A Comparison of Erythrocyte Sedimentation Rate and C-Reactive Protein Measurements from Randomized Clinical Trials of Golimumab in Rheumatoid Arthritis. The Journal of Rheumatology, 36(8):1606-1610. https://doi.org/10.3899/jrheum.081188.
Cruccu, G. (2017) A Review of Neuropathic Pain: From Guidelines to Clinical Practice. Pain Ther, 6(Suppl 1):S35-S42.
Cryan, J.F. & Sweeney, F.F. (2011). The age of anxiety: Role of animal models of anxiolytic action in drug discovery. British Journal of Pharmacology, 164:1129-1161.
Csicsvari, J. et al. (2003). Mechanisms of gamma oscillations in the hippocampus of the behaving rat. Neuron, 37:311-322.
Culbert, K.M. et al. (2015). Research Review: What we have learned about the causes of eating disorders—A synthesis of sociocultural, psychological, and biological research. Journal of Child Psychology and Psychiatry, 56:11, pp. 1141-1164. https://doi.org/10.1111/jcpp.12441.
Curatolo, P. et al. (2010) The neurobiological basis of ADHD. Ital J Pediatr, 36:79, http://www.ijponline.net/content/36/1/79, 7 pages.
Cuthbert, P.C. et al. (2007). Synapse-associated protein 102/dlgh3 couples the NMDA receptor to specific plasticity pathways and learning strategies. Journal of Neuroscience, 27(10):2673-2682. https://doi.org/10.1523/JNEUROSCI.4457-06.2007.
Da Silveira, D.X. et al. (2005). Ayahuasca in adolescence: A preliminary psychiatric assessment. Journal of Psychoactive Drugs, 37:2, 129-133. https://doi.org/10.1080/02791072.2005.10399792.
Dahan, A. et al. (Oct. 2014) Comorbidities and the Complexities of Chronic Pain. Anesthesiology, 121(4):675-677.
Dalic, L., & Cook, M. (2016). Managing drug-resistant epilepsy: challenges and solutions. Neuropsychiatric Disease and Treatment, vol. 12, p. 2605-2616. https://doi.org/10.2147/NDT.S84852.
Dansie, E.J. & Turk, D.C. (2013) Assessment of patients with chronic pain. Br J Anaesth. 111(1):19-25.
Darveaux, J., & Busse, W. W. (2015). Biologics in Asthma—The Next Step Toward Personalized Treatment. J Allergy Clin Immunol Pract, 3(2), 152-160. https://doi.org/10.1016/j.jaip.2014.09.014.
Dash, S. (2019). The impact of genetic and cultural factors on anorexia and bulimia. Life Research, 2(2), 71-79. https://doi.org/10.12032/life2019-0425-004.
Dauer, W., & Przedborski, S. (2003). Parkinson's Disease: Mechanisms and Models. Neuron, 39(6), 889-909. https://doi.org/10.1016/S0896-6273(03)00568-3.
Dauvilliers, Y. & Barateau, L. (2017). Narcolepsy and Other Central Hypersomnias. Continyyn (Minneap Minn), 23(4):989-1004. https://doi.org/10.1212/CON.0000000000000492.
Dauvilliers, Y. et al. (2007). Narcolepsy with cataplexy. Lancet 369, 499-511. https://doi.org/10.1016/S0140-6736(07)60237-2.
Dauvilliers, Y. et al. (2009). Psychological health in central hypersomnias: The French Harmony study. J. Neurol. Neurosurg. Psychiatry, 80, 636-641. https://doi.org/10.1136/jnnp.2008.161588.
Davis, C. (2015). The epidemiology and genetics of binge eating disorder (BED). CNS Spectrums, 20(6), pp. 522-529.
Davis, H., & Attia, E. (2017). Pharmacotherapy of eating disorders. Current Opinion in Psychiatry, 30(6), 452-457. https://doi.org/10.1097/YCO.0000000000000358.
De Veen, B.T.H. et al. (2017) "Psilocybin for treating substance use disorders?" Exp Rev Neurotherapeutics, 17(2):203-212; DOI: 10.1080/14737175.2016.1220834.
Deacon, R.M.J. & Rawlins, J.N.P. (2006) T-maze alternation in the rodent. Nat Protoc, 1(1):7-12. Available from: http://www.ncbi.nlm.nih.gov/pubmed/17406205.
DeBacker, W.A. et al. (1995). Central apnea index decreases after prolonged treatment with acetazolamide. Am. J. Respir. Crit. Care Med., 151:87-91, https://doi.org/10.1164/ajrccm.151.1.7812578.
Debotton, N. and A. Dahan (2017) Applications of Polymers as Pharmaceutical Excipients in Solid Oral Dosage Forms. Med Res Rev, 37(1):52-97.
Decaluwé, V. and Braet, C. (2003). Prevalence of binge-eating disorder in obese children and adolescents seeking weight-loss treatment. International Journal of Obesity, 27(3), pp. 404-409.
DeJong, H. et al. (2013). Quality of life in anorexia nervosa, bulimia nervosa and eating disorder not-otherwise-specified. Journal of Eating Disorders, 1:43, http://www.jeatdisord.com/content/1/1/43, 8 pages.
DeLisi, M. et al. (Jul. 2019) The etiology of antisocial personality disorder: The differential roles of adverse childhood experiences and childhood psychopathology. Compr Psychiatry, 92:1-6.
Dell'Osso, B. et al. (2018). Prevalence of suicide attempt and clinical characteristics of suicide attempters with obsessive-compulsive disorder: A report from the International College of Obsessive-Compulsive Spectrum Disorders (ICOCS). CNS Spectrums, 23(1), 59-66. https://doi.org/10.1017/S1092852917000177.
Depboylu, C. et al. (2015). Systemically administered neuregulin-1β1 rescues nigral dopaminergic neurons via the ErbB4 receptor tyrosine kinase in MPTP mouse models of Parkinson's disease. Journal of Neurochemistry, 133(4), 590-597. https://doi.org/10.1111/jnc.13026.
Di Lodovico, L., & Gorwood, P. (2020). The relationship between moderate to vigorous physical activity and cognitive rigidity in anorexia nervosa. Psychiatry Research, 284:112703, https://doi.org/10.1016/j.psychres.2019.112703, 9 pages.
Dijkstra, P.U. et al. (2002) Phantom pain and risk factors: A multivariate analysis. J Pain Symptom Manage. 24(6):578-585.
Diniz, J.B. et al. (2010) "Quetiapine versus clomipramine in the augmentation of selective serotonin reuptake inhibitors for the treatment of obsessive-compulsive disorder: A randomized, open-label trial" Journal of Psychopharmacology, 24(3):297-307.
Dold, M. et al. (2015). Antipsychotic Augmentation of Serotonin Reuptake Inhibitors in Treatment-Resistant Obsessive-Compulsive Disorder: An Update Meta-Analysis of Double-Blind, Randomized, Placebo-Controlled Trials. The International Journal of Neuropsychopharmacology, 1-11, https://doi.org/10.1093/ijnp/pyv047.
Dold, M. et al. (2015) "Second-Generation Antipsychotic Drugs in Anorexia Nervosa: A Meta-Analysis of Randomized Controlled Trials" Psychotherapy and Psychosomatics, 84(2):110-116. https://doi.org/10.1159/000369978.
Dotterer, H.L. et al. (2017) Amygdala reactivity predicts adolescent antisocial behavior but not callous-unemotional traits. Dev Cogn Neurosci, 24:84-92.
Drakatos, P. et al (2017). Safety and efficacy of long-term use of sodium oxybate for narcolepsy with cataplexy in routine clinical practice. Sleep Med, 35:80-84. https://doi.org/10.1016/j.sleep.2017.03.028.
Dürk, T. et al. (2005). 5-Hydroxytryptamine modulates cytokine and chemokine production in LPS-primed human monocytes via stimulation of different 5-HTR subtypes. International Immunology, 17(5), 599-606. https://doi.org/10.1093/intimm/dxh242.
Droogleever Fortuyn, H.A. et al. (2011). Narcolepsy and psychiatry: An evolving association of increasing interest. Sleep Med. 12, 714-719. https://doi.org/10.1016/j.sleep.2011.01.013.
Drover, D.R., 2004. Comparative pharmacokinetics and pharmacodynamics of short-acting hypnosedatives: Zaleplon, zolpidem

(56) References Cited

OTHER PUBLICATIONS and zopiclone. Clin. Pharmacokinet. 423(4):227-238. https://doi.org/10.2165/00003088-200443040-00002.

drugs.com (2014) Venlafaxine. Drugs.com, Web Archives [online]. Retrieved from: https://web.archive.org/web/20140502180823/https://www.drugs.com/venlafaxine.html; on May 2, 2014; 5 pages.

Dunning, C.J.R. et al. (2016). Multisite tyrosine phosphorylation of the N-terminus of Mint1/X11α by Src kinase regulates the trafficking of amyloid precursor protein. Journal of Neurochemistry, 137(4), 518-527. https://doi.org/10.1111/jnc.13571.

Dávila González, I. et al. (2019). Benralizumab: A New Approach for the Treatment of Severe Eosinophilic Asthma. Journal of Investigational Allergology and Clinical Immunology, 29(2), 84-93. https://doi.org/10.18176/jiaci.0385.

Earle, W. J. (2014) "DSM-5" The Philosophical Forum [online]. Retrieved from: https://doi.org/10.1111/phil.12034; pp. 179-196.

Eckert, D.J. et al. (Feb. 2007). Central sleep apnea: Pathophysiology and treatment. Chest, 131:595-607. NIH Public Access Author Manuscript, available Apr. 3, 2008, 22 pages.

Edfawy, M. et al. (2019). Abnormal mGluR-mediated synaptic plasticity and autism-like behaviours in Gprasp2 mutant mice. Nature Communications. 10:1431, https://doi.org/10.1038/s41467-019-09382-9, 15 pages.

Edwards, A. (Jun. 2010) Book Review: Handbook of Depression (2nd ed.). Gotlib, I.H., Hammen, C.L. (Eds.), The Guilford Press: New York, 2009. Psychology Medicine, 40:1051-1052.

Eijk, S. et al. (2018). Autism Spectrum Disorder in an Unselected Cohort of Children with Neurofibromatosis Type 1 (NF1). Journal of Autism and Developmental Disorders, 15:2278-2285. https://doi.org/10.1007/s10803-018-3478-0.

Ekbom, K. et al. (Mar. 2002) Age at onset and sex ratio in cluster headache: Observations over three decades. Cephalalgia, 22(2):94-100.

Elbassuoni, E. A., & Ahmed, R. F. (2019). Mechanism of the neuroprotective effect of GLP-1 in a rat model of Parkinson's with pre-existing diabetes. Neurochemistry International, 131, 104583. https://doi.org/10.1016/j.neuint.2019.104583, 8 pages.

El-Emshaty, H. M., Nasif, W. A., & Mohamed, I. E. (2015). Serum Cytokine of IL-10 and IL-12 in Chronic Liver Disease: The Immune and Inflammatory Response. Disease Markers, https://doi.org/10.1155/2015/707254, 7 pages.

El-Gabalawy, H., Guenther, L. C., & Bernstein, C. N. (2010). Epidemiology of Immune-Mediated Inflammatory Diseases: Incidence, Prevalence, Natural History, and Comorbidities. The Journal of Rheumatology Supplement, 85, 2-10. https://doi.org/10.3899/jrheum.091461.

Epstein JN, Loren REA. (2013) Changes in the definition of ADHD in DSM-5: Subtle but important. Neuropsychiatry, 3(5):455-8.

Erdur, L. et al. (2012). Somatic comorbidity in anorexia nervosa: First results of a 21-year follow-up study on female inpatients. BioPsychoSocial Medicine, 6:4, https://doi.org/10.1186/1751-0759-6-4, 6 pages.

Erskine, H. and Whiteford, H. (Nov. 2018). Epidemiology of binge eating disorder. Current Opinion in Psychiatry, 31(6), pp. 462-470.

Essau, C.A. et al. (2014). Anxiety disorders in adolescents and psychosocial outcomes at age 30. J. Affect. Disord. 163, 125-132. https://doi.org/10.1016/j.jad.2013.12.033. NIH Public Access Author Manuscript, 19 pages.

Evans, M.M. et al. (2016) Ego-dissolution and psychedelics: Validation of the Ego-Dissolution Inventory (EDI). Front Human Neurosci, 10:269, doi: 10.3389/fnhum.2016.00269, 13 pages.

Everitt, H. et al. (2018). Antidepressants for insomnia in adults (Review). Cochrane Database Syst. Rev., Issue 5, Art. No. CD010753, https://doi.org/10.1002/14651858.CD010753.pub2, 117 pages.

Fadiman, J. & Korb, S. (2019) Might Microdosing Psychedelics Be Safe and Beneficial? An Initial Exploration. J Psychoactive Drugs, 51(2):118-22. Available from: https://doi.org/10.1080/02791072.2019.1593561.

Fan, L.Y. et al. (Oct. 2018) Visual processing as a potential endophenotype in youths with attention-deficit/hyperactivity disorder: A sibling study design using the counting Stroop functional MRI. Hum Brain Mapp, 39(10):3827-35. Available from: http://www.ncbi.nlm.nih.gov/pubmed/29749060.

Fayaz, A. et al. (2016) Prevalence of chronic pain in the UK: a systematic review and meta-analysis of population studies. BMJ Open [Internet]. 6:e010364, doi:10.1136/bmjopen-2015-010364, 12 pages.

FDA mulls drug to slow late-stage Alzheimer's [online], [retrieved on Sep. 23, 2003]. Retrieved from the internet, http://www.cnn.com/2003/HEALTH/conditions/09/24/alzheimers.drug.ap/index.html.

Feinstein, A.R. (1970). The pre-therapeutic classification of co-morbidity in chronic disease. Journal of Chronic Diseases, 23(7), 455-468. https://doi.org/10.1016/0021-9681(70)90054-8.

Ferguson, S.A. et al. (2010). Melatonin agonists and insomnia. Expert Rev. Neurother., 10(2):305-318. https://doi.org/10.1586/ern.10.1.

Fernandez, B. A., & Scherer, S.W. (2017). Syndromic autism spectrum disorders: Moving from a clinically defined to a molecularly defined approach. Dialogues in Clinical Neuroscience, 19:353-371.

Feyder, M. et al. (2010). Association of mouse Dlg4 (PSD-95) gene deletion and human DLG4 gene variation with phenotypes relevant to autism spectrum disorders and Williams' syndrome. American Journal of Psychiatry, 167:1508-1517. https://doi.org/10.1176/appi.ajp.2010.10040484.

Fiebich, B.L. et al. (2004). Antiinflammatory effects of 5-HT3 receptor antagonists in lipopolysaccharide-stimulated primary human monocytes. Scandinavian Journal of Rheumatology. 33:28-32. https://doi.org/15515409.

Fisher, G. (1970). The psycholytic treatment of a childhood schizophrenic girl. International Journal of Social Psychiatry. 16(2):112-130. https://doi.org/10.1177/002076407001600204.

Fisher, K.A & Hany, M. (Jun. 24, 2020) Antisocial Personality Disorder. StatPearls [Internet]. NCBI Bookshelf. Retrieved from: http://www.ncbi.nlm.nih.gov/pubmed/31536279, 6 printed pages.

Fisher, R.S. et al. (2005). Epileptic Seizures and Epilepsy: Definitions Proposed by the International League Against Epilepsy (ILAE) and the International Bureau for Epilepsy (IBE). Epilepsia, 46(4), 470-472. https://doi.org/10.1111/j.0013-9580.2005.66104.x.

Flament, M.F. et al. (2012) Evidence-based pharmacotherapy of eating disorders. The International Journal of Neuropsychopharmacology, 15(02), 189-207. https://doi.org/10.1017/S1461145711000381.

Flanagan, T.W. et al. (2019). 5-HT2 receptor activation alleviates airway inflammation and structural remodeling in a chronic mouse asthma model. Life Sciences, 236:116790, https://doi.org/10.1016/j.lfs.2019.116790, 9 pages.

FMC Product Overview (2017) Avicel® SMCC HD 50 Silicified Microcrystalline cellulose NF. Product Specifications, 2 pages.

FMC Product Overview (2017) Avicel® SMCC HD 90 Silicified Microcrystalline cellulose NF. Product Specifications, 2 pages.

Folen, V. (1975) X-ray powder diffraction data for some drugs, excipients, and adulterants in illicit samples. Journal of Forensic Science. 1975, 20, 348-372.

Fond, G. et al. (2014). Anxiety and depression comorbidities in irritable bowel syndrome (IBS): a systematic review and meta-analysis. Eur. Arch. Psychiatry Clin. Neurosci. 264, 651-660. https://doi.org/10.1007/s00406-014-0502-z.

Fornasari, D. (2017) Pharmacotherapy for Neuropathic Pain: A Review. Pain Ther, 6(Suppl 1):S25-S33.

Fortuyn, H.A.D. et al. (2008). High Prevalence of Eating Disorders in Narcolepsy with Cataplexy: A Case-Control Study. Sleep 31, 335-341. https://doi.org/10.1093/sleep/31.3.335.

Fortuyn, H.A.D. et al. (2010). Anxiety and mood disorders in narcolepsy: a case-control study. Gen. Hosp. Psychiatry, 32:49-56. https://doi.org/10.1016/j.genhosppsych.2009.08.007.

*Freedom to Operate, Inc. v. Compass Pathways Limited.* Case PGR2022-00012, U.S. Pat. No. 10,947,257: Petitioner's Request for Rehearing Under 37 C.F.R. § 42.71 (PTAB Jul. 22, 2022); 17 pages.

*Freedom to Operate, Inc. v. Compass Pathways Limited.* Case PGR2022-00018, U.S. Pat. No. 10,954,259: Petitioner's Request for Rehearing Under 37 C.F.R. § 42.71 (PTAB Jul. 22, 2022); 17 pages.

(56) References Cited

OTHER PUBLICATIONS

*Freedom to Operate, Inc. v. Compass Pathways Limited.* Case PGR2022-00012, U.S. Pat. No. 10,947,257. Exhibit 1006: Declaration of Sven Lidin, Ph.D. (PTAB Dec. 15, 2021).
*Freedom to Operate, Inc. v. Compass Pathways Limited.* Case PGR2022-00012, U.S. Pat. No. 10,947,257. Exhibit 1007: Curriculum Vitae—Sven Lidin, Ph.D. (PTAB Dec. 15, 2021).
*Freedom to Operate, Inc. v. Compass Pathways Limited.* Case PGR2022-00012, U.S. Pat. No. 10,947,257. Exhibit 1008: Declaration of James A. Kaduk, Ph.D. (PTAB Dec. 15, 2021).
*Freedom to Operate, Inc. v. Compass Pathways Limited.* Case PGR2022-00012, U.S. Pat. No. 10,947,257. Exhibit 1009: Curriculum Vitae—James A. Kaduk, Ph.D. (PTAB Dec. 15, 2021).
*Freedom to Operate, Inc. v. Compass Pathways Limited.* Case PGR2022-00012, U.S. Pat. No. 10,947,257. Exhibit 1010: Declaration of Raj Suryanarayanan, Ph.D. (PTAB Dec. 15, 2021).
*Freedom to Operate, Inc. v. Compass Pathways Limited.* Case PGR2022-00012, U.S. Pat. No. 10,947,257. Exhibit 1011: Curriculum Vitae—Raj Suryanarayanan, Ph.D. (PTAB Dec. 15, 2021).
*Freedom to Operate, Inc. v. Compass Pathways Limited.* Case PGR2022-00012, U.S. Pat. No. 10,947,257. Exhibit 1012: Declaration of Charles L. Raison, M.D. (PTAB Dec. 15, 2021).
*Freedom to Operate, Inc. v. Compass Pathways Limited.* Case PGR2022-00012, U.S. Pat. No. 10,947,257. Exhibit 1013: Hancock, B.C. and G. Zografi. Characteristics and Significance of the Amorphous State in Pharmaceutical Systems. Journal of Pharmaceutical Sciences, vol. 86, No. 1. (PTAB Dec. 15, 2021).
*Freedom to Operate, Inc. v. Compass Pathways Limited.* Case PGR2022-00012, U.S. Pat. No. 10,947,257. Exhibit 1014: Arlin, J.B. et al. Experimental Crystal Structure Determination, 1-3, 2021 (PTAB Dec. 15, 2021).
*Freedom to Operate, Inc. v. Compass Pathways Limited.* Case PGR2022-00012, U.S. Pat. No. 10,947,257. Exhibit 1015: Bernstein J. Polymorphism in Molecular Crystals, International Union of Crystallography, Oxford, 2002 (PTAB Dec. 15, 2021).
*Freedom to Operate, Inc. v. Compass Pathways Limited.* Case PGR2022-00012, U.S. Pat. No. 10,947,257. Exhibit 1016: Boratto, M. H. Semiconducting and Insulating Oxides Applied to Electronic Devices. Thesis Ph.D. UNESP, School of Science, Bauru, 2018. (PTAB Dec. 15, 2021).
*Freedom to Operate, Inc. v. Compass Pathways Limited.* Case PGR2022-00012, U.S. Pat. No. 10,947,257. Exhibit 1017: D.E. Nichols, Synthesis of High Purity Psilocybin: Lot 10415-25, Nov. 1, 2009. (PTAB Dec. 15, 2021).
*Freedom to Operate, Inc. v. Compass Pathways Limited.* Case PGR2022-00012, U.S. Pat. No. 10,947,257. Exhibit 1018: Jun. 6, 2012 Letter from D. Nichols to R. Griffiths. (PTAB Dec. 15, 2021).
*Freedom to Operate, Inc. v. Compass Pathways Limited.* Case PGR2022-00012, U.S. Pat. No. 10,947,257. Exhibit 1019: Apr. 15, 2014 Letter from C. Kim to E. Elder. (PTAB Dec. 15, 2021).
*Freedom to Operate, Inc. v. Compass Pathways Limited.* Case PGR2022-00012, U.S. Pat. No. 10,947,257. Exhibit 1020: Declaration of Brett D. Bobzien. (PTAB Dec. 15, 2021).
*Freedom to Operate, Inc. v. Compass Pathways Limited.* Case PGR2022-00012, U.S. Pat. No. 10,947,257. Exhibit 1021: Triclinic Labs Report, Characterization of Psilocybin, Dec. 2, 2021. (PTAB Dec. 15, 2021).
*Freedom to Operate, Inc. v. Compass Pathways Limited.* Case PGR2022-00012, U.S. Pat. No. 10,947,257. Exhibit 1023: USP35-(941) Physical Tests/X-Ray Powder Diffraction. (PTAB Dec. 15, 2021).
*Freedom to Operate, Inc. v. Compass Pathways Limited.* Case PGR2022-00012, U.S. Pat. No. 10,947,257. Exhibit 1024: Ottoboni S. et al. Understanding API Static Drying with Hot Gas Flow: Design and Test of a Drying Rig Prototype and Drying Modeling Development. Org. Process Res. Dev. 2020, 24, 2505-2520. (PTAB Dec. 15, 2021).
*Freedom to Operate, Inc. v. Compass Pathways Limited.* Case PGR2022-00012, U.S. Pat. No. 10,947,257. Exhibit 1025: Airaksinen S. et al. Comparison of the effects of two drying methods on polymorphism of theophylline. International Journal of Pharmaceutics 276 (2004) 129-141. (PTAB Dec. 15, 2021).
*Freedom to Operate, Inc. v. Compass Pathways Limited.* Case PGR2022-00012, U.S. Pat. No. 10,947,257. Exhibit 1026: Lim, H.L. et al., Understanding and preventing agglomeration in a filter drying process. Powder Technology, 300 (2016) 146-156. (PTAB Dec. 15, 2021).
*Freedom to Operate, Inc. v. Compass Pathways Limited.* Case PGR2022-00012, U.S. Pat. No. 10,947,257. Exhibit 1028: Curriculum Vitae—Charles L. Raison, M.D. (PTAB Dec. 15, 2021).
*Freedom to Operate, Inc. v. Compass Pathways Limited.* Case PGR2022-00012, U.S. Pat. No. 10,947,257. Exhibit 1029: Excerpt from Diagnostic and Statistical Manual of Mental Disorders, Fifth Edition, DSM-5. Am. Psychiatric Assn., 2013; pp. 160-168. (PTAB Dec. 15, 2021).
*Freedom to Operate, Inc. v. Compass Pathways Limited.* Case PGR2022-00012, U.S. Pat. No. 10,947,257. Exhibit 1030: Declaration of Roland R. Griffiths, Ph.D. (PTAB Dec. 15, 2021).
*Freedom to Operate, Inc. v. Compass Pathways Limited.* Case PGR2022-00012, U.S. Pat. No. 10,947,257. Exhibit 1031: Excerpt from A. Dictionary of Chemistry, 6th Edition. John Daintith (Ed.) Oxford University Press; p. 428 (PTAB Dec. 15, 2021).
*Freedom to Operate, Inc. v. Compass Pathways Limited.* Case PGR2022-00012, U.S. Pat. No. 10,947,257. Exhibit 1032: *Astrazeneca AB v. Reddy's Laboratories, Inc.*, Civil Action No. 11-2317 (May 1, 2013). 2013 U.S. Dist. LEXIS 62149; Dec. 13, 2021. (PTAB Dec. 15, 2021).
*Freedom to Operate, Inc. v. Compass Pathways Limited.* Case PGR2022-00012, U.S. Pat. No. 10,947,257. Exhibit 1033: Baker R.W. et al. Molecular Structures of Hallucinogenic Substances: Lysergic Acid Diethylamide, Psilocybin, and 2,4,5-Trimethoxyamphetamine. Molecular Pharmacology, 9, 1973, 23-32. (PTAB Dec. 15, 2021).
*Freedom to Operate, Inc. v. Compass Pathways Limited.* Case PGR2022-00012, U.S. Pat. No. 10,947,257. Exhibit 1034: Petcher, T.J. and Weber, H.P. Crystal Structures of the Teonanácatl Hallucinogens. J. Chem Soc. Perkins Trans., 2, 8, 946-948, 1974.
*Freedom to Operate, Inc. v. Compass Pathways Limited.* Case PGR2022-00012, U.S. Pat. No. 10,947,257. Exhibit 1035: Kuhnert-Brandstätter, M. and Heindl, W. Polymorphe Modifikationen und Solvate von Psilocin und Psilocybin. Arch. Pharm, 1976, 309, 625-631 (German, English abstract on p. 626) (PTAB Dec. 15, 2021).
*Freedom to Operate, Inc. v. Compass Pathways Limited.* Case PGR2022-00012, U.S. Pat. No. 10,947,257. Exhibit 1036: Hofmann, A. et al. (1959) Psylocybin and Psilocin, zwei psychotrope Wirkstoffe aus mexikanischen Rauschpilzen. Helvetica Chimica Acta, vol. XLII (v), 1557-1572. (PTAB Dec. 15, 2021).
*Freedom to Operate, Inc. v. Compass Pathways Limited.* Case PGR2022-00012, U.S. Pat. No. 10,947,257. Exhibit 1041: Sherwood A.M. et al. An Improved, Practical, and Scalable Five-Step Synthesis of Psilocybin. Synthesis 2020, 52, 688-694 (PTAB Dec. 15, 2021).
*Freedom to Operate, Inc. v. Compass Pathways Limited.* Case PGR2022-00012, U.S. Pat. No. 10,947,257. Exhibit 1042: dos Santos, R.G. et al. Antidepressive, anxiolytic, and antiaddictive effects of ayahuasca, psilocybin and lysergic acid diethylamide (LSD): a systematic review of clinical trials published in the last 25 years. Ther Adv Psychopharmacol, 2016, vol. 6(3), 193-213. (PTAB Dec. 15, 2021).
*Freedom to Operate, Inc. v. Compass Pathways Limited.* Case PGR2022-00012, U.S. Pat. No. 10,947,257. Exhibit 1043: Hill, R.J. Expanded Use of the Rietveld Method in Studies of Phase Abundance in Multiphase Mixtures. Powder Diffraction, Jun. 1991, vol. 6, No. 2, pp. 74-77. (PTAB Dec. 15, 2021).
*Freedom to Operate, Inc. v. Compass Pathways Limited.* Case PGR2022-00012, U.S. Pat. No. 10,947,257. Exhibit 1044: Groom, C.R. et al. The Cambridge Structural Database. Acta Cryst. (2016). B72, 171-179. (PTAB Dec. 15, 2021).
*Freedom to Operate, Inc. v. Compass Pathways Limited.* Case PGR2022-00012, U.S. Pat. No. 10,947,257. Exhibit 1045: Lee, P.L.

(56) References Cited

OTHER PUBLICATIONS et al. A twelve-analyzer detector system for high-resolution powder diffraction. J Synchrotron Rad. (2008). 15, 427-432. (PTAB Dec. 15, 2021).
*Freedom to Operate, Inc.* v. *Compass Pathways Limited.* Case PGR2022-00012, U.S. Pat. No. 10,947,257. Exhibit 1046: Wang, J. et al. A dedicated powder diffraction beamline at the Advanced Photon Source: Commissioning and early operational results. Review of Scientific Instruments, 79, 085105 (2008). (PTAB Dec. 15, 2021).
*Freedom to Operate, Inc.* v. *Compass Pathways Limited.* Case PGR2022-00012, U.S. Pat. No. 10,947,257. Exhibit 1047: Antao, S.M. et al. State-of-the-Art High-Resolution Powder X-Ray Diffraction (HRPXRD) Illustrated With Rietveld Structure Refinement of Quartz, Sodalite, Tremolite, and Meionite. The Canadian Mineralogist, vol. 46, pp. 1501-1509 (2008). (PTAB Dec. 15, 2021).
*Freedom to Operate, Inc.* v. *Compass Pathways Limited.* Case PGR2022-00012, U.S. Pat. No. 10,947,257. Exhibit 1048: Toby B.H. and Von Dreele, B. GSAS-II: The genesis of a modern open-source all purpose crystallography software package. J Appl Cryst, (2013) 46, 544-549. (PTAB Dec. 15, 2021).
*Freedom to Operate, Inc.* v. *Compass Pathways Limited.* Case PGR2022-00012, U.S. Pat. No. 10,947,257. Exhibit 1049: Sykes, R.A. et al. New software for statistical analysis of Cambridge Structural Database data. J Appl Cryst, (2011) vol. 44, pp. 882-886. (PTAB Dec. 15, 2021).
*Freedom to Operate, Inc.* v. *Compass Pathways Limited.* Case PGR2022-00012, U.S. Pat. No. 10,947,257. Exhibit 1050: Bruno, I.J. et al. Retrieval of Crystallographically-Derived Molecular Geometry Information, J Chem Inf Comput Sci (2004) vol. 44, pp. 2133-2144. (PTAB Dec. 15, 2021).
*Freedom to Operate, Inc.* v. *Compass Pathways Limited.* Case PGR2022-00012, U.S. Pat. No. 10,947,257. Exhibit 1051: Kresse, G. and Furthmüller, J. Efficiency of ab-initio total energy calculations for metals and semiconductors using a plane-wave basis set. Computational Materials Science (1996) vol. 6, pp. 15-50. (PTAB Dec. 15, 2021).
*Freedom to Operate, Inc.* v. *Compass Pathways Limited.* Case PGR2022-00012, U.S. Pat. No. 10,947,257. Exhibit 1052: Dovesi, R. et al. Quantum-mechanical condensed matter simulations with Crystal. WIREs Comput Mol Sci (2018) e1360, pp. 1-36. (PTAB Dec. 15, 2021).
*Freedom to Operate, Inc.* v. *Compass Pathways Limited.* Case PGR2022-00012, U.S. Pat. No. 10,947,257. Exhibit 1053: Gatti, C. et al. Crystal field effects on the topological properties of the electron density in molecular crystals: The case of urea. J Chem Phys (1994) vol. 101, 10686. (PTAB Dec. 15, 2021).
*Freedom to Operate, Inc.* v. *Compass Pathways Limited.* Case PGR2022-00012, U.S. Pat. No. 10,947,257. Exhibit 1054: Peintinger, M.F. et al. Consistent Gaussian Basis Sets of Triple-Zeta Valence with Polarization Quality for Solid-State Calculations. Journal of Computational Chemistry (2012) 1-9. (PTAB Dec. 15, 2021).
*Freedom to Operate, Inc.* v. *Compass Pathways Limited.* Case PGR2022-00012, U.S. Pat. No. 10,947,257. Exhibit 1055: Louër, D. and Boultif, A. Some further considerations in powder diffraction pattern indexing with the dichotomy method. Powder Diffraction, 29(S2), S7-S12, Dec. 2014. (PTAB Dec. 15, 2021).
*Freedom to Operate, Inc.* v. *Compass Pathways Limited.* Case PGR2022-00012, U.S. Pat. No. 10,947,257. Exhibit 1056: Kourkoumelis, K. Powdl: a Reusable .net Component for Interconverting Powder Diffraction Data. Recent Developments. Powder Diffr., vol. 28, No. 2, Jun. 2013, p. 142. (PTAB Dec. 15, 2021).
*Freedom to Operate, Inc.* v. *Compass Pathways Limited.* Case PGR2022-00012, U.S. Pat. No. 10,947,257. Exhibit 1057: Curriculum Vitae—Roland R. Griffiths. (PTAB Dec. 15, 2021).
*Freedom to Operate, Inc.* v. *Compass Pathways Limited.* Case PGR2022-00012, U.S. Pat. No. 10,947,257. Exhibit 1058: Zeeh Pharmaceutical Experiment Station, University of Wisconsin—Madison School of Pharmacy. Certificate of Analysis for Lot No. 10415-25. (PTAB Dec. 15, 2021).
*Freedom to Operate, Inc.* v. *Compass Pathways Limited.* Case PGR2022-00012, U.S. Pat. No. 10,947,257. Exhibit 1059: Barrett, F.S. et al. Double-blind comparison of the two hallucinogens psilocybin and dextromethorphan: Effects on cognition. Psychopharmacology (Berl), Oct. 2018; 235(10): 2915-2927. HHS Public Access Author Manuscript. (PTAB Dec. 15, 2021).
*Freedom to Operate, Inc.* v. *Compass Pathways Limited.* Case PGR2022-00012, U.S. Pat. No. 10,947,257. Exhibit 1060: Non-Final Office Action, dated Aug. 13, 2020 (PTAB Dec. 15, 2021).
*Freedom to Operate, Inc.* v. *Compass Pathways Limited.* Case PGR2022-00012, U.S. Pat. No. 10,947,257. Exhibit 1061: Applicant-Initiated Interview Summary, filed Oct. 14, 2020 (PTAB Dec. 15, 2021).
*Freedom to Operate, Inc.* v. *Compass Pathways Limited.* Case PGR2022-00012, U.S. Pat. No. 10,947,257. Exhibit 1062: Amendment/Response to Non-Final Office Action, filed Nov. 13, 2020 (PTAB Dec. 15, 2021).
*Freedom to Operate, Inc.* v. *Compass Pathways Limited.* Case PGR2022-00012, U.S. Pat. No. 10,947,257. Exhibit 1063: Lakshmana Prabhu, S. and Suriyaprakash, T.N.K. Impurities and Its Importance in Pharmacy. Int Journal of Pharmaceutical Sciences Review and Research, vol. 3, Issue 2, Jul.-Aug. 2010, Article 012, pp. 66-71. (PTAB Dec. 15, 2021).
*Freedom to Operate, Inc.* v. *Compass Pathways Limited.* Case PGR2022-00012, U.S. Pat. No. 10,947,257. Exhibit 1064: ICH Topic Q 3 A (R2) Impurities in New Drug Substances, 2006. (PTAB Dec. 15, 2021).
*Freedom to Operate, Inc.* v. *Compass Pathways Limited.* Case PGR2022-00012, U.S. Pat. No. 10,947,257. Exhibit 1065: Excerpts of Handbook of Pharma Excipients, Sixth Edition. Rowe, R.C. et al. (Eds.) London, UK: Pharmaceutical Press, 2011; pp. 129-133, 139-141 (PTAB Dec. 15, 2021).
*Freedom to Operate, Inc.* v. *Compass Pathways Limited.* Case PGR2022-00012, U.S. Pat. No. 10,947,257. Exhibit 1066: Martin's Physical Pharmacy and Pharmaceutical Sciences, Sixth Edition. P.J. Sinko (Ed.) Lippincott Williams & Wilkins, 2011; p. 564 (PTAB Dec. 15, 2021).
*Freedom to Operate, Inc.* v. *Compass Pathways Limited.* Case PGR2022-00012, U.S. Pat. No. 10,947,257. Exhibit 1067: Supplemental Amendment, filed Nov. 19, 2020 (PTAB Dec. 15, 2021).
*Freedom to Operate, Inc.* v. *Compass Pathways Limited.* Case PGR2022-00012, U.S. Pat. No. 10,947,257. Exhibit 1068: The Manufacturing Process. Solid Dose Experts Techceuticals, vol. 15. (2015). (PTAB Dec. 15, 2021).
*Freedom to Operate, Inc.* v. *Compass Pathways Limited.* Case PGR2022-00012, U.S. Pat. No. 10,947,257. Exhibit 1069: Documentation of shipment of sample from Johns Hopkins University Batch to Triclinic Labs, Jul. 21, 2021. (PTAB Dec. 15, 2021).
*Freedom to Operate, Inc.* v. *Compass Pathways Limited.* Case PGR2022-00012, U.S. Pat. No. 10,947,257. Exhibit 1070: USP 24|NF 19. The Official Compendia of Standards, U.S. Pharmacopeia, 2000; pp. 738-739, 865-866. (PTAB Dec. 15, 2021).
*Freedom to Operate, Inc.* v. *Compass Pathways Limited.* Case PGR2022-00012, U.S. Pat. No. 10,947,257. Exhibit 1071: Sixsmith, D. The effect of compression on some physical properties of microcrystalline cellulose powders. J Pharm Pharmac, 1977, 29, 33-36. (PTAB Dec. 15, 2021).
*Freedom to Operate, Inc.* v. *Compass Pathways Limited.* Case PGR2022-00012, U.S. Pat. No. 10,947,257. Exhibit 1072: Curriculum Vitae—Brett D. Bobzien. (PTAB Dec. 15, 2021).
*Freedom to Operate, Inc.* v. *Compass Pathways Limited.* Case PGR2022-00012, U.S. Pat. No. 10,947,257. Exhibit 1073: Documentation of shipment of sample from Johns Hopkins University Batch to Triclinic Labs, Jul. 21, 2021. (PTAB Dec. 15, 2021).
*Freedom to Operate, Inc.* v. *Compass Pathways Limited.* Case PGR2022-00012, U.S. Pat. No. 10,947,257. Exhibit 1074: Altomare, A. et al. Expo2013: A kit of tools for phasing crystal structures from powder data. Journal of Applied Crystallography (2013) 46, 1231-1235. (PTAB Dec. 15, 2021).
*Freedom to Operate, Inc.* v. *Compass Pathways Limited.* Case PGR2022-00012, U.S. Pat. No. 10,947,257. Exhibit 1078: Petzoldt, C. et al. An example of how to handle amorphous fractions in API during early pharmaceutical development: SAR114137—A success-

(56) References Cited

OTHER PUBLICATIONS ful approach. European Journal of Pharmaceutics and Biopharmaceutics, 86 (2014) 337-350. (PTAB Dec. 15, 2021).
*Freedom to Operate, Inc. v. Compass Pathways Limited.* Case PGR2022-00012, U.S. Pat. No. 10,947,257. Exhibit 1079: Sivén, M. et al. Challenge of paediatric compounding to solid dosage forms sachets and hard capsules—Finnish perspective. Journal of Pharmacy and Pharmacol (2017) vol. 69, pp. 593-602 (PTAB Dec. 15, 2021).
*Freedom to Operate, Inc. v. Compass Pathways Limited.* Case PGR2022-00012, U.S. Pat. No. 10,947,257. Exhibit 1080: Tobyn, M. et al. (1998) Physicochemical comparison between microcrystalline cellulose and silicified microcrystalline cellulose. International Journal of Pharmaceutics, 169 (1998) 183-194. (PTAB Dec. 15, 2021).
*Freedom to Operate, Inc. v. Compass Pathways Limited.* Case PGR2022-00012, U.S. Pat. No. 10,947,257. Exhibit 1081: Packing Slip, Johns Hopkins BPRU Pharmacy to Triclinic Laboratories, Inc., Jul. 21, 2021. (PTAB Dec. 15, 2021).
*Freedom to Operate, Inc. v. Compass Pathways Limited.* Case PGR2022-00012, U.S. Pat. No. 10,947,257. Exhibit 1082: Triclinic Labs Inc., Standard Operating Procedure. Controlled Substances, No. G026.10 (PTAB Dec. 15, 2021).
*Freedom to Operate, Inc. v. Compass Pathways Limited.* Case PGR2022-00012, U.S. Pat. No. 10,947,257. Exhibit 1085: Sherwood, A.M. et al. Psilocybin: crystal structure solutions enable phase analysis of prior art and recently patented examples. Acta Cryst. (2022) C78. (PTAB Dec. 15, 2021).
*Freedom to Operate, Inc. v. Compass Pathways Limited.* Case PGR2022-00012, U.S. Pat. No. 10,947,257. Paper No. 18: Decision Denying Institution of Post-Grant Review (PTAB Jun. 22, 2022); 25 pages.
*Freedom to Operate, Inc. v. Compass Pathways Limited.* Case PGR2022-00012, U.S. Pat. No. 10,947,257. Paper No. 2: Petition for Post-Grant Review (PTAB Dec. 15, 2021).
*Freedom to Operate, Inc. v. Compass Pathways Limited.* Case PGR2022-00018, U.S. Pat. No. 10,954,259. Exhibit 1106: Declaration of Sven Lidin, Ph.D. (PTAB Dec. 22, 2021).
*Freedom to Operate, Inc. v. Compass Pathways Limited.* Case PGR2022-00018, U.S. Pat. No. 10,954,259. Exhibit 1108: Declaration of James A. Kaduk, Ph.D. (PTAB Dec. 22, 2021).
*Freedom to Operate, Inc. v. Compass Pathways Limited.* Case PGR2022-00018, U.S. Pat. No. 10,954,259. Exhibit 1110: Declaration of Raj Suryanarayanan, Ph.D. (PTAB Dec. 22, 2021).
*Freedom to Operate, Inc. v. Compass Pathways Limited.* Case PGR2022-00018, U.S. Pat. No. 10,954,259. Exhibit 1112: Declaration of Charles L. Raison, M.D. (PTAB Dec. 22, 2021).
*Freedom to Operate, Inc. v. Compass Pathways Limited.* Case PGR2022-00018, U.S. Pat. No. 10,954,259. Exhibit 1113: Roy, J. an Introduction to Pharmaceutical Sciences, Biohealthcare, UK (2011) (PTAB Dec. 22, 2021).
*Freedom to Operate, Inc. v. Compass Pathways Limited.* Case PGR2022-00018, U.S. Pat. No. 10,954,259. Exhibit 1120: Declaration of Brett D. Bobzien. (PTAB Dec. 22, 2021).
*Freedom to Operate, Inc. v. Compass Pathways Limited.* Case PGR2022-00018, U.S. Pat. No. 10,954,259. Exhibit 1130: Declaration of Roland R. Griffiths, Ph.D. (PTAB Dec. 22, 2021).
*Freedom to Operate, Inc. v. Compass Pathways Limited.* U.S. Pat. No. 10,954,259. Exhibit 1160: Claims of '739 Application as Filed and Preliminary Amendment filed Dec. 9, 2020. (PTAB Dec. 22, 2021).
*Freedom to Operate, Inc. v. Compass Pathways Limited.* Case PGR2022-00018, U.S. Pat. No. 10,954,259. Exhibit 1161: Terminal Disclaimer. (PTAB Dec. 22, 2021).
*Freedom to Operate, Inc. v. Compass Pathways Limited.* Case PGR2022-00018, U.S. Pat. No. 10,954,259. Paper No. 16: Decision Denying Institution of Post-Grant Review (PTAB Jun. 22, 2022); 25 pages.
*Freedom to Operate, Inc. v. Compass Pathways Limited.* Case PGR2022-00018, U.S. Pat. No. 10,954,259. Paper No. 2: Petition for Post-Grant Review (PTAB Dec. 22, 2021).
Freudenberg, F., Alttoa, A., & Reif, A. (2015). Neuronal nitric oxide synthase (NOS1) and its adaptor, NOS1AP, as a genetic risk factors for psychiatric disorders. Genes, Brain and Behavior, 14(1), 46-63. https://doi.org/10.1111/gbb.12193.
Fuchs, X. et al. (2018) Psychological factors associated with phantom limb pain: A review of recent findings. Pain Res Manag, 2018:5080123, http://doi.org/10.1155/2018/5080123, 12 pages.
Funk, C. D., & FitzGerald, G. A. (2007). COX-2 Inhibitors and Cardiovascular Risk. Journal of Cardiovascular Pharmacology, 50(5), 470-479. https://doi.org/10.1097/FJC.0b013e318157f72d.
Galbiati, A. et al. (2019). The risk of neurodegeneration in REM sleep behavior disorder: A systematic review and meta-analysis of longitudinal studies. Sleep Medicine Reviews, 43, 37-46. https://doi.org/10.1016/j.smrv.2018.09.008.
Galimberti, D. et al. (2008). Association of a NOS1 promoter repeat with Alzheimer's disease. Neurobiology of Aging, 29(9), 1359-1365. https://doi.org/10.1016/j.neurobiolaging.2007.03.003.
Galmiche, M. et al. (2019). Prevalence of eating disorders over the 2000-2018 period: a systematic literature review. The American Journal of Clinical Nutrition, 109(5), pp. 1402-1413.
Gan, W., Mohamad, N. and Law, L. (2018). Factors Associated with Binge Eating Behavior among Malaysian Adolescents. Nutrients, 10:66, doi:10.3390/nu10010066, 12 pages.
Gandal, M. J. et al. (Feb. 2018). Shared molecular neuropathology across major psychiatric disorders parallels polygenic overlap. Science, 359:693-697. https://doi.org/10.1126/science.aad6469.
Gandy, M. et al. (2013). Rates of DSM-IV mood, anxiety disorders, and suicidality in Australian adult epilepsy outpatients: A comparison of well-controlled versus refractory epilepsy. Epilepsy Behav. 26, 29-35. https://doi.org/10.1016/j.yebeh.2012.10.023.
Ganesan, H. et al. (2019). mTOR signalling pathway—a root cause for idiopathic autism? BMB Reports, 52(7):424-433.
García-Rayado, G., Navarro, M., & Lanas, A. (2018). NSAID induced gastrointestinal damage and designing GI-sparing NSAIDs. Expert Review of Clinical Pharmacology, 11(10), 1031-1043. https://doi.org/10.1080/17512433.2018.1516143.
Garcia-Romeu, A., Griffiths, R. and Johnson, M. (2015). Psilocybin-Occasioned Mystical Experiences in the Treatment of Tobacco Addiction. Current Drug Abuse Reviews, 7(3), pp. 157-164.
Gasior, M. et al. (2017). A Phase 3, Multicenter, Open-Label, 12-Month Extension Safety and Tolerability Trial of Lisdexamfetamine Dimesylate in Adults With Binge Eating Disorder. Journal of Clinical Psychopharmacology, 37(3), pp. 315-322.
Gau, S.S .-F. & Huang, W.L. (2014) Rapid visual information processing as a cognitive endophenotype of attention deficit hyperactivity disorder. Psychol Med, 44(2):435-446.
Gaul, C. et al. (2011) Cluster Headache—Clinical Features and Therapeutic Options. Deutsches Ärzteblatt International, 108(33):543-549.
GBD 2016 Parkinson's Disease Collaborators. (2018). Global, regional, and national burden of Parkinson's disease, 1990-2016: a systematic analysis for the Global Burden of Disease Study 2016. The Lancet. Neurology, 17(11), 939-953. https://doi.org/10.1016/S1474-4422(18)30295-3.
Gessner, P.K. et al. (1960) The relationship between the metabolic fate and pharmacological actions of serotonin, bufotenine and psilocybin. J. Pharmacol. Exp. Ther., 130:126-133.
Agh, T. et al. (2015). Epidemiology, health-related quality of life and economic burden of binge eating disorder: a systematic literature review. Eating and Weight Disorders, 20:1-12.
Ghanizadeh, A. (2015) A systematic review of reboxetine for treating patients with attention deficit hyperactivity disorder. Nord J Psychiatry. 69(4):241-8.
Gibb, A. & Deeks, E.D. (2014). Vortioxetine: First global approval. Drugs 74:135-145, https://doi.org/10.1007/s40265-013-0161-9, 11 pages.
Gilon Mann, T. et al. (2018). Different attention bias patterns in anorexia nervosa restricting and binge/purge types. European Eating Disorders Review, 26(4):293-301. https://doi.org/10.1002/erv.2593.

(56) References Cited

OTHER PUBLICATIONS

Giovinazzo, S. et al. (2019). Anorexia nervosa and heart disease: a systematic review. Eating and Weight Disorders—Studies on Anorexia, Bulimia and Obesity, vol. 24, Issue 2, pp. 199-207. https://doi.org/10.1007/s40519-018-0567-1.

Glaesmer, H. et al. (2012) Psychometric properties and population-based norms of the Life Orientation Test Revised (LOT-R). British Journal of Health Psychology, 17:432-445.

Glashouwer, K. A., van der Veer, R. M. L., Adipatria, F., de Jong, P. J., & Vocks, S. (2019). The role of body image disturbance in the onset, maintenance, and relapse of anorexia nervosa: A systematic review. Clinical Psychology Review, 74:101771; DOI:10.1016/j.cpr.2019.101771, 21 pages.

Glenn, A.L. et al. (2013) Antisocial personality disorder: A current review. Current Psychiatry Reports, 15:427, DOI: 10.1007/s11920-013-0427-7, 9 pages.

Global Burden of Disease Study 2013 Collaborators. (2015). Global, regional, and national incidence, prevalence, and years lived with disability for 301 acute and chronic diseases and injuries in 188 countries, 1990-2013: a systematic analysis for the Global Burden of Disease Study 2013. Lancet (London, England), 386(9995), 743-800. https://doi.org/10.1016/S0140-6736(15)60692-4.

Gámez, W. et al. (2014) The Brief Experiential Avoidance Questionnaire: Development and Initial Validation. Psychological Assessment. 26:35-45.

Golden, E.C. & Lipford, M.C. (2018). Narcolepsy: Diagnosis and management. Cleveland Clin. J. Med., 85(12):959-969. https://doi.org/10.3949/ccjm.85a.17086.

Goldstein-Piekarski, A.N. et al. (2016). A trans-diagnostic review of anxiety disorder comorbidity and the impact of multiple exclusion criteria on studying clinical outcomes in anxiety disorders. Transl. Psychiatry, 6:e847, doi.org/10.1038/tp.2016.108, 9 pages.

Golyala, A., & Kwan, P. (2017). Drug development for refractory epilepsy: The past 25 years and beyond. Seizure, 44, 147-156. https://doi.org/10.1016/j.seizure.2016.11.022.

Golzari, S.E.J. et al. Lidocaine and pain management in the emergency department: A review article. Anesthesiol Pain Med. 2014;4(1):1-6.

Gong, D. et al. (2012). TGFβ signaling plays a critical role in promoting alternative macrophage activation. BMC Immunology, 13:31, https://doi.org/10.1186/1471-2172-13-31, 10 pages.

González-Maeso, J. et al. (2007) "Hallucinogens Recruit Specific Cortical 5-$HT_{2a}$ Receptor-Mediated Signaling Pathways to Affect Behavior" Neuron, 53(3):439-452.

González-Maeso J. et al. (Mar. 24, 2008) "Identification of a serotonin/glutamate receptor complex implicated in psychosis" Nature, 452(7183):93-7. Available from: http://www.nature.com/articles/nature06612.

Gooriah, R. et al. (2015) Evidence-based treatments for cluster headache. Ther Clin Risk Manag, 11:1687-1696. Available from: http://dx.doi.org/10.2147/TCRM.S94193.

Gorla, K., & Mathews, M. (2005). Pharmacological treatment of eating disorders. Psychiatry, 2(6), 43-48. http://www.ncbi.nlm.nih.gov/pubmed/21152155.

Gouzoulis-Mayfrank, E. et al (2002). Effects of the hallucinogen psilocybin on covert orienting of visual attention in humans. Neuropsychobiology, 45(4):205-212. Available from: http://www.ncbi.nlm.nih.gov/pubmed/12097810.

Grant, A.M. et al. (2002) The Self-Reflection and Insight Scale: A New Measure of Private Self-Consciousness. Social Behavior and Personality, 30(8), 821-836.

Grant, J. et al. (Jul. 2019). A double-blind, placebo-controlled study of vortioxetine in the treatment of binge-eating disorder. International Journal of Eating Disorders, 52(7), pp. 786-794.

Greenan, C. et al. (Feb. 13, 2020) "Preparation and Characterization of Novel Crystalline Solvates and Polymorphs of Psilocybin and Identification of Solid Forms Suitable for Clinical Development" Preprint [online]. Retrieved from ResearchGate: https://www.researchgate.net/publication/339238710, 29 printed pages.

Greten, F.R. et al. (Sep. 2007). NF-κB Is a Negative Regulator of IL-1β Secretion as Revealed by Genetic and Pharmacological Inhibition of IKKβ. Cell, 130(5), 918-931. https://doi.org/10.1016/j.cell.2007.07.009.

Grieco, M. et al. (Oct. 2019). Glucagon-Like Peptide-1: A Focus on Neurodegenerative Diseases. Frontiers in Neuroscience, 13, Article 1112, 7 pages. https://doi.org/10.3389/fnins.2019.01112.

Grieshaber, A. F., Moore, K. A., & Levine, B. (2001). The detection of psilocin in human urine. Journal of Forensic Sciences, 46(3), 627-630. http://www.ncbi.nlm.nih.gov/pubmed/11373000.

Griffin, C.E. et al. (2013). Benzodiazepine pharmacology and central nervous system-mediated effects. Ochsner J. 13, 214-223.

Griffiths, K. (2019). Understanding the neural mechanisms of lisdexamfetamine dimesylate (LDX) pharmacotherapy in Binge Eating Disorder (BED): a study protocol. Journal of Eating Disorders, 7:23, https://doi.org/10.1186/s40337-019-0253-3, 10 pages.

Griffiths, K.R. et al. (2017). "Sustained attention and heart rate variability in children and adolescents with ADHD." Biol Psychol [Internet]. 124:11-20. Available from: http://www.ncbi.nlm.nih.gov/pubmed/28099875.

Griffiths, R.R. (Dec. 2011) Psilocybin occasioned mystical-type experiences: Immediate and persisting dose-related effects. Psychopharmacol, 218(4):649-665. NIH Public Access Author Manuscript, 27 pages.

Griffiths, R.R. et al. (Aug. 2006) Psilocybin can occasion mystical-type experiences having substantial and sustained meaning and spiritual significance. Psychopharmacol (Berl), 187(3):268-283.

Griffiths, R.R. et al. (2016) Psilocybin produces substantial and sustained decreases in depression and anxiety in patients with life-threatening cancer: A randomized double-blind trial. Journal of Psychopharmacology, 30(12):1181-1197.

Griffiths, S. (2019). "The Vulnerability Experiences Quotient (VEQ): A Study of Vulnerability, Mental Health and Life Satisfaction in Autistic Adults." Autism Research. (10):1516-28. https://doi.org/10.1002/aur.2162.

Grilo, C. et al. (2012). 12-month follow-up of fluoxetine and cognitive behavioral therapy for binge eating disorder. Journal of Consulting and Clinical Psychology, 80(6), pp. 1108-1113.

Grilo, C., Reas, D. and Mitchell, J. (2016). Combining Pharmacological and Psychological Treatments for Binge Eating Disorder: Current Status, Limitations, and Future Directions. Current Psychiatry Reports, 18:55, doi:10.1007/s11920-016-0696-z, 11 pages.

Grob, C.S. et al. (Jan. 2011) Pilot Study of Psilocybin Treatment for Anxiety in Patients with Advanced-Stage Cancer. Arch Gen Psychiatry, 68(1):71-78.

Grob, C.S. et al. (2013) Chapter 17: Use of the Classic Hallucinogen Psilocybin for Treatment of Existential Distress Associated with Cancer. In B.I. Carr and J. Steel (Eds.) Psychological Aspsects of Cancer. Springer Science + Business Media; p. 291-308.

Guerdjikova, A. et al. (2016). Novel pharmacologic treatment in acute binge eating disorder—role of lisdexamfetamine. Neuropsychiatric Disease and Treatment, 12:833-841.

Guerreiro, R. et al. (2015). "The age factor in Alzheimer's disease." Genome Medicine, 7:106, https://doi.org/10.1186/s13073-015-0232-5, 3 pages.

Guo, M. et al. (2003) "Potential Application of Silicified Microcrystalline Cellulose in Direct-Fill Formulations for Automatic Capsule-Filling Machines," Pharmaceutical Development and Technology, vol. 8, No. 1, pp. 47-59.

Gupta, S. P. et al. (2016). "Association of Polymorphism of Neuronal Nitric Oxide Synthase Gene with Risk to Parkinson's Disease." Molecular Neurobiology, 53(5), 3309-3314. https://doi.org/10.1007/s12035-015-9274-3.

Guze, S.B. (1995) Diagnostic and Statistical Manual of Mental Disorders, 4th ed. (DSM-IV). Am. J. Psychiatry, 152, 1228. https://doi.org/10.1176/ajp.152.8.1228.

Hajihosseini, A. et al. (2012). "The role of beta-gamma oscillations in unexpected rewards processing." Neuroimage. 60(3):1678-85. https://doi.org/10.1016/j.neuroimage.2012.01.125.

Halberstadt, A. L. et al. (2011). "Multiple receptors contribute to the behavioral effects of indoleamine hallucinogens." Neuropharmacology, 61(3):364-381, https://doi.org/10.1016/j.neuropharm.2011.01.017.

(56) References Cited

OTHER PUBLICATIONS

Hall N. et al. (2018). "Phantom limb pain: a review of pharmacological management." Br J Pain [Internet]. 12(4):202-7. Available from: https://doi.org/10.1177/2049463717747307.

Halpern, J.H. (2003) Hallucinogens: An Update. Current Psychiatry Reports, 5:347-354.

Hama, Y. et al. (2015). "Level of plasma neuregulin-1 SMDF is reduced in patients with idiopathic Parkinson's disease." Neuroscience Letters, 587, 17-21. https://doi.org/10.1016/j.neulet.2014.12.024.

Hamadjida, A. et al. (2020). "The highly selective mGlu2 receptor positive allosteric modulator LY-487,379 alleviates I-DOPA-induced dyskinesia in the 6-OHDA-lesioned rat model of Parkinson's disease." The European Journal of Neuroscience. 51(12):2412-2422. https://doi.org/10.1111/ejn.14679.

Hamilton, M. (1960) A Rating Scale for Depression. Journal of Neurology, Neurosurgery & Psychiatry. 23:56-62.

Hanes, K.R. (1996). "Serotonin, Psilocybin, and Body Dysmorphic Disorder." Journal of Clinical Psychopharmacology, 16(2), pp. 188-189.

Hanyu-Deutmeyer, A.A. et al. (2020) Phantom Limb Pain. StatPearls. StatPearls Publishing. [online]. Available from NCBI Bookshelf: http://www.ncbi.nlm.nih.gov/pubmed/28846343, 6 pages.

Haroon, E. et al. (2018). Antidepressant treatment resistance is associated with increased inflammatory markers in patients with major depressive disorder. Psychoneuroendocrinology, 95:43-49. https://doi.org/10.1016/j.psyneuen.2018.05.026.

Hasler, F. et al. (1997). "Determination of psilocin and 4-hydroxyindole-3-acetic acid in plasma by HPLC-ECD and pharmacokinetic profiles of oral and intravenous psilocybin in man." Pharmaceutica Acta Helvetiae, 72(3), 175-184. https://doi.org/10.1016/S0031-6865(97)00014-9.

Hasler, F. et al. (2002). "Renal excretion profiles of psilocin following oral administration of psilocybin: A controlled study in man." Journal of Pharmaceutical and Biomedical Analysis, 30(2), 331-339. https://doi.org/10.1016/S0731-7085(02)00278-9.

Hasler, F. et al. (2004) Acute psychological and physiological affects of psilocybin in healthy humans: A double-blind, placebo-controlled dose-effect study. Psychopharmacology, 172(2):145-156.

Heal, D. et al. (2017). Dopamine and µ-opioid receptor dysregulation in the brains of binge-eating female rats—possible relevance in the psychopathology and treatment of binge-eating disorder. Journal of Psychopharmacology, 31 (6), pp. 770-783.

Hebert, L.E. et al. (2013). "Alzheimer disease in the United States (2010-2050) estimated using the 2010 census." Neurology, 80(19), 1778-1783. https://doi.org/10.1212/WNL.0b013e31828726f5.

Heim, R. et al. (Mar. 3, 1958) "Mycologie—Determinisme de la formation des carpophores et des sclerotes dans la culture du Psilocybe mexicana Heim, Agaric hallucinogene du Mexique, et mise en evidence de la psilocybine et de la psilocine [Mycology—Determinism in the formation of carpophores and sclerotia in the cultivation of Psilocybe mexicana Heim, an hallucinogenic Agaric of Mexico, and isolation of psilocybin and psilocyn]" Comptes Rendus Hebdomadaires des Seances de L'Academie des Sciences [Weekly Reports of the Sessions of the Academy of Sciences], 246(9):1346-1351.

Herr, N. et al. (Jul. 2017). "The Effects of Serotonin in Immune Cells." Frontiers in Cardiovascular Medicine, 4, Article 48, 11 pages. https://doi.org/10.3389/fcvm.2017.00048.

Herring, W.J. et al. (2012). "Orexin receptor antagonism for treatment of insomnia: A randomized clinical trial of suvorexant." Neurology 79, 2265-2274. https://doi.org/10.1212/WNL.0b013e31827688ee.

Hibicke, M. et al. (Apr. 1, 2019). "Psychedelics Improve the Mental Health of Rats." FASEB J., 33(S1):666.1; https://doi.org/10.1096/fasebj.2019.33.1_supplement.666.1, 3 pages.

Hilbert, A. et al. (2019). Meta-analysis of the efficacy of psychological and medical treatments for binge-eating disorder. Journal of Consulting and Clinical Psychology, 87(1), pp. 91-105.

Hill, L.S. et al. (2010) Scoff, the development of an eating disorder screening questionnaire. International Journal of Eating Disorders, 43(4):344-351. https://doi.org/10.1002/eat.20679.

Himmerich, H. et al. (2019). "Psychiatric comorbidity as a risk factor for mortality in people with anorexia nervosa." European Archives of Psychiatry and Clinical Neuroscience, 269(3), 351-359. https://doi.org/10.1007/s00406-018-0937-8.

Hoek, H. et al. (2003). "Review of the Prevalence and Incidence of Eating Disorders." International Journal of Eating Disorders, vol. 34, Issue 4, pp. 383-396. https://doi.org/10.1002/eat.10222.

Hofmann, A. et al. (1958) "Konstitutionsaufklärung und Synthese von Psilocybin [Constitutional elucidation and synthesis of psilocybin]" Experientia, 14(11):397-399, with English translation (3 pages).

Hofmann, A. et al. (Mar. 15, 1958) "Psilocybin, ein psychotroper Wirkstoff aus dem mexikanischen Rauschpilz Psilocybe mexicana Heim [Psilocybin, a psychotropic substance from Mexican magic mushrooms Psilocybe mexicana Heim]" Experientia, 14(3):107-109, with English translation (3 pages).

Hofmann, A. et al. (1959) "Psilocybin und Psilocin, zwei psychotrope Wirkstoffe aus mexikanischen Rauschpilzen [Psilocybin and Psilocin, two psychotropic active substances from Mexican magic mushrooms" Helvetica Chimica Acta, vol. XLII, Issue v, No. 168, pp. 1557-1572, with English translation (17 pages).

Holtkamp, K. et al. (2005). "A retrospective study of SSRI treatment in adolescent anorexia nervosa: Insufficient evidence for efficacy." Journal of Psychiatric Research, 39(3), 303-310. https://doi.org/10.1016/j.jpsychires.2004.08.001.

Hood, S.D. et al. (2014). "Benzodiazepine dependence and its treatment with low dose flumazenil." Br. J. Clin. Pharmacol. 77, 285-294. https://doi.org/10.1111/bcp.12023.

Howell, M. J. et al. (2015). "Rapid Eye Movement Sleep Behavior Disorder and Neurodegenerative Disease." JAMA Neurology, 72(6), 707-712. https://doi.org/10.1001/jamaneurol.2014.4563.

Hoyer, D. et al. (1985). "Molecular pharmacology of 5-HT1 and 5-HT2 recognition sites in rat and pig brain membranes: Radioligand binding studies with [3H]5-HT, [3H]8-OH-DPAT, (-)[125I]iodocyanopindolol, [3H]mesulergine and [3H]Ketanserin." Eur J Pharmacol. 118(1-2):13-23.

Hsu, E. et al. (2013). "Postamputation pain: Epidemiology, mechanisms, and treatment." J Pain Res, 6:121-136. http://dx.doi.org/10.2147/JPR.S32299.

Huang, H. et al. (2016). "Genetic association of NOS1 exon18, NOS1 exon29, ABCB1 1236C/T, and ABCB1 3435C/T polymorphisms with the risk of Parkinson's disease: A meta-analysis." Medicine, 95(40), e4982. https://doi.org/10.1097/MD.0000000000004982.

Hudson, C.C. et al. (2019). "Prevalence of Depressive Disorders in Individuals with Autism Spectrum Disorder: a Meta-Analysis." Journal of Abnormal Child Psychology. 47(1):165-75. https://doi.org/10.1007/s10802-018-0402-1.

Hudson, J.I. et al. (1992). "Polysomnographic Characteristics of Young Manic Patients: Comparison with Unipolar Depressed Patients and Normal Control Subjects." Arch. Gen. Psychiatry 49, 378-383. https://doi.org/10.1001/archpsyc.1992.01820050042006.

Hudson, J.I. et al. (2007). "The Prevalence and Correlates of Eating Disorders in the National Comorbidity Survey Replication." Biological Psychiatry, 61(3), 348-358. https://doi.org/10.1016/j.biopsych.2006.03.040.

Huecker, M. et al. (2020). Bupropion. StatPearls. NCBI Bookshelf [online]. Retrieved from: https://www.ncbi.nlm.nih.gov/books/NBK470212/; retrieved on Jul. 30, 2020, 4 pages.

Huedo-Medina, T.B. et al. (2012). "Effectiveness of non-benzodiazepine hypnotics in treatment of adult insomnia: Meta-analysis of data submitted to the Food and Drug Administration." BMJ, 345:e8343,. https://doi.org/10.1136/bmj.e8343, 13 pages.

Huff, T. and Daly, D.T. (2020) Neuroanatomy, Cranial Nerve 5 (Trigeminal). StatPearls. StatPearls Publishing; Available from NCBI Bookshelf: http://www.ncbi.nlm.nih.gov/pubmed/29489263.

Hughes, J.R. (2008). "Gamma, fast, and ultrafast waves of the brain: Their relationships with epilepsy and behavior." Epilepsy Behav. 13(1):25-31. https://doi.org/10.1016/j.yebeh.2008.01.011.

(56) References Cited

OTHER PUBLICATIONS

Hussman, J.P. et al. (2011). "A noise-reduction GWAS analysis implicates altered regulation of neurite outgrowth and guidance in autism." Molecular Autism. 2, 1. https://doi.org/10.1186/2040-2392-2-1.

Hutson, P., Balodis, I. and Potenza, M. (2018). Binge-eating disorder: Clinical and therapeutic Advances. Pharmacology & Therapeutics, 182:15-27.

Hutten, N.R.P.W. et al. (2019). "Self-Rated Effectiveness of Microdosing With Psychedelics for Mental and Physical Health Problems Among Microdosers." Front Psychiatry [Internet]. 10:672. Available from: http://www.ncbi.nlm.nih.gov/pubmed/31572246.

Huysmans, S. et al. (2019). "Melatonin and sleep disorders: Overview of literature and testing in psychiatric practice." Tijdschr. Psychiatr. 61, 854-861.

Hvolby, A. (2015). "Associations of sleep disturbance with ADHD: implications for treatment." ADHD Atten. Deficit Hyperact. Disord. 7(1):1-8. https://doi.org/10.1007/s12402-014-0151-0.

Hwang, J.Y. et al. (2008) The development of the Santa Clara brief compassion scale: An abbreviation of Sprecher and Fehr's compassionate love scale. Pastoral Psychology, 56(4):421-428.

ICH (Jun. 2017) Q3C—Tables and List Guidance for Industry. U.S. Department of Health and Human Services, Food and Drug Administration, Center for Drug Evaluation and Research (CDER), Center for Biologics Evaluation and Research (CBER) Revision 3, 10 pages.

Infliximab Side Effects. (2019). Drugs.Com [online]. Retrieved from: https://www.drugs.com/sfx/infliximab-side-effects.html, 11 pages.

Institute for Quality and Efficiency in Health Care (IQWiG) (Oct. 2017). Treatment options for generalized anxiety disorder [online]. InformedHealth.org. Retrieved from: https://www.ncbi.nlm.nih.gov/books/NBK279594/?report=printable; retrieved on Jul. 30, 2020, 3 pages.

Institute for Quality and Efficiency in Health Care (IQWiG) (Feb. 2018). What is an inflammation? [online]. Retrieved from: https://www.ncbi.nlm.nih.gov/books/NBK279298/; retrieved on Jul. 30, 2020, 1 page.

International Search Report and Written Opinion for PCT/IB2018/057811 dated Mar. 11, 2019, 10 pages.

International Search Report and Written Opinion issued in International Patent Application No. PCT/EP2022/058483, dated Aug. 4, 2022, with Notification of Transmittal; 17 pages.

International Search Report and Written Opinion issued in International Patent Application No. PCT/IB2020/053684, dated Aug. 26, 2020, with Notification of Transmittal; 24 total pages.

International Search Report and Written Opinion issued in International Patent Application No. PCT/IB2020/053687, dated Aug. 26, 2020, with Notification of Transmittal; 22 total pages.

International Search Report and Written Opinion issued in International Patent Application No. PCT/IB2020/053688, dated Aug. 26, 2020, with Notification of Transmittal; 30 total pages.

Isaacson, R.S. et al. (2018). "The clinical practice of risk reduction for Alzheimer's disease: A precision medicine approach." Alzheimer's & Dementia : The Journal of the Alzheimer's Association, 14(12), 1663-1673. https://doi.org/10.1016/j.jalz.2018.08.004.

Isooka, N. et al. (2020) "Dopaminergic neuroprotective effects of rotigotine via 5-HT1A receptors: Possibly involvement of metallothionein expression in astrocytes." Neurochemistry International, 132:104608, https://doi.org/10.1016/j.neuint.2019.104608, 13 pages.

Ivarsson, M. et al. (2005). "Antidepressants and REM sleep in Wistar-Kyoto and Sprague-Dawley rats" Eur. J. Pharmacol., 522(1-3):63-71. https://doi.org/10.1016/j.ejphar.2005.08.050.

Jack, C. R. et al. (2018). "NIA-AA Research Framework: Toward a biological definition of Alzheimer's disease." Alzheimer's & Dementia : The Journal of the Alzheimer's Association, 14(4), 535-562. https://doi.org/10.1016/j.jalz.2018.02.018.

Jaeger, J. and Domingo, S.Z. (2016) The Digit Symbol Substitution Test (DSST): Psychometric properties and clinical utility in major depressive disorder. Poster presented at the 29th ECNP Congress, Sep. 17-20, 2016, Vienna, Austria. Retrieved from ResearchGate [online], http://www.researchgate.net/publication/309602300.

Jafarian, S. et al. (2008). "High-altitude sleep disturbance: Results of the Groningen Sleep Quality Questionnaire survey." Sleep Med. 9, 446-449. https://doi.org/10.1016/j.sleep.2007.06.017.

Jagielska et al. (2017). "Outcome, comorbidity and prognosis in anorexia nervosa." Psychiatr. Pol, 51(2), 205-218. https://doi.org/10.12740/PP/64580.

Jagmag, S.A. et al. (2016). "Evaluation of Models of Parkinson's Disease." Frontiers in Neuroscience, 9: 503. https://doi.org/10.3389/fnins.2015.00503.

Jankovic, J. (2008). "Parkinson's disease: clinical features and diagnosis." Journal of Neurology, Neurosurgery & Psychiatry, 79(4), 368-376. https://doi.org/10.1136/jnnp.2007.131045.

Jansen, C. et al. (2019). "Interictal psychiatric comorbidities of drug-resistant focal epilepsy: Prevalence and influence of the localization of the epilepsy." Epilepsy Behav. 94, 288-296. https://doi.org/10.1016/j.yebeh.2018.06.046.

Javaheri, S. (2006). "Acetazolamide improves central sleep apnea in heart failure: a double-blind, prospective study." Am. J. Respir. Crit. Care Med. 173, 234-237.

Javaheri, S. et al. (1996). "Effect of theophylline on sleep-disordered breathing in heart failure." N. Engl. J. Med. 335, 562-567. https://doi.org/10.1056/NEJM199608223350805.

Jayakumar, A.R. & Norenberg, M.D. (2016). Glutamine Synthetase: Role in Neurological Disorders. The Glutamate/GABA-Glutamine Cycle. A. Schousboe, R. Sonnewald (eds.), Springer International Publishing. Advances in Neurobiology, vol. 13, https://doi.org/10.1007/978-3-319-45096-4_13; pp. 327-350.

Jennings, K. M. et al. (2017). "Eating Disorder Examination-Questionnaire (EDE-Q): Norms for Clinical Sample of Female Adolescents with Anorexia Nervosa." Archives of Psychiatric Nursing, 31(6), 578-581. https://doi.org/10.1016/j.apnu.2017.08.002.

Jiang, H.-R. et al. (2002). "Secretion of interleukin-10 or interleukin-12 by LPS-activated dendritic cells is critically dependent on time of stimulus relative to initiation of purified DC culture" Journal of Leukocyte Biology, 72(5):978-985.

Jiao, J.-J. et al. (2017). "GLP-1/GIP/Gcg receptor Triagonist improves the cognitive behaviors in triple-transgenic mice of Alzheimer's disease." Sheng Li Xue Bao : [Acta Physiologica Sinica], 69(2), 135-145. Retrieved from http://www.ncbi.nlm.nih.gov/pubmed/28435972.

Jin, L. et al. (2019). "Antidepressants for the treatment of narcolepsy: A prospective study of 148 patients in northern China." J. Clin. Neurosci. 63, 27-31. https://doi.org/10.1016/j.jocn.2019.02.014.

Johanson, M. et al. (Feb. 2020) A Systematic Literature Review of Neuroimaging of Psychopathic Traits. Front Psychiatry. 10:1027, doi: 10.3389/fpsyt.2019.01027, 20 pages.

John, O. P., & Srivastava, S. (1999). The Big-Five trait taxonomy: History, measurement, and theoretical perspectives. In L. A. Pervin & O. P. John (Eds.), Handbook of personality: Theory and Research (vol. 2, pp. 102-138). New York: Guilford Press.

Johns, M. (1991). "New Method for Measuring Daytime Sleepiness: The Epworth Sleepiness Scale." Sleep. 14(6):540-5 [online]. Retrieved from: https://academic.oup.com/sleep/article/14/6/540/2742871 (accessed Mar. 26, 2020).

Johnson et al., "Potential Therapeutic Effects of Psilocybin," Neurotherapeutics (2017) 14:734-740 (published Jun. 5, 2017).

Johnson, M.W. (2008) Human hallucinogen research: guidelines for safety. J Psychopharmacol, 22(6):603-620.

Johnson, M.W. et al. (Jan. 2017) Long-term follow-up of psilocybin-facilitated smoking cessation. Am J Drug Alcohol Abuse. 2017;43(1):55-60. doi:10.3109/00952990.2016.1170135 [published correction appears in Am J Drug Alcohol Abuse. Jan. 2017;43(1):127]. HHS Public Access Author Manuscript, 10 pages.

Johnstad, P.G. (2018). "Powerful substances in tiny amounts: An interview study of psychedelic microdosing" Nord Stud Alcohol Drugs, 35(1):39-51.

Jyonouchi, H. (2013). "Immunological abnormalities in autism spectrum disorders." Advances in Neuroimmune Biology. vol. 4, No. 3, pp. 141-159. https://doi.org/10.3233/NIB-130061.

(56) References Cited

OTHER PUBLICATIONS

Kaelen, M. et al. (2015) LSD enhances emotional response to music. Psychopharmacology, 232(19):3607-3614.
Kaelen, M. et al. (2018) "The hidden therapist: evidence for a central role of music in psychedelic therapy" Psycopharmacology, 235:505-519.
Kaladjian, A. et al. (2014). "Troubles affectifs et comorbidités anxieuses." Encephale 40, S18-S22. https://doi.org/10.1016/S0013-7006(14)70126-5.
Kalliolias, G. D. et al. (2016). "TNF biology, pathogenic mechanisms and emerging therapeutic strategies." Nature Reviews Rheumatology, 12(1), 49-62. https://doi.org/10.1038/nrrheum.2015.169.
Kandel, S.A. and Mandiga P. (2020) Cluster Headache. StatPearls. StatPearls Publishing [Internet]. Available from NCI Bookshelf: http://www.ncbi.nlm.nih.gov/pubmed/31334961, 6 pages.
Kandil, E. et al. (2017). "Lidocaine Infusion: A Promising Therapeutic Approach for Chronic Pain." J Anesth Clin Res. 08(01): 697.
Kandratavicius, L. et al. (2014). Animal models of epilepsy: use and limitations. Neuropsychiatric Disease and Treatment, 1693. https://doi.org/10.2147/NDT.S50371.
Kang, D. W. et al. (2019). "Long-term benefit of Microbiota Transfer Therapy on autism symptoms and gut microbiota." Scientific Reports. 9(1):1-9. https://doi.org/10.1038/s41598-019-42183-0.
Kang Y. et al. (2018). "Self-report pain assessment tools for cognitively intact older adults: Integrative review." International journal of older people nursing. 13(2):e12170.
Kanner, A.M. (2011). "Anxiety disorders in epilepsy: The forgotten psychiatric comorbidity." Epilepsy Curr. 11(3):90-1. https://doi.org/10.5698/1535-7511-11.3.90.
Kantojärvi, K. et al. (2011). "Fine mapping of Xq11.1-q21.33 and mutation screening of RPS6KA6, ZNF711, ACSL4, DLG3, and IL1RAPL2 for autism spectrum disorders (ASD)." Autism Research. 4(3):228-33. https://doi.org/10.1002/aur.187.
Kargbo, R.B. et al. (2020) "Direct Phosphorylation of Psilocin Enables Optimized cGMP Kilogram-Scale Manufacture of Psilocybin" ACS Omega, 5:16959-16966.
Karimi, P. et al. (2017). Environmental factors influencing the risk of autism. J Res Med Sci. 22:27, https://doi.org/10.4103/1735-1995.200272, 12 pages.
Kasper LJ et al. (2012). "Moderators of working memory deficits in children with attention-deficit/hyperactivity disorder (ADHD): A meta-analytic review." Clinical Psychology Review. vol. 32, p. 605-17.
Kasper, S. et al. (2009). "Efficacy of pregabalin and venlafaxine-XR in generalized anxiety disorder: Results of a double-blind, placebo-controlled 8-week trial." Int. Clin. Psychopharmacol. 24, 87-96. https://doi.org/10.1097/YIC.0b013e32831d7980.
Katzman, M.A. et al. (2017). "Adult ADHD and comorbid disorders: Clinical implications of a dimensional approach." BMC Psychiatry. 17(1):1-15.
Kaur A et al. (2018). "Phantom limb pain: A literature review." Chinese Journal of Tramatology, 21(6):366-8. https://doi.org/10.1016/j.cjtee.2018.04.006.
Kaur, H. et al. (2018). Chronic Insomnia. StatPearls. NLM Bookshelf [online]. Retrieved from: https://www.ncbi.nih.gov/books/NBK526136/?report=reader; retrieved on Jul. 30, 2002; 5 pages.
Keezer, M. R. et al. (2016). "Comorbidities of epilepsy: current concepts and future perspectives." The Lancet Neurology, 15(1), 106-115. https://doi.org/10.1016/S1474-4422(15)00225-2.
Kelly, W.E. et al. (2019). "A brief self-report measure for frequent distressing nightmares: The Nightmare Experience Scale (NEXS)." Dreaming 29, 180-195. https://doi.org/10.1037/drm0000106.
Kelton, M.C. et al. (Jun.-Aug. 2000). The effects of nicotine on Parkinson's disease. Brain and Cognition, 43(1-3):274-282 (abstract). Retrieved from http://www.ncbi.nlm.nih.gov/pubmed/10857708, 1 page.
Kessler, R. et al. (2016). The neurobiological basis of binge-eating disorder. Neuroscience & Biobehavioral Reviews, 63, pp. 223-238.
Kessler, R.C. et al. (2013). The prevalence and correlates of binge eating disorder in the World Health Organization World Mental Health Surveys. Biological Psychiatry, 73(9):904-914.
Khajehpour, H. et al. (2019). "Disrupted resting-state brain functional network in methamphetamine abusers: A brain source space study by EEG." PLoS One 14, e0226249. https://doi.org/10.1371/journal.pone.0226249.
Khalifa, N. et al. (2010) Pharmacological interventions for antisocial personality disorder. Cochrane Database Syst Rev. (8):CD007667, doi: 10.1002/14651858.CD007667.pub2. Europe PMC Funders Group Author Manuscript, 83 pages.
Khemka, S. et al. (2017). "Dissecting the function of hippocampal oscillations in a human anxiety model." J. Neurosci. 37, 6869-6876.
Khurshid KA. (2018). "Comorbid insomnia and psychiatric disorders: an update." Innovations in Clinical Neuroscience. 15(3-4):28.
Kim, J.W. et al. (2014). "Subchronic treatment of donepezil rescues impaired social, hyperactive, and stereotypic behavior in valproic acid-induced animal model of autism." PLoS One. 9(8):e104927.
Kim, Y. E., & Jeon, B. S. (2014). Clinical Implication of REM Sleep Behavior Disorder in Parkinson's Disease. Journal of Parkinson's Disease, 4(2), 237-244. https://doi.org/10.3233/JPD-130293.
Kinnaird, E. et al. (2019). Same behaviours, different reasons: what do patients with co-occurring anorexia and autism want from treatment? International Review of Psychiatry, 31(4), 308-317. https://doi.org/10.1080/09540261.2018.1531831.
Kirsh, K.L. (2010). "Differentiating and Managing Common Psychiatric Comorbidities Seen in Chronic Pain Patients." J Pain Palliat Care Pharmacother, 24(1):39-47. Available from: https://www.tandfonline.com/action/journalInformation?journalCode=ippc20.
Kishi, T. et al. (Jun. 2012). Are Antipsychotics Effective for Anorexia Nervosa? Are Antipsychotics Effective for the Treatment of Anorexia Nervosa? Results From a Systematic Review and Meta-Analysis. J Clin Psychiatry, 73(6), 757-766. https://doi.org/10.4088/JCP.12r07691.
Kishi, T. et al. (2015). "Suvorexant for primary insomnia: A systematic review and meta-analysis of randomized placebo-controlled trials." PLoS One. 10(8):e0136910. https://doi.org/10.1371/journal.pone.0136910.
Klinkenberg I et al. (2010). "The validity of scopolamine as a pharmacological model for cognitive impairment: A review of animal behavioral studies." Neuroscience and Biobehavioral Reviews. vol. 34, p. 1307-50.
Knotkova, H. et al. (2012). "Current and future options for the management of phantom-limb pain." J Pain Res [Internet]. 5:39-49. Available from: http://dx.doi.org/10.2147/JPR.S16733.
Knyazev, G.G. et al. (2005). "Uncertainty, anxiety, and brain oscillations." Neurosci. Lett. 387, 121-125. https://doi.org/10.1016/j.neulet.2005.06.016.
*Kohn & Associates PLLC* v. *Compass Pathways Limited*, Case PGR2020-00030, U.S. Pat. No. 10,519,175, Exhibit 1005: The United States Pharmacopeial Convention (USP). 941 Characterization of Crystalline and Partially Crystalline Solids by X-Ray Powder Diffraction (XRPD). The United States Pharmacopeia. 35th Revision: The National Formulary. 30th ed (USP 35). 2011 (Official from May 1, 2012); pp. 427-433 (Exhibit E) (PTAB Feb. 21, 2020).
*Kohn & Associates PLLC* v. *Compass Pathways Limited*, Case PGR2020-00030, U.S. Pat. No. 10,519,175, Exhibit 1008: Declaration of Poncho Meisenheimer and Alex Sherwood (Exhibit H), (PTAB Feb. 21, 2020).
*Kohn & Associates PLLC* v. *Compass Pathways Limited*, Case PGR2020-00030, U.S. Pat. No. 10,519,175, Exhibit 1016: Abstracts of articles resulting from search of psilocybin treating depression and treatment resistant depression (Exhibit P) (PTAB Feb. 21, 2020).
*Kohn & Associates PLLC* v. *Compass Pathways Limited*, Case PGR2020-00030, U.S. Pat. No. 10,519,175, Exhibit 1017: Declaration of Jordan Sloshower, MD (Exhibit Q) (PTAB Feb. 21, 2020).
*Kohn & Associates PLLC* v. *Compass Pathways Limited*, Case PGR2020-00030, U.S. Pat. No. 10,519,175, Exhibit 1018: Declaration of Charles L. Raison, MD (Exhibit R) (PTAB Feb. 21, 2020).
*Kohn & Associates PLLC* v. *Compass Pathways Limited*, Case PGR2020-00030, U.S. Pat. No. 10,519,175, Exhibit 2004: Email

(56) References Cited

OTHER PUBLICATIONS

Correspondence Between Petitioner and Patent Owner, dated Mar. 19-Apr. 1, 2020 (PTAB May 26, 2020).
*Kohn & Associates PLLC* v. *Compass Pathways Limited*, Case PGR2020-00030, U.S. Pat. No. 10,519,175, Exhibit 2005: Delaware Division of Corporations Details for Freedom to Operate, Inc., dated Apr. 1, 2020 (PTAB May 26, 2020).
*Kohn & Associates PLLC* v. *Compass Pathways Limited*, Case PGR2020-00030, U.S. Pat. No. 10,519,175, Exhibit 2006: A. Harrison, "Challenges to a Company's Psilocybin Patent Highlight Contrasting Business Strategies for Developers of Psychedelic Therapies," https://www.lucid.news/challenges-to-a-companyspsilocybin-patent-highlight-contrasting-business-strategies-fordevelopers-of-psychedelic-therapies/ (Apr. 7, 2020) (PTAB May 26, 2020).
*Kohn & Associates PLLC* v. *Compass Pathways Limited*, Case PGR2020-00030, U.S. Pat. No. 10,519,175, Exhibit 2007: Biography of Alexander Sherwood, Ph.D. (PTAB May 26, 2020).
*Kohn & Associates PLLC* v. *Compass Pathways Limited*, Case PGR2020-00030, U.S. Pat. No. 10,519,175, Exhibit 2008: Biography of Poncho Meisenheimer, Ph.D. (PTAB May 26, 2020).
*Kohn & Associates PLLC* v. *Compass Pathways Limited*, Case PGR2020-00030, U.S. Pat. No. 10,519,175, Exhibit 2009: Biography of Chuck Raison, M.D. (PTAB May 26, 2020).
*Kohn & Associates PLLC* v. *Compass Pathways Limited*, Case PGR2020-00030, U.S. Pat. No. 10,519,175, Exhibit 2010: Biography of Jordon Sloshower, M.D., MSc (PTAB May 26, 2020).
*Kohn & Associates PLLC* v. *Compass Pathways Limited*, Case PGR2020-00030, U.S. Pat. No. 10,519,175, Exhibit 2011: Biography of Bill Linton (PTAB May 26, 2020).
*Kohn & Associates PLLC* v. *Compass Pathways Limited*, Case PGR2020-00030, U.S. Pat. No. 10,519,175, Exhibit 2017: Clinical Trials.gov, "A Study of Psilocybin for Major Depressive Disorder (MDD)" Identifier: NCT03866174, Apr. 22, 2020, 12 pages (PTAB Jul. 22, 2020).
*Kohn & Associates PLLC* v. *Compass Pathways Limited*, Case PGR2020-00030, U.S. Pat. No. 10,519,175, Exhibit 2018: Sloshower, J. (May 6, 2020) "Psychedelics in the Treatment of Mood and Substance Use Disorders" Presentation, 31 pages (PTAB Jul. 22, 2020).
*Kohn & Associates PLLC* v. *Compass Pathways Limited*, Case PGR2020-00030, U.S. Pat. No. 10,519,175, Paper 1: Petition for Post Grant Review of U.S. Pat. No. 10,519,175 under 35 U.S.C. 321 (PTAB Feb. 21, 2020).
*Kohn & Associates PLLC* v. *Compass Pathways Limited*, U.S. Pat. No. 10,519,175, Paper 11: Patent Owner's Exhibit List (PTAB Mar. 13, 2020).
*Kohn & Associates PLLC* v. *Compass Pathways Limited*, Case PGR2020-00030, U.S. Pat. No. 10,519,175, Paper 12: Notice Accepting Corrected Petition (PTAB Mar. 17, 2020).
*Kohn & Associates PLLC* v. *Compass Pathways Limited*, Case PGR2020-00030, U.S. Pat. No. 10,519,175, Paper 13: Corrected Petition for Post Grant Review of U.S. Pat. No. 10,519,175 Under 35 U.S.C. 321 (PTAB Mar. 20, 2020).
*Kohn & Associates PLLC* v. *Compass Pathways Limited*, Case PGR2020-00030, U.S. Pat. No. 10,519,175, Paper 15: Patent Owner's Preliminary Response (PTAB May 26, 2020).
*Kohn & Associates PLLC* v. *Compass Pathways Limited*, Case PGR2020-00030, U.S. Pat. No. 10,519,175, Paper 17: Reply to Patent Owner's Preliminary Response (PTAB Jul. 7, 2020).
*Kohn & Associates PLLC* v. *Compass Pathways Limited*, Case PGR2020-00030, U.S. Pat. No. 10,519,175, Paper 2: Petition for Post Grant Review of U.S. Pat. No. 10,519,175 Under 35 U.S.C. 321 Petitioner's List of Exhibits (PTAB Feb. 21, 2020).
*Kohn & Associates PLLC* v. *Compass Pathways Limited*, Case PGR2020-00030, U.S. Pat. No. 10,519,175, Paper 23: Patent Owner's Sur-Reply to Petitioner's Reply (PTAB Jul. 22, 2020).
*Kohn & Associates PLLC* v. *Compass Pathways Limited*, Case PGR2020-00030, U.S. Pat. No. 10,519,175, Paper 25: Decision Denying Institution of Post-Grant Review (PTAB Aug. 20, 2020).
*Kohn & Associates PLLC* v. *Compass Pathways Limited*, Case PGR2020-00030, U.S. Pat. No. 10,519,175, Paper 5: Notice of Filing Date Accorded to Petition and Time for Filing Patent Owner Preliminary Response (PTAB Feb. 26, 2020).
*Kohn & Associates PLLC* v. *Compass Pathways Limited*, Case PGR2020-00030, U.S. Pat. No. 10,519,175, Paper 6: Corrected Petition for Post Grant Review of U.S. Pat. No. 10,519,175 Under 35 U.S.C. 321 (PTAB Mar. 6, 2020).
*Kohn & Associates PLLC* v. *Compass Pathways Limited*, Case PGR2020-00030, U.S. Pat. No. 10,519,175, Paper 8: Patent Owner's Mandatory Notices (PTAB Mar. 13, 2020).
Kolar, D. et al. (2008) Treatment of adults with attention-deficit/hyperactivity disorder. Neuropsychiatric Dis Treat, 4(2):389-403.
Kolarik, J. (1967). Eeg-Veranderungen nach Psilocybin bei Epilepsien. Acta Univ. Palackianae Olomucensis, 47:253-263. (English Summary on p. 262).
Kolden, G.G. et al. (2000) The Therapeutic Realizations Scale-Revised (TRS-R): Psychometric Characteristics and Relationship to Treatment Process and Outcome. Journal of Clinical Psychology. 56(9):1207-1220.
Kolla, B. et al. (2017). "The prevalence of hypersomnolence, its correlates and associated role impairment in the National Comorbidity Survey Replication (NCS-R)." Sleep. 40(suppl_1), pp. A239-A239. https://doi.org/10.1093/sleepj/zsx050.645.
Kometer, M. et al. (2013). "Activation of Serotonin 2A Receptors Underlies the Psilocybin-Induced Effects on Oscillations, N170 Visual-Evoked Potentials, and Visual Hallucinations." Journal of Neuroscience, 33(25), 10544-10551. https://doi.org/10.1523/JNEUROSCI.3007-12.2013.
Korecka, J.A. et al. (2017). "Repulsive Guidance Molecule a (RGMa) Induces Neuropathological and Behavioral Changes That Closely Resemble Parkinson's Disease." The Journal of Neuroscience : The Official Journal of the Society for Neuroscience, 37(39), 9361-9379. https://doi.org/10.1523/JNEUROSCI.0084-17.2017.
Kornum, B.R. et al. (2017). "Narcolepsy." Nat. Rev. Dis. Prim. 3(1):1-9. https://doi.org/10.1038/nrdp.2016.100.
Kothare, S.V. et al. (2008) "Zonisamide: review of pharmacology, clinical efficacy, tolerability, and safety." Expert Opinion on Drug Metabolism & Toxicology, 4(4), 493-506. https://doi.org/10.1517/17425255.4.4.493.
Kotov, S.B. Bellman, and D.B. Watson (2004) Multidimensional Iowa Suggestibility Scale (MISS) Brief Manual. [online] Retrieved from: https://renaissance.stonybrookmedicine.edu/sites/default/files/MISSBriefManual.pdf, 16 pages.
Kouli, A. et al. (2018). Parkinson's Disease: Etiology, Neuropathology, and Pathogenesis. In Parkinson's Disease: Pathogenesis and Clinical Aspects. Thomas B. Stoker & Julia C. Greenland (Eds.) Codon Publications, pp. 3-26. Retrieved from http://www.ncbi.nlm.nih.gov/pubmed/30702842.
Kountza, M. et al. (2018). "La comorbidité psychiatrique de l'anorexie mentale : une étude comparative chez une population de patients anorexiques français et grecs." L'Encéphale, 44(5), 429-434. https://doi.org/10.1016/j.encep.2017.07.005. English abstract on p. 429.
Kryzhanovskiĭ, G.N. et al. (1992). [The antiepileptic effects of sodium valproate and the calcium antagonist riodipine when used jointly in a model of generalized korazol-induced epileptic activity]. Biulleten' Eksperimental'noi Biologii i Meditsiny, 114(10), 376-378 [Abstract]. Retrieved from http://www.ncbi.nlm.nih.gov/pubmed/1288691, 1 page.
Krzyszkowiak, W. et al. (2019) "Treatment of obsessive-compulsive disorders (OCD) and obsessive-compulsive-related disorders (OCRD)" Psychiatr Pol, 53(4):825-843; DOI: https://doi.org/10.12740/PP/105130.
Kubera, M. et al. (2005). Effects of serotonin and serotonergic agonists and antagonists on the production of tumor necrosis factor α and interleukin-6. Psychiatry Research, 134(3), 251-258. https://doi.org/10.1016/j.psychres.2004.01.014.
Kuhnert, M. et al. (1976) "Polymorphe Modifikationen und Solvate von Psilocin und Psilocybin [Polymorphic Modifications and Solvates of Psilocin and Psilocybin]" Archiv der Pharmazie, 309:625-631, with English translation from GoogleTranslate (14 total pages).

(56) References Cited

OTHER PUBLICATIONS

Kurrasch-Orbaugh, D.M. et al. (2003). Serotonin 5-Hydroxytryptamine$_{2a}$ Receptor-Coupled Phospholipase C and Phospholipase A$_2$ Signaling Pathways Have Different Receptor Reserves. J Pharmacol Exp Ther., 304(1), 229-237.

Kwan, P., & Brodie, M. J. (2001). Neuropsychological effects of epilepsy and antiepileptic drugs. The Lancet, 357(9251), 216-222. https://doi.org/10.1016/S0140-6736(00)03600-X.

Kwan, P. et al. (2009). Definition of drug resistant epilepsy: Consensus proposal by the ad hoc Task Force of the ILAE Commission on Therapeutic Strategies. Epilepsia, 51(6), 1069-1077. https://doi.org/10.1111/j.1528-1167.2009.02397.x.

Lader, M., 2015. Generalized Anxiety Disorder BT—Encyclopedia of Psychopharmacology, in: Stolerman, I.P., Price, L.H. (Eds.). Springer Berlin Heidelberg, pp. 699-702. https://doi.org/10.1007/978-3-642-36172-2_317.

Lahdenpaa et al., "Direct compression with silicified and non-silicified microcrystalline cellulose: study of some properties of powders and tablets," S.T.P. Pharma Sciences, 2001;11(2):129-135. Supplied by the British Library Oct. 12, 2019, 8 pages.

Lahey, B.B. et al. (2005) Predicting Future Antisocial Personality Disorder in Males From a Clinical Assessment in Childhood. J Consult Clin Psychol, 73(3):389-399.

Lahmame, A. et al. (1997). "Are Wistar-Kyoto rats a genetic animal model of depression resistant to antidepressants?" Eur. J. Pharmacol. 337(2-3):115-23. https://doi.org/10.1016/S0014-2999(97)01276-4.

Lai, M.C. et al. (2019). "Prevalence of co-occurring mental health diagnoses in the autism population: a systematic review and meta-analysis." The Lancet Psychiatry. 6(10):819-29. https://doi.org/10.1016/S2215-0366(19)30289-5.

Landau, A.M. et al. (2005). "Defective Fas expression exacerbates neurotoxicity in a model of Parkinson's disease." The Journal of Experimental Medicine, 202(5), 575-581. https://doi.org/10.1084/jem.20050163.

Larrosa, O. et al. (2001). "Stimulant and Anticataplectic Effects of Reboxetine in Patients with Narcolepsy: A Pilot Study." Sleep. 24(3):282-5.

Lecavalier, L. (2006). "Behavioral and emotional problems in young people with pervasive developmental disorders: Relative prevalence, effects of subject characteristics, and empirical classification." Journal of Autism and Developmental Disorders. 36(8):1101-14. https://doi.org/10.1007/s10803-006-0147-5.

Lecendreux, M. et al. (2015). Attention-Deficit/Hyperactivity Disorder (ADHD) Symptoms in Pediatric Narcolepsy: A Cross-Sectional Study. Sleep 38, 1285-1295. https://doi.org/10.5665/sleep.4910.

LeClerc, S. et al. (Jun. 2015). "Pharmacological therapies for autism spectrum disorder: A review." Pharmacy and Therapeutics. 40(6):389-397.

Ledonne, A., & Mercuri, N. B. (2020). On the modulatory roles of neuregulins/ErbB signaling on synaptic plasticity. International Journal of Molecular Sciences, 21:275, 23 pages. https://doi.org/10.3390/ijms21010275.

Lee, P. H. et al. (2019). "Genomic Relationships, Novel Loci, and Pleiotropic Mechanisms across Eight Psychiatric Disorders." Cell. 179(1469-1482):e11. https://doi.org/10.1016/j.cell.2019.11.020.

Lee, R.M. and Robbins, S.B. (1995) Measuring belongingness: the social connectedness and the social assurance scales Journal of Counseling Psychology. 42:232-241.

Lee, T. J. et al. (2017). "Repeated adolescent activity-based anorexia influences central estrogen signaling and adulthood anxiety-like behaviors in rats." Physiology and Behavior, 171, 199-206. https://doi.org/10.1016/j.physbeh.2016.12.039.

Lee, Y.C. et al. (2010). "A review of SSRIs and SNRIs in neuropathic pain." Expert Opin Pharmacother. 11(17):2813-25.

Leigh, J. P. et al. (2015). "Brief Report: Forecasting the Economic Burden of Autism in 2015 and 2025 in the United States." Journal of Autism and Developmental Disorders. 45(12):4135-9. https://doi.org/10.1007/s10803-015-2521-7.

Leonard, H.L., & Rapoport, J.L. (Sep. 1987) "Letter to the Editor: Relief of obsessive-compulsive symptoms by LSD and psilocin" American Journal of Psychiatry, 144(9):1239-1240.

Leroux, E. and Ducros, A. (2008) Cluster headache. Orphanet J Rare Dis, 3:20, doi: 10.1186/1750-1172-3-20, 11 pages.

Levin, E. D., & Rezvani, A. H. (2000). Development of nicotinic drug therapy for cognitive disorders. European Journal of Pharmacology, 393(1-3), 141-146. https://doi.org/10.1016/s0014-2999(99)00885-7.

Leysen, J.E. et al. (1982). [$^3$H]Ketanserin (R 41 468), a selective $^3$H-ligand for serotonin$_2$ receptor binding sites. Binding properties, brain distribution, and functional role. Molecular Pharmacology, 21(2), 301-314.

Li, T. et al. (2017). A scored human protein-protein interaction network to catalyze genomic interpretation. Nature Methods, 14(1), 61-64. https://doi.org/10.1038/nmeth.4083.

Li, Y. et al. (2011) "Quantification of polymorphic impurity in an enantiotropic polymorph system using differential scanning calorimetry, X-ray powder diffraction and Raman spectroscopy" Intl J Pharma, 415:110-118.

Liang, H. et al. (2019). Mammalian Target of Rapamycin at the Crossroad Between Alzheimer's Disease and Diabetes. In Diabetes Mellitus. A Risk Factor for Alzheimer's Disease. Advances in Experimental Medicine and Biology, 1128, 185-225. https://doi.org/10.1007/978-981-13-3540-2_10.

Limakatso K et al. (2019). "The prevalence of phantom limb pain and associated risk factors in people with amputations: A systematic review protocol." Syst Rev. 8:17, 5 pages. https://doi.org/10.1186/s13643-018-0938-8.

Lindenblatt, H et al. (1998). "Quantitation of psilocin in human plasma by high-performance liquid chromatography and electrochemical detection: Comparison of liquid—liquid extraction with automated on-line solid-phase extraction." J Chromatogr B Biomed Appl. 709(2):255-63.

Liu, L. et al. (2018). "Deficiency of Sustained Attention in ADHD and Its Potential Genetic Contributor MAOA" J Atten Disord, 22(9):878-885.

Liu, P.-P. et al. (2019). "History and progress of hypotheses and clinical trials for Alzheimer's disease." Signal Transduction and Targeted Therapy, 4:29, https://doi.org/10.1038/s41392-019-0063-8, 22 pages.

Lopez-Castejon, G. et al. (2011). "Understanding the mechanism of IL-1β secretion." Cytokine & Growth Factor Reviews, 22(4), 189-195. https://doi.org/10.1016/j.cytogfr.2011.10.001.

Loth, E. et al. (2018). "Facial expression recognition as a candidate marker for autism spectrum disorder: how frequent and severe are deficits?" Molecular Autism, 9:7, https://doi.org/10.1186/s13229-018-0187-7, 11 pages.

Lu, T.-T., Wan, C., Yang, W., & Cai, Z. (2019). Role of Cdk5 in Amyloid-beta Pathology of Alzheimer's Disease. Current Alzheimer Research, 16(13), 1206-1215. https://doi.org/10.2174/1567205016666191210094435.

Lucchina, L. et al. (2014). "Altered Peripheral and Central Inflammatory Responses in a Mouse Model of Autism." Autism Research. 7(2):273-89. https://doi.org/10.1002/aur.1338.

Lucza, T. et al. (2015). "Screening Mild and Major Neurocognitive Disorders in Parkinson's Disease." Behavioural Neurology, 2015, Article ID 983606, 10 pages. https://doi.org/10.1155/2015/983606.

Lugli, S.M. et al. (1997). "Tumor Necrosis Factor a Enhances the Expression of the Interleukin (IL)-4 Receptor α-Chain on Endothelial Cells Increasing IL-4 or IL-13-induced Stat6 Activation." Journal of Biological Chemistry, 272(9), 5487-5494. https://doi.org/10.1074/jbc.272.9.5487.

Lynch ME et al. (2006). "The pharmacotherapy of chronic pain: A review." Pain Res Manag. 11(1):11-38.

Lyons, T and R.L. Carhart-Harris (2018) Increased nature relatedness and decreased authoritarian political views after psilocybin for treatment-resistant depression. Journal of Psychopharmacology, 32(7):811-819.

Čiž, M. et al. (2007). Serotonin modulates the oxidative burst of human phagocytes via various mechanisms. Platelets, 18(8):583-590. https://doi.org/10.1080/09537100701471865.

(56) References Cited

OTHER PUBLICATIONS

Maïano, C. et al. (2019). Psychometric Properties of the Body Checking Questionnaire (BCQ) and of the Body Checking Cognitions Scale (BCCS): A Bifactor-Exploratory Structural Equation Modeling Approach. Assessment, 1-15, https://doi.org/10.1177/1073191119858411.
Mabunga, D.F.N. et al. (2015). "Exploring the Validity of Valproic Acid Animal Model of Autism." Experimental Neurobiology. 24(4):285-300. https://doi.org/10.5607/en.2015.24.4.285.
Macy, A.S. et al. (2013) "Quality of life in obsessive compulsive disorder" CNS Spectrums, 18(1):21-33.
Mahapatra et al., "Role of psilocybin in the treatment of depression," Ther Adv Psychopharmacol, Jan. 2017; 7(1): 54-56.
Mahfoud, Y. et al. (Sep. 2009). Sleep disorders in substance abusers: How common are they? Psychiatry, 6(9):38-42.
Mahone EM et al. (2017). "Attention-Deficit/Hyperactivity Disorder: A Historical Neuropsychological Perspective." J Int Neuropsychol Soc [Internet]. 23:916-29. Available from: http://www.rmtcnet.com/resources/Phenylbutazone_Review-Dr._Lawrence_R._Soma.pdf.
Maina, G. et al. (2003) "Antipsychotic augmentation for treatment resistant obsessive-compulsive disorder: What if antipsychotic is discontinued?" International Clinical Psychopharmacology, 18(1):23-28; DOI: 10.1097/01.yic.0000047784.24295.2b.
Maïmoun, L. et al. (2018). Effects of the two types of anorexia nervosa (binge eating/purging and restrictive) on bone metabolism in female patients. Clinical Endocrinology, 88(6):863-872. https://doi.org/10.1111/cen.13610.
Manavalan, A. et al. (2013). Brain site-specific proteome changes in aging-related dementia. Experimental & Molecular Medicine. 45:e39, 17 pages. https://doi.org/10.1038/emm.2013.76.
Marras, C. et al. (2018). Prevalence of Parkinson's disease across North America. npjParkinson's Disease. 4:21, https://doi.org/10.1038/s41531-018-0058-0, 7 pages.
Martin, W., Vaupel, D., Nozaki, M. and Bright, L. (1978). The identification of LSD-like hallucinogens using the chronic spinal dog. Drug and Alcohol Dependence, 3(2), pp. 113-123.
Martins, G.R. et al. (2016). Proinflammatory and Anti-Inflammatory Cytokines Mediated by NF-κ B Factor as Prognostic Markers in Mammary Tumors. Mediators of Inflammation, 2016:1-10. https://doi.org/10.1155/2016/9512743.
Martinussen R. et al. (2005). A meta-analysis of working memory impairments in children with attention-deficit/hyperactivity disorder. J Am Acad Child Adolesc Psychiatry, 44(4):377-84.
Marvanova, M. & Gramith, K. (2018). Role of antidepressants in the treatment of adults with anorexia nervosa. Ment Health Clin [Internet] 8(3):127-37. DOI: 10.9740/mhc.2018.05.127.
Mason, N.L. et al. (2019). Sub-Acute Effects of Psilocybin on Empathy, Creative Thinking, and Subjective Well-Being. Journal of Psychoactive Drugs, https://doi.org/10.1080/02791072.2019.1580804, 13 pages.
Mathes, B.M. et al. (2019). Epidemiological and Clinical Gender Differences in OCD. In Current Psychiatry Reports (vol. 21, Issue 5, pp. 1-7). Curr Psychiatry Rep, 21:36, 7 pages, https://doi.org/10.1007/s11920-019-1015-2.
Matheson, E. & Hainer, B.L. (2017) Insomnia: Pharmacologic Therapy—American Family Physician. Am Fam Physician, 96(1):29-35.
Matsushima, Y. et al. (2009). Effects of Psilocybe argentipes on Marble-Burying Behavior in Mice. Bioscience Biotechnology and Biochemistry, 73(8):1866-1868. https://doi.org/10.1271/bbb.90095.
Mattingly, G. et al. (2012). Attention deficit hyperactivity disorder subtypes and symptom response in adults treated with lisdexamfetamine dimesylate. Innov Clin Neurosci, 9(5-6):22-30.
Maxwell, C.R. et al. (2013). Atypical Laterality of Resting Gamma Oscillations in Autism Spectrum Disorders, 45(2):292-297, doi:10.1007/s10803-013-1842-7.
Mayhew A. & Argáez, C. (2018). Intravenous lidocaine for chronic pain: a review of the clinical effectiveness and guidelines. Ottawa: CADTH; Jan. 2018 (CADTH rapid response report: summary with critical appraisal), 22 pages.

Mazza M, Marano G, Janiri L. (2016) An update on pharmacotherapy for personality disorders. Expert Opinion on Pharmacotherapy. 17:(15):1977-1979.
McCarberg, B. & Billington, R. (2006). Consequences of neuropathic pain: Quality-of-life issues and associated costs. Am J Manag Care, 12(Suppl. 9):S263-8.
McCuen-Wurst, C. et al. (Jan. 2018). Disordered eating and obesity: associations between binge-eating disorder, night-eating syndrome, and weight-related comorbidities. Annals of the New York Academy of Sciences, 1411(1), pp. 96-105.
McCullough, M.E. et al. (2002) The grateful disposition: A conceptual and empiracal topography. Journal of Personality and Social Psychology, 82:112-127.
McElroy, S. et al. (2012). Pharmacological management of binge eating disorder: current and emerging treatment options. Therapeutics and Clinical Risk Management, 8:219-241.
McElroy, S. et al. (2013). A placebo-controlled pilot study of the novel opioid receptor antagonist ALKS-33 in binge eating disorder. International Journal of Eating Disorders, 46(3), pp. 239-245.
McElroy, S. et al. (2015). Efficacy and Safety of Lisdexamfetamine for Treatment of Adults With Moderate to Severe Binge-Eating Disorder. JAMA Psychiatry, 72(3), p. 235-246.
Mcguire-Snieckus, R. et al. (2007) A new scale to assess the therapeutic relationship in community mental health care: STAR. Psychological Medicine. 37:85-95.
Medical News Today, M. (2020). What to know about Parkinson's dementia. Retrieved from https://www.medicalnewstoday.com/articles/314486, 14 pages.
Medzhitov, R. (2008). Origin and physiological roles of inflammation. Nature, 454(7203):428-435. https://doi.org/10.1038/nature07201.
Mei, L., & Nave, K.-A. (2014). Neuregulin-ERBB signaling in the nervous system and neuropsychiatric diseases. In Neuron, 83:27-49, https://doi.org/10.1016/j.neuron.2014.06.007.
Meier, S.M. et al. (2016). Mortality among persons with obsessive-compulsive disorder in Denmark. JAMA Psychiatry, 73(3):268-274. https://doi.org/10.1001/jamapsychiatry.2015.3105.
Meldrum, B.S. & Naquet, R. (1970). Effects of psilocybin, dimethyltryptamine and various lysergic acid derivatives on photically-induced epilepsy in the baboon (*Papio papio*). British Journal of Pharmacology, 40(1):144P-145P. Retrieved from http://www.ncbi.nlm.nih.gov/pubmed/4992165.
Meyer, A.-C. et al. (2010). Global disparities in the epilepsy treatment gap: a systematic review. Bulletin of the World Health Organization, 88(4):260-266. https://doi.org/10.2471/BLT.09.064147.
Miller, A.H., & Raison, C. L. (2016). Role of inflammation in depression from evolutionary imperative to modern treatment target. Nat Rev Immunol, 16(1):22-34. https://doi.org/10.1038/nri.2015.5.
Mills, S.E.E. et al. (2019). Chronic pain: a review of its epidemiology and associated factors in population-based studies. Br J Anaesth. 123(2):273-83.
Milos, G. et al. (2002). Comorbidity of obsessive-compulsive disorders and duration of eating disorders. International Journal of Eating Disorders, 31(3):284-289. https://doi.org/10.1002/eat.10013.
Min, S.S. et al. (2011). Neuregulin-1 prevents amyloid β-induced impairment of long-term potentiation in hippocampal slices via ErbB4. Neuroscience Letters, 505(1):6-9. https://doi.org/10.1016/j.neulet.2011.05.246.
Minen, M.T. et al. (2016). Migraine and its psychiatric comorbidities. J. Neurol. Neurosurg. Psychiatry, 87:741-749. https://doi.org/10.1136/jnnp-2015-312233.
Miniati, M. et al. (2016). Psychopharmacological options for adult patients with anorexia nervosa. CNS Spectrums, 21:134-142. https://doi.org/10.1017/S1092852914000790.
Mitsuyama, F. et al. (2009). Amyloid beta: a putative intra-spinal microtubule-depolymerizer to induce synapse-loss or dentritic spine shortening in Alzheimer's disease. Italian Journal of Anatomy and Embryology, 114(2-3), 109-120. [Abstract]. Retrieved from http://www.ncbi.nlm.nih.gov/pubmed/20198823, 1 page.
Molero, P. et al. (2018). Antidepressant Efficacy and Tolerability of Ketamine and Esketamine: A Critical Review. CNS Drugs 32:411-420). https://doi.org/10.1007/s40263-018-0519-3.

(56) References Cited

OTHER PUBLICATIONS

Montejo, A.L. et al. (2008) Psychometric Properties of the Psychotropic-Related Sexual Dysfunction Questionnaire (PRSexDQ-SALSEX) in Patients with Schizophrenia and Other Psychotic Disorders. Journal of Sex Marital Therapy. 34(3):227-39.

Montigny, C. (1989). Cholecystokinin Tetrapeptide Induces Panic-like Attacks in Healthy Volunteers: Preliminary Findings. Archives of General Psychiatry, 46:511-517. https://doi.org/10.1001/archpsyc.1989.01810060031006.

Moran, P. et al. (2003) Standardised Assessment of Personality—Abbreviated Scale (SAPAS): preliminary validation of a brief screen for personality disorder. The British Journal of Psychiatry, 183(3):228-232.

Moreno, F. A., & Delgado, P. L. (1997). Hallucinogen-induced relief of obsessions and compulsions. American Journal of Psychiatry, vol. 154, Issue 7, pp. 1037-1038. https://doi.org/10.1176/ajp.154.7.1037b.

Moreno, F.A. et al. (Nov. 2006). Safety, tolerability, and efficacy of psilocybin in 9 patients with obsessive-compulsive disorder. Journal of Clinical Psychiatry, 67(11), 1735-1740. https://doi.org/10.4088/JCP.v67n1110.

Morgan, C. et al. (2017). Tripping up addiction: the use of psychedelic drugs in the treatment of problematic drug and alcohol use. Current Opinion in Behavioral Sciences, 13, pp. 71-76.

Morilak, D.A. et al. (2005). Role of brain norepinephrine in the behavioral response to stress. Prog. Neuro-Psychopharmacology Biol. Psychiatry, 29:1214-1224. https://doi.org/10.1016/j.pnpbp.2005.08.007.

Moscovich, M. et al. (2017). Death certificate data and causes of death in patients with parkinsonism. Parkinsonism & Related Disorders, 41:99-103. https://doi.org/10.1016/j.parkreldis.2017.05.022.

Mukherjee, S. et al. (2009). Lipopolysaccharide-driven Th2 Cytokine Production in Macrophages Is Regulated by Both MyD88 and TRAM. Journal of Biological Chemistry, 284(43):29391-29398. https://doi.org/10.1074/jbc.M109.005272.

Mula, M. et al. (2006). Psychopharmacology of topiramate: From epilepsy to bipolar disorder. Neuropsychiatric Disease and Treatment, 2(4):475-488. https://doi.org/10.2147/nedt.2006.2.4.475.

Mulvey, M.R. (2017) Neuropathic pain in cancer: systematic review, performance of screening tools and analysis of symptom profiles. British Journal of Anaesthesia, 119(4):765-774.

Municio, C. et al. (2018). Methotrexate limits inflammation through an A20-dependent cross-tolerance mechanism. Annals of the Rheumatic Diseases, 77(5):752-759. https://doi.org/10.1136/annrheumdis-2017-212537.

Murphy-Beiner, A. & Soar, K. (2020). Ayahuasca's 'afterglow': improved mindfulness and cognitive flexibility in ayahuasca drinkers. Psychopharmacology, published online, https://doi.org/10.1007/s00213-019-05445-3, 9 pages.

Murrough, J.W. et al. (2015). Emerging drugs for the treatment of anxiety. Expert Opin. Emerg. Drugs, 20(3):393-406. https://doi.org/10.1517/14728214.2015.1049996.

Nam, H. et al. (2014). Learned helplessness and social avoidance in the Wistar-Kyoto rat. Front. Behav. Neurosci., 8(109), https://doi.org/10.3389/fnbeh.2014.00109, 18 pages.

National Institute for Health and Care Excellence (NICE) (Jan. 28, 2019) Antisocial Personality Disorder: Prevention and Management. Clinical guidance CG77 [online]. Available from www.nice.org.uk/guidance/cg77, 35 pages.

National Institute of Mental Health (NIMH) (Nov. 2017) Eating Disorders. Mental Health Information—Statistics (online). Retrieved Mar. 5, 2020, from https://www.nimh.nih.gov/health/statistics/eating-disorders.shtml#part_155063,.

Nau, F. et al. (2015). Serotonin 5-HT$_2$ receptor activation prevents allergic asthma in a mouse model. American Journal of Physiology. Lung Cellular and Molecular Physiology, 308(2), L191-8. https://doi.org/10.1152/ajplung.00138.2013.

Nau, F., Yu, B., Martin, D., & Nichols, C. D. (2013). Serotonin 5-HT$_{2a}$ Receptor Activation Blocks TNF-α Mediated Inflammation In Vivo. PLoS One, 8(10):2-9. https://doi.org/10.1371/journal.pone.0075426.

Naviaux, J.C. et al. (2014). Reversal of autism-like behaviors and metabolism in adult mice with single-dose antipurinergic therapy. Translational Psychiatry, 4:e400, 11 pages. https://doi.org/10.1038/tp.2014.33.

Nechita, D. et al. (2018). A review of the influence the anxiety exerts on human life. Rom. J. Morphol. Embryol., 59(4):1045-1051.

Nelis, S.M. et al. (2019). The impact of co-morbidity on the quality of life of people with dementia: findings from the IDEAL study. Age and Ageing, 48(3):361-367. https://doi.org/10.1093/ageing/afy155.

Nelson, R. J. et al. (2006). Pleiotropic contributions of nitric oxide to aggressive behavior. Neuroscience and Biobehavioral Reviews, 30(3):346-355. https://doi.org/10.1016/j.neubiorev.2005.02.002.

Newman-Tancredi, A. et al. (2018). Effects of the Serotonin 5-HT1A Receptor Biased Agonists, F13714 and F15599, on Striatal Neurotransmitter Levels Following L-DOPA Administration in Hemi-Parkinsonian Rats. Neurochemical Research, 43(5):1035-1046. https://doi.org/10.1007/s11064-018-2514-y.

Ngugi, A.K. et al. (2010). Estimation of the burden of active and life-time epilepsy: A meta-analytic approach. Epilepsia, 51(5):883-890. https://doi.org/10.1111/j.1528-1167.2009.02481.x.

Ni, H.C. et al. (Oct. 2013) A head-To-head randomized clinical trial of methylphenidate and atomoxetine treatment for executive function in adults with attention-deficit hyperactivity disorder. Int J Neuropsychopharmacol, 16(9):1959-1973.

Nichols, D.E. (2004) Hallucinogens. Pharmacology & Therapeutics, 101:131-181.

Nichols, D.E. (Apr. 2016) Psychedelics. Pharmacol Reviews, 68:264-355.

Nichols et al., "Improvements to the Synthesis of Psilocybin and a Facile Method for Preparing the 0-Acetyl Prodrug of Psilocin," Synthesis. 1999; 6:935-938.

Nicholson, B. & Verma S. (2004). Comorbidities in chronic neuropathic pain. Pain Medicine. 5(S1):S9-25. Retrieved from: https://academic.oup.com/painmedicine/article-abstract/5/suppl_1/S9/1884243, on Jul. 30, 2020.

Nicolini, C. et al. (2015). Decreased mTOR signaling pathway in human idiopathic autism and in rats exposed to valproic acid. Acta Neuropathologica Communications, 3:3, 13 pages, https://doi.org/10.1186/s40478-015-0184-4.

Niederhofer, H. (2005). Atomoxetine Also Effective in Patients Suffering From Narcolepsy? Sleep, 28(9):1189, 1 page. https://www.researchgate.net/publication/7500498_Atomoxetine_Also_Effective_in_Patients_Suffering_From_Narcolepsy (accessed Mar. 26, 2020).

Nielsen, S. (2017). Benzodiazepines. Curr. Top. Behav. Neurosci. 34:141-159. https://doi.org/10.1007/7854_2015_425.

Nimmo-Smith, V. et al. (2020). Anxiety Disorders in Adults with Autism Spectrum Disorder: A Population-Based Study. Journal of Autism and Developmental Disorders, 50:308-318. https://doi.org/10.1007/s10803-019-04234-3.

Nisbet, E. et al. (Sep. 2009) The nature relatedness scale. Linking individuals' connection with nature to environmental concern and behavior. Environment and Behavior 41(5):715-740.

Norris, M.L. et al. (2011). Olanzapine Use for the Adjunctive Treatment of Adolescents with Anorexia Nervosa. Journal of Child and Adolescent Psychopharmacology, 21(3):213-220. https://doi.org/10.1089/cap.2010.0131.

Nour, M.M. et al. (Jun. 2016) Ego-Dissolution and Psychedelics: Validation of the Ego-Dissolution Inventory (EDI) Frontiers in Human Neuroscience, 10:269, doi: 10.3389/fnhum.2016.00269, 13 pages.

Nour, M.M. et al. (2017) Psychedelics, Personality and Political Perspectives. Journal of Psychoactive Drugs, 49(3):182-191.

Nowacka, A. & Borczyk, M. (2019). Ketamine applications beyond anesthesia—A literature review. European Journal of Pharmacology, 860, 172547, 14 pages. https://doi.org/10.1016/j.ejphar.2019.172547.

Oerbeck, B. et al. (2017) ADHD, comorbid disorders and psychosocial functioning: How representative is a child cohort study?

(56) References Cited

OTHER PUBLICATIONS

Findings from a national patient registry. BMC Psychiatry, 17:23, 9 pages. Available from: http://dx.doi.org/10.1186/s12888-017-1204-7.

Olguin, P. et al. (2017). Medical comorbidity of binge eating disorder. Eat Weight Disord 22, 13-26.

Onakpoya, I.J. et al. (2019). Benefits and harms of pregabalin in the management of neuropathic pain: A rapid review and meta-analysis of randomised clinical trials. BMJ Open 9, e023600, 19 pages. https://doi.org/10.1136/bmjopen-2018-023600.

Opbroek, A. et al. (2002) Emotional blunting associated with SSRI-induced sexual dysfunction. Do SSRIs inhibit emotional responses? International Journal of Neuropsychopharmacology, 5:147-151.

Orekhova, E.V. et al. (2008). Sensory gating in young children with autism: Relation to age, IQ, and EEG gamma oscillations. Neurosci. Lett., 434:218-223. https://doi.org/10.1016/j.neulet.2008.01.066.

Osland, S. et al. (2018). The prevalence of diagnosed obsessive compulsive disorder and associated comorbidities: A population-based Canadian study. Psychiatry Research, 268:137-142. https://doi.org/10.1016/j.psychres.2018.07.018.

Ottman, R. et al. (2011). Comorbidities of epilepsy: results from the Epilepsy Comorbidities and Health (EPIC) survey. Epilepsia, 52(2):308-315. https://doi.org/10.1111/j.1528-1167.2010.02927.x.

Otto, M.W. et al. (2001). An effect-size analysis of the relative efficacy and tolerability of serotonin selective reuptake inhibitors for panic disorder. Am. J. Psychiatry 158:1989-1992. https://doi.org/10.1176/appi.ajp.158.12.1989.

Page, J. & Henry, D. (Mar. 2000). Consumption of NSAIDs and the Development of Congestive Heart Failure in Elderly Patients. Archives of Internal Medicine, 160(6):777-784. https://doi.org/10.1001/archinte.160.6.777.

Pahwa, R. et al. (2020). Chronic Inflammation. Statpearls [Internet]. NCBI Bookshelf. Retrieved from: https://www.ncbi.nlm.nih.gov/books/NBK493173/, 9 printed pages.

Palsson-McDermott, E. M. & O'Neill, L. A. J. (2004). Signal transduction by the lipopolysaccharide receptor, Toll-like receptor-4. Immunology, 113(2):153-162. https://doi.org/10.1111/j.1365-2567.2004.01976.x.

Papakostas, G.I. et al. (2006) "The combination of duloxetine and bupropion for treatment-resistant major depressive disorder" Depression and Anxiety, 23:178-181.

Parameswaran, N. & Patial, S. (2010). Tumor necrosis factor-α signaling in macrophages. Critical Reviews in Eukaryotic Gene Expression, 20(2):87-103. https://doi.org/10.1615/critreveukargeneexpr.v20.i2.10.

Park, A. (Dec. 2021) Characterization of Psilocybin. Freedom to Operate, LLC. Triclinic Labs Report No. R2021638.01, 11 pages.

Park, J.H. & Park, H.J. (2017) Botulinum toxin for the treatment of neuropathic pain. Toxins. 9:290, doi:10.3390/toxins9090260, 15 pages.

Parkinson's Foundation (2020). Prescription Medications for Parkinson Disease. Retrieved from https://www.parkinson.org/Understanding-Parkinsons/Treatment/Prescription-Medications; retrieved on Jul. 30, 2020; 6 pages.

Parkinson's Foundation, P. (2020). Stages of Parkinson's disease. Retrieved from https://www.parkinson.org/Understanding-Parkinsons/What-is-Parkinsons/Stages-of-Parkinsons, 8 pages.

Parnas, J. et al. (2005) EASE: Examination of Anomalous Self-Experience. Psychopathology. 38:236-258.

Passie, T. et al. (2002) The pharmacology of psilocybin. Addiction Biology, 7:357-364.

Patra, S. (Dec. 2016) "Return of the psychedelics: Psilocybin for treatment resistant depression," Asian Journal of Psychiatry, vol. 24, p. 51-52.

Patton, J.H. (Nov. 1995) Factor structure of the Barratt Impulsiveness Scale. Journal of Clinical Psychology. 51:768-774.

Pauli, D. et al. (2017). Motivation to change, coping, and self-esteem in adolescent anorexia nervosa: A validation study of the Anorexia Nervosa Stages of Change Questionnaire (ANSOCQ). Journal of Eating Disorders, 5(1):11, 11 pages. https://doi.org/10.1186/s40337-016-0125-z.

Peciña, S., & Berridge, K.C. (Dec. 2005). Hedonic hot spot in nucleus accumbens shell: Where do μ opioids cause increased hedonic impact of sweetness? The Journal of Neuroscience, 25(50):11777-11786.

Pelletier, M. & Siegel, R. M. (2009). Wishing away inflammation? New links between serotonin and TNF signaling. Molecular Interventions, 9(6):299-301. https://doi.org/10.1124/mi.9.6.5.

Pennington, S. et al. (2010). The cause of death in idiopathic Parkinson's disease. Parkinsonism & Related Disorders, 16(7):434-437. https://doi.org/10.1016/j.parkreldis.2010.04.010.

Perini, G. I. et al. (1996). Interictal mood and personality disorders in temporal lobe epilepsy and juvenile myoclonic epilepsy. Journal of Neurology, Neurosurgery & Psychiatry, 61(6):601-605. https://doi.org/10.1136/jnnp.61.6.601.

Perlis, M.L. et al. (2001). Beta/Gamma EEG Activity in Patients with Primary and Secondary Insomnia and Good Sleeper Controls. Sleep, 24(1):110-117.

Persson, S. A. (1978). LSD and related drugs as DA antagonists: receptor-mediated effects on the synthesis and turnover of DA. Life Sciences, 23(5):523-526. https://doi.org/10.1016/0024-3205(78)90165-0.

Peters, E. et al. (2004) Measuring Delusional Ideation: the 21-item Peters et al. Delusions Inventory (PDI). Schizophrenia Bulletin, 30(4):1005-1022.

Piedmont, R.L. (1999) Does spirituality represent the sixth factor of personality? Spiritual transcendence and the five-factor model. Journal of Personality. 67:985-1013.

Piton, A. et al. (2011). Systematic resequencing of X-chromosome synaptic genes in autism spectrum disorder and schizophrenia. Molecular Psychiatry, 16(8):867-880. https://doi.org/10.1038/mp.2010.54.

Pittenger, C. et al. (2014). Pharmacological treatment of obsessive-compulsive disorder. In Psychiatric Clinics of North America, 37(3):375-391. https://doi.org/10.1016/j.psc.2014.05.006.

Polat, G. et al. (2017). Sepsis and Septic Shock: Current Treatment Strategies and New Approaches. Eurasian Journal of Medicine, 49(1):53-58. https://doi.org/10.5152/eurasianjmed.2017.17062.

Polito, V. & Stevenson, R.J. (2019) A systematic study of microdosing psychedelics. PLoS One. 14(2):e0211023, https://doi.org/10.1371/journal.pone.0211023, 26 pages.

Postal, M. et al. (2016). Depressive symptoms are associated with tumor necrosis factor alpha in systemic lupus erythematosus. Journal of Neuroinflammation, 13(1):5. https://doi.org/10.1186/s12974-015-0471-9, 7 pages.

Pérez-Carbonell, L. et al. (2020). Adherence to wakefulness promoting medication in patients with narcolepsy. Sleep Med. 70:50-54. https://doi.org/10.1016/j.sleep.2020.02.013.

Price, J. et al. (2012) The Oxford Questionnaire on the Emotional Side-effects of Antidepressants (OQuESA): Development, validity, reliability and sensitivity to change. Journal of Affective Disorders. 140:66-74.

Prince J. (2008) Catecholamine dysfunction in attention-deficit/hyperactivity disorder. An update. Journal of Clinical Psychopharmacology. 48(3 Suppl 2):39-45.

Prochazkova, L. et al. (2018). Exploring the effect of microdosing psychedelics on creativity in an open-label natural setting. Psychopharmacology, 235(12):3401-3413. https://doi.org/10.1007/s00213-018-5049-7.

Prosolv® SMCC. Retrieved from Web Archive, Reset https://web.archive.org/web/20160318071326/http://www.jrspharma.com/pharmaen/products-services/excipients/hfe/prosolvs-mcc.php Retrieved Mar. 18, 2016.

Pryor, T. et al. (1996). Clinical correlates of anorexia nervosa subtypes. The International Journal of Eating Disorders, 19(4):371-379. http://www.ncbi.nlm.nih.gov/pubmed/9156690.

Psilocybin for the Treatment of Cluster Headache. ClinicalTrials.gov [Internet]. Identifier: NCT02981173. Retrieved from: https://clinicaltrials.gov/ct2/show/NCT02981173, 8 pages.

(56) References Cited

OTHER PUBLICATIONS

Psilocybin Patent Tracker. Psilocybin Alpha, 2020 [online]. Retrieved from: https://psilocybinalpha.com/data/psilocybin-patent-tracker; retrieved on Oct. 1, 2020, 2 printed pages.
Pugazhenthi, S. et al. (2013). Induction of an Inflammatory Loop by Interleukin-1β and Tumor Necrosis Factor-α Involves NF-κB and STAT-1 in Differentiated Human Neuroprogenitor Cells. PLOS ONE, 8(7):1-12. https://doi.org/10.1371/journal.pone.0069585.
Pulikkan, J. et al. (2019). Role of the Gut Microbiome in Autism Spectrum Disorders. In Advances in Experimental Medicine and Biology, 1118:253-269. https://doi.org/10.1007/978-3-030-05542-4_13.
Quadri, S. et al. (2009). Improvement of idiopathic central sleep apnea with zolpidem. J. Clin. Sleep Med. 5:122-129. https://doi.org/10.5664/jcsm.27439.
Quan, Q. et al. (2019). CDK5 Participates in Amyloid-β Production by Regulating PPARγ Phosphorylation in Primary Rat Hippocampal Neurons. Journal of Alzheimer's Disease : JAD, 71(2):443-460. https://doi.org/10.3233/JAD-190026.
Quan, X. et al. (2020). Related Network and Differential Expression Analyses Identify Nuclear Genes and Pathways in the Hippocampus of Alzheimer Disease. Medical Science Monitor : International Medical Journal of Experimental and Clinical Research, 26:e919311, 11 pages. https://doi.org/10.12659/MSM.919311.
Quintero J. et al. (2010). Reboxetine for ADHD in children non-responders or with poor tolerance to methylphenidate: A prospective long-term open-label study. ADHD Atten Deficit Hyperact Disord., 2(3):107-113.
Raffaeli, W. & Arnaudo, E. (2017). Pain as a disease: An overview. J Pain Res., 10:2003-2008.
Rai, D. et al. (2012). Epilepsy and psychiatric comorbidity: A nationally representative population-based study. Epilepsia 53:1095-1103. https://doi.org/10.1111/j.1528-1167.2012.03500.x.
Ramachandran, V. et al. (2018). Relief from intractable phantom pain by combining psilocybin and mirror visual-feedback (MVF). Neurocase, 24(2):105-110. Available from: https://doi.org/10.1080/13554794.2018.1468469.
Ramadan, M.I. et al. (2006). Protect against drug-drug interactions with anxiolytics. Current Psychiatry, 5(5):16-28.
Ramos, A.A. et al. (2019). A meta-analysis on verbal working memory in children and adolescents with ADHD. Clinical Neuropsychologist, 34(5):873-898.
Rautiainen, M-R. et al. (2016) Genome-wide association study of antisocial personality disorder. Transl Psychiatry. 6:e883, doi:10.1038/tp.2016.155, 10 pages.
Raval et al., "Silicified Microcrystalline Cellulose as a Multifunctional Pharmaceutical Excipient," Drug Delivery Technology, 2009;9(4):28 and 30-32. Supplied by the British Library Oct. 12, 2019, 6 pages.
Ravindran, L.N. & Stein, M.B. (2010). The pharmacologic treatment of anxiety disorders: A review of progress. J. Clin. Psychiatry. 71(7):839-854. https://doi.org/10.4088/JCP.10r06218blu.
Reas, D. and Grilo, C. (Mar. 2014). Current and emerging drug treatments for binge eating disorder. Expert Opinion on Emerging Drugs, 19(1), pp. 99-142.
Reimherr, F.W. et al. (2017). ADHD and Anxiety: Clinical Significance and Treatment Implications. Curr. Psychiatry Rep., 19:109, 10 pages. https://doi.org/10.1007/s11920-017-0859-6.
Reitz, C. & Mayeux, R. (2014). Alzheimer disease: Epidemiology, diagnostic criteria, risk factors and biomarkers. Biochemical Pharmacology, 88(4):640-651. https://doi.org/10.1016/j.bcp.2013.12.024.
Remes, O. et al. (2016). A systematic review of reviews on the prevalence of anxiety disorders in adult populations. Brain Behav. https://doi.org/10.1002/brb3.497, 33 pages.
Repke et al., Psilocin Analogs. 1. Synthesis of 3-[2-(Dialkylamino)ethyl]- and 3-[2-(Cycloalkylamino)ethyl] indol-4-ols, J. Heterocyclic Chem., 14, 71 (1977), 4 pages.
Rickels, K. et al. (Sep. 2005). Pregabalin for treatment of generalized anxiety disorder: A 4-week, multicenter, double-blind, placebo-controlled trial of pregabalin and alprazolam. Arch. Gen. Psychiatry 62, 1022-1030. https://doi.org/10.1001/archpsyc.62.9.1022.
Riediger, C. et al. (2017). Adverse effects of antidepressants for chronic pain: A systematic review and meta-analysis. Front. Neurol. 8:307, 23 pages. doi: 10.3389/fneur.2017.00307.
Rintala, H. et al. (2017). Register-based study of the incidence, comorbidities and demographics of obsessive-compulsive disorder in specialist healthcare. BMC Psychiatry, 17(1):64, 8 pages. https://doi.org/10.1186/s12888-017-1224-3.
Ripoll, L.H. et al. (2011) Evidence-based pharmacotherapy for personality disorders. 14:1257-1288.
Robbins, M.S. (2013) The psychiatric comorbidities of cluster headache. Curr Pain Headache Rep, 17(2):313, DOI:10.1007/s11916-012-0313-8, 8 pages.
Robner, A. et al. (2017). Cognitive Flexibility in Juvenile Anorexia Nervosain Relation to Comorbid Symptoms of Depression, Obsessive Compulsive Symptoms and Duration of Illness. Zeitschrift für Kinder- und Jugendpsychiatrie und Psychotherapie, 45 (5):371-380. https://doi.org/10.1024/1422-4917/a000493.
Rodríguez, C. et al. (2016). Attention deficit/hyperactivity disorder (ADHD) diagnosis: An activation-executive model. Front. Psychol. 7:1406, 13 pages. doi: 10.3389/fpsyg.2016.01406.
Rojas, D.C. & Wilson, L.B. (2014). γ-band abnormalities as markers of autism spectrum disorders. Biomark Med. Mar. 2014; 8(3):353-368. doi:10.2217/bmm.14.15.
Rosen, E. et al. (2017). Hepatic Complications of Anorexia Nervosa. Dig Dis Sci, 62:2977-2981. doi:10.1007/s10620-017-4766-9.
Rosenberg, M. (1965) Society and the adolescent self-image. Science, 148(3671):804, DOI:10.1126/science.148.3671.804.
Rosenblat, J.D. et al. (2014). Inflamed moods: A review of the interactions between inflammation and mood disorders. Progress in Neuro-Psychopharmacology and Biological Psychiatry, 53:23-34. https://doi.org/10.1016/j.pnpbp.2014.01.013.
Ross, S. et al. (2016). Rapid and sustained symptom reduction following psilocybin treatment for anxiety and depression in patients with life-threatening cancer: A randomized controlled trial. J. Psychopharmacol. 30:1165-1180. https://doi.org/10.1177/0269881116675512.
Rossi, P. and Whelan, J. (2016) What is cluster headache? Fact sheet for patients and their families. A publication to mark Cluster Headache Day 2016. Functional Neurology. 31(3):181-183.
Roth, T. et al. (2007). Efficacy and safety of doxepin 1 mg, 3 mg, and 6 mg in adults with primary insomnia. Sleep 30, 1555-61. https://doi.org/10.1093/sleep/30.11.1555.
Roth, T. et al. (2007). Insomnia: Definition, prevalence, etiology, and consequences. J. Clin. Sleep Med. Supplement to vol. 3, No. 5, https://doi.org/10.5664/jcsm.26929.
Råstam, M., et al. (2003). Outcome of teenage-onset anorexia nervosa in a Swedish community-based sample. European Child and Adolescent Psychiatry, 12(Suppl. 1):78-90. https://doi.org/10.1007/s00787-003-1111-y.
Ruffolo, S. et al. (2006). Comorbidity of body dysmorphic disorder and eating disorders: Severity of psychopathology and body image disturbance. International Journal of Eating Disorders, 39(1), pp. 11-19.
Rupprecht, R. et al. (2009). Translocator protein (18 kD) as target for anxiolytics without benzodiazepine-like side effects. Science, New Series, vol. 325, No. 5939, pp. 490-493. https://doi.org/10.1126/science.1175055.
Ruscio, A. M. et al. (2010). The epidemiology of obsessive-compulsive disorder in the National Comorbidity Survey Replication. Molecular Psychiatry, 15(1), 53-63. https://doi.org/10.1038/mp.2008.94.
Rush, A.J. et al. (2003) The 16-Item Quick Inventory of Depressive Symptomatology (QIDS), Clinician Rating (QIDS-C), and Self-Report (QIDS-SR): A Psychometric Evaluation in Patients with Chronic Major Depression. Biol Psy, 54(5):573-583.
Russell, E.J. et al. (2013). Risk of obsessive-compulsive disorder in pregnant and postpartum women: A meta-analysis. Journal of Clinical Psychiatry, 74(4), 377-385. https://doi.org/10.4088/JCP.12r07917.
Russo, A.J. (2014). Increased Epidermal Growth Factor Receptor (EGFR) Associated with Hepatocyte Growth Factor (HGF) and

(56) References Cited

OTHER PUBLICATIONS

Symptom Severity in Children with Autism Spectrum Disorders (ASDs). Journal of Central Nervous System Disease. 6:79-83. https://doi.org/10.4137/jcnsd.s13767.

Ryder, S. & A, Stannard C.F. (2005). Treatment of chronic pain: Antidepressant, antiepileptic and antiarrhythmic drugs. Contin Educ Anaesthesia, Crit Care Pain. 5(1):18-21.

Rylander, M. et al. (2017). A comparison of the metabolic complications and hospital course of severe anorexia nervosa by binge-purge and restricting subtypes. Eating Disorders, 25(4), 345-357. https://doi.org/10.1080/10640266.2016.1269555.

Sagata, N. et al. (2017). Dysregulated gene expressions of MEX3D, FOS and BCL2 in human induced-neuronal (iN) cells from NF1 patients: A pilot study. Scientific Reports. https://doi.org/10.1038/s41598-017-14440-7.

Sahu, A. & Gupta, R. (2017). A study of psychiatric comorbidity after traumatic limb amputation: A neglected entity. Ind Psychiatry J. 26(6):228-32.

Sakashita, Y. et al. (2015). Effect of Psilocin on Extracellular Dopamine and Serotonin Levels in the Mesoaccumbens and Mesocortical Pathway in Awake Rats. Biol. Pharm. Bull. 38, 134-138 (2015).

Salama, R. M. et al. (2020). Neuroprotective effect of crocin against rotenone-induced Parkinson's disease in rats: Interplay between PI3K/Akt/mTOR signaling pathway and enhanced expression of miRNA-7 and miRNA-221. Neuropharmacology, 164, 107900., 12 pages. https://doi.org/10.1016/j.neuropharm.2019.107900.

Salisbury-Afshar, E. (2018). Management of Insomnia Disorder in Adults—Implementing AHRQ Effective Health Care Reviews. Am Fam Physician. 98(5), 5 pages. https://www.aafp.org/afp/2018/0901/p319.html#afp20180901p319-b4.

Sandbank, M. et al. (2020). Project AIM: Autism intervention meta-analysis for studies of young children. Psychological Bulletin. 146(1):1-29. https://doi.org/10.1037/bul0000215.

Sandiego, C.M. et al. (2015). Imaging robust microglial activation after lipopolysaccharide administration in humans with PET. Proceedings of the National Academy of Sciences, 112(40), 12468-12473. https://doi.org/10.1073/pnas.1511003112.

Santiago, J.A. et al. (2017). Biological and Clinical Implications of Comorbidities in Parkinson's Disease. Frontiers in Aging Neuroscience, 9, 16 pages. https://doi.org/10.3389/fnagi.2017.00394.

Santini, E. et al. (2013). Exaggerated translation causes synaptic and behavioural aberrations associated with autism. Nature, 493, https://doi.org/10.1038/nature11782, 6 pages.

Saraf, G. et al. (2017). Bipolar disorder comorbidity in patients with a primary diagnosis of OCD, International Journal of Psychiatry in Clinical Practice, 21:1, 70-74, doi: 10.1080/13651501.2016.1233344.

Saraiva, M., & O'Garra, A. (2010). The regulation of IL-10 production by immune cells. Nature Reviews Immunology, 10(3), 170-181. https://doi.org/10.1038/nri2711.

Sard, H. et al. (2005). SAR of psilocybin analogs: Discovery of a selective 5-HT2C agonist. Bioorganic and Medicinal Chemistry Letters, 15(20), 4555-4559. https://doi.org/10.1016/j.bmcl.2005.06.104.

Saunders, A.M. et al. (1993). Association of apolipoprotein E allele ε4 with late-onset familial and sporadic Alzheimer's disease. Neurology, 43(8):1467-1467. https://doi.org/10.1212/WNL.43.8.1467.

Savage, C. (1952) Lysergic Acid Diethylamide (LSD-25). A Clinical-Psychological Study. The American Journal of Psychiatry, 108:896-900.

Savioz, A., Leuba, G., & Vallet, P. G. (2014). A framework to understand the variations of PSD-95 expression in brain aging and in Alzheimer's disease. Ageing Research Reviews, 18, 86-94. https://doi.org/10.1016/j.arr.2014.09.004.

Saxton, R. A. & Sabatini, D.M. (Mar. 2017). mTOR Signaling in Growth, Metabolism, and Disease. Cell, 168(6):960-976. https://doi.org/10.1016/j.cell.2017.02.004.

Sayal, K. et al. (2018) ADHD in children and young people: prevalence, care pathways, and service provision. The Lancet Psychiatry, 5(2):175-186. Available from: http://dx.doi.org/10.1016/S2215-0366(17)30167-0cdc.gov.

Scammell, T.E. (2015) Narcolepsy. N. Engl. J. Med., 373:4654-2662. https://doi.org/10.1056/NEJMra1500587.

Schachter, M. & Parkes, J.D. (1980). Fluvoxamine and clomipramine in the treatment of cataplexy. Journal of Neurology, Neurosurgery, and Psychiatry, 43:171-174.

Scheller, J. et al. (2011). The pro- and anti-inflammatory properties of the cytokine interleukin-6. Biochimica et Biophysica Acta, 1813(5):878-888. https://doi.org/10.1016/j.bbamcr.2011.01.034.

Schülke, S. (2018). Induction of Interleukin-10 Producing Dendritic Cells as a Tool to Suppress Allergen-Specific T Helper 2 Responses. Frontiers in Immunology, 9:455, https://doi.org/10.3389/fimmu.2018.00455, 18 pages.

Schneider, T. et al. (2008). Gender-specific behavioral and immunological alterations in an animal model of autism induced by prenatal exposure to valproic acid. Psychoneuroendocrinology, 33:728-740. https://doi.org/10.1016/j.psyneuen.2008.02.011.

Schwalberg, M.D. et al. (1992). Comparison of Bulimics, Obese Binge Eaters, Social Phobics, and Individuals With Panic Disorder on Comorbidity Across DSM-III-R Anxiety Disorders. J. Abnorm. Psychol., 101:675-681. https://doi.org/10.1037/0021-843X.101.4.675.

Sedgwick, O. et al. (2017) Neuropsychology and emotion processing in violent individuals with antisocial personality disorder or schizophrenia: The same or different? A systematic review and meta-analysis. Australian and New Zealand Journal of Psychiatry, 51(12):1178-1197.

Sedley, W. & Cunningham, M.O. (2013). Do cortical gamma oscillations promote or suppress perception? An under-asked question with an over-assumed answer. Front. Hum. Neurosci., 7:595, https://doi.org/10.3389/fnhum.2013.00595, 17 pages.

Serrano-Pozo, A. et al. (2011). Neuropathological Alterations in Alzheimer Disease. Cold Spring Harbor Perspectives in Medicine, 1(1):a006189, https://doi.org/10.1101/cshperspect.a006189, 23 pages.

Sewell, R.A. et al. (Jun. 2006) "Response of cluster headache to psilocybin and LSD" Neurology, 66(12):1920-1922.

Shah, K., & Lahiri, D.K. (2014). Cdk5 activity in the brain—multiple paths of regulation. Journal of Cell Science, 127(11):2391-2400. https://doi.org/10.1242/jcs.147553.

Shannon, P. et al. (2003). Cytoscape: a software environment for integrated models of biomolecular interaction networks. Genome Research, 13(11):2498-2504. https://doi.org/10.1101/gr.1239303.

Sharma, S.R. et al. (2018). Autism Spectrum Disorder: Classification, diagnosis and therapy. Pharmacology and Therapeutics, 190:91-104. https://doi.org/10.1016/j.pharmthera.2018.05.007.

Sherman, E.M.S. et al. (2011). Neuropsychological outcomes after epilepsy surgery: Systematic review and pooled estimates. Epilepsia, 52(5):857-869. https://doi.org/10.1111/j.1528-1167.2011.03022.x.

Sherwood, A.M. et al. (2021) Psilocybin: crystal structure solutions enable phase analysis of prior art and recently patented examples. Acta Crystallographica, 78(1):1-20.

Shier, A.C. et al. (2013) Pharmacological Treatment of Attention Deficit Hyperactivity Disorder in Children and Adolescents: Clinical Strategies. J Cent Nerv Syst Dis, 5, doi: 10.4137/JCNSD.S6691, 17 pages.

Shirota et al. (Jun. 2003) "Concise large-scale synthesis of psilocin and psilocybin, principal hallucinogenic constituents of 'magic mushroom'" J Nat Prod, 66(6):885-887.

Shofty, B. et al. (Apr. 26, 2019). Loss of function in the autism and learning disabilities associated gene Nf1 disrupts corticocortical and corticostriatal functional connectivity in human and mouse. BioRxiv, preprint, https://doi.org/10.1101/618223, 35 pages.

Shoja Shafti, S., & Kaviani, H. (2015). Aripiprazole versus quetiapine in treatment-resistant obsessive-compulsive disorder: A double-blind clinical trial. Therapeutic Advances in Psychopharmacology, 5(1):32-37. https://doi.org/10.1177/2045125314560739.

Shulgin et al., "TIHKAL: The Continuation," Transform Press, 1997, pp. 468-473.

Sid-Otmane, L. et al. (2020). Selective metabotropic glutamate receptor 2 positive allosteric modulation alleviates L-DOPA-

(56) References Cited

OTHER PUBLICATIONS induced psychosis-like behaviours and dyskinesia in the MPTP-lesioned marmoset. European Journal of Pharmacology, 873:172957, https://doi.org/10.1016/j.ejphar.2020.172957, 6 pages.

Siervo, M. et al. (Jun. 2005). Application of the SCOFF, Eating Attitude Test 26 (EAT 26) and Eating Inventory (TFEQ) questionnaires in young women seeking diet-therapy. Eating and Weight Disorders, 10(2):76-82. https://doi.org/10.1007/BF03327528.

Silber, M.H. et al. (2002) The epidemiology of narcolepsy in Olmsted County, Minnesota: A population-based study. Sleep, 25(2):197-202. https://doi.org/10.1093/sleep/25.2.197.

Silva, N. et al. (2014) Searching for a neurobiological basis for self-medication theory in ADHD comorbid with substance use disorders: An in vivo study of dopamine transporters using $^{99m}$Tc-TRODAT-1 SPECT. Clin Nucl Med, 39(2):e129-e134.

Simon, N.M. (2009) Generalized Anxiety Disorder and Psychiatric Comorbidities Such as Depression, Bipolar Disorder, and Substance Abuse. J Clin Psychiatry, 70(suppl 2):10-14.

Singh, A., & Trevick, S. (2016). The Epidemiology of Global Epilepsy. Neurologic Clinics, 34(4):837-847. https://doi.org/10.1016/j.ncl.2016.06.015.

Siniscalco, D. et al. (Jun. 2018). Inflammation and neuro-immune dysregulations in autism spectrum disorders. Pharmaceuticals, 11:56, https://doi.org/10.3390/ph11020056, 14 pages.

Skapinakis, P. et al. (2016) "Pharmacological and psychotherapeutic interventions for management of obsessive-compulsive disorder in adults: a systematic review and network meta-analysis" The Lancet Psychiatry, 3(8):730-739. https://doi.org/10.1016/S2215-0366(16)30069-4.

Smith, B.W. et al. (2008) The Brief Resilience Scale: Assessing the Ability to Bounce Back. International Journal of Behavioral Medicine. 15:194-200.

Smith, K.N. et al. (2019). Changes in meal-related anxiety predict treatment outcomes in an intensive family-based treatment program for adolescents with anorexia nervosa. Eating Disorders, DOI: 10.1080/10640266.2019.1688008, 13 pages.

Snaith, R.P. et al. (1995) A scale for the assessment of hedonic tone. The Snaith-Hamilton Pleasure Scale. The British Journal of Psychiatry, 167:99-103.

Soler, J. et al. (2018). Genetic variability in scaffolding proteins and risk for schizophrenia and autism-spectrum disorders: A systematic review. Journal of Psychiatry and Neuroscience, 43(4):223-244. https://doi.org/10.1503/jpn.170066.

Souery, D. et al. (2007). Clinical Factors Associated With Treatment Resistance in Major Depressive Disorder: Results From a European Multicenter Study. The Journal of Clinical Psychiatry, 68(07):1062-1070. https://doi.org/10.4088/JCP.v68n0713.

Spangler, E.L., Rigby, P., & Ingram, D.K. (1986). Scopolamine impairs learning performance of rats in a 14-unit T-maze. Pharmacology, Biochemistry and Behavior, 25:673-679. https://doi.org/10.1016/0091-3057(86)90158-9.

Spielberger, C.D. (2020) State-Trait Anxiety Inventory for AdultsTM. STAI—Adult Manual. Mind Garden Inc., www.mindgarden.com, 87 pages.

Spowart-Manning L. et al. (May 2004) The T-maze continuous alternation task for assessing the effects of putative cognition enhancers in the mouse. Behav Brain Res, 151(1-2):37-46.

Srinivas, H.V. & Shah, U. (2017). Comorbidities of epilepsy. Neurology India, 65(Supplement):S18-S24. https://doi.org/10.4103/neuroindia.NI_922_16, 15 pages.

Srivastava, R.K. et al. (2011). Role of Donepezil in Autism: Its Conduciveness in Psychopharmacotherapy. Case Reports in Psychiatry, 2011:563204, https://doi.org/10.1155/2011/563204, 2 pages.

Stahl, S.M. (1998) Mechanism of action of serotonin selective reuptake inhibitors. Serotonin receptors and pathways mediate therapeutic effects and side effects. J. Affect. Disord., 51:215-235. https://doi.org/10.1016/S0165-0327(98)00221-3.

Stancil, S. et al. (2019). Naltrexone Reduces Binge Eating and Purging in Adolescents in an Eating Disorder Program. Journal of Child and Adolescent Psychopharmacology, 29(9):721-724.

Stancu, C., & Sima, A. (2001). Statins: mechanism of action and effects. Journal of Cellular and Molecular Medicine, 5(4), 378-387. https://doi.org/10.1111/j.1582-4934.2001.tb00172.x.

Starr, M.S. (1996). The role of dopamine in epilepsy. Synapse. 22:159-194.

Stefano, S. et al. (2008). Antidepressants in short-term treatment of binge eating disorder: Systematic review and meta-analysis. Eating Behaviors, 9(2), pp. 129-136.

Steger, M.F. et al. (2008) Understanding the search for meaning in life: Personality, cognitive style, and the dynamic between seeking and experiencing meaning. Journal of Personality, 76:199-228.

Stein, D.J. et al. (2017). Epidemiology of anxiety disorders: From surveys to nosology and back. Dialogues Clin Neurosci, 19:127-135.

Stein, D.J. et al. (2019) "Obsessive-compulsive disorder" Nature Reviews Disease Primers, 5(1):52; doi: 10.1038/s41572-019-0102-3, 21 pages.

Stein, M.B. & Sareen, J. (2015). Generalized anxiety disorder. N. Engl. J. Med., 373:2059-2068. https://doi.org/10.1056/NEJMcp1502514.

Steinhausen, H-C. (2009). Outcome of Eating Disorders. Child and Adolescent Psychiatric Clinics of North America, 18(Issue 1):225-242. https://doi.org/10.1016/j.chc.2008.07.013.

Stevenson, R.A. et al. (2019). Conjunctive visual processing appears abnormal in Autism. Frontiers in Psychology, 9:2668, https://doi.org/10.3389/fpsyg.2018.02668, 7 pages.

Stice, L. V., & Lavner, J. A. (2019). Social Connectedness and Loneliness Mediate the Association Between Autistic Traits and Internalizing Symptoms Among Young Adults. Journal of Autism and Developmental Disorders, 49(3), 1096-1110. https://doi.org/10.1007/s10803-018-3812-6.

Sticht, G., & Käferstein, H. (2000). Detection of psilocin in body fluids. Forensic Science International, 113(1-3):403-407. https://doi.org/10.1016/S0379-0738(00)00213-9.

Stojanovic, A. et al. (2014). Increased serum interleukin-6 levels in early stages of psychosis: Associations with at-risk mental states and the severity of psychotic symptoms. Psychoneuroendocrinology, 41, 23-32. https://doi.org/10.1016/j.psyneuen.2013.12.005.

Strawbridge, R. et al. (2019). Inflammatory profiles of severe treatment-resistant depression. Journal of Affective Disorders, 246:42-51. https://doi.org/10.1016/j.jad.2018.12.037.

Strunk, D.R. et al. (2006) Depressive symptoms are associated with unrealistic negative predictions of future life events. Behavior Research and Therapy, 44:861-882.

Studerus, E. et al. (2010) Psychometric evaluation of the altered states of consciousness rating scale (OAV). PloS One, 5:e12412, 19 pages.

Studerus, E. et al. (2011) "Acute, subacute and long-term subjective effects of psilocybin in healthy humans: a pooled analysis of experimental studies" J Psychopharmacol, 25(11):1434-1452.

Su, H., Lei, C.-T., & Zhang, C. (Apr. 2017). Interleukin-6 Signaling Pathway and Its Role in Kidney Disease: An Update. Frontiers in Immunology, 8:405, https://doi.org/10.3389/fimmu.2017.00405, 10 pages.

Subedi, B. & Grossberg, G.T. (2011) Phantom limb pain: Mechanisms and treatment approaches. Pain Res Treat, 2011:864605, doi:10.155/2011/864605, 8 pages.

Substance Abuse and Mental Health Services Administration. (Jun. 2016) Table 3.35, DSM-IV to DSM-5 Hypersomnolence Disorder Comparison. In: Impact of the DSM-IV to DSM-5 Changes on the National Survey on Drug Use and Health [Internet]. Rockville (MD): Substance Abuse and Mental Health Services Administration (US). Retrieved from NCBI Bookshelf, https://www.ncbi.nlm.nih.gov/books/NBK519704/table/ch3_.t35/, on Jul. 30, 2020, 3 printed pages.

Suda, S. et al. (2011). Decreased expression of axon-guidance receptors in the anterior cingulate cortex in autism. Molecular Autism, 2:14, https://doi.org/10.1186/2040-2392-2-14, 5 pages.

Suto, F. et al. (2005). Plexin-A4 mediates axon-repulsive activities of both secreted and transmembrane semaphorins and plays roles in nerve fiber guidance. Journal of Neuroscience, 25(14):3628-3637. https://doi.org/10.1523/JNEUROSCI.4480-04.2005.

(56) References Cited

OTHER PUBLICATIONS

Swieboda, P. et al. (2013) Assessment of pain: types, mechanism and treatment. Ann Agric Environ Med, 1(1):2-7.
Sztainberg, Y. & Zoghbi, H. Y. (2016). Lessons learned from studying syndromic autism spectrum disorders. Nature Neuroscience, 19(11):1408-1418. https://doi.org/10.1038/nn.4420.
Tai, J. et al. (2018). Neuroprotective effects of a triple GLP-1/GIP/glucagon receptor agonist in the APP/PS1 transgenic mouse model of Alzheimer's disease. Brain Research, 1678:64-74. https://doi.org/10.1016/j.brainres.2017.10.012.
Takamori, S. (Feb. 2016). Presynaptic Molecular Determinants of Quantal Size. Frontiers in Synaptic Neuroscience, 8:2, https://doi.org/10.3389/fnsyn.2016.00002, 9 pages.
Tan, L.L. et al. (2019). Gamma oscillations in somatosensory cortex recruit prefrontal and descending serotonergic pathways in aversion and nociception. Nat. Commun. 10:983, https://doi.org/10.1038/s41467-019-08873-z, 17 pages.
Tan, T. et al. (2018). Low-frequency rTMS ameliorates autistic-like behaviors in rats induced by neonatal isolation through regulating the synaptic GABA transmission. Frontiers in Cellular Neuroscience, 12:Article 46, https://doi.org/10.3389/fncel.2018.00046, 12 pages.
Tanaka, T. et al. (2014). IL-6 in Inflammation, Immunity, and Disease. Cold Spring Harbor Perspectives in Biology, 6(10):a016295, https://doi.org/10.1101/cshperspect.a016295, 16 pages.
Tarpey, P. et al. (2004). Mutations in the DLG3 gene cause nonsyndromic X-linked mental retardation. American Journal of Human Genetics, 75:318-324. https://doi.org/10.1086/422703.
Tatsumi, M. et al. (1997). Pharmacological profile of antidepressants and related compounds at human monoamine transporters. Eur. J. Pharmacol., 340, 249-258. https://doi.org/10.1016/S0014-2999(97)01393-9.
Taylor, J.F. et al. (1994) Self-Report Assessment of Female Sexual Function: Psychometrie Evaluation of the Brief Index of Sexual Functioning for Women. Archives of Sexual Behavior. 23(6):627-643.
Tecott, L. et al. (1995). Eating disorder and epilepsy in mice lacking 5-HT2C serotonin receptors. Nature, 374(6522), pp. 542-546.
Tellegen, A. and Atkinson, G. (1974) Openness to Absorbing and Self-Altering Experiences ("Absorption"), a Trait Related to Hypnotic Susceptibility. Journal of Abnormal Psychology, 83:268-277.
Tennant, R. et al. (2007) The Warrwick-Edinburgh Mental Wellbeing Scale (WEMWBS): development and the UK validation. Health and Quality of Life Outcomes, 5:63 doi:10.1186/1477-7525-5-63, 14 pages.
Terrando, N. et al. (2010). Tumor necrosis factor-α triggers a cytokine cascade yielding postoperative cognitive decline. Proceedings of the National Academy of Sciences, 107(47):20518-20522. https://doi.org/10.1073/pnas.1014557107.
Thamby, A., & Jaisoorya, T. S. (2019) "Antipsychotic augmentation in the treatment of obsessive-compulsive disorder" Indian Journal of Psychiatry, 61(7):S51-S57. https://doi.org/10.4103/psychiatry.IndianJPsychiatry_519_18.
Thapar, A. et al. (2005). Do depression symptoms predict seizure frequency—or vice versa? Journal of Psychosomatic Research, 59(5):269-274. https://doi.org/10.1016/j.jpsychores.2005.04.001.
Thase, M.E. (1999). Antidepressant treatment of the depressed patient with insomnia. Journal of Clinical Psychiatry, 60(suppl. 17):28-31.
Thomas, A. et al. (2009) "Marble burying reflects a repetitive and perseverative behavior more than novelty-induced anxiety" Psychopharmacology, 204(2):361-373. NIH Public Access Author Manuscript, available in PMC Jul. 8, 2010, 22 pages.
Tokudome, K. et al. (2016). Synaptic vesicle glycoprotein 2A (SV2A) regulates kindling epileptogenesis via GABAergic neurotransmission. Scientific Reports, 6(1):27420. https://doi.org/10.1038/srep27420, 12 pages.
Tolba, R. et al. (2018) The opioid epidemic and pain medicine specialists: Where to begin and what is next? Ochsner J, 18(1):20-22.
Toronto Research Chemicals; Certificate of Analysis; Product available for sale (Catalog No. P839650); Test Date: Apr. 5, 2013.
Torres, A.R. et al. (2006) "Obsessive-compulsive disorder: Prevalence, Comorbidity, impact, and help-seeking in the British National Psychiatric Morbidity Survey of 2000" American Journal of Psychiatry, 163(11):1978-1985. https://doi.org/10.1176/ajp.2006.163.11.1978.
Tramutola, A. et al. (2015). Alteration of mTOR signaling occurs early in the progression of Alzheimer disease (AD): analysis of brain from subjects with pre-clinical AD, amnestic mild cognitive impairment and late-stage AD. Journal of Neurochemistry, 133(5), 739-749. https://doi.org/10.1111/jnc.13037.
Treynor, W. et al. (Jun. 2003) Rumination Reconsidered: A Psychometric Analysis. Cognitive Therapy and Research, 27:247-259.
Trulson, M. E., Stark, A. D., & Jacobs, B. L. (1977). Comparative effects of hallucinogenic drugs on rotational behavior in rats with unilateral 6-hydroxydopamine lesions. European Journal of Pharmacology, 44(2), 113-119. https://doi.org/10.1016/0014-2999(77)90097-8.
Trunko, M.E. et al. (2011). Aripiprazole in anorexia nervosa and low-weight bulimia nervosa: Case reports. International Journal of Eating Disorders, 44(3):269-275. https://doi.org/10.1002/eat.20807.
Tsai, S.-J. (2017). Effects of interleukin-1beta polymorphisms on brain function and behavior in healthy and psychiatric disease conditions. Cytokine & Growth Factor Reviews, 37:89-97. https://doi.org/10.1016/j.cytogfr.2017.06.001.
Tucha, L. et al. (2017) Sustained attention in adult ADHD: time-on-task effects of various measures of attention. J Neural Transm, 124(Suppl. 1):S39-S53.
Tully, P.J. et al. (2014). The anxious heart in whose mind? A systematic review and meta-regression of factors associated with anxiety disorder diagnosis, treatment and morbidity risk in coronary heart disease. J. Psychosom. Res., 77:439-448. https://doi.org/10.1016/j.jpsychores.2014.10.001.
Tully, P.J. et al. (2016). Anxiety and Cardiovascular Disease Risk: a Review. Curr. Cardiol. Rep., 18:120, https://doi.org/10.1007/s11886-016-0800-3, 8 pages.
Tumolo, J. (Sep. 2018) "Uncovering the Therapeutic Potential of Psychedelics" Retrieved from Psychiatry & Behavioral Health Learning Network [online]. Retrieved from: https://www.hmpgloballearningnetwork.com/site/pcn/article/uncovering-therapeutic-potential-psychedelics, 8 pages.
Tyrer, P. and Baldwin, D. (2006). Generalised anxiety disorder. Lancet, 368:2156-2166. https://doi.org/10.1016/S0140-6736(06)69865-6.
Ulfvebrand, S. et al. (2015). Psychiatric comorbidity in women and men with eating disorders results from a large clinical database. Psychiatry Research, 230(2), 294-299. https://doi.org/10.1016/j.psychres.2015.09.008.
United Kingdom Office Action for Application GB2012911.0, dated Jan. 11, 2022, 3 pages.
United Kingdom Patent Application GB1816438.4: Examination Report, dated Jan. 10, 2022, 1 page.
United Kingdom Patent Application GB1816438.4: Search Report, dated Dec. 2, 2019, 7 pages.
United Kingdom Patent Application GB2012911.0: Examination Report, dated Jan. 11, 2022, 1 page.
United Kingdom Patent Application GB2012911.0: Search and Examination Report, dated Feb. 18, 2021, 4 pages.
United Kingdom Patent Application GB2012914.4: Search and Examination Report, dated Feb. 18, 2021, 4 pages.
United Kingdom Patent Application GB2012914.4: Examination Report, dated Jan. 11, 2022, 1 page.
United Kingdom Patent GB 2527023 (GB1810588.2): Examination Report, dated Nov. 18, 2019, 2 pages.
United Kingdom Patent GB 2527023 (GB1810588.2): Request for Opinion—Statement in Reply with Supplemental Statement of Truth, dated Jun. 24, 2021, 9 pages.
United Kingdom Patent GB 2527023 (GB1810588.2): Search Report, dated Aug. 21, 2018, 9 pages.
United Kingdom Patent GB 2527023 (GB1810588.2): Third Party Observations, dated Jan. 23, 2020, 13 pages.

(56) References Cited

OTHER PUBLICATIONS

United Kingdom Patent GB 2527023 (GB1810588.2): Opinion Under Section 74A, dated Jul. 28, 2021, including Letters to Proprietor and Requester; 17 pages.
United Kingdom Patent GB 2527023 (GB1810588.2): Third Party Request for Opinion dated Aug. 27, 2020, with Statement of Truth; 12 pages.
United Kingdom Patent GB 2571696 (GB1716505.1): Decision on Request for Opinion filed Jun. 11, 2020, by Kohn & Associates; Apr. 27, 2021, 14 pages.
United Kingdom Patent GB2571696 (GB1716505.1): Examination Report, dated Nov. 18, 2019, 2 pages.
United Kingdom Patent GB2571696 (GB1716505.1): Search Report, dated Dec. 19, 2017, 10 pages.
United Kingdom Patent GB2571696 (GB1716505.1): Search Report, dated Jan. 25, 2018, 2 pages.
United Kingdom Patent GB2571696 (GB1716505.1): Third Party Observations, Jan. 24, 2020, 10 pages.
Unruh, K. E., Bodfish, J. W., & Gotham, K. O. (2018). Adults with Autism and Adults with Depression Show Similar Attentional Biases to Social-Affective Images. Journal of Autism and Developmental Disorders, 50:2336-2347. https://doi.org/10.1007/s10803-018-3627-5.
U.S. Appl. No. 16/155,386: Third Party Observations with Concise Description of Relevance, filed Jul. 26, 2019, 22 pages.
U.S. Appl. No. 16/155,386: Third Party Observations with Concise Description of Relevance, filed May 23, 2019, 27 pages.
U.S. Appl. No. 16/155,386: Third Party Observations with Concise Description of Relevance, filed May 28, 2019, 31 pages.
U.S. Appl. No. 17/604,610: Third Party Pre-Issuance Submission Under 37 C.F.R. 1.290 with Concise Description of Relevance, filed Mar. 9, 2022, 128 pages.
Uyeno, E.T. (1967). Effects of mescaline and psilocybin on dominance behavior of the rat. Archives Internationales de Pharmacodynamie et de Therapie, 166(1), 60-64. http://www.ncbi.nlm.nih.gov/pubmed/6034329.
Valbrun, L. and Zvonarev, V. (2020). The Opioid System and Food Intake: Use of Opiate Antagonists in Treatment of Binge Eating Disorder and Abnormal Eating Behavior. Journal of Clinical Medicine Research, 12(2), pp. 41-63.
Van Ameringen, M. et al. (2014) "DSM-5 obsessive-compulsive and related disorders: Clinical implications of new criteria" Depression and Anxiety, 31(6):487-493. https://doi.org/10.1002/da.22259.
Van den Beuken-van Everdingen, M.H.J et al. (Jun. 2006) Update on Prevalence of Pain in Patients with Cancer: Systematic Review and Meta-Analysis. Journal of Pain and Symptom Management. 51(6):1070-1090, with Appendix I, 1090:e1-e9.
Van Hecke, A.V. et al. (2013). Measuring the Plasticity of Social Approach: A Randomized Controlled Trial of the Effects of the PEERS Intervention on EEG Asymmetry in Adolescents with Autism Spectrum Disorders. J. Autism Dev. Disord., 45(2):316-335. https://doi.org/10.1007/s10803-013-1883-y.
Van Spijker, B.A.J. et al. (2014) The Suicidal Ideation Attributes Scale (SIDAS): Community-Based Validation Study of a New Scale for the Measurement of Suicidal Ideation. Suicide and Life-Threatening Behavior, 44(4):408-419.
Varga, Z. et al. (2017). Cardiovascular Risk of Nonsteroidal Anti-Inflammatory Drugs: An Under-Recognized Public Health Issue. Cureus, 9(4):e1144, https://doi.org/10.7759/cureus.1144, 12 pages.
Vaupel, D. et al. (1979). The inhibition of food intake in the dog by LSD, mescaline, psilocin, -amphetamine and phenylisopropylamine derivatives. Life Sciences, 24(26), pp. 2427-2431.
Veale, D. et al. (2014) "Atypical antipsychotic augmentation in SSRI treatment refractory obsessive-compulsive disorder: A systematic review and meta-analysis" BMC Psychiatry, 14(1):317, https://doi.org/10.1186/s12888-014-0317-5, 13 pages.
Velikonja, T., Fett, A. K., & Velthorst, E. (2019). Patterns of Nonsocial and Social Cognitive Functioning in Adults with Autism Spectrum Disorder: A Systematic Review and Meta-analysis. JAMA Psychiatry, 76(2):135-151. https://doi.org/10.1001/jamapsychiatry.2018.3645.
Venlafaxine Hydrochloride (Sep. 23, 2020). Drugs.com (online). Retrieved from: https://www.drugs.com/monograph/venlafaxine-hydrochloride.html, 19 printed pages.
Verbeeck, W. et al. (2017). Bupropion for attention deficit hyperactivity disorder (ADHD) in adults. Cochrane Database of Systematic Reviews, 2017, Issue 10, Art. No. CD009504, DOI: 10.1002/14651858.CD009504.pub2, 58 pages.
Vinik, A. et al. Diabetic Neuropathies. Table 7, Drugs Approved by the FDA for Treatment of Neuropathic Pain Syndromes. [Updated Feb. 5, 2018]. In: Feingold, K.R., Anawalt, B., Boyce, A. et al., editors. Endotext [Internet]. South Dartmouth (MA): MDText.com, Inc.; 2000-. Retrieved from: https://www.ncbi.nlm.nih.gov/books/NBK279175/table/diab-neuropathies.medication/, retrieved on Jul. 30, 2020, 2 printed pages.
Volkow, N.D. et al. (Aug. 2007) Depressed dopamine activity in caudate and preliminary evidence of limbic involvement in adults with attention-deficit/hyperactivity disorder. Arch Gen Psychiatry, 64(8):932-940.
Volkow, N.D. et al. (Feb. 1, 2007) Brain dopamine transporter levels in treatment and drug naïve adults with ADHD. Neuroimage [Internet]. 34(3):1182-90. Available from: http://www.ncbi.nlm.nih.gov/pubmed/17126039.
Vollenweider, F. (1998) Advances and Pathophysiological Models of Hallucinogenic Drug Actions in Humans: A Preamble to Schizophrenia Research. Pharmacopsychiatry, 31(Suppl):92-103. https://doi.org/10.1055/s-2007-979353.
Vollenweider, F.X. et al. (1999). 5-HT modulation of dopamine release in basal ganglia in psilocybin-induced psychosis in man—a PET study with [$^{11}$C]raclopride. Neuropsychopharmacology, 20(5):424-433. https://doi.org/10.1016/S0893-133X(98)00108-0.
Vollenweider, F.X. et al. (Sep. 2007) The effects of the preferential 5-HT2A agonist psilocybin on prepulse inhibition of startle in healthy human volunteers depend on interstimulus interval. Neuropsychopharmacology, 32(9):1876-1887.
Von Bernhardi, R. et al. (Oct. 28, 2015). Role of TGFβ signaling in the pathogenesis of Alzheimer's disease. Frontiers in Cellular Neuroscience, 9:426, https://doi.org/10.3389/fncel.2015.00426, 21 pages.
Voon, P. et al. (2017). Chronic pain and opioid misuse: a review of reviews. Substance Abuse Treatment, Prevention and Policy, 12:36, DOI 10.1186/s13011-017-0120-7, 9 pages.
Vossler, D.G. (2016). Antiepileptic drugs. Are generics as effective as brand name? Neurology, 87(17):e211-e214. https://doi.org/10.1212/WNL.0000000000003323.
Wade, A.G. et al. (2011). Prolonged release melatonin in the treatment of primary insomnia: Evaluation of the age cut-off for short- and long-term response. Curr. Med. Res. Opin., 27:87-98. https://doi.org/10.1185/03007995.2010.537317.
Wagner, J. and Wagner, M.L. (2000). Non-benzodiazepines for the treatment of insomnia. Sleep Med. Rev., 4(6):551-581. https://doi.org/10.1053/smrv.2000.0126.
Wahlberg (2015) "UW-Madison tunes in to 'magic mushroom' medicine" Oct. 11, 2015; retrieved from Web Archive, https://web.archive.org/web/20181214181711/https://madison.com/wsi/news/local/health-med-fit/uw-madison-tunes-in-to-magic-mushroom-medicine/article5c229322-1132-5328-90cl-017e917f0696.html, retrieved Dec. 14, 2018.
Walia, K.S. et al. (2004) Side Effects of Antiepileptics—a Review. Pain Pract, (3):194-203.
Walsh, B.T. et al. (2006). Fluoxetine after weight restoration in anorexia nervosa: A randomized controlled trial. Journal of the American Medical Association, 295(22):2605-2612. https://doi.org/10.1001/jama.295.22.2605.
Wang, G. et al. (2017). Resveratrol mitigates lipopolysaccharide-mediated acute inflammation in rats by inhibiting the TLR4/NF-κBp65/MAPKs signaling cascade. Scientific Reports, 7:45006, https://doi.org/10.1038/srep45006, 13 pages.
Wang, J. et al. (2016). Enhanced Gamma oscillatory activity in rats with chronic inflammatory pain. Front. Neurosci. 10:489, https://doi.org/10.3389/fnins.2016.00489, 8 pages.

(56) References Cited

OTHER PUBLICATIONS

Wang, L. et al. (2003). IL-6 Induces NF-κB Activation in the Intestinal Epithelia. The Journal of Immunology, 171(6):3194-3201. https://doi.org/10.4049/jimmunol.171.6.3194.
Wang, Q. et al. (2018). CDK5-Mediated Phosphorylation-Dependent Ubiquitination and Degradation of E3 Ubiquitin Ligases GP78 Accelerates Neuronal Death in Parkinson's Disease. Molecular Neurobiology, 55(5):3709-3717. https://doi.org/10.1007/s12035-017-0579-2.
Wang, X. et al. (2018). Gastrodin Rescues Autistic-Like Phenotypes in Valproic Acid-Induced Animal Model. Frontiers in Neurology, 9:1052, https://doi.org/10.3389/fneur.2018.01052, 10 pages.
Wang, Z.-J. et al. (2020). A dual GLP-1 and Gcg receptor agonist rescues spatial memory and synaptic plasticity in APP/PS1 transgenic mice. Hormones and Behavior, 118:104640. https://doi.org/10.1016/j.yhbeh.2019.104640, 9 pages.
Washburn, J.J. et al. (Apr. 2007) Development of Antisocial Personality Disorder in Detained Youth: The Predictive Value of Mental Disorders. J Consult Clin Psychol, 75(2):221-231. NIH Public Access Author Manuscript, 20 pages.
Watson, J. et al. (Jul. 2019). Use of multiple inflammatory marker tests in primary care: using Clinical Practice Research Datalink to evaluate accuracy. British Journal of General Practice, 69(684), e462-e469. https://doi.org/10.3399/bjgp19X704309.
Weber, A. et al. (2010). Interleukin-1 (IL-1) Pathway. Science Signaling, 3(105):cm1, https://doi.org/10.1126/scisignal.3105cm1, 7 pages.
Weber et al. (1974) "Crystal structures of the teonanacatl hallucinogens. Part 1. Psilocybin C12HI7N204P" J Chem Soc, Perkin Trans, 2:942-946.
Wegner, D.M. and Zanakos, S. (1994) Chronic Thought Suppression. Journal of Personality, 62:615-640.
Wei, D. Y-T. et al. (2018) Cluster headache: Epidemiology, pathophysiology, clinical features, and diagnosis. Annals of Indian Academy of Neurology, 21(5):3-8.
Weissman, A.N. (1979) The Dysfunctional Attitude Scale: A validation study. [Dissertation in Education, Doctor of Philosophy]. University of Pennsylvania. Publicly Accessible Penn Dissertations. 1182. https://repository.upenn.edu/edissertations/1185, 209 pages.
Welch, E. et al. (2016). Treatment-seeking patients with binge-eating disorder in the Swedish national registers: clinical course and psychiatric comorbidity. BMC Psychiatry, 16:163, doi:10.1186/s12888-016-0840-7, 8 pages.
Werner, K.B. et al. (Apr. 2015) Epidemiology, comorbidity, and behavioral genetics of antisocial personality disorder and psychopathy. Psychiatr Ann. 45(4):195-199. HHS Public Access Author Manuscript, 8 pages.
Westmoreland, P. et al. (2016). Medical Complications of Anorexia Nervosa and Bulimia. The American Journal of Medicine, 129:30-37.
White, H. K., & Levin, E. D. (1999). Four-week nicotine skin patch treatment effects on cognitive performance in Alzheimer's disease. Psychopharmacology, 143(2):158-165. https://doi.org/10.1007/s002130050931.
Whitfield, D.R. et al. (2014). Assessment of ZnT3 and PSD95 protein levels in Lewy body dementias and Alzheimer's disease: association with cognitive impairment. Neurobiology of Aging, 35(12):2836-2844. https://doi.org/10.1016/j.neurobiolaging.2014.06.015.
Whyatt, C., & Craig, C. (Jul. 18, 2013). Sensory-motor problems in autism. Frontiers in Integrative Neuroscience. 7:51, https://doi.org/10.3389/fnint.2013.00051, 12 pages.
Wiedemann, K. et al. (2001). Anxiolyticlike effects of atrial natriuretic peptide on cholecystokinin tetrapeptide-induced panic attacks. Preliminary findings. Archives of General Psychiatry, 58:371-377. https://doi.org/10.1001/archpsyc.58.4.371.
Wilcox, J.A. (2014) "Psilocybin and obsessive compulsive disorder" Journal of Psychoactive Drugs, 46(5):393-395: DOI: 10.1080/02791072.2014.963754.

Wilens, T.E. et al. (Oct. 2011) An update on the pharmacotherapy of attention-deficit/hyperactivity disorder in adults. Expert Rev Neurother, 11(10):1443-1465. NIH Public Access Author Manuscript; available in PMC Aug. 1, 2012, 34 pages.
Williams, J.M.G. et al. (1986) Autobiographical Memory in Suicide Attempters. Journal of Abnormal Psychology, 95:144-149.
Williams, K. et al. (2013). Selective serotonin reuptake inhibitors (SSRIs) for autism spectrum disorders (ASD). Cochrane Database of Systematic Reviews, 8:CD004677, https://doi.org/10.1002/14651858.CD004677.pub3, 46 pages.
Willoughby, J.O. et al. (2003). Persistent abnormality detected in the non-ictal electroencephalogram in primary generalised epilepsy. J. Neurol. Neurosurg. Psychiatry, 74:51-55. https://doi.org/10.1136/jnnp.74.1.51.
Wilson, S. et al. (Jul. 2017) Interpersonal dysfunction in personality disorders: A meta-analytic review. Psychol Bull, 143(7):677-734. HHS Public Access Author Manuscript, 120 pages.
Wingo A, Ghaemi S. (2007) A systematic review of rates and diagnostic validity of comorbid adult attention-deficit/hyperactivity disorder and bipolar disorder. J Clin Psychiatry, 68(11):1775-1784.
Winkelman, J.W. et al. (2011). Randomized polysomnography study of gabapentin enacarbil in subjects with restless legs syndrome. Mov. Disord., 26:2065-2072. https://doi.org/10.1002/mds.23771.
Winter, J.C. et al. (2007). Psilocybin-induced stimulus control in the rat. Pharmacology Biochemistry and Behavior, 87(4):472-480. NIH Public Access Author Manuscript; available in PMC Oct. 3, 2007, 18 pages.
Witkin, J.M. (2008) "Animal models of obsessive-compulsive disorder" Current Protocols in Neuroscience. 45:9.30.1-9.30.9. DOI: 10.1002/0471142301.ns0930s45.
Wong, M. et al. (2008). TNFα blockade in human diseases: Mechanisms and future directions. Clinical Immunology, 126(2):121-136. https://doi.org/10.1016/j.clim.2007.08.013.
World Health Organization (WHO) (2015). International statistical classification of diseases and related health problems (ICD-10), 10th revision, Fifth edition. vol. 1, Tabular List. Geneva, Switzerland: WHO Press, www.who.int; 1076 pages.
World Health Organization (WHO) (2019). Risk reduction of cognitive decline and dementia—WHO Guidelines. Foreward and Executive Summary, pp. 3-11.
World Health Organization (WHO) (Sep. 19, 2019). Dementia. Retrieved from https://www.who.int/news-room/fact-sheets/detail/dementia, 5 pages.
Worrell, G.A. et al. (2004). High-frequency oscillations and seizure generation in neocortical epilepsy. Brain 127, 1496-1506. https://doi.org/10.1093/brain/awh149.
Wu, H. et al. (Sep. 2016). Field potential oscillations in the bed nucleus of the Stria terminalis correlate with compulsion in a rat model of obsessive-compulsive disorder. J. Neurosci. 36, 10050-10059.
Wultsch, T. et al. (2007) "Behavioural and expressional phenotyping of nitric oxide synthase-I knockdown animals" Journal of Neural Transmission, (Suppl 72):69-85. https://doi.org/10.1007/978-3-211-73574-9_10.
Xie, Z. et al. (2017). A review of sleep disorders and melatonin. Neurol. Res., 39:559-565. https://doi.org/10.1080/01616412.2017.1315864.
Xu, C. et al. (2019). Integrative analysis of shared genetic pathogenesis by obsessive-compulsive and eating disorders. Molecular Medicine Reports, 19(3):1761-1766. https://doi.org/10.3892/mmr.2018.9772.
Xu, P. et al. (2016). Activation of serotonin 2C receptors in dopamine neurons inhibits binge-like eating in mice. Biological Psychiatry, 81, 737-747.
Yang, S. et al. (Apr. 19, 2018). Role of TNF—TNF Receptor 2 Signal in Regulatory T Cells and Its Therapeutic Implications. Frontiers in Immunology, 9:784, https://doi.org/10.3389/fimmu.2018.00784, 11 pages.
Yilmaz, Z. et al. (2015). Genetics and epigenetics of eating disorders. Advances in Genomics and Genetics, 5:131-150. HHS Public Access Author Manuscript, 36 pages.

(56) References Cited

OTHER PUBLICATIONS

Ypsilantis, E. and Tang, T.Y. (2010) Pre-emptive analgesia for chronic limb pain after amputation for peripheral vascular disease: A systematic review. Annals of Vascular Surgery, 24:1139-1146.
Yu, B. et al. (2008). Serotonin 5-hydroxytryptamine$_{2a}$ receptor activation suppresses tumor necrosis factor-alpha-induced inflammation with extraordinary potency. The Journal of Pharmacology and Experimental Therapeutics, 327(2):316-323.
Zammit, G. et al. (2007). Evaluation of the efficacy and safety of ramelteon in subjects with chronic insomnia. J. Clin. Sleep Med., 3:495-504. https://doi.org/10.5664/jcsm.26914.
Zetner, M. et al. (2008) Emotions evoked by the sound of music: Characterization, classification, and measurement. Emotion. 8:494-521.
Zhai, H. et al. (2019). Baicalin attenuated substantia nigra neuronal apoptosis in Parkinson's disease rats via the mTOR/AKT/GSK-3β pathway. Journal of Integrative Neuroscience, 18(4), 423-429. https://doi.org/10.31083/j.jin.2019.04.192.
Zhang, J.-M., & An, J. (2007). Cytokines, Inflammation and Pain. Int Anesthesiol Clin., 69(2):482-489. NIH Public Access Author Manuscript, available in PMC Nov. 30, 2009, 10 pages.
Zhou, R. et al. (2018). Elevated Resting State Gamma Oscillatory Activities in Electroencephalogram of Patients With Post-herpetic Neuralgia. Front. Neurosci. 12, 750, 10 pages. https://doi.org/10.3389/fnins.2018.00750.
Zhou, Y. et al. (2017). Comorbid generalized anxiety disorder and its association with quality of life in patients with major depressive disorder. Sci. Rep. 7:40511, https://doi.org/10.1038/srep40511, 8 pages.
Zipfel, S. et al. (2015). Anorexia nervosa: Aetiology, assessment, and treatment. The Lancet Psychiatry, vol. 2, Issue 12, pp. 1099-1111. https://doi.org/10.1016/S2215-0366(15)00356-9.
Zulauf, C.A. et al. (Mar. 2014). The complicated relationship between attention deficit/hyperactivity disorder and substance use disorders. Curr Psychiatry Rep, 16(3):436; doi:10.1007/s11920-013-0436-6. HHS Public Access Author Manuscript; available in PMC Apr. 29, 2015, 17 pages.
Anonymous: "Compass Pathways announces positive outcome of 25mg COMP360 psilocybin therapy as adjunct to SRI antidepressants in open-label treatment-resistant depression study", Dec. 13, 2021 (Dec. 13, 2021), XP093033918., 7 pages.
Anonymous: "Psilocybin in Depression Resistant to Standard Treatments—Full Text View—ClinicalTrials.gov", Jul. 13, 2021 (Jul. 13, 2021), XPO93024023, Retrieved from the Internet: URL:https://clinicaltrials.gov/ct2/show/NCT04959253?term=depression&cond=psilocybin&draw=2&rank=11 [retrieved on Feb. 15, 2023], 5 pages.
Becker Anna M. et al: "Acute Effects of Psilocybin After Escitalopram or Placebo Pretreatment in a Randomized, Double-Blind, Placebo-Controlled, Crossover Study in Healthy Subjects", Clinical Pharmacology and Therapeutics, vol. 111, No. 4, Nov. 22, 2021 (Nov. 22, 2021), pp. 886-895, XP093033911.
*Freedom to Operate, Inc. v. Compass Pathways Limited.* Case PGR2022-00012, U.S. Pat. No. 10,947,257. and *Freedom to Operate, Inc. v. Compass Pathways Limited.* Case PGR2022-00018, U.S. Pat. No. 10,954,259; Order that the requests for POP review are denied and original panel maintains authority over all matters, including considering the submitted rehearing requests, dated Feb. 10, 2023, 3 pages.
*Freedom to Operate, Inc. v. Compass Pathways Limited.* Case PGR2022-00012, U.S. Pat. No. 10,947,257. and *Freedom to Operate, Inc. v. Compass Pathways Limited.* Case PGR2022-00018, U.S. Pat. No. 10,954,259; Paper No. 21, Order Denying Petitioners Request on Rehearing, dated May 23, 2023, 9 pages.
Fekadu et al., "Standardisation framework for the Maudsley staging method for treatment resistance in depression," BMC Psychiatry (Apr. 11, 2018) 18:100.
Greyson, B., The Near-Death Experience Scale, the Journal of Nervous and Mental Disease, 171:369-375 (1983).
Halberstadt et al., "Correlation between the potency of hallucinogens in the mouse head-twitch response assay and their behavioral and subjective effects in other species," Neuropharmacology. May 1, 2020;167:107933, pp. 1-35. doi: 10.1016/j.neuropharm.2019.107933. Epub Jan. 7, 2020.
International Search Report and Written Opinion for International Application No. PCT/US2022/052368 dated Mar. 30, 2023, 14 Pages.
International Search Report and Written Opinion for PCT/US2022/048713 dated Feb. 24, 2023, 17 pages.
Jones, S.A.V., et al., "Psychedelics as a Treatment for Alzheimer's Disease Dementia," Frontiers in Synaptic Neuroscience, Aug. 21, 2020, vol. 12, pp. 34.
Mertens, L.J., et al., "Therapeutic mechanisms of psilocybin: Changes in amygdala and prefrontal functional connectivity during emotional processing after psilocybin for treatment-resistant depression," Journal of Psychopharmacology, Feb. 2020, vol. 34 (2), pp. 167-180.
Rucker, J. et al. (Dec. 25, 2017) "Psychiatry & the psychedelic drugs. Past, present & future," Neuropharmacol, 142:200-218.

Wash with citric acid (14) and
NaHCO3 (15) Dry with MgSO4 (16)
Partition with heptane (17)

PREPARATION OF PSILOCYBIN, DIFFERENT POLYMORPHIC FORMS, INTERMEDIATES, FORMULATIONS AND THEIR USE

This application is a continuation of U.S. patent application Ser. No. 16/679,009, filed Nov. 8, 2019; which is a continuation of U.S. patent application Ser. No. 16/155,386, filed Oct. 9, 2018 (now U.S. Pat. No. 10,519,175); which claims priority to United Kingdom Application No. 1816438.4, filed Oct. 9, 2018; United Kingdom Application No. 1810588.2, filed Jun. 28, 2018; and United Kingdom Application No. 1716505.1, filed Oct. 9, 2017. The disclosure of the above applications are incorporated by reference herein in their entireties.

This invention relates to the large-scale production of psilocybin for use in medicine.

By large scale is meant producing batches of psilocybin with a weight of greater than 10 g, more preferably greater than 100 g, more preferably still greater than 250 g and up to, and above, Kg levels.

It also relates to the production of intermediates, including but not limited to psilocin, different polymorphic forms of psilocybin, including isostructural variants, and their formulation for use in medicine, particularly, but not exclusively for the treatment of treatment resistant depression, as defined in Diagnostic and Statistical Manual, 5$^{th}$ Edition, either alone or in combination with psychological support which may be provided digitally.

BACKGROUND

Psilocybin was first synthesised in 1958 by Sandoz, see GB912714 and U.S. Pat. No. 3,075,992, and was widely available as a research chemical until the mid-1960's.

A plant based psychedelic it has been used as an aide to psychotherapy for the treatment of mood disorders and alcoholic disorders and recently 3 clinical trials have reported its use for depressive symptoms.
Griffiths et al 2016; J Psychopharmacol 30 (12):1181-1197;
Ross et al 2016; J Psychopharmacol 30 (12):1165-1180; and
Carhart-Harris et al 2016, Lancet Psychiatry 3(7): 619-627.
Methods of manufacture of psilocybin are limited and include:
J Nat Prod 2003, 66, pages 885-887;
Helv Chim Acta 1959, 42, 2073-2103;
Experientia 1958, 15, 397-399; and
Synthesis 1999, 935-938.

Based on this literature Applicant believed that the process disclosed in J Nat Prod 2003, 66, pages 885-887 (hereafter JNP) was the most suitable method for development into a commercial scaled process.

The process disclosed therein produced quantities in the order of 10 g and comprised 6 steps numbered (i) to (vi).

By analogy with the Applicants process, steps ii and iii are hereafter discussed as a single step, (Step 2) and the JNP process is reproduced as FIG. 1 herein.

Step 1 (i) comprised reacting 4-hydroxyindole ("3") with acetic anhydride ($Ac_2O$) in pyridine and anhydrous dichloromethane ($CH_2Cl_2$) at 0° C. Water was added, the mixture evaporated, and the resulting concentrate was dissolved in ethyl acetate, washed with water, and saturated sodium chloride, and the organic phase dried over sodium sulphate and evaporated to obtain 4-acetylindole ("4"), which was collected by filtration and washed with water and ethyl acetate.

Step 2 (ii and iii), a two-step acylation (ii)—amidation step (iii), comprised forming 3-Dimethylaminooxalyl-4-acetylindole ("6") by: (ii) reacting 4-acetylindole ("4") with oxalyl chloride (($COCl)_2$) in anhydrous diethylether, stirring, adding n-hexane and holding at −20° C. to produce an intermediate 3-(2-chloro-2-oxoacetyl)-1H-indol-4-yl acetate ("5") which was separated by filtration. The intermediate was dissolved in anhydrous tetrahydrofuran (THF) and reacted with dimethylamine (($CH_3)_2NH$) in tetrahydrofuran and pyridine. Anhydrous ether was added because of solidification, and the reaction product separated by filtration and washed with n hexane, ethyl acetate, and water to obtain 3-Dimethylaminooxalyl-4-acetylindole ("6").

Step 3 (iv) comprised the formation of psilocin ("1") by reacting the 3-Dimethylaminooxalyl-4-acetylindole ("6") with lithium aluminium hydride ($LiAlH_4$) in anhydrous THF under an argon atmosphere. After refluxing and cooling, anhydrous sodium sulphate was added, followed by a solution of sodium sulphate, and further anhydrous sodium sulphate. The reaction mixture was diluted with ethyl acetate, quickly concentrated in vacuo, and the resulting psilocin crystals briefly washed with methanol.

Step 4 (v) comprised the formation of benzyl [2-(4-oxyindol-3-yl) ethyl]dimethylammonio-4-O-benzyl phosphate ("8") by reacting psilocin, dissolved in anhydrous THF, with n-butyl lithium (n-BuLi) in n-hexane at −78° C. and tetrabenzylpyrophosphate [$(BnO)_2PO]_2O$, and the reaction allowed to warm to 0° C., and the production of intermediate dibenzyl 3-[2-(dimethylamino)ethyl]-1H-indol-4-yl phosphate ("7") monitored. On checking for its presence, aminopropyl silica gel was added, the mixture diluted with ethyl acetate and filtered through a Celite pad by suction, the filtrate concentrated in vacuo, re-dissolved in $CH_2Cl_2$, and the precipitate collected by filtration.

Step 5 (vi) comprised the formation of psilocybin ("2") by reaction of ("8"), in methanol (MeOH), with hydrogen ($H_2$) using a palladium-activated carbon catalyst (Pd/C). Water was added, because of product deposition, and ("8"), its mono de-benzylated derivative were monitored along with the appearance of psilocybin, the reaction solution was filtered through a Celite pad. The product was collected by filtration and washed with ethanol to provide a white needle crystalline form with a melting point 190° C.-198° C.

In contrast to most processes, such as JNP, which use non-aqueous solvents, such as methanol or ethanol, Experientia 1958, 15, 397-399 used a single re-crystalisation from water to obtain psilocybin from a mushroom extraction. The teaching was to use boiling water to dissolve the starting material, obtained at small scale by chromatography, and the resulting high vacuum dried material was stated to melt indistinctly between 185 and 195° C., and showed a weight loss of 25.4%, suggesting it clearly differs in purity and form to that obtained by Applicant.

During the development of a synthesis to produce Psilocybin the applicant conducted a number of hydrogenation reactions on a 5 g scale which resulted in different crystalline forms of Psilocybin being obtained. The initial hydrogenation reaction yielded Hydrate A (JCCA2157E) which exhibited a XRPD diffractogram as shown in FIG. 7d and DSC and TGA thermograms as shown in FIG. 8d. The DSC exhibits an endotherm at ~97° C. which is coincidental with a weight reduction in the TGA indicative of dehydration, and an endothermic event with an onset temperature of ~216° C. which was presumed to be the melt. Another hydrogenation reaction yielded an ethanol solvate (JCCA2158D) which when analysed by XRPD (FIG. 7e), DSC (FIG. 8e), TGA (FIG. 8e) and by $^1H$ NMR indicated 11% entrapped ethanol.

The DSC thermogram shows an endotherm having an onset of ~154° C. that appeared to be a melt concurrent with the ~13% weight loss in the TGA. In another experiment performed during development, the applicant performed a crystallisation of psilocybin; rather than remain in solution in hot water allowing for a polish filtration step, precipitation occurred at high temperature (>90° C.). The solids formed did not re-dissolve upon further heating or addition of extra water. Upon cooling and isolation of the solid (CB646E) XRPD was performed. The XRPD diffractogram (FIG. 7f) suggested a mixed phase of Polymorph A' (JCCA2160-F-D4) and Polymorph B (JCCA2160-F-TM2-C5). These findings highlight the importance of developing a process which can consistently produce the desired crystalline form so the Applicants set about experiments to determine what these forms were in order they could produce a chemically pure psilocybin, in a controlled form suitable for use in medicine.

For clinical trials any New Active Substance (NAS) should be capable of large scale production (typically 100 g plus, more typically greater than 250 g, more preferably still greater than 500 g, to Kg plus batches), depending on the amount of active to be dosed to a human subject. It should also be chemically pure, well defined, and stable on storage.

Furthermore, any method of manufacture must be readily reproducible, and provide batch to batch consistency.

It is a first object of this invention to provide psilocybin, of consistent polymorphic form, for administration to human subjects.

It is another object of this invention to provide chemically pure psilocybin, of consistent polymorphic form, for administration to human subjects.

It is yet a further object to provide chemically pure psilocybin, in large scale batch quantities since for commercial use, the pure psilocybin must be produced at scale.

It is yet a further object of the invention to provide a method of crystallising psilocybin in a desired polymorphic form.

It is yet a further object of the present invention to provide a scalable method for manufacturing psilocybin, from psilocin or 4 hydroxy-indole.

In developing suitable methodology Applicant experienced numerous problems and difficulties which they had to be overcome, and it is a separate, independent, object to overcome those problems identified at each step, and use the inventions either alone or in combination.

It is yet a further object of the invention to formulate the psilocybin of the invention in a form suitable for administration to human subjects and use it in medicine, particularly in the treatment of central nervous system disorders (CNS), and more particularly, but not exclusively, in the treatment of depression, particularly, drug resistant depression either alone or in combination with a digital health product or digital solution.

BRIEF SUMMARY OF THE DISCLOSURE

In accordance with a first aspect of the present inventions there is provided crystalline psilocybin in the form Polymorph A or Polymorph A', characterised by one or more of:
a. peaks in an XRPD diffractogram at 11.5, 12.0 and 14.5 °2θ±0.1 °2θ;
b. peaks in an XRPD diffractogram at 11.5, 12.0 and 14.5 °2θ±0.1 °2θ, further characterised by at least one further peak at 19.7, 20.4, 22.2, 24.3 or 25.7 °2θ±0.1 °2θ;
c. an XRPD diffractogram as substantially illustrated in FIG. 7a or 7b; or
d. an endothermic event in a DSC thermogram having an onset temperature of between 205 and 220° C. substantially as illustrated in FIG. 8a or 8b.

Polymorph A

In accordance with a preferred embodiment of the present invention there is provided crystalline psilocybin in the form Polymorph A, characterised by one or more of:
a. peaks in an XRPD diffractogram at 11.5, 12.0, 14.5, and 17.5, °2θ±0.1 °2θ;
b. peaks in an XRPD diffractogram at 11.5, 12.0, 14.5 and 17.5, °2θ±0.1 °2θ, further characterised by at least one further peak at 19.7, 20.4, 22.2, 24.3 or 25.7 °2θ±0.1 °2;
c. an XRPD diffractogram as substantially illustrated in FIG. 7a; or
d. an endothermic event in a DSC thermogram having an onset temperature of between 205 and 220° C. substantially as illustrated in FIG. 8a.

The peak at 17.5 °2θ±0.1 °2θ has a relative intensity compared to the peak at 14.5 °2θ±0.1 °2θ of at least 5%, preferably at least 6%, more preferably still at least 7%, through 8%, and 9% to at least 10%.

In one embodiment, psilocybin Polymorph A exhibits an XRPD diffractogram characterised by the diffractogram summarised in Table 1. In one embodiment, described herein, the crystalline psilocybin Polymorph A comprises at least 3 peaks of (±0.1 °2θ) of Table 1. In a certain embodiment, described herein, the crystalline psilocybin Polymorph A comprises at least 4 peaks of (±0.1 °2θ) of Table 1. In a certain embodiment, described herein the crystalline psilocybin Polymorph A comprises at least 5 peaks of (±0.1 °2θ) of Table 1. In a certain embodiment, described herein the crystalline psilocybin Polymorph A comprises at least 6 peaks of (±0.1 °2θ) of Table 1. In a certain embodiment, described herein the crystalline psilocybin Polymorph A comprises at least 8 peaks of (±0.1 °2θ) of Table 1. In a certain embodiment, described herein the crystalline psilocybin Polymorph A comprises at least 10 peaks of (±0.1 °2θ) of Table 1. In a certain embodiment, described herein the crystalline psilocybin Polymorph A comprising at least 15 peaks of (±0.1 °2θ) of Table 1. A peak at about 17.5, °2θ±0.1 °2θ distinguishes psilocybin Polymorph A from Polymorph A', in which the peak is absent or substantially absent (i.e. has a relative intensity compared to the peak at 14.5 °2θ±0.1 °2θ of less than 2%, more preferably less than 1%).

TABLE 1

XRPD peak positions for Polymorph A

| Position [°2 Th.] | Relative Intensity [%] |
| --- | --- |
| 5.6 | 8.42 |
| 11.5 | 13.05 |
| 12.0 | 26.45 |
| 14.5 | 100 |
| 17.5 | 10.71 |
| 19.7 | 37.29 |
| 20.4 | 20.06 |
| 22.2 | 17.83 |
| 23.2 | 6.99 |
| 24.3 | 17.93 |
| 25.7 | 16.4 |
| 26.8 | 3.15 |
| 27.8 | 4.54 |
| 29.7 | 9.53 |
| 31.2 | 6.51 |
| 32.6 | 2.45 |
| 33.7 | 1.75 |

In one embodiment, crystalline psilocybin Polymorph A is characterised by XRPD diffractogram peaks at 11.5, 12.0, 14.5, and 17.5 °2θ±0.1 °2θ. In another embodiment, crystalline psilocybin Polymorph A is further characterised by at least one additional peak appearing at 19.7, 20.4, 22.2, 24.3 or 25.7 °2θ±0.1 °2θ. In another embodiment, crystalline psilocybin Polymorph A is further characterised by at least two additional peaks appearing at 19.7, 20.4, 22.2, 24.3 or 25.7 °2θ±0.1 °2θ. In another embodiment, crystalline psilocybin Polymorph A is further characterised by at least three additional peaks appearing at 19.7, 20.4, 22.2, 24.3 or 25.7 °2θ±0.1 °2θ. In yet a further embodiment, crystalline psilocybin Polymorph A exhibits an XRPD diffractogram substantially the same as the XRPD diffractogram shown in FIG. 7a.

In one embodiment, crystalline psilocybin Polymorph A is characterised by XRPD diffractogram peaks at 14.5 and 17.5 °2θ±0.1 °2θ with the peak at 17.5 °2θ having an intensity which is at least 5% of the intensity of the peak at 14.5 °2θ, more preferably still at least 6%, through at least 7%, at least 8%, at least 9%, to at least 10%.

In one embodiment, crystalline psilocybin Polymorph A is absent or substantially absent of an XRPD diffractogram peaks at 10.1. By substantially absent is meant than any XRPD diffractogram peaks at 10.1 is less than 2% of the intensity of the peak at 14.5 °2θ, such as less than 1%, or is not detectable in the XRPD diffractogram, In one embodiment, crystalline psilocybin Polymorph A is characterised by an endothermic event in a DSC thermogram having an onset temperature of between 205 and 220° C., such as between 210 and 220° C., such as between 210 and 218° C., or such as between 210 and 216° C. In another embodiment, crystalline psilocybin Polymorph A is further characterised by an endothermic event in the DSC thermogram having an onset temperature of between 145 and 165° C., such as between 145 and 160° C., or such as between 145 and 155° C. In another embodiment, crystalline psilocybin Polymorph A is characterised by an endothermic event having an onset temperature of between 205 and 220° C., such as between 210 and 220° C., such as between 210 and 218° C., or such as between 210 and 216° C., and an endothermic event having an onset temperature of between 145 and 165° C., such as between 145 and 160° C., or such as between 145 and 155° C., in a DSC thermogram. In yet another embodiment, crystalline psilocybin Polymorph A exhibits a DSC thermogram substantially the same as the DSC thermogram in FIG. 8a.

In another embodiment, crystalline psilocybin Polymorph A is characterised by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In one embodiment, crystalline psilocybin Polymorph A is characterised by having <0.5% w/w loss, such as <0.4% w/w, such as <0.3% w/w, such as <0.2% w/w, such as <0.1% w/w, in the TGA thermogram between ambient temperature, such as about 25° C., and 200° C. In one embodiment, crystalline psilocybin Polymorph A loses less than 2% by weight in a loss on drying test, such as less than 1% by weight, such as less than 0.5% by weight. The loss on drying test is performed at 70° C.

In one embodiment, crystalline psilocybin Polymorph A is a highly pure crystalline form of Polymorph A, for example, psilocybin comprises at least 90% by weight, such as 95%, such as 99%, such as 99.5% of Polymorph A.

In one embodiment, crystalline psilocybin Polymorph A is a white to off white solid.

In another embodiment, crystalline psilocybin Polymorph A is chemically pure, for example the psilocybin has a chemical purity of greater than 97%, such as greater than 98%, or such as greater than 99% by HPLC. In one embodiment, crystalline psilocybin Polymorph A has no single impurity of greater than 1%, more preferably less than 0.5%, including phosphoric acid as measured by $^{31}$P NMR, and psilocin as measured by HPLC. In one embodiment, crystalline psilocybin Polymorph A has a chemical purity of greater than 97 area %, more preferably still greater than 98 area %, and most preferably greater than 99 area % by HPLC. In one embodiment, crystalline psilocybin Polymorph A has no single impurity greater than 1 area %, more preferably less than 0.5 area % as measured by HPLC. In one embodiment, crystalline psilocybin Polymorph A does not contain psilocin at a level greater than 1 area %, more preferably less than 0.5 area % as measured by HPLC. In one embodiment, crystalline psilocybin Polymorph A does not contain phosphoric acid at a level greater than 1 weight %, more preferably less than 0.5 weight % as measured by $^{31}$P NMR. In one embodiment, crystalline psilocybin Polymorph A has a chemical assay of at least 95 weight %, such as at least 96 weight %, or such as at least 98 weight %.

Polymorph A'

In accordance with another embodiment of the invention, there is provided crystalline psilocybin Polymorph A' characterised by one or more of:

a. peaks in an XRPD diffractogram at 11.5, 12.0 and 14.5 °2θ±0.1 °2θ, but absent or substantially absent of a peak at 17.5 °2θ±0.1 °2θ;

b. peaks in an XRPD diffractogram at 11.5, 12.0 and 14.5 °2θ±0.1 °2θ, but absent or substantially absent of a peak at 17.5 °2θ±0.1 °2θ, further characterised by at least one further peak at 19.7, 20.4, 22.2, 24.3 or 25.7 °2θ±0.1 °2θ;

c. an XRPD diffractogram as substantially illustrated in FIG. 7b; or d. an endothermic event in a DSC thermogram having an onset temperature of between 205 and 220° C. substantially as illustrated in FIG. 8b.

By substantially absent of a peak at 17.5 °2θ±0.1 °2θ is meant, if present, the peak has a relative intensity, compared to a peak at 14.5 °2θ±0.1 °2θ, of less than 5%, more preferably less than 4%, through less than 3%, to 2%, 1% or less.

In one embodiment, psilocybin Polymorph A' exhibits an XRPD diffractogram characterised by the diffractogram summarised in Table 2. In one embodiment, described herein the crystalline psilocybin Polymorph A' comprises at least 3 peaks of (±0.1 °2θ) of Table 2 but absent or substantially absent of a peak at 17.5 °2θ±0.1 °2θ. In a certain embodiment, described herein the crystalline psilocybin Polymorph A' comprising at least 4 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 5 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 6 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 8 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 10 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 15 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 20 peaks of (±0.1 °2θ) of Table 2 but absent or substantially absent of a peak at 17.5 °2θ±0.1 °2θ. In a certain embodiment, described herein the crystalline psilocybin Polymorph A' comprises at least 25 peaks of (±0.1 °2θ) of Table 2 but absent or substantially absent of a peak at 17.5 °2θ±0.1 °2θ.

TABLE 2

XRPD peak positions for Polymorph A'

| Position [°2 Th.] | Relative Intensity [%] |
|---|---|
| 5.5 | 4.89 |
| 10.1 | 4.09 |
| 11.5 | 22.05 |
| 12.0 | 22.77 |
| 14.5 | 100 |
| 14.9 | 11.29 |
| 17.5 | 1.08 |
| 18.7 | 2.44 |
| 19.4 | 23.02 |
| 19.6 | 33.7 |
| 20.3 | 17.01 |
| 21.1 | 12.08 |
| 21.6 | 8.51 |
| 22.2 | 15.54 |
| 22.6 | 8.78 |
| 23.1 | 10.11 |
| 24.3 | 21.83 |
| 25.1 | 4.36 |
| 25.8 | 15.4 |
| 26.3 | 4.28 |
| 26.8 | 2.86 |
| 27.8 | 5.96 |
| 28.6 | 1.91 |
| 29.7 | 10.56 |
| 31.1 | 7.35 |
| 32.6 | 3.72 |
| 33.8 | 1.54 |

In one embodiment, crystalline psilocybin Polymorph A' is characterised by XRPD diffractogram peaks at 11.5, 12.0, and 14.5 °2θ±0.1 °2θ but substantially absent of a peak at 17.5 °2θ±0.1 °2θ. In another embodiment, crystalline psilocybin Polymorph A' is further characterised by at least one additional peak appearing at 19.7, 20.4, 22.2, 24.3, or 25.7 °2θ±0.1 °2θ. In another embodiment, crystalline psilocybin Polymorph A' is further characterised by at least two additional peaks appearing at 19.7, 20.4, 22.2, 24.3, or 25.7 °2θ±0.1 °2θ. In another embodiment, crystalline psilocybin Polymorph A' is further characterised, and distinguished from Polymorph A by the presence of a peak appearing at 10.1 °2θ±0.1 °2θ. In yet a further embodiment, crystalline psilocybin Polymorph A' exhibits an XRPD diffractogram substantially the same as the XRPD diffractogram shown in FIG. 7b.

In one embodiment, crystalline psilocybin Polymorph A' is characterised by XRPD diffractogram peaks at 14.5 and 17.5 °2θ±0.1 °2θ wherein the intensity of the peak at 17.5 °2θ is less than 5% of the intensity of the peak at 14.5 °2θ, such as less than 4%, such as less than 3%, as at less than 2%, such as less than 1%, or such as about 1%.

In one embodiment, crystalline psilocybin Polymorph A' is characterised by XRPD diffractogram peaks at 10.1 and 14.5 °2θ±0.1 °2θ wherein the intensity of the peak at 10.1 °2θ is at least 1% of the intensity of the peak at 14.5 °2θ, such as at least than 2%, such as at least than 3%, or such as about 4%.

In one embodiment, crystalline psilocybin Polymorph A' is characterised by an endothermic event in a DSC thermogram having an onset temperature of between 205 and 220° C., such as between 210 and 220° C., such as between 210 and 218° C., or such as between 210 and 216° C. In another embodiment, crystalline psilocybin Polymorph A' is further characterised by an endothermic event in the DSC thermogram having an onset temperature of between 145 and 165° C., such as between 145 and 160° C., or such as between 145 and 155° C. In another embodiment, crystalline psilocybin Polymorph A' is characterised by an endothermic event having an onset temperature of between 205 and 220° C., such as between 210 and 220° C., such as between 210 and 218° C., or such as between 210 and 216° C., and an endothermic event having an onset temperature of between 145 and 165° C., such as between 145 and 160° C., or such as between 145 and 155° C., in a DSC thermogram. In yet another embodiment, crystalline psilocybin Polymorph A' exhibits a DSC thermogram substantially the same as the DSC thermogram in FIG. 8b.

In another embodiment, crystalline psilocybin Polymorph A' is characterised by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In one embodiment, crystalline psilocybin Polymorph A' is characterised by having <0.5% w/w loss, such as <0.4% w/w, such as <0.3% w/w, such as <0.2% w/w, such as <0.1% w/w, in the TGA thermogram between ambient temperature, such as 25° C., and 200° C. In one embodiment, crystalline psilocybin Polymorph A' loses less than 2% by weight in a loss on drying test, such as less than 1% by weight, such as less than 0.5% by weight. The loss on drying test is performed at 70° C.

In one embodiment, crystalline psilocybin Polymorph A' is a highly pure crystalline form of Polymorph A', for example, psilocybin comprises at least 90% by weight, such as 95%, such as 99%, such as 99.5% of Polymorph A'.

In one embodiment, crystalline psilocybin Polymorph A's is a white to off white solid.

In another embodiment, crystalline psilocybin Polymorph A' is chemically pure, for example the psilocybin has a chemical purity of greater than 97%, more preferably still greater than 98%, and most preferably greater than 99% by HPLC. In one embodiment, crystalline psilocybin Polymorph A' has no single impurity of greater than 1%, more preferably less than 0.5%, including phosphoric acid as measured by $^{31}P$ NMR, and psilocin as measured by HPLC. In one embodiment, crystalline psilocybin Polymorph A' has a chemical purity of greater than 97 area %, more preferably still greater than 98 area %, and most preferably greater than 99 area % by HPLC. In one embodiment, crystalline psilocybin Polymorph A' has no single impurity greater than 1 area %, more preferably less than 0.5 area % as measured by HPLC. In one embodiment, crystalline psilocybin Polymorph A' does not contain psilocin at a level greater than 1 area %, more preferably less than 0.5 area % as measured by HPLC. In one embodiment, crystalline psilocybin Polymorph A' does not contain phosphoric acid at a level greater than 1 weight %, more preferably less than 0.5 weight % as measured by $^{31}P$ NMR. In one embodiment, crystalline psilocybin Polymorph A' has a chemical assay of at least 95 weight %, such as at least 96 weight %, or such as at least 98 weight %.

XRPD diffractograms and XRPD peak positions are acquired using Cu Kα radiation.

DSC and TGA thermograms are acquired using a heating rate of 20° C./min.

In one embodiment, there is provided high purity crystalline psilocybin, Polymorph A or Polymorph A' (12A or 12A'), exhibiting an XRPD diffractogram as substantially illustrated in FIG. 7a or 7b and a DSC thermograph as substantially illustrated in FIG. 8a or 8b or a mixture thereof.

Preferably the crystalline psilocybin Polymorph A (12A) exhibits an XRPD diffractogram as illustrated in FIG. 7a and a DSC thermograph as illustrated in FIG. 8a.

Preferably the crystalline psilocybin Polymorph A' (12A') exhibits an XRPD diffractogram as substantially illustrated in FIG. 7b and a DSC thermograph as substantially illustrated in FIG. 8b.

Preferably the high purity crystalline psilocybin Polymorph A (12A) is characterised by a XRPD diffractogram as substantially illustrated in FIG. 7a and a DSC thermograph as substantially illustrated in FIG. 8a.

Preferably the high purity crystalline psilocybin Polymorph A (12A') is characterised by a XRPD diffractogram as illustrated in FIG. 7b and a DSC thermograph as illustrated in FIG. 8b.

Polymorph A (including its isostructural variant Polymorph A') (FIGS. 7a and 7b) differs from Polymorph B (FIG. 7c), the Hydrate A (FIG. 7d) and the ethanol solvate (FIG. 7e: Solvate A), and the relationship between some of the different forms is illustrated in FIG. 9.

The crystalline psilocybin Polymorph A or Polymorph A', is a white to off white solid, and/or has a chemical purity of greater than 97%, more preferably still greater than 98%, and most preferably greater than 99% by HPLC, and has no single impurity of greater than 1%, more preferably less than 0.5%, including phosphoric acid as measured by $^{31}$P NMR, and psilocin as measured by HPLC. In one embodiment, there is provided high purity crystalline psilocybin, Polymorph A or Polymorph A'. In one embodiment, crystalline psilocybin, Polymorph A or Polymorph A', has a chemical purity of greater than 97 area %, more preferably still greater than 98 area %, and most preferably greater than 99 area % by HPLC. In one embodiment, crystalline psilocybin, Polymorph A or Polymorph A', has no single impurity greater than 1 area %, more preferably less than 0.5 area % as measured by HPLC. In one embodiment, crystalline psilocybin, Polymorph A or Polymorph A', does not contain psilocin at a level greater than 1 area %, more preferably less than 0.5 area % as measured by HPLC. In one embodiment, crystalline psilocybin, Polymorph A or Polymorph A', does not contain phosphoric acid at a level greater than 1 weight %, more preferably less than 0.5 weight % as measured by $^{31}$P NMR. In one embodiment, crystalline psilocybin, Polymorph A or Polymorph A', has a chemical assay of at least 95 weight %, such as at least 96 weight %, or such as at least 98 weight %.

The heating of Polymorph A or A' results in an endothermic event having an onset temperature of circa 150° C. corresponding to solid-solid transition of Polymorph A or Polymorph A' to Polymorph B. Continued heating of the resulting solid, i.e., Polymorph B, results in a second endothermic event corresponding to a melting point having an onset temperature of between 205 and 220° C. (see FIGS. 8a and 8b).

In accordance with another independent aspect of the present invention there is provided a crystalline form of psilocybin, Hydrate A, characterised by one or more of:
  a. peaks in an XRPD diffractogram at 8.9, 12.6 and 13.8 °2θ±0.1 °2θ;
  b. peaks in an XRPD diffractogram at 8.9, 12.6 and 13.8 °2θ±0.1 °2θ, further characterised by at least one further peak at 6.5, 12.2, 19.4, 20.4 or 20.8 °2θ± 0.1 °2θ;
  c. an XRPD diffractogram as substantially illustrated in FIG. 7d; or
  d. an endothermic event in a DSC thermogram having an onset temperature of between 205 and 220° C. substantially as illustrated in FIG. 8d.

In one embodiment, psilocybin Hydrate A exhibits an XRPD diffractogram characterised by the diffractogram summarised in Table 3. In one embodiment, described herein the crystalline psilocybin Hydrate A comprises at least 3 peaks of (±0.1 °2θ) of Table 3. In a certain embodiment, described herein the crystalline psilocybin Hydrate A comprises at least 4 peaks of (±0.1 °2θ) of Table 3. In a certain embodiment, described herein the crystalline psilocybin Hydrate A comprises at least 5 peaks of (±0.1 °2θ) of Table 3. In a certain embodiment, described herein the crystalline psilocybin Hydrate A comprises at least 8 peaks of (±0.1 °2θ) of Table 3. In a certain embodiment, described herein the crystalline psilocybin Hydrate A comprises at least 10 peaks of (±0.1 °2θ) of Table 3.

TABLE 3

XRPD peak positions for Hydrate A

| Position [°2 Th.] | Relative Intensity [%] |
| --- | --- |
| 5.6 | 14.4 |
| 6.5 | 18.84 |
| 8.9 | 100 |
| 12.2 | 11.51 |
| 12.6 | 18.65 |
| 13.8 | 44.22 |
| 16.2 | 21.22 |
| 18.9 | 6.62 |
| 19.4 | 38.68 |
| 20.4 | 21.32 |
| 20.8 | 19.73 |
| 21.5 | 20.75 |
| 22.3 | 12.8 |
| 22.5 | 19.38 |
| 23.1 | 47.53 |
| 23.5 | 25.79 |
| 24.3 | 5.62 |
| 24.8 | 14.62 |
| 25.4 | 5.27 |
| 26.9 | 6.53 |
| 27.9 | 7.82 |
| 28.4 | 5.78 |
| 29.0 | 5.09 |
| 29.7 | 4.83 |
| 32.1 | 8.27 |
| 32.8 | 4.81 |
| 33.4 | 3.74 |
| 34.2 | 5.96 |

In one embodiment, crystalline psilocybin Hydrate A is characterised by XRPD diffractogram peaks at 8.9, 12.6 and 13.8 °2θ±0.1 °2θ. In another embodiment, crystalline psilocybin Hydrate A is further characterised by at least one peak appearing at 6.5, 12.2, 19.4, 20.4 or 20.8 °2θ±0.1 °2θ. In another embodiment, crystalline psilocybin Hydrate A is further characterised by at least two peaks appearing at 6.5, 12.2, 19.4, 20.4 or 20.8 °2θ±0.1 °2θ. In yet a further embodiment, crystalline psilocybin Hydrate A exhibits an XRPD diffractogram substantially the same as the XRPD diffractogram shown in FIG. 7d.

In one embodiment, crystalline psilocybin Hydrate A is characterised by an endothermic event in a DSC thermogram having an onset temperature of between 205 and 220° C., such as between 210 and 220° C., such as between 210 and 218° C., or such as between 210 and 216° C. In another embodiment, crystalline psilocybin Hydrate A is further characterised by an endothermic event in the DSC thermogram having an onset temperature of between 85 and 105° C., or such as between 90 and 100° C. In another embodiment, crystalline psilocybin Hydrate A is characterised by an endothermic event having an onset temperature of between 205 and 220° C., such as between 210 and 220° C., such as between 210 and 218° C., or such as between 210 and 216° C., and an endothermic event having an onset temperature of between 85 and 105° C., or such as between 90 and 100° C., in a DSC thermogram. In yet another embodiment, crystalline psilocybin Hydrate A exhibits a DSC thermogram substantially the same as the DSC thermogram in FIG. 8d.

In another embodiment, crystalline psilocybin Hydrate A is characterised by having a water content of between 10 and 18%, such as between 12 and 16%, or such as about 13%. The skilled person would know of methods to determine the water content of a compound, for example Karl Fischer Titration. In one embodiment, crystalline psilocybin Hydrate A is characterised by having a weight loss in the TGA thermogram of between 10 and 18%, such as between 12 and 16%, or such as about 13%, between ambient temperature, such as about 25° C., and 120° C.

In one embodiment, crystalline psilocybin Hydrate A is a highly pure crystalline form of Hydrate A, for example, psilocybin comprises at least 90% by weight, such as 95%, such as 99%, such as 99.5% of Hydrate A.

In accordance with another independent aspect of the present invention there is provided a crystalline form of psilocybin, Polymorph B, characterised by one or more of:
 a. peaks in an XRPD diffractogram at 11.1, 11.8 and 14.3 °2θ±0.1 °2θ;
 b. peaks in an XRPD diffractogram at 11.1, 11.8 and 14.3 °2θ±0.1 °2θ, further characterised by at least one further peak at 14.9, 15.4, 19.3, 20.0 or 20.6 °2θ± 0.1 °2θ;
 c. an XRPD diffractogram as substantially illustrated in FIG. 7c; or
 d. an endothermic event in a DSC thermogram having an onset temperature of between 205 and 220° C. substantially as illustrated in FIG. 8c.

In one embodiment, psilocybin Polymorph B exhibits an XRPD diffractogram characterised by the diffractogram summarised in Table 4. In one embodiment, described herein the crystalline psilocybin Polymorph B comprises at least 3 peaks of (±0.1 °2θ) of Table 4. In a certain embodiment, described herein the crystalline psilocybin Polymorph B comprises at least 4 peaks of (±0.1 °2θ) of Table 4. In a certain embodiment, described herein the crystalline psilocybin Polymorph B comprises at least 5 peaks of (±0.1 °2θ) of Table 4. In a certain embodiment, described herein the crystalline psilocybin Polymorph B comprising at least 8 peaks of (±0.1 °2θ) of Table 4. In a certain embodiment, described herein the crystalline psilocybin Polymorph B comprises at least 10 peaks of (±0.1 °2θ) of Table 4.

TABLE 4

XRPD peak positions for Polymorph B

| Position [°2 Th.] | Relative Intensity [%] |
| --- | --- |
| 5.5 | 21.33 |
| 11.1 | 36.91 |
| 11.8 | 100.00 |
| 12.5 | 12.73 |
| 14.3 | 70.23 |
| 14.9 | 50.01 |
| 15.4 | 23.67 |
| 17.1 | 51.58 |
| 17.4 | 91.25 |
| 18.0 | 12.61 |
| 19.3 | 39.33 |
| 20.0 | 76.61 |
| 20.6 | 50.26 |
| 21.5 | 20.77 |
| 22.3 | 40.19 |
| 23.9 | 13.32 |
| 24.3 | 16.03 |
| 25.3 | 32.94 |
| 28.3 | 7.60 |
| 28.9 | 17.89 |
| 29.3 | 8.96 |
| 31.3 | 6.57 |
| 32.2 | 6.90 |
| 33.8 | 2.37 |

In one embodiment, crystalline psilocybin Polymorph B is characterised by XRPD diffractogram peaks at 11.1, 11.8 and 14.3 °2θ±0.1 °2θ. In another embodiment, crystalline psilocybin Polymorph B is further characterised by at least one peak appearing at 14.9, 15.4, 19.3, 20.0 or 20.6 °2θ± 0.1 °2θ. In another embodiment, crystalline psilocybin Polymorph B is further characterised by at least two peaks appearing at 14.9, 15.4, 19.3, 20.0 or 20.6 °2θ±0.1 °2θ. In yet a further embodiment, crystalline psilocybin Polymorph B exhibits an XRPD diffractogram substantially the same as the XRPD diffractogram shown in FIG. 7c.

In one embodiment, crystalline psilocybin Polymorph B is characterised by an endothermic event in a DSC thermogram having an onset temperature of between 205 and 220° C., such as between 210 and 220° C., such as between 210 and 218° C., or such as between 210 and 216° C. In yet another embodiment, crystalline psilocybin Polymorph B exhibits a DSC thermogram substantially the same as the DSC thermogram in FIG. 8c.

In another embodiment, crystalline psilocybin Polymorph B is characterised by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In one embodiment, crystalline psilocybin Polymorph B is characterised by having <0.5% w/w loss, such as <0.4% w/w, such as <0.3% w/w, such as <0.2% w/w, such as <0.1% w/w, in the TGA thermogram between ambient temperature, such as about 25° C., and 200° C. In one embodiment, crystalline psilocybin Polymorph B loses less than 2% by weight in a loss on drying test, such as less than 1% by weight, such as less than 0.5% by weight. The loss on drying test is performed at 70° C.

In one embodiment, crystalline psilocybin Polymorph B is a highly pure crystalline form of Polymorph B, for example, psilocybin comprises at least 90% by weight, such as 95%, such as 99%, such as 99.5% of Polymorph B.

In another embodiment, crystalline psilocybin Polymorph B is chemically pure, for example the psilocybin has a chemical purity of greater than 97%, such as greater than 98%, or such as greater than 99% by HPLC. In one embodiment, crystalline psilocybin Polymorph B has no single impurity of greater than 1%, more preferably less than 0.5%, including phosphoric acid as measured by $^{31}$P NMR, and psilocin as measured by HPLC. In one embodiment, crystalline psilocybin Polymorph B has a chemical purity of greater than 97 area %, more preferably still greater than 98 area %, and most preferably greater than 99 area % by HPLC. In one embodiment, crystalline psilocybin Polymorph B has no single impurity greater than 1 area %, more preferably less than 0.5 area % as measured by HPLC. In one embodiment, crystalline psilocybin Polymorph B does not contain psilocin at a level greater than 1 area %, more preferably less than 0.5 area % as measured by HPLC. In one embodiment, crystalline psilocybin Polymorph B does not contain phosphoric acid at a level greater than 1 weight %, more preferably less than 0.5 weight % as measured by $^{31}$P NMR. In one embodiment, crystalline psilocybin Polymorph B has a chemical assay of at least 95 weight %, such as at least 96 weight %, or such as at least 98 weight %.

The psilocybin of the invention in the form Polymorph A or A' has the general properties illustrated in Table 5 below:

TABLE 5

| Appearance: | White to off white solid |
| --- | --- |
| Major endothermic event in DSC (onset temperature) (corresponding to a melt): | 210-215° C. |

TABLE 5-continued

| Appearance: | White to off white solid |
| --- | --- |
| Hygroscopicity: | Psilocybin forms Hydrate A at high humidity and when added to water but the water of hydration is lost rapidly on drying. The anhydrous form is therefore being developed. |
| Crystalline form: | Anhydrous Polymorph A and/ or A' |
| pKa (calculated): | 1.74, 6.71, 9.75 |
| Solubility | approx. 15 mg/ml in Water |

The psilocybin conforms to the spectra as set out in Table 6 below and illustrated in the spectra of FIGS. 10-13.

TABLE 6

| Technique | Conclusions |
| --- | --- |
| Proton ($^1$H) and Carbon ($^{13}$C) NMR | Assignment of the proton (FIG. 10) and carbon spectra (FIG. 11) are concordant with Psilocybin. |
| FT-Infrared Spectroscopy (FT-IR) | Assignment of the FT-IR spectrum (FIG. 12) is concordant with Psilocybin. |
| Mass Spectroscopy (MS) | Assignment of the mass spectrum (FIG. 13) is concordant with Psilocybin. |

The high purity is attained by careful control of reaction conditions to ensure that potential organic impurities are significantly reduced.

Known and potential impurities in Psilocybin are shown in Table 7 below:

TABLE 7

| Impurity | Relative Retention Time (RRT) | Structure | Origin |
| --- | --- | --- | --- |
| Psilocin | 1.65 | *(structure)* | Starting material (stage 3). Also generated by hydrolysis of Psilocybin. Only significant impurity observed in psilocybin batches. |
| Stage 4A | | *(structure)* | Initial product formed in the stage 4 reaction. Converts to stage 4 on stirring in THF. Converts to Psilocybin in stage 5. |
| Stage 4 | 2.74 | *(structure)* | Intermediate |

TABLE 7-continued

| Impurity | Relative Retention Time (RRT) | Structure | Origin |
|---|---|---|---|
| N-Denzylated stage 4 | | (structure) | Identified by MS in Stage 4. Converts to Psilocybin in stage 5. |
| Stage 4 Anhydride Impurity | | (structure) | Identified by MS in Stage 4. Converts to Stage 5 Pyrophosphoric acid impurity in stage 5. |
| Stage 5 Pyrophosphoric acid impurity | | (structure) | Identified by MS Formed from the stage 4 anhydride. Removed in the stage 6 re-crystallisation by a combination of hydrolysis to Psilocybin and increased solubility due to the extra phosphate group. |
| Stage 5 (intermediates) | 1.89 and 2.45 | (structures) | 2 Intermediates are formed during the hydrogenation. These subsequently convert to product (structures based on chemistry). Monitored and controlled in stage 5 reaction. |

Similarly, the careful processing ensures solvent levels are kept to below levels as indicated in Table 8.

TABLE 8

| Solvent | Controlled to | Chemical Stage solvent is used in |
|---|---|---|
| Methanol | 3000 ppm | Stage 5 |
| Ethanol | 5000 ppm | Stage 5 |
| THF | 720 ppm | Stage 4 |
| Toluene | 890 ppm | Generated as a by-product in stage 5 |

Through careful selection of operating methodology the psilocybin drug substance of the invention meets the acceptance criteria set out in Table 9 below:

TABLE 9

| Quality attribute | Acceptance criteria | Test method |
|---|---|---|
| 1. Appearance | For information only. | Visual |
| 2. Identity by $^1$H NMR | Compares well with reference. FIG. 10 | $^1$H NMR |
| 3. Identity by $^{13}$C NMR | Compares well with reference. FIG. 11 | $^{13}$C NMR |
| 4. Identity by MS | Compares well with reference. FIG. 12 | MS |
| 5. Identity by FT-IR | Compares well with reference. FIG. 13 | FT-IR |
| 6. Loss on drying | NMT 2% w/w | European Pharmacopoeia 2.2.32 |
| 7. Residue on Ignition | NMT 0.5% w/w | US Pharmacopoeia <281> |
| 8. Chemical purity | NLT 97 area % | HPLC |
| 9. Drug Related Impurities | No single impurity NMT 1.0 area % | HPLC |
| 10. Assay (on a dry basis) | 95-103 weight % | HPLC |
| 11. Residual Solvent Content | Methanol NMT 3000 ppm<br>Ethanol NMT 5000 ppm<br>THF NMT 720 ppm<br>Toluene NMT 890 ppm | HRGC |
| 12. Phosphoric acid content | NMT 1% w/w | $^{31}$P NMR |
| 13. Elemental analysis by ICP-MS | Cd NMT 1.5 ppm<br>Pb NMT 1.5 ppm<br>As NMT 4.5 ppm<br>Hg NMT 9.0 ppm<br>Co NMT 15 ppm<br>V NMT 30 ppm<br>Ni NMT 60 ppm<br>Li NMT 165 ppm<br>Pd NMT 30 ppm | US Pharmacopoeia <233> |
| 14. Polymorphism | Conforms to reference FIG. 7a | XRPD |
| 15. Melting Point | Report result FIG. 8a | DSC |

Abbreviations used in table:
NMT = not more than,
NLT = not less than.

The methodology used to verify the purity is provided in the detailed description.

In fact, the criteria 6-13 are far exceeded in practice, as noted in Table 10 below:

TABLE 10

| Quality attribute | Acceptance criteria | Typically | Test method |
|---|---|---|---|
| 1. Loss on drying | | Typically less than 1% w/w | European Pharmacopoeia 2.2.32 |
| 2. Residue on Ignition | | Typically less than 0.2% w/w | US Pharmacopoeia <281> |
| 3. Chemical purity | | Typically NLT 99% | HPLC |
| 4. Drug Related Impurity | No single impurity NMT 1.0% | RRT 1.49: 0.06%<br>RRT 1.69 (Psilocin): 0.39%<br>RRT 1.70: 0.05%<br>Others LT 0.05%: 0.22% | HPLC |
| 5. Assay (on a dry basis) | 95-103 | 98.65% | HPLC |
| 6. Residual Solvent Content | Methanol NMT 3000 ppm<br>Ethanol NMT 5000 ppm<br>THF NMT 720 ppm<br>Toluene NMT 890 ppm | NMT 5 ppm<br>NMT 10 ppm<br>NMT 5 ppm<br>NMT 5 ppm | HRGC |
| 7. Phosphoric acid content | NMT 1% w/w | 0.2% Absence of phosphoric acid ($H_3PO_4$) which comes at approx. 0 ppm | $^{31}$P NMR |
| 8. Elemental analysis by ICP-MS | Cd NMT 1.5 ppm<br>Pb NMT 1.5 ppm<br>As NMT 4.5 ppm<br>Hg NMT 9.0 ppm<br>Co NMT 15 ppm<br>V NMT 30 ppm<br>Ni NMT 60 ppm<br>Li NMT 165 ppm<br>Pd NMT 30 ppm | LT 0.5 ppm<br>LT 0.5 ppm<br>LT 1 ppm<br>LT 1 ppm<br>LT 5 ppm<br>LT 20 ppm<br>LT 10 ppm<br>LT 20 ppm<br>LT 5 ppm | US Pharmacopoeia <233> |

Abbreviations used in table:
NMT = not more than,
LT = less than.

Thus, crystalline psilocybin, in the form Polymorph A or Polymorph A', has spectra that conform with Proton ($^1$H) and Carbon ($^{13}$C) NMR, FT-Infrared Spectroscopy (FT-IR), and Mass Spectroscopy (MS)—FIGS. 10-13.

It also conforms to any of the criteria specified in Table 9 or Table 10.

In accordance with a second aspect of the present invention there is provided a batch of crystalline psilocybin, in the form Polymorph A or Polymorph A' according to the first aspect of the present invention. In one embodiment, there is provided a batch of crystalline psilocybin, Polymorph A or Polymorph A', comprising at least 10 g, more preferably at least 100 g, and most preferably at least 250 g. In one embodiment, there is provided a batch of crystalline psilocybin, Polymorph A or Polymorph A', comprising at least 10 g, more preferably at least 100 g, and most preferably at least 250 g. In one embodiment, there is provided a batch of high purity psilocybin comprising at least 10 g, more preferably at least 100 g, and most preferably at least 250 g. In one embodiment, there is provided a batch of high purity psilocybin Polymorph A comprising at least 10 g, more preferably at least 100 g, and most preferably at least 250 g. In one embodiment, there is provided a batch of high purity psilocybin Polymorph A' comprising at least 10 g, more preferably at least 100 g, and most preferably at least 250 g.

Alternatively, and independently, the crystalline psilocybin may take the form of Hydrate A or Polymorph B.

In accordance with a third aspect of the present invention there is provided a pharmaceutical formulation comprising crystalline psilocybin and one or more excipients.

In one embodiment, there is provided a pharmaceutical formulation comprising high purity psilocybin and one or more excipients. In another embodiment, there is provided a pharmaceutical formulation comprising crystalline psilocybin Polymorph A and one or more excipients. In another embodiment, there is provided a pharmaceutical formulation comprising crystalline psilocybin Polymorph A' and one or more excipients. In another embodiment, there is provided a pharmaceutical formulation comprising high purity crystalline psilocybin, Polymorph A or Polymorph A', and one or more excipients. In another embodiment, there is provided a pharmaceutical formulation comprising high purity crystalline psilocybin Polymorph A and one or more excipients. In another embodiment, there is provided a pharmaceutical formulation comprising high purity crystalline psilocybin Polymorph A' and one or more excipients.

Alternatively, and independently, the crystalline psilocybin in the formulation may take the form of Hydrate A or Polymorph B.

Preferred pharmaceutical excipients for an oral formulation include: diluents, such as, microcrystalline cellulose, starch, mannitol, calcium hydrogen phosphate anhydrous or co-mixtures of silicon dioxide, calcium carbonate, microcrystalline cellulose and talc; disintegrants, such as, sodium starch glycolate or croscarmellose sodium; binders, such as, povidone, co-povidone or hydroxyl propyl cellulose; lubricants, such as, magnesium stearate or sodium stearyl fumurate; glidants, such as, colloidal silicon dioxide; and film coats, such as, Opadry II white or PVA based brown Opadry II.

Psilocybin is a difficult active to formulate for a number of reasons. Firstly it has poor flow characteristics, and secondly it is used in relatively low doses which combination makes it challenging to ensure content uniformity in tabletting.

A good blend will have an Acceptance Value, AV value of less than 15, and more preferably less than 10.

It will also have a % Label claim of greater than 90% more preferably greater than 94%.

Between them these parameters indicate consistent dosing of the psilocybin between tablets.

For most pharmaceutical tablets, standard excipients, particularly fillers, can be used. However, in the course of formulating psilocybin tablets, applicant found that in order to achieve a satisfactory product, a non-standard filler was preferred.

In this regard a functional filler was selected. The functional filler was a silicified filler, preferably a silicified microcrystalline cellulose. The preferred forms comprises high compactability grades with a particle size range of from about 45 to 150 microns.

In fact a mixture of two functional fillers having different particle size ranges may be used with the wt percentages of the two favouring the larger sized particles.

In one embodiment the silicified microcrystalline filler may comprise a first filler, having a particle size range of from about 45 to 80 microns in an amount of up to 30%, more preferably up to 20%, more preferably still up to 15% or less and a second filler, having a particle size range of from about 90 to 150 microns, in an amount of up to 70%, more preferably up to 80, and more preferably still up to 85% or more, by weight.

The formulation may further comprise or consist of a disintegrant, preferably sodium starch glycolate, a glidant, preferably colloidal silicon dioxide and a lubricant, preferably sodium stearyl fumarate.

Further details of formulation development are given in Example 12.

It should be noted that the formulations may comprise psilocybin in any form, not only the preferred polymorphic forms disclosed.

Studerus et al (2011) J Psychopharmacol 25(11) 1434-1452 classified oral doses of psilocybin as follows: Very low doses at 0.045 mg·kg; low doses between 0.115-0.125 mg/kg, medium doses between 0.115-0.260 mg/kg, and high doses at 0.315 mg/kg.

The psilocybin would typically be present in a formulated dose in an amount of from 0.01 mg/kg to 1 mg/kg. A typical human dose (for an adult weighing 60-80 kg) would equate to a dose of somewhere between 0.60 mg and 80 mg. In one embodiment, between 2 and 50 mg of crystalline psilocybin, most preferably Polymorph A or Polymorph A', is present in a formulated dose, such as between 2 and 40 mg, such as between 2 and 10 mg, such as 5 mg, such as between 5 and 30 mg, such as between 5 and 15 mg, such as 10 mg, such as between 20 and 30 mg, or such as 25 mg. In one embodiment, between 2 and 50 mg of crystalline psilocybin, particularly Polymorph A, is present in a formulated dose, such as between 2 and 40 mg, such as between 2 and 10 mg, such as 5 mg, such as between 5 and 30 mg, such as between 5 and 15 mg, such as 10 mg, such as between 20 and 30 mg, or such as 25 mg. In one embodiment, between 2 and 50 mg of crystalline psilocybin, particularly Polymorph A' is present in a formulated dose, such as between 2 and 40 mg, such as between 2 and 10 mg, such as 5 mg, such as between 5 and 30 mg, such as between 5 and 15 mg, such as 10 mg, such as between 20 and 30 mg, or such as 25 mg.

Favoured adult oral doses are likely to be in the range 1 mg to 40 mg, preferably 2 to 30 mg, more preferably 15 to 30 mg, for example 5 mg, 10 mg or 25 mg. Micro-dosing, typically at about a tenth of these doses, is also possible with micro dose formulations typically lying within the range 0.05 mg to 2.5 mg.

A preferred pharmaceutical formulation is an oral dosage form.

The oral dosage form may be a tablet or a capsule.

For a tablet it is necessary to be able to accurately disperse the active. This is challenging due to the low doses and the hygroscopic and sticky nature of the active which limits its flowability.

The psilocybin will be present together with one or more excipients. Preferred excipients include microcrystalline cellulose and starch, more particularly still a silicified microcrystalline cellulose.

In accordance with a fourth aspect of the present invention there is provided the crystalline psilocybin in the form Polymorph A or Polymorph A' according to the first aspect of the present invention for use in medicine. In one embodiment, there is provided crystalline psilocybin Polymorph A for use in medicine. In one embodiment, there is provided crystalline psilocybin Polymorph A' for use in medicine. In one embodiment, there is provided a high purity crystalline psilocybin Polymorph A for use in medicine. In one embodiment, there is provided a high purity crystalline psilocybin Polymorph A' for use in medicine.

Alternatively, and independently, the crystalline psilocybin may take the form of Hydrate A or Polymorph B.

In accordance with a fifth aspect of the present invention there is provided crystalline psilocybin in the form Polymorph A or Polymorph A' of the first aspect of the present invention for use in treating central nervous disorders.

Alternatively, and independently, the crystalline psilocybin may take the form of Hydrate A or Polymorph B.

In one embodiment, there is provided crystalline psilocybin, Polymorph A or Polymorph A', for use in treating depression. In one embodiment, there is provided crystalline psilocybin, Polymorph A or Polymorph A', for use in treating drug resistant depression. In one embodiment, there is provided crystalline psilocybin Polymorph A for use in treating drug resistant depression. In one embodiment, there is provided crystalline psilocybin Polymorph A' for use in treating drug resistant depression. In one embodiment, there is provided a high purity crystalline psilocybin Polymorph A for use in treating drug resistant depression. In one embodiment, there is provided a high purity crystalline psilocybin Polymorph A' for use in treating drug resistant depression.

Other conditions that may be treated include: anxiety disorders, including anxiety in advanced stage illness e.g. cancer as well as Generalized Anxiety Disorder, Depression including Major Depressive Disorder, Cluster Headaches, Obsessive Compulsive Disorder, Personality Disorders including Conduct Disorder, Drug Disorders including: alcohol dependence, nicotine dependence, opioid dependence, cocaine dependence and other addictions including Gambling Disorder, Eating Disorder and Body Dysmorphic Disorder. A still further condition is the treatment of pain.

In accordance with a sixth aspect of the present invention there is provided a method of treating central nervous disorders comprising administering to a subject in need thereof an effective dose of crystalline psilocybin in the form Polymorph A or Polymorph A' according to the first aspect of the present invention.

In one embodiment, there is provided a method of treating depression comprising administering to a subject in need thereof an effective dose of crystalline psilocybin in the form of Polymorph A or Polymorph A'. In one embodiment, there is provided a method of treating drug resistant depression comprising administering to a subject in need thereof an effective dose of crystalline psilocybin in the form Polymorph A or Polymorph A'. In one embodiment, there is provided a method of treating drug resistant depression comprising administering to a subject in need thereof an effective dose of psilocybin Polymorph A. In one embodiment, there is provided a method of treating drug resistant depression comprising administering to a subject in need thereof an effective dose of psilocybin Polymorph A'. In one embodiment, there is provided a method of treating drug resistant depression comprising administering to a subject in need thereof an effective dose of a high purity crystalline psilocybin Polymorph A. In one embodiment, there is provided a method of treating drug resistant depression comprising administering to a subject in need thereof an effective dose of a high purity crystalline psilocybin Polymorph A'.

Alternatively, and independently, the crystalline psilocybin may take the form of Hydrate A or Polymorph B.

To produce the psilocybin of the invention the psilocybin was crystallised from water in a controlled manner.

According to a seventh aspect of the present invention there is provided a method for large scale manufacture of psilocybin characterised in that the method comprises subjecting psilocybin to a water crystallization step, with controlled drying, to produce crystalline psilocybin Polymorph A according to the first aspect of the present invention.

In one embodiment, there is provided a method for large scale manufacture of psilocybin characterised in that the method comprises subjecting psilocybin to a water crystallization step, with controlled drying, to produced crystalline psilocybin Polymorph A with an XRPD diffractogram as illustrated in FIG. 7a and a DSC and TGA thermograph as illustrated in FIG. 8a. In one embodiment, there is provided a method for large scale manufacture of psilocybin characterised in that the method comprises subjecting psilocybin to a water crystallization step, with controlled drying, to produce a high purity crystalline psilocybin—Polymorph A with an XRPD diffractogram as illustrated in FIG. 7a and a DSC thermograph as illustrated in FIG. 8a.

Preferably Polymorph A is an isostructural variant with an XRPD diffractogram as illustrated in FIG. 7a and a DSC thermograph as illustrated in FIG. 8a.

More preferably the psilocybin is recrystallized in typically about 10-20 volumes of water, heated with agitation to a temperature of at least 70° C., polish filtered with a suitable cut off (typically, below 5 µm), seeded at a temperature of about 70° C., and cooled in a controlled manner to about 5° C. over a period of more than 2 hours.

More preferably the method comprises controlled cooling which drops the temperature by about 5° C.-15° C. an hour, more preferably about 10° C. an hour.

Preferably the polish filter step is done through an appropriately sized filter such as a 1.2 µm in line filter.

Preferably the agitation is by stirring at about 400-500 rpm, typically about 450 rpm.

Preferably the seed is psilocybin Hydrate A. In one embodiment, 0.1% weight or less of seed is added to the process.

Preferably the crystalline psilocybin is isolated by vacuum filtration.

In one embodiment, the isolated crystals are dried in vacuo at a temperature of at least 30° C., such as between 30 and 50° C., or such as between 40 and 50° C. In one embodiment, the isolated crystals are dried in vacuo for at least 10 hours, such as between 12 and 18 hours, or such as about 30 hours. In one embodiment, the isolated crystals are dried in vacuo at a temperature of at least 30° C., such as between 30 and 50° C., or such as between 40 and 50° C., for at least 10 hours, such as between 12 and 18 hours, or such as about 30 hours. In one embodiment, the isolated crystals are dried until the isolated crystals lose less than 2% weight in a loss on drying test, such as less than 0.5% weight.

Preferably the isolated crystals are washed, several times, in water and dried in vacuo at about 50° C. for at least 12 hours.

The crystals obtained are typically relatively large (range 50 to 200 microns) and uniform when viewed under the microscope×10, as illustrated in FIG. 16a.

This differs from crystals obtained without controlled cooling which are much smaller in size (typically 5 to 50 microns) when viewed under the microscope×10, as illustrated in FIG. 16b.

In accordance with an eighth aspect of the present invention there is provided Psilocybin according to the first aspect of the present invention obtained by the method of crystallisation of the invention.

In accordance with a ninth aspect of the present invention there is provided a pharmaceutical formulation comprising psilocybin according to the first aspect of the present invention obtained by the method of crystallisation of the invention.

The psilocybin manufactured prior to crystallisation may be produced using any method: synthetic or biological, e.g. by fermentation or obtained by extraction from mushrooms.

Preferred manufacturing methods use psilocin, or 4 hydroxy-indole, as a starting material.

In accordance with a tenth aspect of the present invention there is provided a method for large scale manufacture of psilocybin from psilocin comprising the steps of:
i) Stage 4—Reacting psilocin with tetrabenzylpyrophosphate to form benzyl 3-[2-(benzyldimethylazaniumyl) ethyl]-1H-indol-4-yl phosphate; and ii) Stage 5—Reacting benzyl 3-[2-(benzyldimethylazaniumyl) ethyl]-1H-indol-4-yl phosphate with hydrogen to form psilocybin.

In accordance with an eleventh aspect of the present invention there is provided a method for large scale manufacture of psilocybin from 4-hydroxyindole comprising the steps of:
i) Stage 1—Reacting 4-hydroxyindole with acetic anhydride to form 1H-indol-4-yl acetate;
ii) Stage 2—Reacting 1H-indol-4-yl acetate with oxalyl chloride and dimethylamine to form 3[(dimethylcarbamoyl)carbonyl]-1H-indol-4yl-acetate;
iii) Stage 3—Reacting 3[(dimethylcarbamoyl)carbonyl]-1H-indol-4yl-acetate with lithium aluminium hydride to form psilocin;
iv) Stage 4—Reacting psilocin with tetrabenzylpyrophosphate to form benzyl 3-[2-(benzyldimethylazaniumyl) ethyl]-1H-indol-4-yl phosphate; and
v) Stage 5—Reacting benzyl 3-[2-(benzyldimethylazaniumyl) ethyl]-1H-indol-4-yl phosphate with hydrogen to form psilocybin.

In accordance with a twelfth aspect of the present invention there is provided a method for large scale manufacture of psilocybin as per the tenth or eleventh aspect of the present invention further comprising:
vi) Stage 6—a water crystallization step, with controlled drying, to produce crystalline psilocybin Polymorph A according to the first aspect of the present invention.

In one embodiment, there is provided a method for large scale manufacture of psilocybin as per the tenth or eleventh aspect of the present invention further comprising:
vi) Stage 6—a water crystallization step, with controlled drying, to produce crystalline psilocybin—Polymorph A with an XRPD diffractogram as substantially illustrated in FIG. 7a and a DSC thermograph as substantially illustrated in FIG. 8a.

In one embodiment, there is provided a method for large scale manufacture of psilocybin as per the tenth or eleventh aspect of the present invention further comprising:
vi) Stage 6—a water crystallization step, with controlled drying, to produce a high purity crystalline psilocybin—Polymorph A with an XRPD diffractogram as illustrated in FIG. 7a and a DSC thermograph as illustrated in FIG. 8a.

Preferably the crystalline psilocybin is Polymorph A.

In developing methodology for the large scale production of psilocin or psilocybin the Applicant overcame one or more significant problems at each of Stages 1 to 5, and whilst these problems are considered in the context of the large scale production of psilocin or psilocybin each step, or rather the way each problem was overcome, are considered separate and independent inventions as they have application in the manufacture of other actives be they intermediates to psilocin, psilocybin, or other derivatives, salts, esters or the like which provide a prodrug.

Preferably the Stage 4 (i) reaction comprises the use of sodium hexamethyldisilazide (NaHMDS).

This has the benefits over the use of Butyl lithium in that: i) it is easier to handle, and ii) it does not introduce lithium into the reaction which causes issues in downstream processing.

Preferably the reaction uses the solvent THF.

This has the benefit that resulting product is obtained in significantly higher purity.

Preferably in (i) the reaction is initiated below −50° C.

This has the benefit of reducing the levels of impurities (m/z 295.2 observed by LCMS) that will subsequently effect purity downstream.

More preferably still the Stage 4 (ii) step uses THF as the solvent.

This has the benefit of ensuring thickening is avoided and facilitates a simple stir out process for obtaining the product.

Preferably the Stage 4 (ii) step comprises a stir out process to obtain benzyl 3-[2-(benzyldimethylazaniumyl) ethyl]-1H-indol-4-yl phosphate.

A stir out process has the advantage that the process is simplified and yields are improved.

To ensure the Stage 4 (ii) reaction is run to completion, levels of Intermediate 4A are monitored, and on completion, the benzyl 3-[2-(benzyldimethylazaniumyl) ethyl]-1H-indol-4-yl phosphate is filtered and oven dried.

This has the advantage that impurities are minimised and a purer product is obtained Preferably the Stage 5 reaction is monitored for levels of intermediates by HPLC, using relative retention times (RRT) and completion is determined by the intermediates being present at less than 0.2%.

Psilocybin crude (Stage 5 product, (12)) has main stage 5 impurities whose relative retention times (RRT) in the HPLC method are about 1.89 and 2.45 respectively, and psilocin (RRT 1.66). These impurities are illustrated in Table 7. Typically, psilocybin crude (Stage 5 product (12)) has 0.24 area % of the RRT 1.89 impurity, 0.03 area % of the RRT 2.45 impurity and 1.86 area % of psilocin. In addition, the pyrophosphoric acid impurity (RRT 0.31) is present in psilocybin crude, for example at a level of about 2-6 area % by HPLC.

At this level subsequent crystallisation processes can be conducted to provide substantially pure psilocybin, for example psilocybin having a purity of at least 95 area % by HPLC, such as at least 98 area %, or such as at least 99 area %. In one embodiment, the pyrophosphoric acid impurity (RRT 0.31) is present in the substantially pure psilocybin at a level of less than 0.3 area % by HPLC, such as less than 0.2 area %, or such as less than 0.1 area %.

In addition, during this stage water is added to the reaction to maintain the psilocybin in solution.

Preferably the catalyst is recovered by filtration.

Preferably in Stage 1 the reaction is conducted in DCM and pyridine.

This has the advantage that flammable solvents are avoided.

Preferably the reaction mixture is washed with citric acid, to give a pH of about 2-3, to remove excess pyridine, and the acid phase is separated from the DCM phase.

This has the advantage that the Intermediate 2A can be isolated, allowing purification away from excess oxalyl chloride.

More preferably the DCM phase is further washed with sodium bicarbonate at about pH 8.

This has the advantage of purer processing.

Preferably the 1H-indol-4-yl acetate is precipitated in heptane.

This aids precipitation and overcomes partial solubility issues.

Preferably magnesium sulphate is used as a drying agent.

Preferably the solvents tert butyl methyl ether (TBME) and tetrahydrofuran (THF) are used.

Preferably the reaction with oxalyl chloride is conducted at about 30° C.-40° C.

This has the advantage that a high reaction rate is ensured giving improved levels of completion.

Preferably Intermediate 2A is isolated by filtration.

This has the advantage that the intermediate is purified away from excess oxalyl chloride.

Preferably in Stage 2, step i the Intermediate 2A is also washed to remove excess oxalyl chloride.

Preferably the Intermediate 2A is washed with TBME.

Preferably a heptane addition is made to precipitate out further Intermediate 2A.

Preferably in Stage 2, step ii, dimethyl amine is used in excess.

This has the advantage that a much improved impurity profile and yield is obtained.

Preferably the pH is maintained at about or above pH 7.

Preferably the reaction is carried out in TBME.

Preferably this stage further comprises a purification step that removes dimethyl amine salts.

This has the advantage that purity is improved.

Preferably this stage comprises a slurry and filtration step.

This has the advantage that handling and purity is improved.

More preferably it comprises slurrying with water and/or IPA, filtering, and drying the isolated 3[(dimethylcarbamoyl)carbonyl]-1H-indol-4yl-acetate.

This has the advantage that purity and yields are improved and hydrolysis reduced.

Preferably in Stage 3 the reaction is conducted in the solvent THF.

This has the advantage that a suspension/emulsion is formed without thickening.

Preferably the 3[(dimethylcarbamoyl)carbonyl]-1H-indol-4yl-acetate is added to a solution of LiAlH$_4$ in THF.

Preferably the reaction is quenched with acetone, followed by citric acid ensuring the mixture remains strongly basic (pH11 or above).

This has the advantage that high yields are obtained.

Preferably the psilocin is filtered and washed in THF and slurried in PrOAc:TBME, filtered, washed in TBME, and dried.

This has the advantage that a high purity product is obtained, for example, at least 95% pure by HPLC, such as at least 98% pure by HPLC, or such as at least 99% pure by HPLC.

The favoured production method comprises each of Stages 1 to 6 but it will be appreciated that each of the features of each stage can stand alone or be used in combination with any other feature from the same or a different step of the reaction.

Psilocybin of a given form, Polymorph A or Polymorph A', and psilocybin of such high purity has not previously been obtained, and to Applicants knowledge their production of Polymorph A and Polymorph A' particularly (as illustrated in FIGS. 7a & 7b and 8a & 8b) is novel. Indeed, the production of large batch quantities of Polymorph A, is new. A consequence of the crystallisation methodology of the invention and, in part, the manufacturing process enable such high chemical purity of crystalline Psilocybin to be obtained.

Furthermore, given the unstable nature of the compound they have obtained a crystalline form which they have shown to be stable, under accelerated conditions, (described later) for at least 12 months.

Polymorph A and A' (FIGS. 7a and 7b) differs from Polymorph B (FIG. 7c), a Hydrate A (FIG. 7d) and ethanol solvate (FIG. 7e) and mixture (FIG. 7f (upper)) as will be apparent from their XRPD diffractograms and DSC thermographs—as described hereafter.

The relationship between the different polymorphs is shown in FIG. 9.

Indeed, the size and shape of the crystals are determined by the crystallisation methodology, and these in turn can affect stability and the ability to formulate the product.

In a particularly preferred embodiment, the psilocybin is manufactured through a 6-stage process as outlined below:

In accordance with another aspect of the present invention there is provided a method for manufacture of crystalline psilocybin according to the first aspect of the present invention, characterised in that the method comprises subjecting psilocybin to a water crystallization step, with controlled drying, to produce crystalline psilocybin Polymorph A or Polymorph A' according to the first aspect of the present invention. In one embodiment, there is provided a method for manufacture of crystalline psilocybin according to the first aspect of the present invention, characterised in that the method comprises a water crystallization step, with controlled drying, to produce crystalline psilocybin—Polymorph A or Polymorph A' with an XRPD diffractogram as substantially illustrated in FIG. 7a or FIG. 7b and a DSC thermograph as substantially illustrated in FIG. 8a or 8b. In one embodiment, there is provided a method for manufacture of psilocybin according to the first aspect of the present invention characterised in that the method comprises a water crystallization step, with controlled drying, to produce a high purity crystalline psilocybin—Polymorph A or Polymorph A' with an XRPD diffractogram as illustrated in FIG. 7a or FIG. 7b and a DSC thermograph as illustrated in FIG. 8a or FIG. 8b.

Preferably Polymorph A and Polymorph A' are isostructural variants with XRPD diffractograms as substantially illustrated in FIG. 7a and FIG. 7b and DSC thermographs as substantially illustrated in FIG. 8a and FIG. 8b.

More preferably the psilocybin is recrystallized in about 10-20 volumes of water, heated with agitation to a temperature of at least 70° C., polish filtered with a suitable cut off (typically, below 5 µm), seeded at a temperature of about 70° C., and cooled in a controlled manner to about 5° C. over a period of more than 2 hours.

More preferably the method comprises controlled cooling which drops the temperature by about 5° C.-15° C. an hour, more preferably about 10° C. an hour.

Preferably the polish filter step is done through an appropriately sized filter such as a 1.2 µm or a 0.45 µm in line filter.

Preferably the agitation is by stirring at about 400-500 rpm, typically about 450 rpm.

Preferably the seed is psilocybin Hydrate A. In one embodiment, 0.1% weight or less of seed is added to the process.

Preferably the crystalline psilocybin is isolated by vacuum filtration.

In one embodiment, the isolated crystals are dried in vacuo at a temperature of at least 30° C., such as between 30 and 50° C., or such as between 40 and 50° C. In one embodiment, the isolated crystals are dried in vacuo for at least 10 hours, such as between 12 and 18 hours, or such as about 30 hours. In one embodiment, the isolated crystals are dried in vacuo at a temperature of at least 30° C., such as between 30 and 50° C., or such as between 40 and 50° C., for at least 10 hours, such as between 12 and 18 hours, or such as about 30 hours. In one embodiment, the isolated crystals are dried until the isolated crystals lose less than 2% weight in a loss on drying test, such as less than 0.5% weight.

Preferably the isolated crystals are washed, several times, in water and dried in vacuo at about 50° C. for at least 12 hours.

The crystals obtained are typically relatively large (range 50 to 200 microns) and uniform when viewed under the microscope×10, as illustrated in FIG. 16a.

This differs from crystals obtained without controlled cooling which are much smaller in size (typically 5 to 50 microns) when viewed under the microscope×10, as illustrated in FIG. 16b.

Stage 1: Synthesis of 1H-indol-4-yl acetate (3)

The core reaction is the reaction of 4-hydroxyindole (1) with acetic anhydride (2) to form 1H-indol-4-yl acetate (3); (FIG. 2)

Most preferably stage 1 is as follows:

4-hydroxyindole (1), DCM (12), and pyridine (13) are added to a vessel and cooled to about 0-5° C. Acetic anhydride (2) is added dropwise, and the mixture warmed to about 20-25° C. and stirred until complete by HPLC. The reactants are washed with aqueous citric acid solution (14) and aqueous $NaHCO_3$ (15), dried over $MgSO_4$ (16) filtered and evaporated to approximately half volume. Heptane (17) is added, and distillation continued to remove the majority of the DCM. The mixture is cooled to about 5-25° C., filtered, washed with heptane and dried in a vacuum oven overnight to isolate 1H-indol-4-yl acetate (3) as a solid suitable for use in the following stage.

Stage 2: Synthesis of 3[(dimethylcarbamoyl)carbonyl]-1H-indol-4yl-acetate (6)

The core reaction is the reaction of 1H-indol-4-yl acetate (3) with Oxalyl chloride (4) and dimethylamine (5) to form 3[(dimethylcarbamoyl)carbonyl]-1H-indol-4yl-acetate (6); (FIG. 3)

Most preferably stage 2 is as follows:

1H-indol-4-yl acetate (3) is dissolved in a mixture of THF (19) and TBME (18) at room temperature. Oxalyl chloride (4) was added dropwise allowing the reaction to exotherm at about 35-40° C. The temperature range is maintained throughout the remainder of the addition. The reaction is then stirred at about 40° C. until complete by HPLC. The reaction is cooled to room temperature and heptane (17) added resulting in precipitation of further solids. The slurry is stirred, then allowed to settle, followed by removal of the majority of the solvent (18/19) by decanting. The solid was washed in the vessel twice with heptane (17). TBME (18) is added to give a yellow slurry and the mixture cooled to about −20° C. Dimethylamine solution (5) is added maintaining the temperature at −20° C. to −10° C. The reaction was then warmed to room temperature and stirred until complete, adding extra dimethylamine if necessary. The reaction was filtered, washed with heptane (17) and dried in a vacuum oven. The crude 3[(dimethylcarbamoyl)carbonyl]-1H-indol-4yl-acetate (6) was further purified by a slurry in water (20), then IPA (21) and then dried in a vacuum oven to yield (6) as a solid suitable for use in the following stage.

Stage 3: Synthesis of 3-(2-(dimethylamino) ethyl)-1H-indol-4-ol (Psilocin) (8)

The core reaction is the reaction of 3[(dimethylcarbamoyl)carbonyl]-1H-indol-4yl-acetate (6) with lithium aluminium hydride (7) to form psilocin (8); (FIG. 4)

Most preferably stage 3 is as follows:

The 3[(dimethylcarbamoyl)carbonyl]-1H-indol-4yl-acetate (6) was slurried in THF (19) and cooled to about 0° C. A THF solution of $LiAlH_4$ (7) was added dropwise maintaining the temperature at about 0-20° C. The reaction was then refluxed until complete by HPLC. The reaction was cooled to 0° C. and the excess $LiAlH_4$ quenched by addition of acetone (22) followed by aqueous citric acid solution (14). The batch was filtered to remove Lithium and Aluminium salts. The filtrate was dried over $MgSO_4$ (16), filtered and concentrated and loaded onto a silica pad (23). The pad was eluted with THF (19) and the product containing fractions evaporated. The resulting solid was slurried in iPrOAc:TBME (24/18) mixture, filtered and washed with TBME. The solid was dried in the oven to yield high purity psilocin (8) as an off white solid.

Stage 4: Synthesis of benzyl 3-[2-(benzyldimethyl-azaniumyl)ethyl]-1H-indol-4-yl phosphate (10)

The core reaction is the reaction of psilocin (8) with tetrabenzylpyrophosphate (9) to form benzyl 3-[2-(benzyldimethylazaniumyl)ethyl]-1H-indol-4-yl phosphate (10), (FIG. 5)

Most preferably stage 4 is as follows:

Charge psilocin (8) to a vessel followed by THF (19). The reaction was cooled to −50° C. to −70° C. and NaHMDS (25) was added dropwise at about −45° C. to −70° C. The temperature was adjusted to about −45° C. to −60° C. and tetrabenzylpyrophosphate in THF was added. The batch was allowed to warm to 0° C. after which the solid by products were removed by filtration and the filtrate concentrated in vacuo. The concentrated mixture was then heated to about 40° C. and stirred until the intermediate had converted to the stage 4 product (10)—controlled by monitoring and the use of HPLC. The batch was cooled to about 0-5° C. and the resulting solid isolated by filtration and dried in vacuo to provide benzyl 3-[2-(benzyldimethylazaniumyl)ethyl]-1H-indol-4-yl phosphate (10) as a solid.

Stage 5: Synthesis of Intermediate Grade 3-[2-(dimethylazaniumyl) ethyl]-1H-indol-4-yl hydrogen phosphate (Psilocybin Crude) (12)

The core reaction comprises reacting benzyl 3-[2-(benzyldimethylazaniumyl) ethyl]-1H-indol-4-yl phosphate (10) with hydrogen (11) to form psilocybin (12), (FIG. 6).

Most preferably stage 5 is as follows:

To a vessel was charged Pd/C (26), methanol (24) and 3-[2-(benzyldimethylazaniumyl)ethyl]-1H-indol-4-yl phosphate (10) and the resulting mixture sparged with hydrogen (11) until complete by HPLC. Purified water (20) is added during this process to retain the product in solution. The mixture was heated to about 35° C.-45° C. and then filtered through a bed of Celite (27) washing with methanol (24) and purified water (20). The filtrate was evaporated in vacuo, azeotroping with ethanol (28) to obtain intermediate grade psilocybin (12).

Stage 6: Synthesis of 3-[2-(dimethylazaniumyl) ethyl]-1H-indol-4-yl hydrogen phosphate (Psilocybin)

The core purifying/polymorph determining step is a water crystallization step, followed by a controlled cooling and drying step, to produce high purity crystalline psilocybin, Polymorph A or Polymorph A'.

Most preferably stage 6 is as follows:

The intermediate grade Psilocybin (12) (stage 5) was charged to a vessel with purified water (20) and the mixture heated until the psilocybin (12) dissolved. The resulting bulk solution was then polish filtered into a pre-warmed vessel. The temperature was adjusted to, preferably, about 68° C.-70° C., and a Psilocybin hydrate seed (i.e., Hydrate A) was added to the reaction. The batch was then cooled in a controlled manner to about 0-10° C. and stirred, and the solids were collected by filtration and washed with purified water. The isolated solids were then dried in vacuo to yield high purity crystalline Psilocybin, Polymorph A or A', as an off white solid.

BRIEF DESCRIPTION OF THE DRAWINGS

Embodiments of the invention are further described hereinafter with reference to the accompanying drawings, in which.

DETAILED DESCRIPTION

Figure 1:
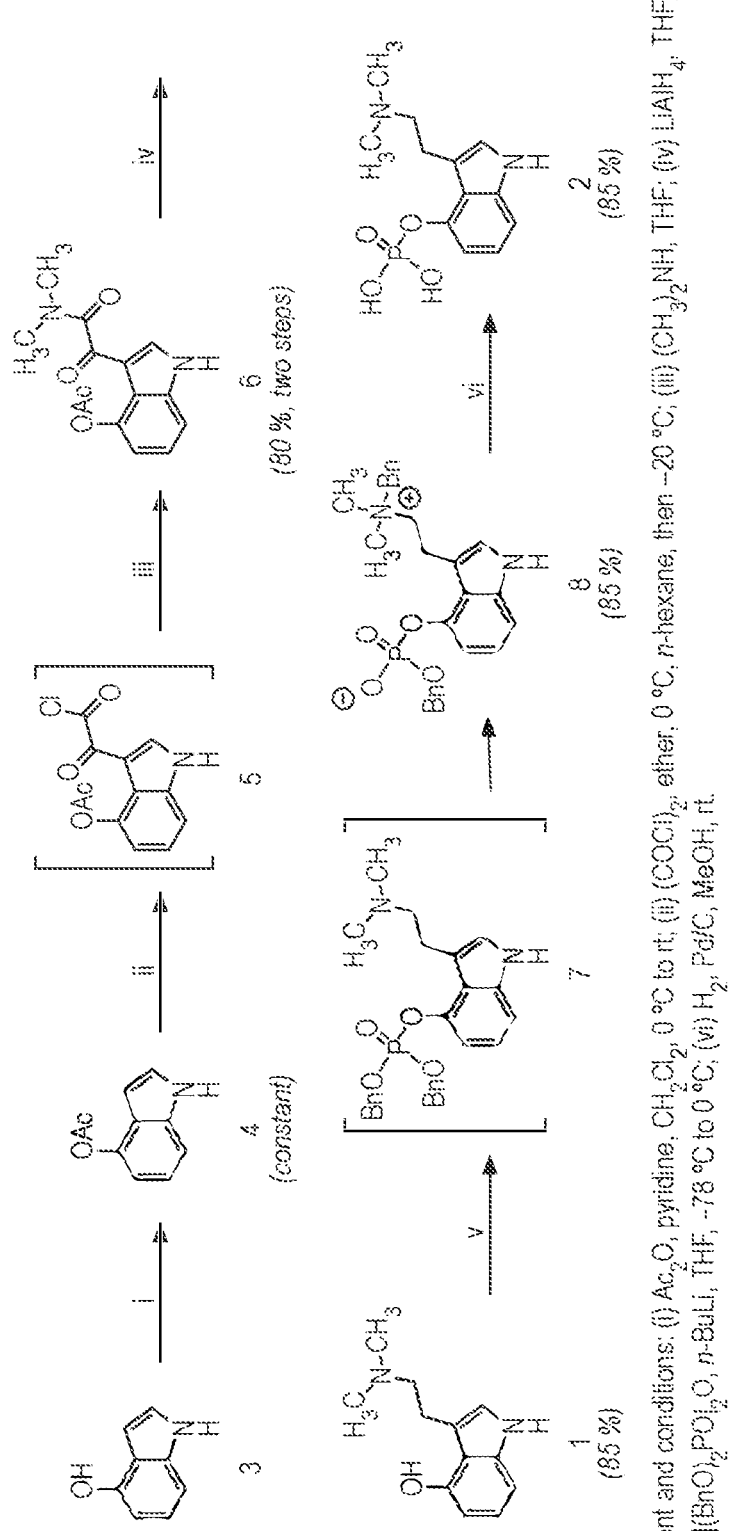
FIG. 1 is a schematic of the reaction taught in JNP.

In contrast to the prior art, the present invention sought to produce psilocybin at a commercial large scale, in amounts or batches of at least 100 g, and more preferably at least 250 g, levels 1 log or 2 logs higher than the levels described in JNP, which describes a "large" scale method to producing gram quantities on a 10 g scale.

To demonstrate the many significant development steps from JNP, the description below sets out details of experiments and investigations undertaken at each of the process stages, which illustrate the selections made to overcome the numerous technical problems faced, in producing psilocybin (7) to GMP at a large scale (including the various intermediates (2-6)) starting from 4-hydroxyindole (1).

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

As used herein, the singular forms "a," "an," and "the" include the plural.

The term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of symptoms, eliminating symptoms and/or the underlying cause of said symptoms, reducing the frequency or likelihood of symptoms and/or their underlying cause, delaying, preventing and/or slowing the progression of diseases and/or disorders and improving or remediating damage caused, directly or indirectly, by the diseases and/or disorders.

The following abbreviations have been used herein:
DSC—Differential Scanning Calorimetry
RT—room temperature
TBME—methyl tert-butyl ether
TGA—Thermogravimetric Analysis
THF—tetrahydrofuran
wrt—with respect to
XRPD—X-Ray Powder Diffraction Example 1

Stage 6 Crystalisation Process and Resulting Polymorphs

Experimental to Produce Form A':

1.0 g of crude Psilocybin was charged to a 25 mL flask. Water (12.8 mL/16 volumes based on activity of input material) was added. The mixture was agitated and heated to 80° C. A dark brown solution with visible undissolved solids was obtained. The mixture was polish filtered through a warmed 0.45 μm filter into a hot 25 mL flask. The undissolved solids were removed to give a dark brown solution. The solution was re-equilibrated at 75° C. and then cooled slowly (10° C./hour) to ambient temperature. The resulting pale brown solution was equilibrated at ambient temperature for 16 hours. The suspension was cooled to 5° C. prior to isolation of the solid by vacuum filtration. The filter cake was washed with water (0.8 mL/1 volume) and dried in vacuo at 50° C. for 16 hours. Yield of 75%, chemical purity 99%, NMR assay >98%.

The procedure above was repeated with 14 volumes (11.2 mL) of water. Yield of 69%, chemical purity 99%, NMR assay >98%.

In both cases, dissolution of crude Psilocybin was achieved at ca. 75° C. On gradual cooling, precipitation was observed at ca. 60° C.

Figure 7B:
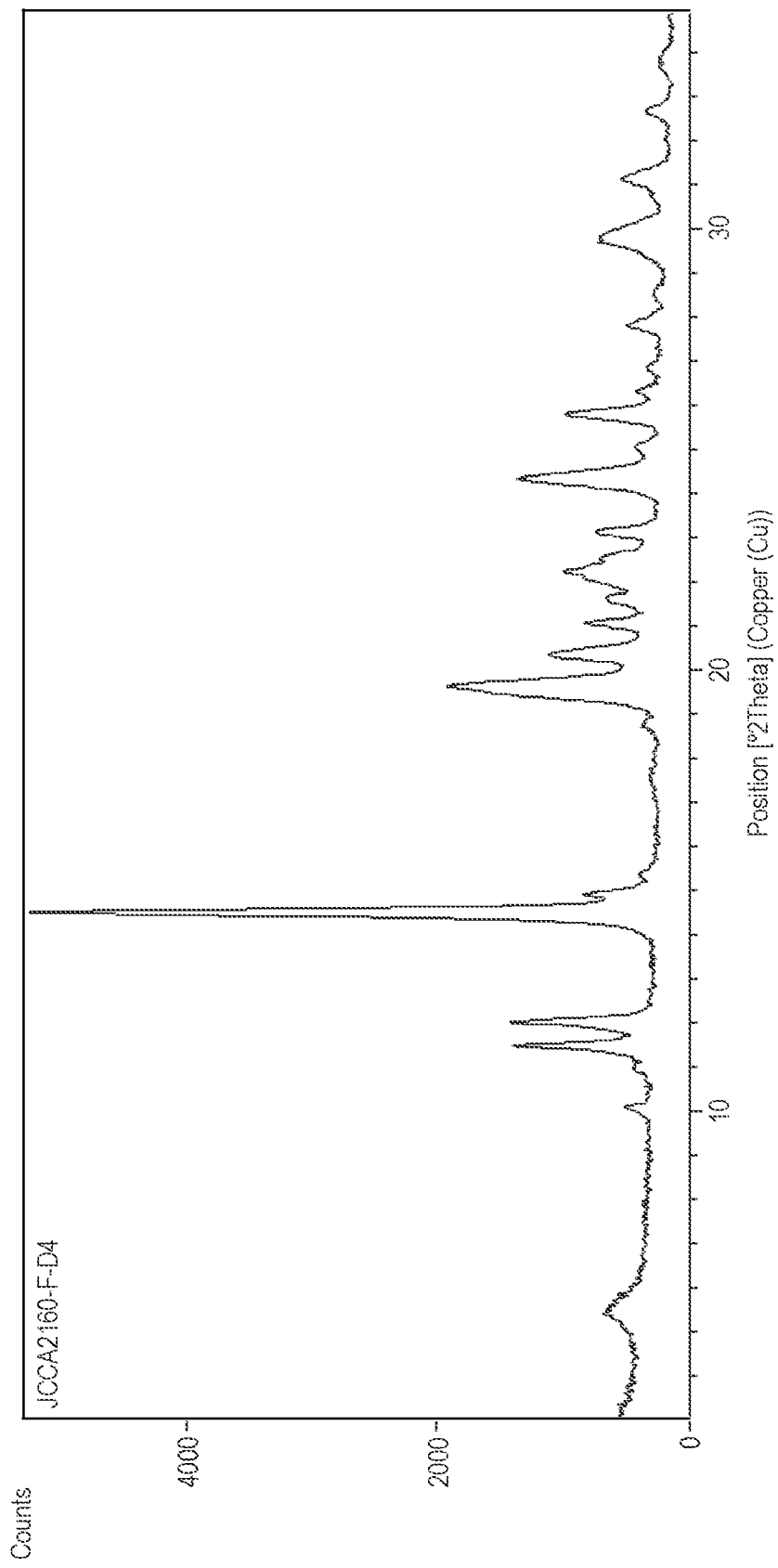
FIG. 7b is a XRPD diffractogram of Polymorph A' (JCCA2160F)
Figure 8A:
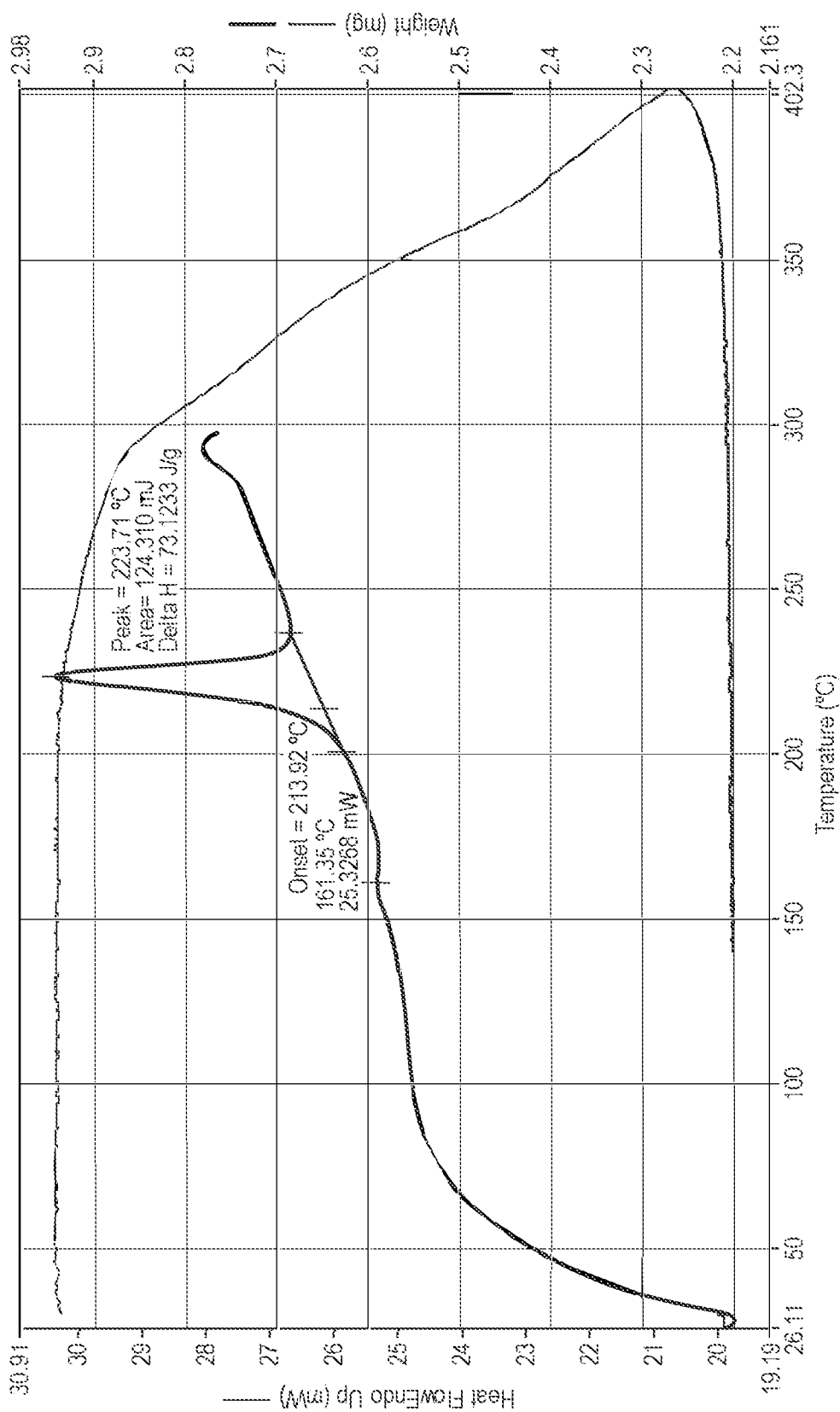
FIG. 8a is a DSC and TGA thermograph of Polymorph A (GM764B)
Figure 8B:
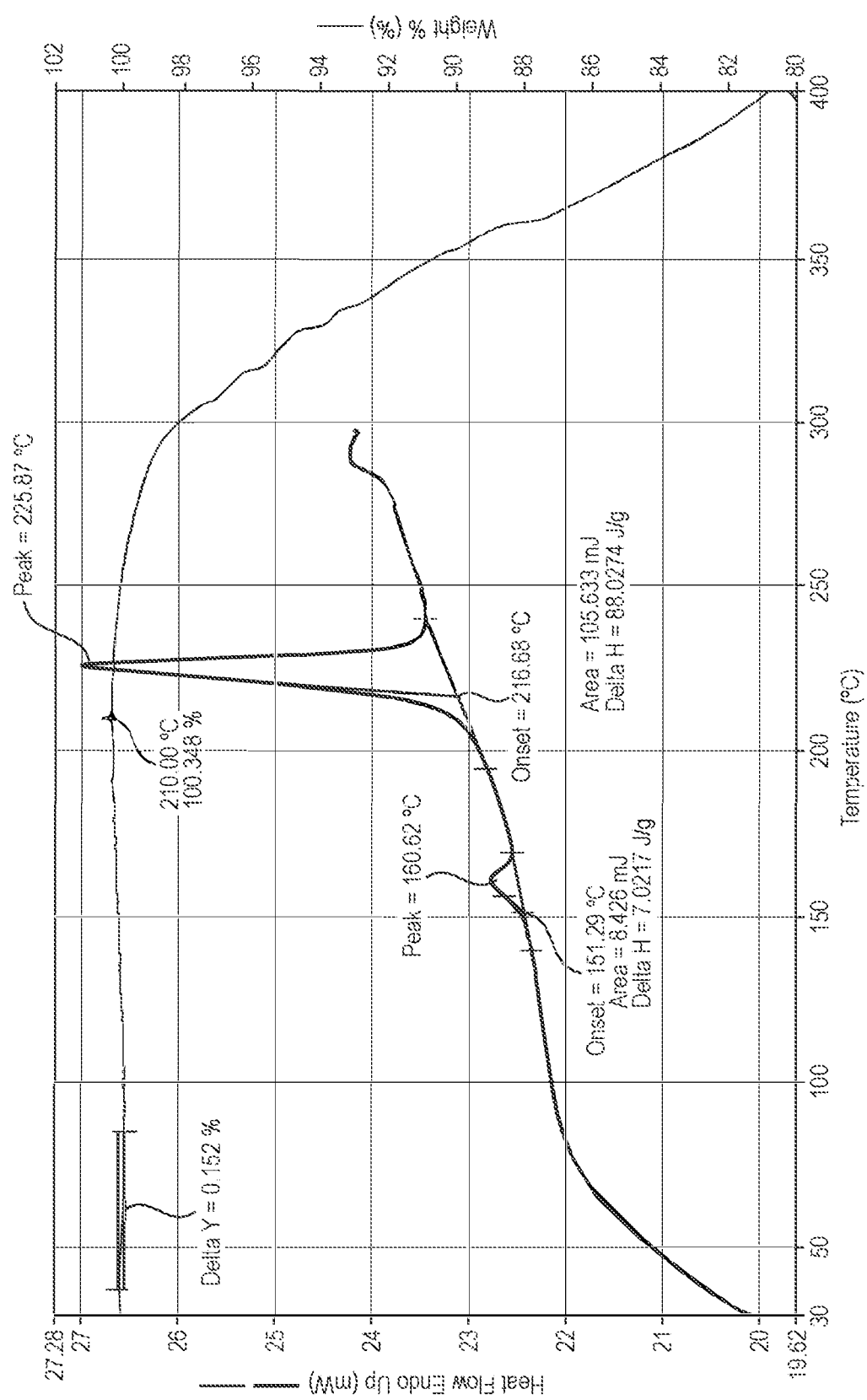
FIG. 8b is a DSC and TGA thermograph of Polymorph A' (JCCA2160F)

In both cases, psilocybin Polymorph A' was produced, confirmed by XRPD (diffractogram consistent with FIG. 7b) and DSC (thermogram consistent with FIG. 8b).

Experimental to Produce Form A:

94 g of crude Psilocybin obtained from the Stage 5 process (about 93% pure by HPLC with about 4% pyrophosphate impurity) was subject to an aqueous re-crystallisation as set out below:

The protocol used sufficient water (12 volumes), a rapid agitation rate (450 rpm) and a controlled cooling profile (10° C./hr).

Psilocybin (94.0 g) (CB650E) was charged to a 2 L flask. Water (902 ml, 12 volumes based upon activity of input material) was added. The mixture was agitated and heated to about 78° C. A dark brown solution with visible undissolved solids was obtained. The mixture was polish filtered through a 1.2 μm in-line filter into a hot 5 L flask fitted with an overhead stirrer (450 rpm). The undissolved solids were removed to give a clarified dark brown solution. The solution was re-equilibrated at about 75° C. for 15 minutes and then cooled slowly (10° C./hour) to ambient temperature. The solution was seeded with Psilocybin Hydrate A (GM758A-XRPD diffractogram consistent with FIG. 7d) following maturation in water) at 68° C.-70° C. The resulting pale brown suspension was equilibrated at ambient temperature for about 16 hours. The suspension was cooled to 5° C. for one hour prior to isolation of the solid by vacuum filtration. The filter cake was washed with water (282 mL, 3 volumes) and dried in vacuo at about 50° C. for 30 hours.

Figure 7A:
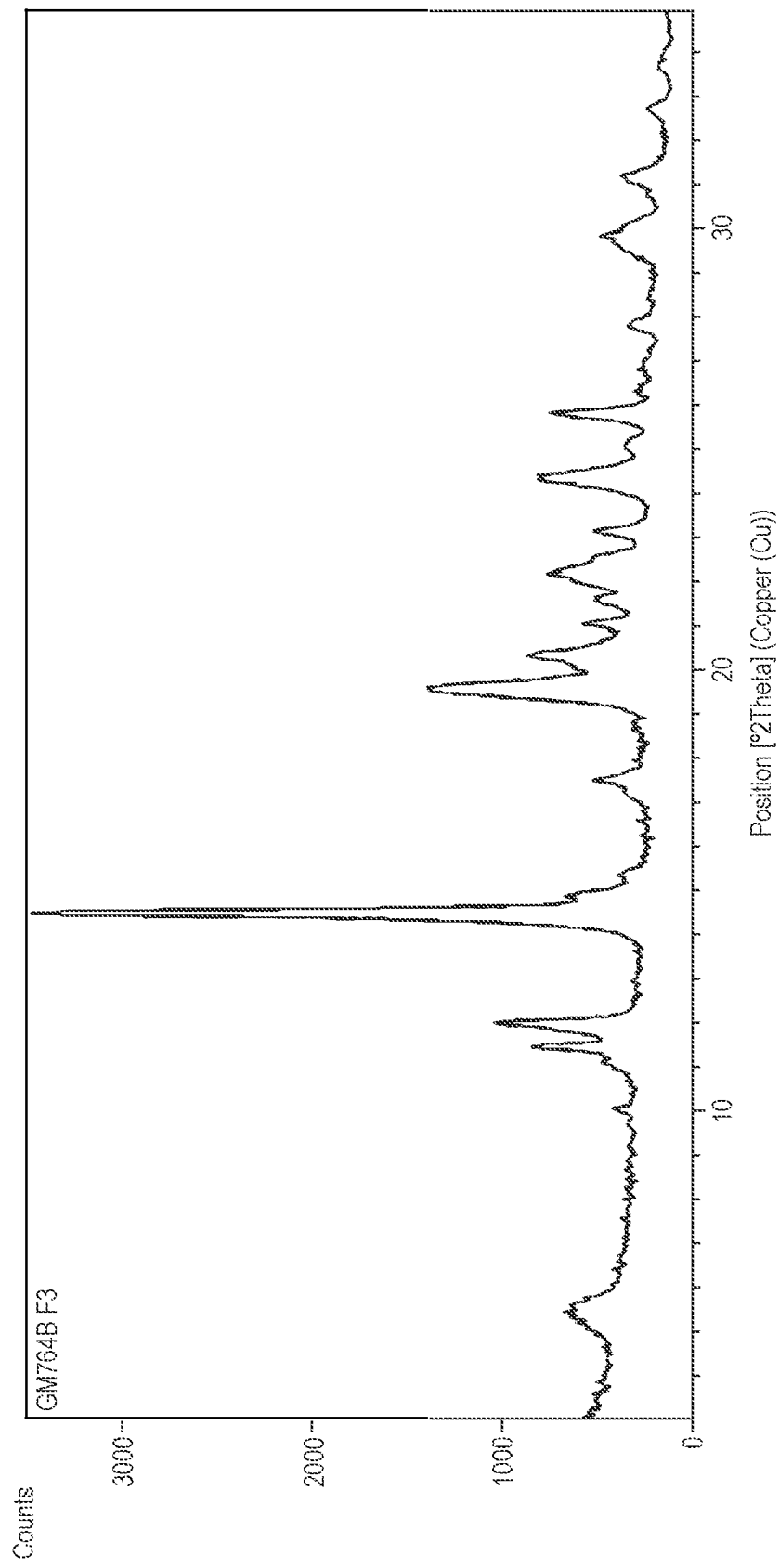
FIG. 7a is a XRPD diffractogram of Polymorph A (GM764B)

The process was completed successfully with a yield of 75% achieved. Chemical purity of the solid was confirmed as 99.3%. Analysis of the solid by XRPD post drying for 30 hours showed Polymorph A (FIG. 7a). A characteristic perturbation was observed at ca ~17 °2θ, such as 17.5 °2θ, and was pronounced in the bulk material.

Solid State Characterisation of Polymorph a and Polymorph A'

The DSC and TGA thermograms (FIG. 8a) obtained for Polymorph A were comparable to the DSC and TGA thermograms obtained for Polymorph A' (FIG. 8b). The TGA thermograms (FIG. 8a) obtained for Polymorph A and Polymorph A' show no weight loss prior to decomposition. This suggested that the difference between the XRPDs obtained for Polymorph A (FIG. 7a; perturbation present at ca. ~17 °2θ) and for Polymorph A' which was obtained at small scale (FIG. 7b; perturbation not present) was not due to excess hydration.

Figure 16A:
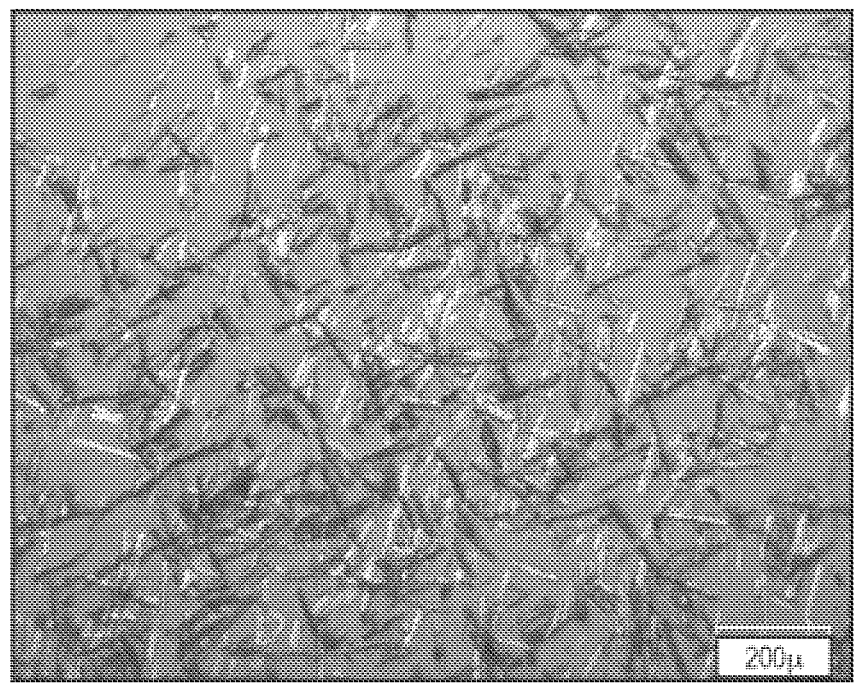
FIG. 16a is a micrograph showing crystals obtained by controlled cooling.

Microscopy of the solid (FIG. 16a) shows rod shaped crystals with good uniformity with a size range of between 50 and 200 micron.

The XRPD diffractogram obtained for Polymorph A' does not demonstrate a perturbation at ca. ~17 °2θ to the same extent as Polymorph A. The perturbation in the XRPD diffractogram at ca. ~17 °2θ is more pronounced for psilocybin produced at large scale (compared to that obtained at small scale) and was unexpected. Applicant has demonstrated that the Hydrate A is the only polymorphic form that exists across a range of temperatures with no diffraction peak in the 17 °2 theta region (see FIG. 7M. This strongly suggests a collapse of Hydrate A upon dehydration to yield Polymorph A or A' that varies with scale and that Polymorph A is the true form with Polymorph A' formed at a small scale being atypical.

To test the robustness of this theory and to demonstrate a return to Polymorph A, a small portion of the bulk was re-dried following another soak in water (to reproduce Hydrate A). A small sample (250 mg—psilocybin Polymorph A) was equilibrated in water (10 vols) for one hour. The suspension was filtered and analysis of the damp solid confirmed that Hydrate A had been generated (FIG. 7d), no perturbation at 17 °2 theta. The material was dried in vacuo for 16 hours and the solid reassessed by XRPD. Polymorph A' material was confirmed by XRPD (FIG. 7b) with the reduction in the XRPD perturbation noted. Additional drying of the original bulk solid and ageing at ambient temperature did not change the XRPD diffractogram of the solid. The two solid versions obtained, the XRPD diffractograms for Polymorph A and Polymorph A' are virtually identical other than the ~17.5° 2 theta peak. The thermal properties are also identical. The distinction between the XRPD diffractograms for Polymorph A versus Polymorph A' is subtle and both polymorphs kinetically convert to the hydrated state very rapidly.

Additional experiments were performed to ascertain if the differences in the XRPD diffractograms for Polymorph A and Polymorph A' were due to the larger scale crystallisation process delivering solids of a larger particle size that subsequently did not dry as effectively and caused the change, or whether the habit and size difference of the crystalline solid was the cause. Psilocybin Polymorph A (polymorphic form confirmed prior to experiment) was ground via a mortar and pestle and assessed by XRPD. No change in polymorph was observed. Another portion (51 mg) was charged with water (<1 mL) and assessed damp to confirm that the hydrate was formed. Both lots were dried in vacuo at 50'C for ca. 18 hours and re-assessed by XRPD. The ground sample remained as Polymorph A. The hydrated sample after dehydration was shown to be Polymorph A'

(i.e., no reflection at ~17.5 °2θ). This suggested that size/habit alone were not the sole reason for the original reflection peaks.

TGA assessment revealed that the input lot demonstrated a small mass loss (0.139% weight) by ca. 70° C. The particle size reduced and subsequently dried solid demonstrated a greater mass loss of 0.343 wt % by ca. 75° C. whereas the hydrated and dried solid demonstrated the smallest mass loss of 0.069 wt % by ca. 80° C. The particle size reduced and subsequently dried solid was held at 80° C. for 10 minutes (past the point of mass loss by TGA) but assessment by XRPD revealed no change from the input, meaning that low levels of hydration and partial swelling of the crystalline lattice were not the cause of the variation It is possible to generate Polymorph A' via the hydration of Polymorph A and subsequent drying of the isolated solid on a small scale.

Psilocybin Polymorph A and Polymorph A', ca. 60 mg each, were charged with water, 0.2 ml, to deliver Hydrate A from both lots. Half of each Hydrate A was dried in vacuo at 25° C. for ca. 17¼ hours and the remainder of each Hydrate A was dried at ambient temperature under a stream of $N_2$ for ca. 17¼ hours. The solids were isolated following drying and assessed by XRPD. XRPD assessment of the solids isolated from the Polymorph A input confirmed that Hydrate A was successfully generated and that the solids dried to give Polymorph A' from both drying methods. XRPD assessment of the solids isolated from the Polymorph A' input confirmed that Hydrate A was successfully generated and that the solids dried to remain as Polymorph A' from both drying methods.

On the small scale investigated, Polymorph A and Polymorph A' will dry to give Polymorph A' via conversion to Hydrate A.

Psilocybin Polymorph A (100 mg) was particle size reduced via mortar and pestle grinding. The ground lot was subject to two different drying regimes in order to assess whether reducing the particle size affected the dehydration of the sample. The first sample was held at 80° C. for 10 minutes and the second sample held at 110° C. for 10 minutes. Both solids were assessed by XRPD which revealed that Polymorph A was retained. It was considered whether the ground lot in the prior isothermal stresses were not held at 110° C. for long enough to impact the form and so a portion of the ground lot was dried in vacuo at 110° C. for ca. 24 hours. Assessment by XRPD revealed a subtle change in form with the Polymorph A reflections at ca. 17 still present but at a slightly reduced intensity.

It was concluded that Polymorph A would not readily convert to Polymorph A' via particle size reduction and/or drying at high temperature.

Methodology

Stability assessments of Psilocybin, not containing the pyrophosphate impurity, indicated that at temperatures in excess of 80° C., the level of the Stage 3 intermediate impurity (psilocin) generated by hydrolysis of Psilocybin is of concern. For example, when a 83 mg/mL Psilocybin aqueous solution is heated to 90° C. and analysed by HPLC at 1, 2 and 4 hours, the level of the Stage 3 impurity were determined as 0.28, 1.82 and 7.79 area % respectively. In comparison, when 50 mg of psilocybin is dissolved in water (1.2-1.8 ml; volume sufficient to maintain a solution) and heated to 70, 75 and 80° C. for 4 hours, the level of the Stage 3 impurity was determined, by HPLC, as 0.53, 0.74 and 2.30 area % respectively. The recrystallization heats the crude Psilocybin to between 75° C. and 80° C. in order to achieve dissolution, and polish filtration. The immediate cooling of the solution limits the level of Psilocybin hydrolysis by reducing the residency time of the material to excessive temperature.

Further trial re-crystallisation's of Psilocybin were conducted introducing the following variations:
Varying the volumes of water used;
Varying agitation;
Having a controlled cooling profile;
Having a rapid (uncontrolled) cooling profile.

Figure 16B:
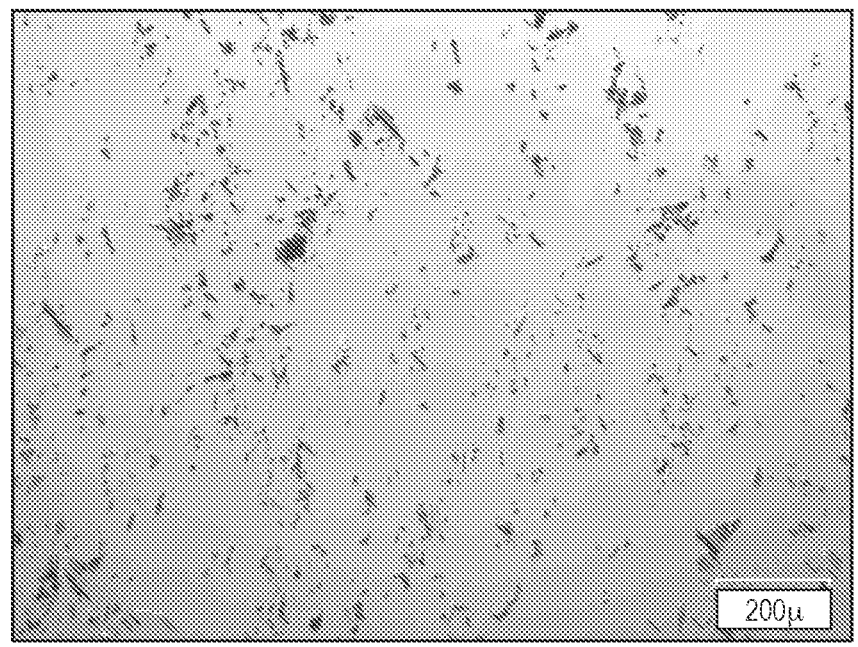
FIG. 16b is a micrograph showing crystals obtained by uncontrolled cooling drying.

Using smaller volumes of water (as little as 12 volumes) did not hinder the re-crystallisation process and dissolution of Psilocybin was achieved at a temperature to enable a polish filtration step. Different cooling rates were shown to result in different crystal size distributions; a slow controlled cool at ca 10° C. per hour produced a relatively larger and more even average crystal size (FIG. 16a) whereas a rapid cooling profile delivered smaller crystals (FIG. 16b). A controlled cooling profile is preferred and this was reflected in an improved purity for the controlled cool.

Using the process resulted in Psilocybin of 99.3% chemical purity, with a 75% yield. Thermal characteristics of the solid corresponded with those desired. Differences in the XRPD diffractogram of the dry solid have suggested that the drying profile may be important in determining how the Hydrate A collapses to give the preferred solid form. Polymorph A has been demonstrated to be stable under accelerated stability testing conditions for 12 months.

Experimental

Stage 5 was charged to vessel under $N_2$ followed by water (approx. 12-15 vol based on active Stage 5). The mixture was heated to about 80° C. to achieve dissolution and polish filtered through a 1.2 µm in-line filter into a clean new flask heated to 80° C. The agitation rate was set to a high level (450 rpm) and the solution equilibrated at 70-75° C. The solution was cooled to ambient temperature, at approx. 10° C./hour, seeding with Psilocybin Hydrate A (0.001×stage 5 charge) at 68-70° C. The suspension was held at ambient temperature overnight then cooled to approx. 5° C. and held for 1 hour. The suspension was filtered, washing with water (2-3 volumes based upon active charge of Stage 5). The pure Psilocybin was dried in vacuo at 50° C. Crystalline material psilocybin (Polymorph A or Polymorph A' dependent on scale) was obtained, for example using 94 g input of psilocybin yielded Polymorph A and using 1 g input of psilocybin yielded Polymorph A'. Typically, batch sizes of greater than 5 g deliver Polymorph A, while batch sizes less than 5 g deliver Polymorph A'.

The differences from JNP and the benefits can be summarised as follows:
i) This additional crystallisation step gives rise to a defined crystalline form—Polymorph A (or A').
ii) Heating to about 80° C., for a short period, has the advantage that solubility is maximised (and hydrolysis avoided), which ensures good yields.
iii) At about 70-80° C. polish filtration can be used to remove insoluble impurities. This is best achieved using an in-line filter—typically about 1.2 µm. This ensures good chemical purity.
iv) Using a high agitation rate (typically about 450 rpm) ensures speedy dissolution allowing the time at which the solution is kept at 80° C. to be minimised, thus avoiding increased levels of the Stage 3 intermediate impurity formed by hydrolysis of Psilocybin.
v) The provision of controlled cooling, typically cooling at about 10° C. per hour, delivers a more uniform crystal size and maintains form as crystalline Hydrate A.

vi) Seeding the solution at about 70° C. with Psilocybin Hydrate A facilitates crystallisation as the Hydrate A.
vii) The crystals are washed in water and dried at about 50° C. to maximise purity and deliver Polymorph A or A' depending on scale.

Examples 2 to 6

Stages 1 to 5 Production of Psilocybin

The following Examples illustrate significant developments from the process described in JNP, and illustrated in FIG. 1, as described herein before.

Example 2

Figure 2:
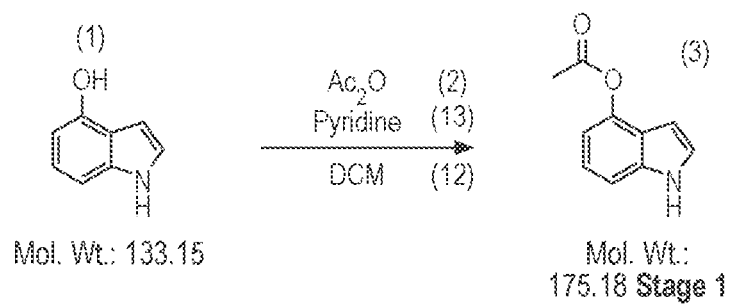
FIG. 2 is a schematic of the Stage 1 reaction of one aspect of the present invention.

Stage 1 (FIG. 2)

The stage 1 conditions in JNP used 1.1 eq $Ac_2O$, and 1.2 eq Pyridine in the solvent DCM. The reaction was found to be complete (99% product, 0% SM) after stirring overnight. The reaction mixture was washed with water and concentrated in vacuo giving a brown oil. In the literature, the oil was taken up in EtOAc and concentrated by evaporation, giving precipitation of solids at low volume.

Investigation

However, in the Applicants hands precipitation of solids from EtOAc was not observed. Precipitation of solids was encouraged by trituration with heptane, however this would not form a scalable process. The solids were collected giving high purity stage 1 product (75% yield, >95% pure by NMR).

While the reaction worked well, the isolation procedure required further development in order that an easy to handle solid could be obtained. It was hoped that isolation of the solids by filtration would then also offer a means of purification.

The reaction was first trialed in EtOAc to see if precipitation of solids could be encouraged allowing isolation directly from the reaction mixture. However, the reaction profile in EtOAc was found to be less favourable than in DCM and therefore the reaction was abandoned.

Applicant washed out the pyridine from the DCM reaction mixture, as it was believed this may be preventing re-crystallisation of the product. The reaction was repeated (completion of 0.4% SM, 98.7% product by HPLC) and the reaction mixture washed with 20% citric acid to achieve pH 2/3, removing pyridine and then saturated $NaHCO_3$ (aq) to avoid low pH in the evaporation steps. The organics were dried and a solvent swap to heptane was carried out giving precipitation of stage 1. The solids were collected by filtration yielding pure stage 1 after drying in vacuo (87% yield, >95% purity by NMR).

Stability trials were carried out that confirmed the reaction mixture was stable overnight when stirred with 20% citric acid, and also saturated $NaHCO_3$. The product was found to be stable when oven dried at 40° C. and 60° C.

Scale Up

The stage 1 reaction was successfully scaled up processing >100 g of 4-hydroxyindole. The reaction progressed as expected and was worked up to give stage 1 product (93% yield, ~98% NMR purity).

GMP Raw Material Synthesis

A large scale stage 1 reaction was carried out to supply GMP starting material (processing >500 g of 4-hydroxyindole). The reaction proceeded as expected giving consumption of SM by HPLC (99.2% product, <0.1% SM). The reaction was worked up using the established procedure to give stage 1 product after drying (94% yield, 99.1% by HPLC, 99% NMR assay).

It was also noted in development that the stage 1 procedure was effective in removing minor impurities present in some batches of 4-hydroxyindole. The low level impurities present in 4-hydroxyindole were completely removed after the stage 1 reaction providing clean material in high yield (89%) and purity (99% by HPLC, 99% by NMR assay).

Experimental 4-hydroxyindole (1 eq. limiting reagent) was charged to a vessel under $N_2$ followed by DCM (dichloromethane; 6 vol based on 4-hydroxyindole charge). The reaction was cooled to 0-5° C. and pyridine added (1.2 eq) dropwise at 0-5° C. Acetic anhydride (1.1 eq) was added dropwise at 0-5° C. and the reaction warmed to 20-25° C. for 1-1.5 hrs and stirred at 20-25° C. for a further 3 hours. The reaction was sampled and analysed for completion. The reaction was then washed three times with 20% aqueous citric acid solution (3×3 vol based on 4-hydroxyindole charge) and once with sat. $NaHCO_3$ (3 vol based on 4-hydroxyindole charge). The DCM solution was dried over $MgSO_4$ and filtered and the DCM layer concentrated to half volume by distillation. Heptane (6 vol based on 4-hydroxyindole charge) was added and further DCM was removed by distillation until full precipitation of the Stage 1 had occurred. The reaction was cooled to 15-25° C. and the solids collected by filtration, washing with heptane (1 vol based on 4-hydroxyindole charge) dried under vacuum overnight at 60° C.

The differences from JNP and the benefits can be summarised as follows:
i) Applicant washed out the pyridine using citric acid at a pH of about 2-3. This facilitated improved isolation and crystallisation. In practice the DCM phase is separated and the aqueous citric acid phase discarded.
ii) An additional wash in sodium bicarbonate resulted in further improvement.
iii) A solvent swap to heptane improved solid precipitation maximising yield and resulting in reproducible high purity Stage 1.

Example 3

Figure 3:
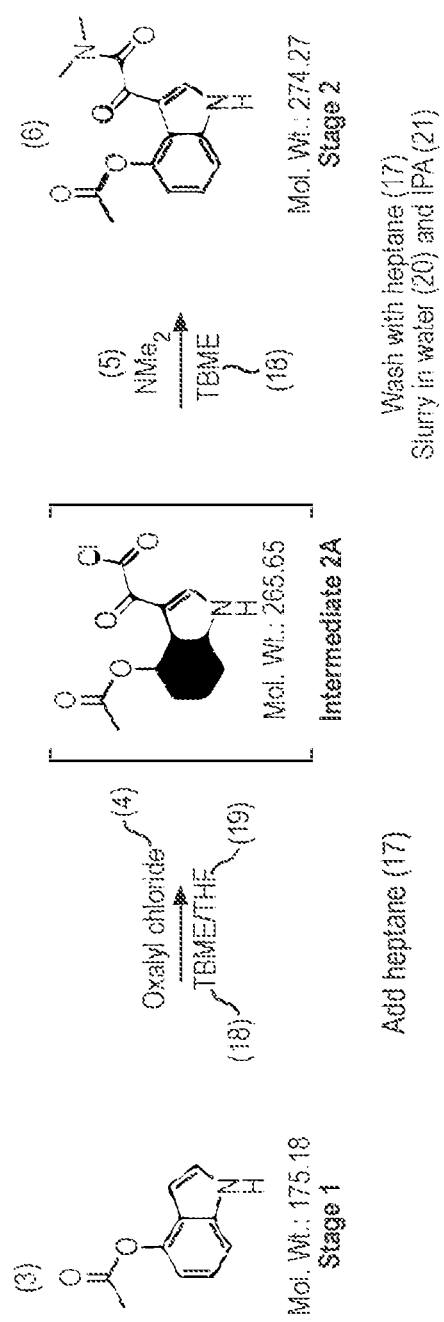
FIG. 3 is a schematic of the Stage 2 reaction of one aspect of the present invention.
Figure 4:
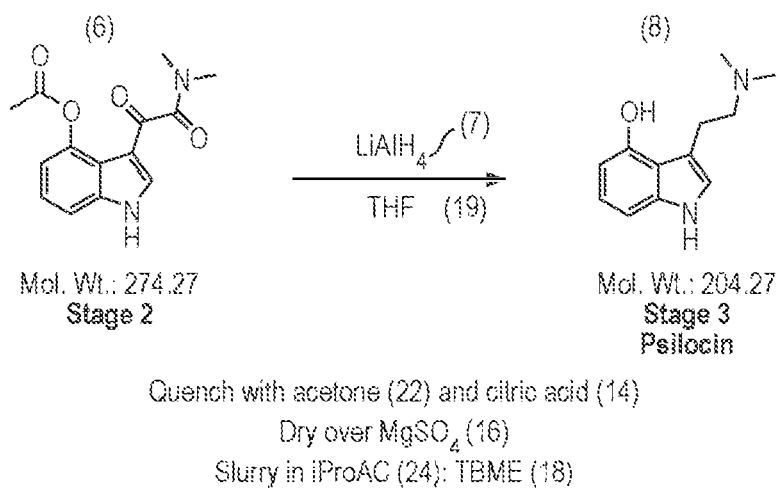
FIG. 4 is a schematic of the Stage 3 reaction of one aspect of the present invention.
Figure 5:
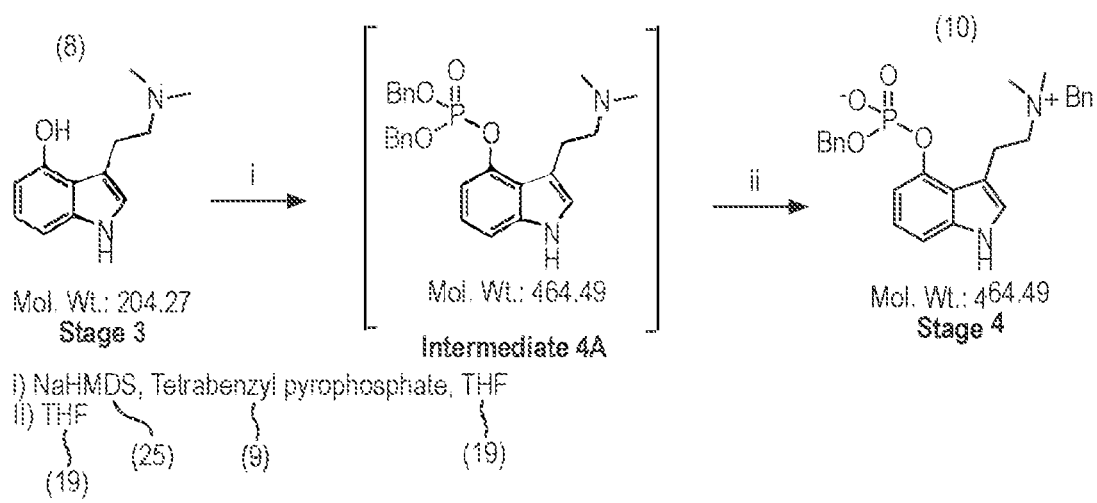
FIG. 5 is a schematic of the Stage 4 reaction of one aspect of the present invention.
Figure 6:
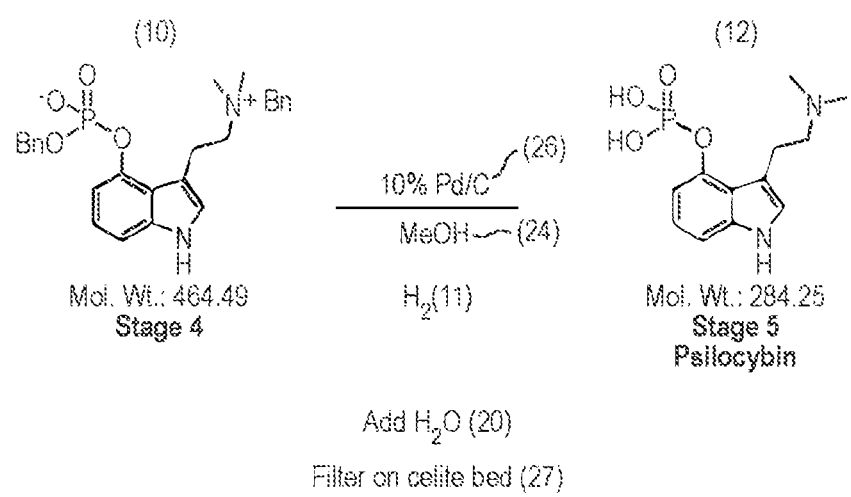
FIG. 6 is a schematic of the Stage 5 reaction of one aspect of the present invention.

Stage 2 (FIG. 3)

Step i—Acid Chloride Formation

Formation of reactive Intermediate 2A by reaction of the stage 1 product with oxalyl chloride (1.5 eq) was initially trialed in a mixture of TBME and THF (6 vol/1 vol) to determine if it was a viable alternative to volatile and highly flammable $Et_2O$ as used in the literature.

The reaction gave completion after ~18 hours with a similar solubility profile to $Et_2O$ (stage 1 in solution, precipitation of stage 2A).

As the acid chloride intermediate is prone to hydrolysis, leading to variable analytical results a more robust sample make up and analysis was developed in which the reaction was quenched into $THF/NMe_2$ (to give stage 2) and then analysed by HPLC. The ratio of TBME and THF was optimised to give the highest purity and yield of intermediate with a preferred ratio of TBME:THF of 6:1 chosen for scale up. Other ratios of TBME:THF may be used.

A scale up reaction was carried out using the preferred solvent mixture (1 vol THF, 6 vol TBME) but with the oxalyl chloride addition carried out at 30-35° C. The resulting solution was then heated at 40° C. for 2.5 hrs giving a completion with ~1% stage 1 product remaining. Carrying out the addition hot to maintain a solution ensures a high reaction rate and gave an improved level of completion with a much shorter reaction time (2.5 hrs vs overnight). The product was still seen to precipitate at temperature after ~15 min and no detrimental effect on the reaction profile was observed by HPLC.

As the stability of Intermediate 2A was not known, telescoping of material through to stage 2 was attempted rather than isolating the intermediate and risking degradation (hydrolysis). The reaction profile was complex with multiple components present at a low level. TBME was added and the precipitate collected. However, this was also found to be a complex mixture by HPLC/NMR.

Due to the poor reaction profile it was deemed necessary to isolate Intermediate 2A to allow for purification away from excess oxalyl chloride. The reaction was repeated and the yellow precipitate collected by filtration and washed with TBME to remove the excess oxalyl chloride (80% yield). NMR analysis confirmed the product to be of sufficient purity (~95% by NMR). However despite storing under nitrogen, some decomposition was noted over the following days giving partial hydrolysis including de-protection of the acetate group.

In order to try and reduce the potential for hydrolysis of the intermediate acid chloride during isolation, further investigations into a telescoped procedure were carried out. It was found that by allowing the reaction mixture to settle the TBME liquors could easily be decanted and then the residual solids washed with further portions of TBME in a similar manner. This allowed purification of Intermediate 2A away from excess oxalyl chloride whilst minimising exposure to moisture.

It was felt that some reaction yield may be lost due to partial solubility of the intermediate in the THF/TBME mixture. This was confirmed by adding heptane to the decantation liquors which gave precipitation of further solids. To limit this solubility, a heptane (8 vol) addition was made prior to decantation. Rather than washing the solids with TBME, heptane was also used for the washes (3×6 vol) which maximised the yield while maintaining the high purity of the intermediate. This methodology was successfully scaled up and is the preferred process.

Step ii—Reaction with Dimethylamine

The literature (Synthesis, 1999, 6, 935-938; D. E. Nichols) suggested $HNMe_2$ gas was effective for this transformation. However to simplify large scale processing this was substituted for either solid $HNMe_2 \cdot HCl$, with an additional excess of base, or a solution of $HNMe_2$ in THF. JNP uses $HNMe_2$ in the presence of excess base (pyridine).

Initially isolated Intermediate 2A was used to optimise the reaction with dimethylamine via a series of trial reactions (see Table 11).

TABLE 11

Stage 2 reaction optimisation trials

| # | Dimethylamine Source | Base | Solvent | HPLC completion | Isolated solids |
|---|---|---|---|---|---|
| 1 | 2M $HNMe_2$/ THF 1.2 eq | Pyridine 1.3 eq | THF/TBME | 80% product, | 64% yield, ~70% pure by NMR, |
| 2 | $HNMe_2 \cdot HCl$ 1.5 eq | $K_2CO_3$ | THF/$H_2O$ | 70% product | 40% yield ~98% by NMR. |
| 3 | 2M $HNMe_2$/ THF 1.33 eq | Pyridine 3.6 eq | $Et_2O$ | 81% product | 63% yield, ~90% by NMR. |
| 4 | 2M $HNMe_2$/ THF 2.9 eq | N/A | $Et_2O$ | 93% product | 72% yield, ~98% by NMR. |

The literature supplied conditions with pyridine (#1) were trialed along with a similar reaction in $Et_2O$ (#3), a biphasic reaction using $Me_2NH \cdot HCl$ and aqueous $K_2CO_3$ (#2) and a reaction with excess 2M $Me_2NH$ in THF (#4). The major component by HPLC was the desired product in all cases with the conditions using aqueous base and excess $Me_2NH$ being generally much cleaner than those with pyridine. While significant hydrolysis product was seen in all cases this was thought to be the result of unreacted Intermediate 2A which was quenched during sample makeup for HPLC analysis. The reactions were worked up by addition of water and then the organic solvent was removed in vacuo giving precipitation of solids.

The reaction with excess amine showed a much improved impurity profile which translated into a higher yield (72% vs 63%) and purity (98% vs 90%). This approach limited the water content of the reaction and therefore minimised the opportunity for hydrolysis to occur. Purification was also expected to be more facile due to the absence of pyridine in the isolated solids. For these reasons the conditions with excess $HNMe_2$ as base were chosen for scale up.

The reaction in $Et_2O$ gave a clean (#4) profile. However, to facilitate large scale processing it proved advantageous to switch to a less volatile solvent, such as TBME. This would facilitate telescoping the acid chloride into this reaction. For these reasons it was chosen to carry out the reaction in TBME using excess 2M $Me_2NH$ in THF.

It was believed that the addition of water would aid the workup by solubilising the $HNMe_2 \cdot HCl$ salts that were present and resulted in a very thick mixture and slow filtrations. This was trialed. However, when water was added to the reactions in TBME and THF a poor recovery was obtained with analysis of the liquors showing additional impurities and extensive acetate de-protection (phenol product). Further development of the purification was therefore required.

Purification Development

It was desirable to develop a purification strategy that would remove the hydrolysis product and other impurities observed. It was also desirable to include water in the crystallisation to reduce the salt content of the isolated material (assumed $HNMe_2 \cdot HCl$). To this end a series of 15 solvents and solvent mixtures were screened (100 mg scale, 10 vol solvent, heat cycling to 60° C.).

TABLE 12

Stage 2 purification trials

| Solvent | Observations | Recovery | HPLC Purity (hydrolysis imp of Intermediate 2A) |
|---|---|---|---|
| TBME | Slurry | 47 mg* | 96.4% (2.8%) |
| DCM | Slurry | 60 mg | 99.5% (0.5%) |
| Toluene | Slurry | 30 mg* | 95.8% (3.4%) |
| EtOAc | Slurry | 66 mg* | 97.8% (1.6%) |
| iPrOAc | Slurry | 40 mg* | 97.3% (2.0%) |
| IPA | Slurry | 65 mg | 99.4% (0.4%) |
| EtOH/$H_2O$, 1:1 | Slurry | 62 mg | 99.4% (0.5%) |
| MeCN/$H_2O$, 1:1 | Partial solution at RT Solution at 60° C. | 30 mg | 99.0% (0.7%) |
| Acetone/$H_2O$, 1:1 | Slurry at RT Solution at 60° C. | 51 mg | 99.4% (0.5%) |
| THF/$H_2O$, 1:1 | Partial solution at RT Solution at 60° C. | No precipitate | n/a |

TABLE 12-continued

Stage 2 purification trials

| Solvent | Observations | Recovery | HPLC Purity (hydrolysis imp of Intermediate 2A) |
|---|---|---|---|
| Heptane | Slurry | 34 mg* | 95.0% (3.6%) |
| MIBK | Slurry | 65 mg | 97.9% (1.4%) |
| MEK | Slurry | 60 mg | 99.6% (0.3%) |
| Cyclohexane | Slurry | 41 mg* | 94.4% (4%) |
| Xylenes | Slurry | 56 mg* | 96.1% (3%) |

*Recovery not representative due to thick suspensions and solids adhering to the glass vial.

From the solvents screened acetone/water gave a re-crystallisation with little observed solubility at room temperature. Since this was an aqueous system it had the advantage of helping to purge $Me_2NH \cdot HCl$ from the solids.

The acetone/water re-crystallisation was scaled up. A solution was obtained at temperature (5 vol acetone, 1 vol water) prior to addition of further water (4 vol) and the mixture cooled to RT giving crystallisation (62% recovery, >99% HPLC purity). This process was subsequently scaled up further with addition of more water to aid the recovery (in total 5 vol acetone, 10 vol water, 78% recovery).

The process was scaled up further (30 g) and the crude solids taken through the re-crystallisation procedure. While product purity was high, there was a drop in yield (56% yield, 99% by NMR assay, 99.4% by HPLC).

In order to improve the recovery, the amount of water added was further increased from 10 vol to 15 vol. This maintained product purity at greater than 99% and gave a higher recovery on a small scale (90% recovery, 56-70% previously observed). However, scale up of this amended procedure again gave a low recovery (58% yield). Therefore, due to the issues encountered when scaling up the re-crystallisation, an alternative means of purification was sought based on the original slurry screen that was carried out (Table 12 above).

Redevelopment of the purification strategy took place using material isolated from a large scale, stage 2, reaction. The reaction progressed as expected to give crude product after oven drying (70% by NMR assay, 79% active yield). To remove the significant salt component (presumed to be $HNMe_2 \cdot HCl$) a portion was water slurried at RT. After drying this gave 75% recovery (95% by NMR assay) showing this to be an effective means of reducing the salt content. HPLC purity remained unchanged at ~93%. A method was then sought to increase the chemical purity of the solids.

From the initial screen both $EtOH:H_2O$, IPA and acetone:$H_2O$ appeared to give high purity product with a good recovery and so these solvent systems were chosen for further investigation. Input purity was 92.7% with the main impurities at levels of 1.4%, 1.0% and 0.8%.

TABLE 13

Further purification development (slurry at 40° C. 1 hr, filtration at RT, 1 vol wash)

| | | HPLC purity (main impurity levels) | | | |
|---|---|---|---|---|---|
| Solvent system | Recovery | Product | Imp 1 | Imp 2 | Imp 3 |
| Acetone/Water 6/16 vol | 67% | 98.8% | 0.7% | 0.2% | 0.1% |
| 1:1 EtOH:H₂O 10 vol | 79% | 98.0% | 0.9% | 0.5% | 0.2% |
| IPA 10 vol | 90% | 97.5% | 0.8% | 0.8% | 0.3% |
| IPA 5 vol | 92% | 97.2% | 1.0% | 0.7% | 0.3% |
| 4.5:2.5 IPA:H₂O * 7 vol | 79% | 98.7% | 0.6% | 0.4% | 0.1% |
| 6:1 IPA:H₂O 7 vol | 82% ** | 98.0% | 0.9% | 0.6% | 0.2% |

* The reaction was initially run in 1:1 IPA:H₂O at 5 vol. However it became too thick to stir and so a further 2 vol of IPA was added.
** The mixture was thick and the solids present were very fine making filtration difficult with some solids beating the filter.

The results of these trials suggested that good recoveries were possible from these systems, particularly those based on IPA. $EtOH:H_2O$ gave a marginally better impurity profile than IPA alone; however the recovery was not as good (79 vs 90%). The impurity profile with IPA was greatly enhanced by the presence of water (98.7% vs ~97.5%) however this led to a lower recovery (79 vs 90%). This suggested a certain level of water solubility for the compound. A final trial in IPA and EtOH:Water was conducted with reduced water volumes to see if a balance could be found that provided high purity and a recovery of ~90%. While this system improved the yield the filtration was slow and therefore further solvent mixtures were also evaluated.

TABLE 14

Examination of further solvent mixtures (500 mg scale, slurry at 40° C. 1 hr, filtration at RT, 1 vol wash)

| | | HPLC purity (impurity levels) | | | |
|---|---|---|---|---|---|
| Solvent system | Recovery | Product | Imp 1 | Imp 2 | Imp 3 |
| IPA 10 vol | 460 mg (92%) | 97.6% | 1.1% | 0.7% | 0.3% |
| 1:3 EtOH:H2O 5 vol | 451 mg (90%) | 96.2% | 1.4% | 0.8% | 0.5% |
| 1:2 EtOH:H2O 5 vol | 440 mg (88%) | 97.5% | 1.3% | 0.7% | 0.4% |
| 1:1 EtOH:H2O 5 vol | 375 mg (75%) | 97.9% | 1.0% | 0.7% | 0.3% |
| 2:1 EtOH:H2O 5 vol | 354 mg (71%) | 97.6% | 1.0% | 0.6% | 0.4% |
| 3:1 EtOH:H2O 5 vol | 369 mg (74%) | 97.9% | 0.9% | 0.5% | 0.3% |

The 5 vol EtOH/Water slurries were very thick and not easily handled. Since the purity of the solids was comparable from all the trials (slight variations are likely due to the quality of the filtration and wash), the 100% IPA conditions were scaled up as they offered a high recovery and the resulting suspension was easily handled.

An initial scale up of the preferred slurry gave (92% recovery) with HPLC purity of 96.4% (Impurity levels of 1.2%, 0.7%, 0.4%). Liquors analysis showed them to be enriched in all of the main impurities—72% (8.6%, 3.8%, 3.4%) by HPLC. This was deemed a suitable purification method offering a high recovery and the material was use tested in the following stage to ensure tracking and removal of the impurities was achieved downstream (>99% at stage 3, no single impurity >0.5%).

The slurry proved scalable when remaining crude stage 2 material (70% assay) was water slurried to remove inorganics, and then slurried in IPA to give material of improved purity (97% by NMR assay, 76% yield for stage 2, 96.8% by HPLC, impurities at 1.1%, 0.8%, 0.4%).

GMP Raw Material Synthesis

A large scale, stage 2 reaction was carried out to supply the GMP campaign. The reaction progressed as expected to provide crude product that was water slurried and filtered to provide stage 2 that was 93% pure by HPLC. This was further slurried in 8 vol IPA and filtered to give stage 2 product (93.7% by HPLC, 92% assay, 66% active yield). Since the purity obtained was lower than that observed during the development campaign, a use test was conducted which confirmed that high purity stage 3 obtained was suitable for onward processing (GMP raw material).

A second batch was carried out under identical conditions to give crude product which after a water slurry was 90% pure by HPLC. This material was subsequently water slurried and purified by IPA slurry to give 384 g of stage 2 product (93.0% by HPLC, 91% NMR assay, 60% active yield).

A third batch was carried out to resupply the GMP synthesis. The crude product was successfully purified by a water then IPA slurry to deliver stage 2 (79% yield) with an increased purity when compared to previous batches (97.3% by HPLC, 96% NMR assay).

Experimental

Stage 1 (1 eq. limiting reagent) was charged to a vessel under $N_2$ followed by THF (1 vol wrt stage 1 charge) and TBME (6 vol wrt stage 1 charge). Oxalyl chloride was then added dropwise to the vessel (1.5 eq,) allowing the exotherm to initially raise the temperature to 35-40° C. and then applying cooling as required to maintain 35-40° C. Immediately following the addition the reaction was heated to 40° C. and stirred for 2-6 hours. The reaction was sampled and analysed for completion, then cooled to RT and heptane (8 vol wrt stage 1 charge) added giving precipitation of further solids. The reaction was stirred for 10 min and then the solids were allowed to settle. The majority of the solvent was decanted from the solid which was then washed twice with heptane (2×6 vol wrt stage 1 charge), decanting in a similar manner after each wash. The solids were then sampled and analysed. TBME was charged to the vessel (4 vol wrt stage 1 charge) to give a yellow slurry which was cooled to −20° C. using a dry ice/acetone bath. A 2M solution of $Me_2NH$ in THF (2 eq,) was added dropwise to the vessel over ~15 min maintaining the temperature at −20° C. to −10° C. The reaction mixture was allowed to warm slowly to RT and stirred overnight. Further $Me_2NH$ can be added at this point if required. The reaction was sampled and analysed for completion. The reaction was filtered, washing with heptane (2×2 vol wrt stage 1 charge) and the isolated solids dried at 60° C. under vacuum. The crude stage 2 was slurried in water (8 vol wrt stage 1 charge) for 2-18 hours and then filtered, washing with water (2 vol wrt stage 1 charge). The solids were dried at 60° C. under vacuum to obtain crude stage 2 with <2% w/w water (determined by Karl Fischer titration (KF)). The crude stage 2 was slurried in IPA (10 vol) for 2-18 hrs and then filtered, washed with IPA (1 vol wrt mass of crude Stage 2) and oven dried under vacuum at 60° C.

The differences from JNP and the benefits can be summarised as follows:

Step 1
  i) Firstly, the use of a THF/TBME solvent system in place of diethyl ether was less volatile and flammable.
  ii) Secondly, the addition of oxalyl chloride was conducted at an elevated temperature, heated to 40° C.,
    giving rise to improved solubility and preventing entrapment of stage 1 product in the precipitate. It also provided a high reaction rate, improved levels of completion and shorter reaction times.
  iii) Thirdly, the Intermediate 2A was isolated to allow for purification away from excess oxalyl chloride.
  iv) Fourthly, heptane was added to help precipitate Intermediate 2A.

Step 2
  v) By ensuring the amine was used in excess much improved purity and yields were obtained, due to minimal water being present, and hence reduced hydrolysis.
  vi) Finally, the use of water and IPA slurries provided good purity of the Stage 2 product.

Example 4

Stage 3

An initial stage 3 trial reaction was carried out using purified stage 2 material (>99% by HPLC) and the supplied reaction conditions. The stage 2 input material was found to be largely insoluble in THF, and so rather than adding a solution of stage 2 to $LiAlH_4$ the reverse addition was carried out. 4 eq of $LiAlH_4$ was used as a 1M solution in THF with the addition made at 20-25° C., over ~2 hrs. At this point 10% product was observed with several intermediate species present. The reaction was heated at reflux for ~7 hrs to give 93% product conversion (by HPLC). The reaction was worked up to give crude stage 3 product (~90% by HPLC, ~90% by NMR, ~87% corrected yield).

A trial reaction was carried out in which the $LiAlH_4$ charge employed was successfully reduced (3 eq vs 4 eq). It was hoped this would benefit the work up by reducing the quantity of Li and Al salts generated. After prolonged heating at reflux (10-18 hrs) the reaction intermediate was largely consumed (2-3% remaining) with ~95% product by HPLC.

Workup Development

Although the first trial reaction was successfully worked up using Rochelles salt, the volumes employed were very high (~100 vol) and this procedure would not form a viable process for scale up. A variety of alternative workup procedures were examined in order to try and reduce the volumes required and aid removal of Li/Al salts.

A reduced volume quench was trialed with EtOAc and then Rochelles salt. Grey solids were present as a thick paste which settled to the bottom of the flask. While filtration failed, the liquors could be decanted and the solids re-slurried in THF/EtOAc to extract the product. An aqueous workup was then carried out and the product isolated by concentration. This yielded product of good purity (90-95% by NMR) in good yield (94% uncorrected for purity). However the process was not readily amenable to scale up.

A reaction was quenched by addition of EtOAc and then sat. $Na_2SO_4$ in the presence of anhydrous $Na_2SO_4$ to act as a binding agent. The reaction gave granular solids which could be readily filtered. An aqueous workup was then carried out and the product isolated by concentration. A good yield was obtained (~94% uncorrected for purity) but the product contained higher levels of the main impurity by NMR (10% vs 2-4% usually observed).

A reaction was quenched with 20% AcOH at 0° C. leading to the formation of a gel which could not be filtered. The reaction was abandoned.

A reaction was quenched with EtOAc and then 20% citric acid to give solids which could be separated by filtration.

The liquors were concentrated to obtain the product. While this procedure was slightly lower yielding (~77% uncorrected for purity), the product was of very high purity (>95%).

A further reaction was quenched by the addition of EtOAc and then water (3 mL per g of LiAlH$_4$ in THF). A gel formed which could not be readily filtered and the reaction was abandoned.

Finally, a reaction was quenched by the Fieser method. An addition of water (1 mL per g of LiAlH$_4$) was made then 15% NaOH (1 mL per g of LiAlH$_4$) and finally water (3 mL per g of LiAlH$_4$). This gave solids which could be filtered from the reaction mixture. The liquors were then partitioned and concentrated in vacuo (87% yield, 90-95% by NMR).

These Experiments are summarised in Table 15 below:

TABLE 15

Summary of alternative workup conditions

| # | Workup procedure | Yield | Purity |
|---|---|---|---|
| 3.1 | EtOAc quench Rochelles salt (reduced vol.) | 2.8 g (94% uncorrected) | 90-95% by NMR |
| 3.2 | EtOAc quench in presence of Na$_2$SO$_4$ | 2.8 g (94% uncorrected) | ~80-85% by NMR, 10% imp. |
| 3.3 | 20% AcOH quench | Emulsion (reaction to waste) | |
| 3.4 | EtOAc quench 20% citric acid | i) 529 mg (71% uncorrected) ii) 2.3 g (77% uncorrected) | >95% purity by NMR |
| 3.5 | Water quench | Emulsion (reaction to waste) | |
| 3.6 | Water/NaOH quench | i) 615 mg (83% uncorrected) ii) 2.6 g (87% uncorrected) | 90-95% by NMR |

Both quenches with citric acid and NaOH gave solids that could be readily filtered from the reaction mixture and required minimal solvent volumes. While the conditions with NaOH were higher yielding (~10%), the product obtained from this procedure was less pure and would likely require further purification before use in the next stage. The lower yield with citric acid was likely due to some precipitation of the product citrate salt. This had a purifying effect with clean product obtained directly after concentration. These conditions were chosen for scale up and it was hoped that further optimisation of the citric acid charge would enable clean product to be isolated in high yield from this process.

The reaction was repeated with a slightly reduced citric acid charge in order to try and maximise the recovery. This reaction yielded product in 57% yield with a further 20% yield obtained by re-slurry of the filter cake in THF (both samples 97.7% by HPLC).

The reaction was scaled up. However during the EtOAc quench, where the reaction was previously seen to thicken, the reaction gummed in the flask to form a thick mass which restricted mixing. While the addition of citric acid then led to the usual slurry/gel this did not represent a viable process. This reaction was worked up with the filter cake re-slurried in THF to maximise the recovery giving 76% active yield, 95.0% by HPLC.

The reaction was repeated in order to develop a better quench and avoid the gum formation seen with EtOAc. A portion was quenched by addition of acetone which led to a readily stirred suspension/emulsion with no sign of thickening. The citric acid treatment was then carried out to give a filterable mixture. This quench was successfully carried out on the remainder of the reaction and worked up to provide crude product in good yield (71% assay, 82% corrected yield, 98.0% by HPLC).

After the quench the reaction mixture was generally found to be pH 8/9. As part of the workup optimisation process different pHs were investigated. A reaction was split for workup with half receiving a slightly reduced citric acid charge (to obtain pH 11/12 after quench) and the other half taken to pH 7 by addition of further citric acid. The pH 11 reaction was worked up to give material of 85% NMR assay (73% yield) with the pH 7 reaction giving 60% NMR assay (62% yield). It was clear from this result that obtaining the correct pH after quench was critical in order to give a >70% yield. By reducing citric acid charge only slightly (still approx. 2 vol of 20% citric acid) an approx. 8% increase in yield was obtained. With this information in hand the pH of future reactions was monitored during the quench in order to ensure the mixture remained strongly basic.

Purification Development

A purification screen was carried out using 100 mg portions of crude Psilocin product which were slurried in 10 vol of solvent with heat cycling to 60° C. The slurries were cooled to RT over the weekend and then any solids collected by filtration. Stability to acid and base was also tested with the view to carrying out an acid/base workup. The results of the screen are presented in Table 16 below:

TABLE 16

Psilocin purification screen. (Input purity and 3 main impurity levels: 90.2%, 3.8%, 0.9%, 0%).

| Solvent | Observations | Recovery (approx.) | HPLC Purity (and main impurity levels) |
|---|---|---|---|
| MeOH | Solution at RT | n/a | n/a |
| EtOH | Solution at 60° C. Precipitate at RT | 35 mg | 97.2%, 0.4%, 1.1%, 0.8% |
| IPA | Slurry at 60° C. | 51 mg | 97.6%, 0.5%, 0.5%, 1.1% |
| MeCN | Solution at 60° C. Precipitate at RT | 46 mg | 96.8%, 0.6%, 0.4%, 1.6% |
| EtOAc | Slurry at 60° C. | 58 mg | 97.1%, 0.9%, 0.2%, 1.3% |
| $^i$PrOAc | Slurry at 60° C. | 58 mg | 98.2%, 0.8%, 0.2%, 0.4% |
| Toluene | Slurry at 60° C. | 70 mg | 93.3%, 3.6%, 0.2%, 0.8% |
| Heptane | Slurry at 60° C. | 77 mg | 91.3%, 3.8%, 0.2%, 0.7% |
| Acetone | Solution at 60° C. Precipitate at RT | 30 mg | 97.7%, 0.4%, 0.3%, 0.9% |
| MEK | Solution at 60° C. Precipitate at RT | 24 mg | 97.3%, 0.5%, 0.5%, 1.2% |
| MIBK | Slurry at 60° C. | 49 mg | 97.4%, 0.6%, 0.2%, 1.3% |
| THF | Solution at RT | n/a | n/a |
| TBME | Slurry at 60° C. | 67 mg | 95.5%, 2.0%, 0.1%, 1.5% |
| DCM | Solution at RT | n/a | n/a |
| 1M HCl | Solution at RT | n/a | 83.7%, new imp 8% |
| 1M KOH | Slurry at RT (black) | n/a | 89.1%, 5.4%, 0.9%, 2.2% |

The first of the three highlighted impurities corresponded with the most stable reaction intermediate that is observed at ~70%, when the LiAlH$_4$ addition is complete (requiring refluxing to convert to product). The third impurity was not present in the input and appeared to be generated during the slurry procedure. Of the solvents that remained as a slurry, $^i$PrOAc gave the highest purity. Several re-crystallisations were found with MeCN having the potential to remove impurities during the crystallisation and having a recovery which had the potential to improve during development.

Some degradation was observed in both acid and base with the KOH sample rapidly turning black.

Purification of the crude stage 3 material was scaled up using the two most promising solvents (MeCN and $^i$PrOAc). The solvent volumes were reduced to a minimum in order to improve the recovery. The results of these trials are presented in Table 17 below.

TABLE 17

Further development of MeCN/$^i$PrOAc purification

| Solvent | Observations | Recovery (%) | HPLC Purity (and main impurity levels) |
|---|---|---|---|
| MeCN (5 vol) | Recryst in 5 vol | 512 mg (51%) | 97.6%, 0.7%, 0.8%, 0% |
| $^i$PrOAc (3 vol) | Slurry in 3 vol | 706 mg (71%) | 95.8%, 1.3%, 0.6%, 0% |

A re-crystallisation was obtained from MeCN in 5 vol and a hot slurry was achieved in $^i$PrOAc at 3 vol (both at 75° C.). The recovery from MeCN was again poor despite reduced volumes, however the product was of very high purity (>>95% by NMR). The recovery from $^i$PrOAc was better with a large increase in product purity when analysed by NMR (~95%).

Although HPLC and NMR purity of material from the iPrOAc slurry was high, a low assay value (85% by NMR assay) was observed. In order to improve the assay value of the material, as well as remove colour, (all materials obtained so far were strongly purple, green or brown) purification by silica pad was investigated.

Crude Psilocin (71% assay, 98.0% by HPLC) was passed through 4 eq of silica eluting with THF. An 80% recovery of an off white solid with slightly improved HPLC purity (98.4%) and assay value (~82% assay) was obtained. This proved to be an effective means of increasing the product assay value and was therefore included as part of the reaction workup.

A series of $^i$PrOAc/anti-solvent slurries (Table 18) were then performed using the silica treated input (100 mg per slurry) to try and improve the recovery, whist maintaining chemical purity (input purity 98.4%).

TABLE 18

Results of $^i$PrOAc/anti-solvent additions.

| Solvent system | Recovery | HPLC purity |
|---|---|---|
| $^i$PrOAc 5 vol | 78% | 99.7% |
| 1:1 $^i$PrOAc:Heptane 5 vol | 70% | 99.6% |
| 1:1 $^i$PrOAc:TBME 5 vol | 83% | 99.7% |
| 1:1 $^i$PrOAc:Toluene 5 vol | 84% | 99.4% |
| $^i$BuOAc 5 vol | 80% | 99.6% |

Since all purity values were comparable, two solvent systems were chosen for scale up based on the highest recoveries obtained. The two favoured slurries (TBME and Toluene as anti-solvent) were scaled up (1.0 g per slurry) to better assess the recovery.

TABLE 19

Scale up of favoured purification methods

| Solvent system | Recovery | HPLC purity |
|---|---|---|
| 1:1 $^i$PrOAc:TBME 5 vol | 79.9% | 99.1% |
| 1:1 $^i$PrOAc:Toluene 5 vol | 79.4% | 99.6% |

Both of these options provided material of >99% HPLC purity at ~80% recovery and, combined with a silica pad, appear to provide an effective means of purification for the Psilocin product. Further colour was removed into the liquors during the slurry giving Psilocin as a white solid. All impurities were effectively removed to below 0.5%. The $^i$PrOAc:TBME slurry was chosen for scale up as this used non-toxic ICH class 3 solvents.

Scale Up

The developed stage 3 conditions were scaled up and the reaction progressed to give a completion of 94.4% product with 2.9% of the reaction intermediate present by HPLC after overnight at reflux (typical of the process). After a silica pad Psilocin was obtained in 83% purity by NMR assay, 66% active yield, 97.0% by HPLC. This material was further purified by slurry in iPrOAc/TBME to give material 100% by NMR assay in 62% yield and 99.7% by HPLC.

Due to the crude yield from the reaction being lower than expected (66% vs ~75%) the filter cake and silica pad were reinvestigated in order to try and recover additional material. However, this was unsuccessful.

The lower than expected yield may have been due to decomposition of the product during workup, although previous stress tests had indicated the material to be stable under the conditions used. To investigate this further the reaction was repeated. The crude product was isolated before the silica pad and additional stress test samples taken to confirm degradation of the product was not occurring during workup.

The reaction progressed as expected to give completion (93.7% product, 2.9% intermediate) and was concentrated yielding crude material (77% NMR assay, 66% active yield). The filter cake was re-slurried in THF/MeOH but no significant Psilocin was isolated. In order to try and displace any product that was coordinated to the aluminium salts, further citric acid was added to take the pH to 4 (from pH 8) and the cake re-slurried in THF, but again no significant Psilocin was isolated. Mass balance was not obtained from the reaction with the 66% active yield closely matching what was previously obtained. This batch was purified by silica pad and slurry in $^i$PrOAc/TBME to give a 62% yield of high purity material (99.8% by HPLC).

Despite the solvent volumes employed being relatively high and a silica pad being required for removal of aluminium and lithium species, the process was still well suited to the required scale.

The stage 3 reaction was further scaled up to process. The reaction proceeded as expected to give completion after 18 hours (~91% product, ~3% reaction intermediate remaining). Workup by silica pad and slurry gave a 57% yield of high purity Psilocin (>99% by HPLC, 99% NMR assay, 0.35% w/w water Karl Fischer).

Experimental

Stage 2 (1 eq. limiting reagent) was charged to the vessel followed by THF (5 vol wrt stage 2 charge). The mixture was cooled to 0° C. and a 1M THF solution of LiAlH$_4$ (3 eq,) added dropwise over 30-45 min maintaining the temperature at 0-20° C. Following the addition, the reaction was stirred for 30 min at 10-20° C. and then heated to reflux and stirred for ~16 hrs. The reaction was sampled and analysed for completion, cooled to 0° C. and quenched by dropwise addition of acetone (9.3 eq.) at 0-30° C. followed by a 20% aq citric acid soln (1.9 vol wrt stage 2 charge) at 0-30° C. The pH of the addition was monitored to ensure that it remains at pH>11 and the addition was stopped early if required. The resulting suspension was stirred for 1 hr and filtered, washing with THF (2 vol wrt stage 2 charge) to remove Li and Al salts. The filter cake was slurried in THF (12.5 vol wrt stage 2 charge) for ~1 hr and filtered, washing with THF (5 vol wrt stage 2 charge) to recover product from the Li and Al salts. The combined organics were dried over $MgSO_4$ and filtered. The filtrate was evaporated in vacuo until approximately 10 volumes remained (wrt stage 2 charge) and this solution was applied to a silica pad (3 eq wrt stage 2 charge). The silica pad was eluted with THF and the product fractions were combined and evaporated to dryness in vacuo. The crude stage 3 (Psilocin) was slurried in 1:1 iPrOAc:TBME (5 vol wrt mass at step 18) for 2-18 hrs, filtered, washing with TBME (2.5 vol wrt mass at step 18) and dried in vacuo at 40° C. to isolate pure Psilocin.

The differences from JNP and the benefits can be summarised as follows:

i) Firstly, Applicant, whilst using THF as a solvent, quenched the reaching using acetone. This lead to a suspension/emulsion without thickening.

ii) Secondly, Applicant quenched with citric acid maintaining a basic pH, typically about 11. The pH control ensured high yields were obtained.

iii) Thirdly, following purification by silica pad, to remove residual Li/Al salts, eluting with THF, a iPrOAc:TBME slurry provides a highly purified product which was then dried.

Example 5

Stage 4

Initially the literature conditions were used to process a 2.58 g sample giving ~88% conversion to Intermediate 4A when analysed by HPLC. The product was purified by the addition of aminopropyl silica and filtration through Celite. The resulting green oil (5.5 g) was slurried in DCM giving benzyl transfer and precipitation of the zwitterionic stage 4 (4.1 g, 70% yield, ~95% by NMR).

Step

Initial development at this stage was focused on finding an alternative to "BuLi that was easier to handle and ideally did not introduce further lithium into the synthesis. An initial screen of alternative conditions was carried out including the following bases: Li$^t$BuO, K$^t$BuO, NaH, NaHMDS, and NaNH$_2$. All of the reactions gave product with NaHMDS performing as well as "BuLi. All of the reactions became very thick with gelling observed and overhead stirring was recommended for efficient stirring.

The initial screen suggested NaHMDS would be a suitable alternative to "BuLi (81% conversion to product/Intermediate 4A). These conditions were scaled up to 1.5 g alongside a reference reaction with "BuLi. Overhead stirring was used in both cases.

TABLE 20

Comparison of "BuLi and NaHMDS

| Timepoint | HPLC - "BuLi | HPLC - NaHMDS |
|---|---|---|
| 1 hr, −30° C. | 6.6% St 3, 78% Int 4A, 1% St 4 | <1% St 3, 78% Int 4A, 4% St 4 |
| 2 hr, 0° C. | 6.5% St 3, 77% Int 4A, 1% St 4 | <1% St 3, 76% Int 4A, 4% St 4 |
| Crude product | 4.89 g <1% St 3, 2% Int 4A, 60% St 4 | 4.38 g <1% St 3, 5% Int4A, 68% St 4 |

Abbreviations used in the table: St 3 = Stage 3, Int 4A = Intermediate 4A, St 4 = Stage 4

The reaction profile obtained in both cases was very similar with the NaHMDS reaction giving consumption of stage 3. Both reactions were filtered on Celite to remove a white precipitate and concentrated. By NMR excess benzyl protons were present in both cases (especially in the example with "BuLi) and the isolated yield was >100%. The NaHMDS conditions proved successful giving a favourable reaction profile and were chosen for further scale up. However, workup and purification development was required.

Step ii

HPLC data indicated the material isolated from the trials above using NaHMDS and "BuLi had rearranged to give zwitterionic stage 4 upon concentration. Purification of this material away from the benzylphosphoric acid by-products and other impurities was attempted by slurry in a number of solvents.

TABLE 21

Trial purification of crude stage 4 product

| Solvent | Mass recovered | HPLC Purity |
|---|---|---|
| DCM | White solid | 84% St 4 |
| EtOH | Gum | — |
| EtOAc | Gum | — |
| IPA | White solid | 88% St 4 |
| Toluene | Gum | — |
| TBME | White solid | 62% St 4 |
| MIBK | Gum | — |
| MeCN | Gum | — |
| Acetone | White solid | 86% St 4 |

Abbreviations used in table: St 4 = Stage 4

White solids were obtained from several solvents however the solids obtained from DCM and TBME turned to a pale purple gum when stored over the weekend. Those obtained from IPA and acetone remained as free flowing white solids on storage suggesting that the stability of these solids was likely to be higher and that they would allow for easier handling.

The slurries in IPA and acetone were scaled up to 1 g. However, gumming was noticed immediately on addition of the solvent. The gum was slowly dispersed by vigorous stirring and eventually showed signs of crystallisation, with a white slurry forming after an overnight stir. However, this process was not suitable for scale up. Solids were isolated in good yield with IPA providing the highest purity.

THF was also investigated as this had advantages in that it was also the reaction solvent. However, when this was trialed initial gum formation was again observed (isolated ~80% yield, ~92% by HPLC). In order to try and avoid the gum formation and give a more controlled crystallisation the crude stage 4 was first solubilised in a low volume of DMSO (2 vol). THF was then added to this (10 vol) and the solution stirred over the weekend. This slowly gave precipitation of the product which was collected by filtration and washed with THF to yield stage 4 (86% yield) with 96% HPLC purity (>95% by NMR).

As the THF crystallisation was successful and it was previously noted that complete conversion to zwitterionic stage 4 occurred during concentration of the reaction liquors (THF/EtOAc) at 40° C., it was hoped that the changes of solvent could be avoided and the product crystallised directly by stirring out the reaction mixture at 40° C.

Two 4 g NaHMDS reactions were carried out with both reactions reaching completion with ~80% conversion to Intermediate 4A. One reaction was diluted with EtOAc and the other with THF and both were filtered to remove phosphate by-products. In order to further reduce the phosphate impurity levels a brine wash was carried out and the organics dried and concentrated to 10 vol. These solutions were stirred overnight at 40° C. to give conversion to, and precipitation of, stage 4 (~1% stage 3, ~0.2% Intermediate 4A, ~82% stage 4). The solids were collected by filtration giving 8.03 g (88% yield) from EtOAc/THF and 5.65 g (62% yield) from THF. The brown/grey solids obtained from EtOAc/THF were of lower purity (~90% by HPLC, 78% assay) when compared to the white solids obtained from THF (97% by HPLC, 88% assay). Analysis of the aqueous layer from the THF reaction showed product to be present and additional losses were incurred to the final THF filtrate.

Due to the higher purity obtained from THF, this solvent was investigated further in order to optimise the recovery. The brine wash was omitted due to product losses to the aqueous layer and the reaction mixture was further concentrated after the reaction to minimise losses during the final filtration step. This new procedure was trialed on a 75 g scale with portions of the reaction mixture concentrated to 8 vol and 6 vol. Upon filtration no difference in yield was noted between the two portions with an overall yield of 140.4 g (90% by NMR assay, 74% active yield, 90% by HPLC).

Impurity Tracking

Three main impurities were observed in the isolated product, with identities for two of these species proposed based on MS data.

The debenzylated impurity (typically ~2-5% by HPLC) was shown to give psilocybin during the following hydrogenation and could therefore be tolerated at a higher level. The main observed impurity in the isolated stage 4 (typically ~5-8% by HPLC) was the anhydride impurity. This was tracked through the subsequent hydrogenation and shown to be readily removed by re-crystallisation from water as the highly soluble pyrophosphorate impurity that results from debenzylation. The other main observed impurity (m/z 295.2 observed by LCMS) was found to be controlled to less than 2% by limiting the reaction temperature (below −50° C.) and was not observed in Psilocybin after hydrogenation.

The impurity profile of the 140 g batch produced above showed 90.0% stage 4, 6.4% anhydride impurity, 0.2% N-debenzylated impurity and 1.2% of the m/z 295.2 impurity.

GMP Synthesis

The first large scale stage 3 batch (544 g input) was completed using the established procedure to give 213.5 g (53% yield, 99% by HPLC). A second batch (628.2 g input) was also processed successfully to give 295.2 g (66% yield, 99% by HPLC).

Some variability in yield at this stage was noted over 3 large scale batches (57%, 53% and 66%). This is probably a consequence of minor differences in the workup and quench procedure.

Experimental

Stage 3 was charged to a vessel followed by THF (15 vol wrt stage 3 charge) and cooled to ≤−50° C. using a dry ice/acetone bath. 1M NaHMDS solution in THF (1.13 eq) was charged maintaining a temperature of ≤−45° C., target <−50° C. The reaction was stirred for 30 minutes at −60 to −50° C. Tetrabenzylpyrophosphate (2.26 eq) was charged to the reaction in a single portion followed by additional THF (20 vol) while maintaining the reaction temperature <−30° C. The reaction was warmed to 0° C., over 1.5-2 hours and sampled for completion. The reaction was filtered to remove phosphate salts washing with THF (8 vol). The filtrate was concentrated until 6-8 vol remains and stirred overnight at 40° C. to convert Intermediate 4A to stage 4 product. The reaction was sampled for completion and then filtered and the solid washed with THF (2 vol). The stage 4 product was dried in a vacuum oven at 40° C.

The differences from JNP and the benefits can be summarised as follows:

Step i
i) Firstly, sodium hexamethyldisilazide was introduced to support deprotonation. This proved an effective alternative to Butyl Lithium, which was easier to handle, and did not introduce further lithium into the reaction.
ii) Secondly, by diluting the reaction with THF, a much higher purity Intermediate 4A was obtained.
iii) Thirdly, by controlling the reaction temperature at below −50° C., undesirable mz 295.2 observed by LCMS was controlled to levels of less than 2%.

Step ii
iv) Fourthly, by monitoring levels of stage 4A impurities, particularly the N-debenzylated Stage 4 (Table 7) and anhydride Stage 4 (Table 7), a pure product can be produced reproducibly.
v) The intermediate stage 4A to stage 4 conversion can be carried out in the reaction solvent, avoiding the need for time consuming solvent swaps.
vi) Finally, the obtained solid is washed with THF and oven dried to obtain stage 4.

Example 6

Stage 5

Catalyst poisoning was noted during development of this stage and a charcolation step can be included in the process when required to prevent incomplete hydrogenation. However, charcolation is not routinely required.

After sparging with hydrogen for 3 hours typical reactions showed high levels of completion (>90% product, 3-5% SM remaining). A small amount of water was added to aid solubility and after sparging with hydrogen for a further 1 hour, consumption of stage 4 was achieved.

A successful reaction was worked up by filtration, followed by evaporation to remove methanol, leaving the product as a thick suspension in water. Ethanol was added and the solid filtered to give Psilocybin in 69% yield. $^1$H NMR confirmed the identity of the product but indicated a minor related impurity was present. LCMS analysis indicated a purity of 95.2% with the major impurity (4.1%) being identified as the pyrophosphoric acid impurity. (Table 7) deriving from the anhydride impurity at stage 4. It was later shown that this impurity was effectively purged during the final product re-crystallisation (Stage 6).

A further reaction was then carried out using stage 4 material from the finalised THF workup which was 88.0% pure by HPLC and contained 7.3% N-debenzylated stage 4 (converted to product), with none of the anhydride impurity.

Again completion was noted and the reaction worked up as previously to give Psilocybin in 46% yield. The low yield was believed to result from precipitation of the product during the catalyst filtration step. $^1$H NMR confirmed the identity of the product and HPLC indicated a purity of 98.9%.

Further development of the reaction conditions was carried out to optimise the water volume employed and minimise product losses during the filtration step. After the reaction, a solution was obtained by addition of 10 volumes of water with heating to 40° C. This allowed for removal of the catalyst by filtration without incurring product losses on the filter.

Some stage 3 was generated by hydrolysis during the reaction and workup with levels of approx. 1-2.5% appearing to be typical of the process. A reduction in the stage 3 level was demonstrated during the final product re-crystallisation.

Scale Up

The large scale stage 4 batch (non-GMP) was processed as a single batch (148 g active input). Consumption of stage 4 was achieved with 88% product and 0.9% stage 3 resulting from hydrolysis. The anhydride impurity (6.4%) was completely converted to the corresponding pyrophosphoric acid impurity (5.2%).

The large scale hydrogenation was filtered and concentrated to yield 109 g of crude product after stripping back from ethanol to reduce the water content (~71% by NMR assay, 86% yield).

Experimental

10% Pd/C (~50% water wet, type 87L, 0.1×stage 4 charge) was charged to a vessel under $N_2$ followed by Methanol (20 vol wrt stage 4) and Stage 4. The $N_2$ was replaced with $H_2$ and the reaction was stirred under $H_2$ (atmospheric pressure) for 1-2 hours. The reaction was sampled for completion and then water was added (10 vol wrt stage 4) maintaining a temperature of <25° C. The mixture stirred for a further 1-2 hours under $H_2$ (atmospheric pressure). The reaction was sampled and checked for completion.

If the reaction was incomplete, $H_2$ was recharged and the reaction continued for a further 1-12 hr until completion was observed. The reaction was then placed under $N_2$ and warmed to 40° C. and held for 15-45 minutes. The reaction was filtered through celite to remove catalyst, washing with methanol (13.3 vol wrt stage 4 charge) and water (6.7 vol wrt stage 4 charge). The filtrate was concentrated in vacuo, azeotroping with ethanol to remove water until a solid was obtained. The differences from JNP and the benefits can be summarised as follows:

Primarily, the reaction is monitored for levels of intermediates by HPLC, using relative retention times (RRT) and completion controlled with intermediates being present at less than 0.2%. The stage 5 pyrophosphoric acid impurity is also carefully monitored to confirm that it can be controlled in the final re-crystallisation.

The final Stage 6 process is as described in Example 1.

Example 7

Testing Methodology and Protocols

To test for purity etc the following methodology/protocols were employed.

7.1 NMR $^1$H and $^{13}$C NMR spectra of Psilocybin in $D_2O$ were obtained using 400 MHz spectrometer. Chemical shifts are reported in ppm relative to $D_2O$ in the $^1$H NMR (☐=4.75 ppm) and relative to MeOH (☐=49.5 ppm), which was added as a reference, in the $^{13}$C NMR the spectrum. Literature values for Psilocybin are reported in JNP. Analysis of Psilocybin by NMR gave data that was consistent with the structure and consistent with that reported in the literature with only minor variations in chemical shifts for protons near the ionisable groups which is expected as the zwitterionic nature of the compound makes the material very sensitive to small changes in pH.

Figure 10:
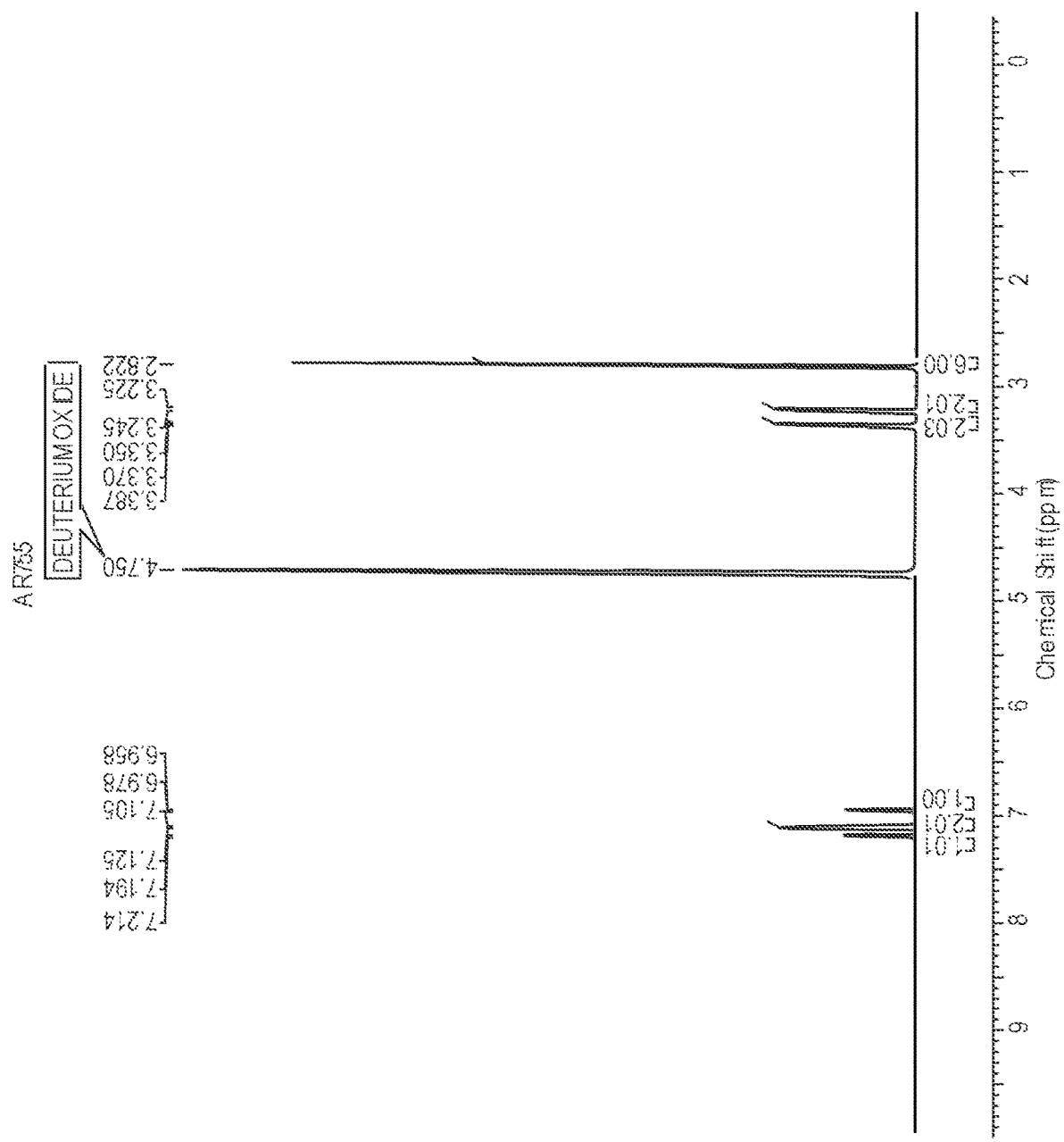
FIG. 10 is a 1H NMR spectrum of Psilocybin; (Read alongside assignment Example 7)
Figure 11:
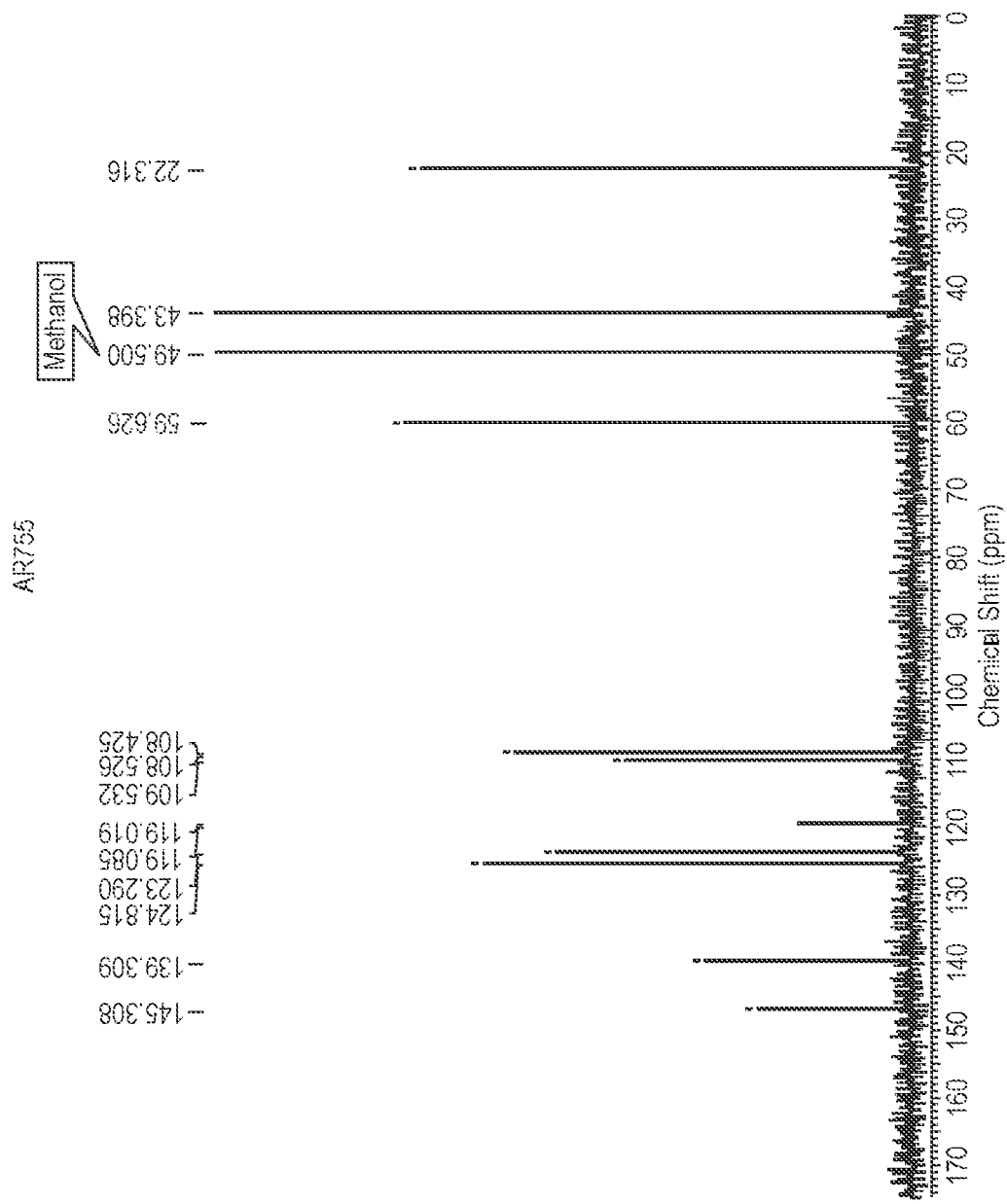
FIG. 11 is a $^{13}C$ NMR spectrum of Psilocybin; (Read alongside assignment Example 7)

The $^1$H NMR and $^{13}$C NMR data are outlined below and the spectra are shown in FIGS. 10 and 11.

$^1$H NMR Data (400 MHz, $D_2O$): 2.79 (s, 3H), 3.18 (t, J=7.4 Hz, 2H), 3.31 (t, J=7.4 Hz, 2H), 6.97 (d, J=8.0 Hz, 1H), 7.08 (s, 1H), 7.10 (t, J=8.0 Hz, 1H), 7.19 (d, 8.2 Hz, 1H).

$^{13}$C NMR Data (400 MHz, $D_2O$ (+trace MeOH): 22.3 (1×$CH_2$), 43.4 (2×$CH_3$), 59.6 (1×$CH_2$), 108.4 (1×CH), 108.6 (1×C), 109.5 (1×CH), 119.1 (d, $^3J_{P-H}$=6.7 Hz, 1×C), 123.3 (1×CH2), 124.8 (1×CH), 139.3 (1×C), 146.3 (d, $^2J_{P-H}$=6.7 Hz, 1×C)

7.2 FT-IR

Figure 12:
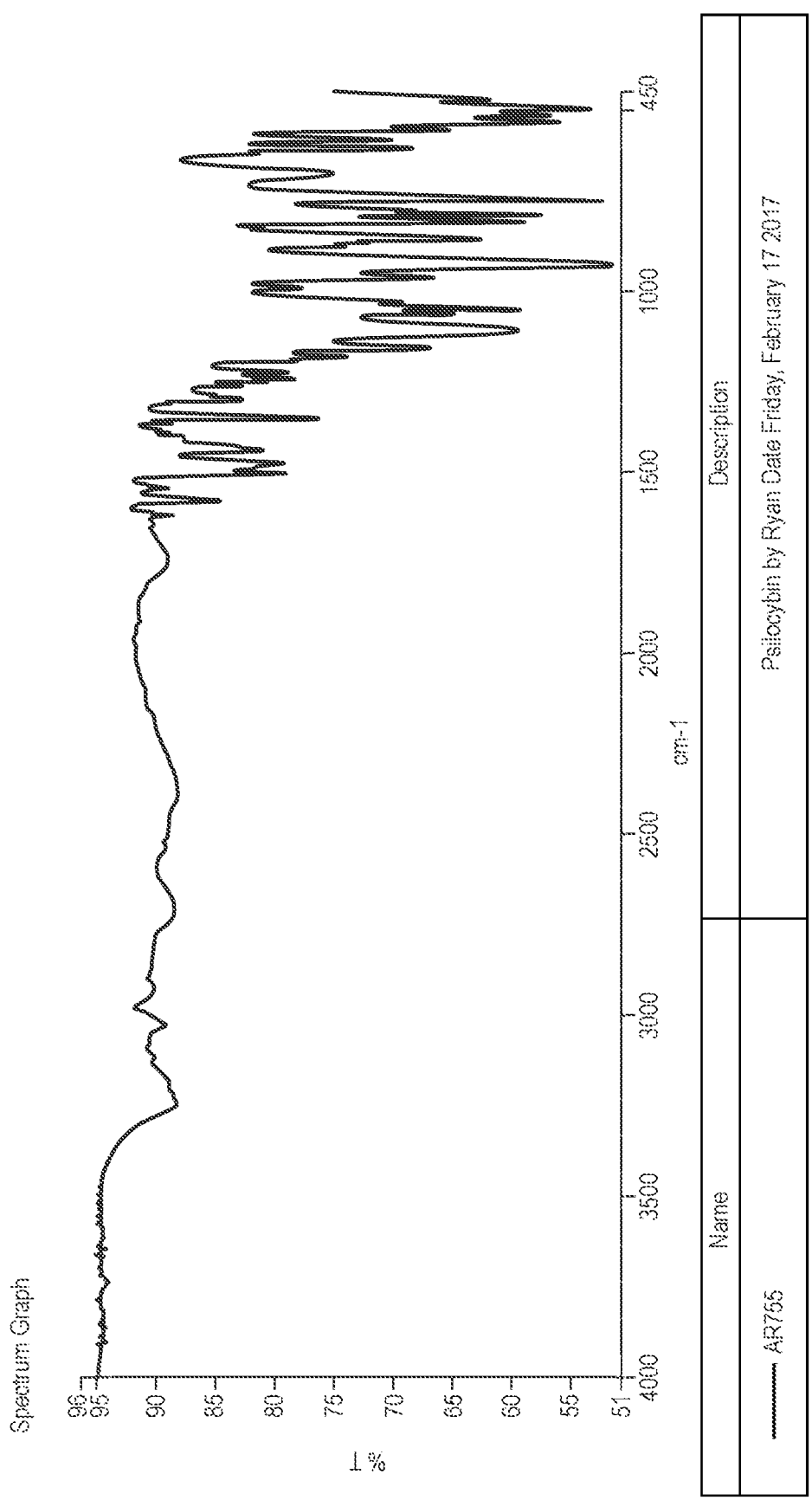
FIG. 12 is a FT-IR Spectrum of Psilocybin.

Data was collected on a Perkin Elmer Spectrum Two™ Spectrometer with UATR Two accessory. Analysis of Psilocybin (Batch: AR755) by FT-IR spectroscopy gave a spectrum (FIG. 12) that is consistent with the proposed structure. The broad peak at 3244 cm$^{-1}$ is typical of an amine salt. The remainder of the peaks are in the fingerprint region and therefore can't be assigned individually.

7.3. Mass Spectrometry

Figure 13:
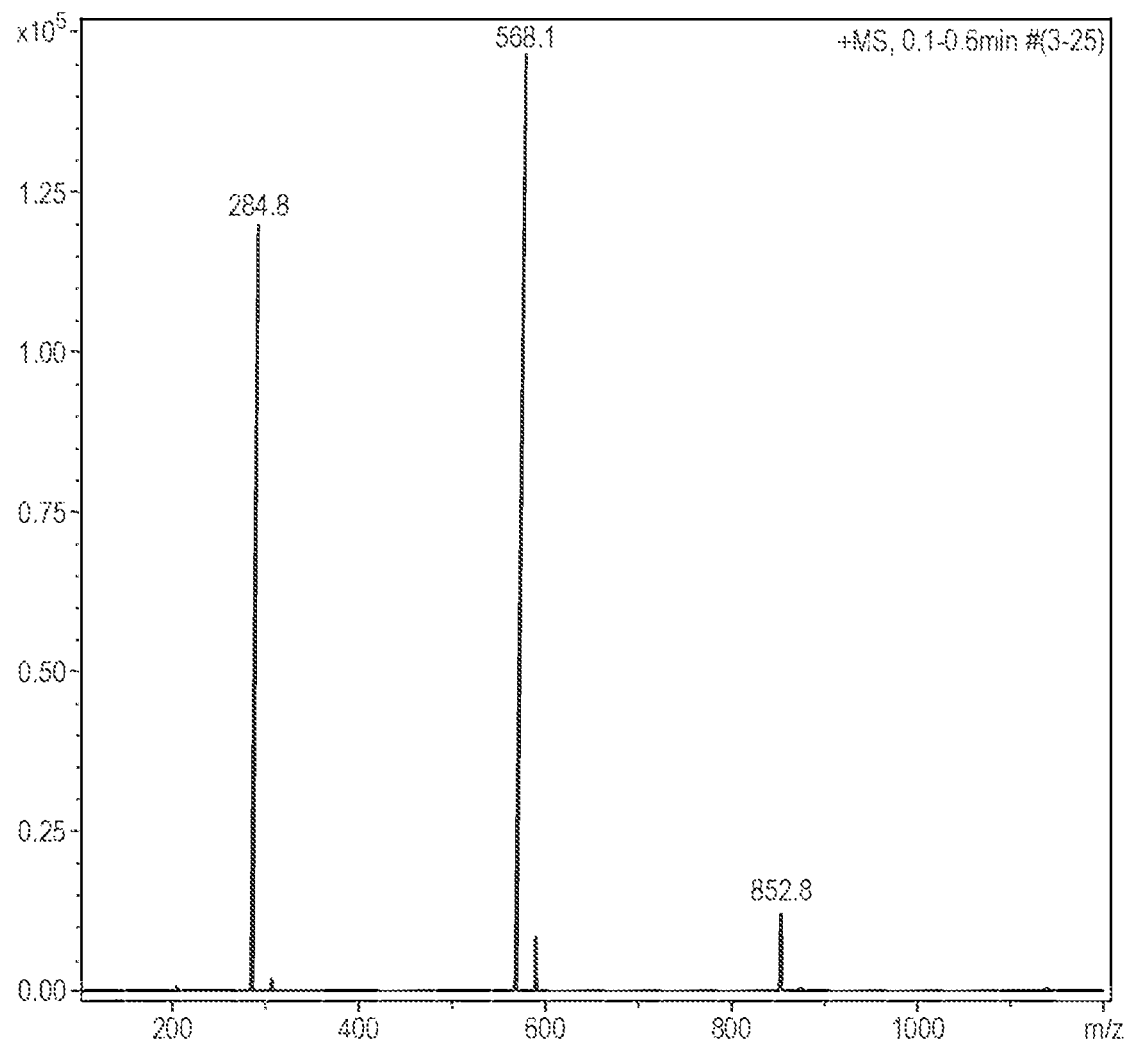
FIG. 13 is a Mass Spectrum of Psilocybin.
Figure 14:
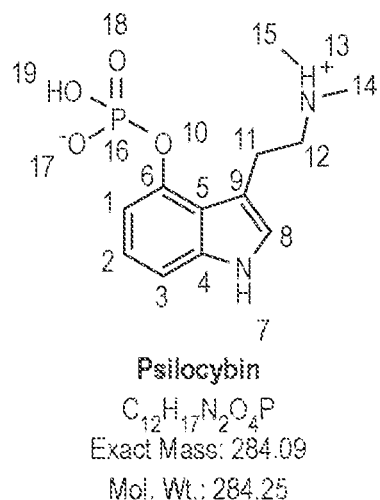
FIG. 14 is a numbered structural formula of Psilocybin.
Figure 15:
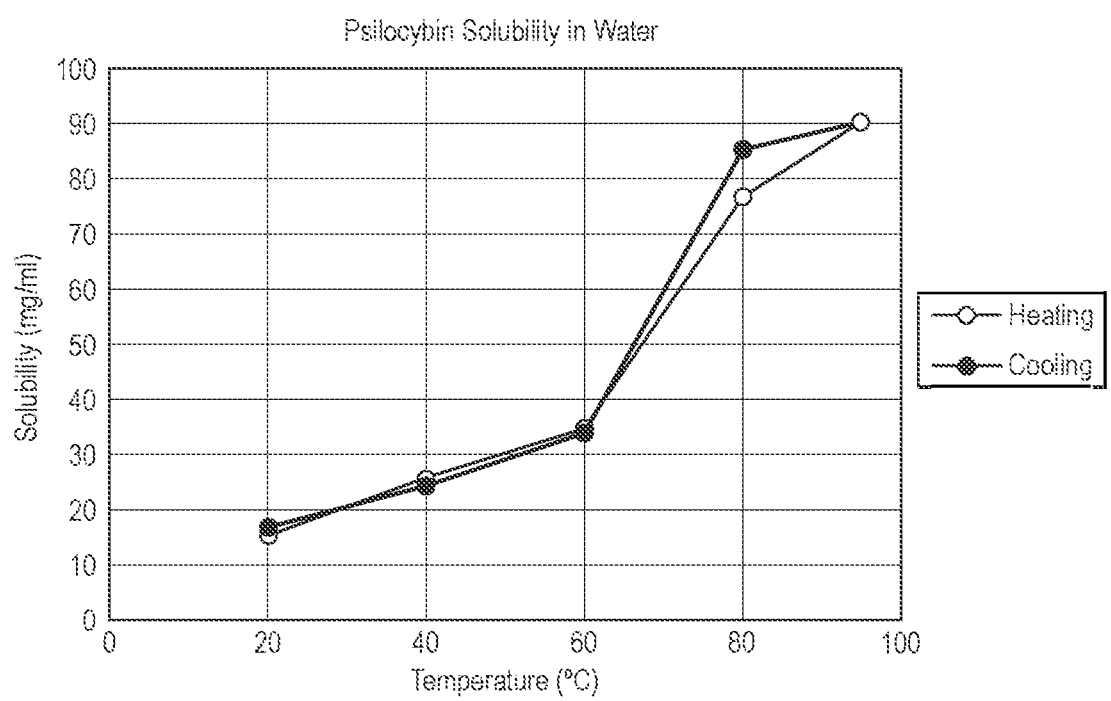
FIG. 15 is a temperature solubility curve for Psilocybin in water.

The mass spectrum of Psilocybin (AR755) was obtained on a Bruker Esquire 3000 plus Ion Trap Mass Spectrometer and was concordant with the structure. The mass spectrum (FIG. 13) showed a main peak at m/z=284.8 and 568.1 that corresponded to $(M+H)^+$ and $(2M+H)^+$ of Psilocybin. This implied the molecular ion has m/z 284 corresponding to the molecular formula of Psilocybin ($C_{12}H_{17}N_2O_4P$) (FIG. 14).

7.4 Residue on Ignition

The residue on ignition method follows the pharmacopeia method with one adjustment. Inconsistent results were obtained when the crucible was heated to 500° C. and it is believed this is due to low volatility of the phosphate residues that are generated. The temperature was therefore increased to 800° C. for Psilocybin and consistent and accurate results were obtained.

7.5 HPLC—Assay and Purity Determination

The HPLC method used for assay, chemical purity and quantifying the impurities of Psilocybin is a gradient HPLC-UV method and the conditions are outlined in Table 22. External standards are used for quantification. Approximately 1 mg/mL of Psilocybin was dissolved in Purified Water:MeOH (95:5). Sonicate to fully dissolve.

Purity by HPLC is calculated in the basis of area % and is correlated against a known retention time standard.

Assay by HPLC is calculated on an anhydrous basis, based on weight % versus a standard of known purity and composition.

TABLE 22

Typical HPLC Conditions for Identification, Purity and Assay

| Parameter | Conditions |
| --- | --- |
| System | Agilent 1100 series liquid chromatograph or equivalent |
| Column | XBridge C18, 4.6 × 150 mm; 3.5 μm (Ex; waters PN:186003034) |
| Flow Rate | 1.0 ml · min$^{-1}$ |

TABLE 22-continued

Typical HPLC Conditions for Identification, Purity and Assay

| | |
|---|---|
| Injection Volume | 5 μl |
| Detection | UV @ 267 nm |
| Column Temperature | 30° C. |
| Mobile Phase | A - Purified Water:Methanol:TFA (95:5:0.1) |
| | B - Methanol:Purified Water:TFA (95:5:0.1) |

| Gradient | Time (mins) | % A | % B |
|---|---|---|---|
| | 0 | 100 | 0 |
| | 2 | 100 | 0 |
| | 15 | 0 | 100 |
| | 20 | 0 | 100 |
| | 22 | 100 | 0 |

7.6 Residual Solvent Content by HRGC

The HRGC method for quantifying residual solvents is a headspace method and is described in Table 23 below:

TABLE 23

Typical Residual Solvent GC Method

| Parameter | Conditions |
|---|---|
| System | Agilent 6890/7890 HRGC or similar |
| Column | DB-624 60 m × 0.32 mm, 1.80 μm film thickness (or equivalent) |
| Oven Program | 40° C. (hold for 15 min) then ramp (20° C. min$^{-1}$) to 200° C. (hold 5 min) |
| Headspace Parameters | |
| Oven Temp | 125° C. |
| Loop Temp | 140° C. |
| Transfer Line Temp | 150° C. |
| Split Ratio | 10:1 |
| Injector temperature | 200° C. |
| Detector temperature | 250° C., FID |
| Head pressure | 15 psi, constant pressure |
| Carrier gas | Nitrogen |
| Column flow | 2.0 ml · min$^{-1}$ @ 40° C. |
| Internal Standard | 1,2-Difluorobenzene |

Levels of the following solvents and reagents are determined: Methanol, Ethanol, THF and Toluene.

7.7 Melting Point by DSC

DSC data was collected on a PerkinElmer Pyris 6000 DSC (or similar). The instrument was verified for energy and temperature calibration using certified indium. The sample was weighed (typically 0.5 to 3.0 mg) into a pin-holed aluminium sample pan. The pan was crimped with an aluminium pan cover. The pan was heated at 20° C./min from 30 to 300° C. with a purge of dry nitrogen at 20 mL/min. During the melting point procedure, each batch of Psilocybin Polymorph A or A' exhibited two endothermic events the latter; the first of which was attributed to solid-solid transition of Polymorph A or A' to Polymorph B, and the second of which was attributed to melting of Polymorph B.

7.8 Polymorphism by XRPD

The solid state form of Psilocybin is determined by XRPD. XRPD diffractograms were collected on a diffractometer (such as a PANalytical X'Pert PRO or equivalent) using Cu Kα radiation (45 kV, 40 mA), θ-θ goniometer, focusing mirror, divergence slit (½"), soller slits at both incident and divergent beam (4 mm) under ambient conditions. The data collection range was 3-35 °2θ with a continuous scan speed of 0.2° s$^{-1}$. The resulting diffractogram is compared to that of a reference diffractogram of Polymorph A or A' to ensure that it is concordant (FIG. 7a or 7b respectively).

7.9 Thermo-Gravimetric Analysis (TGA)

TGA data was collected on a PerkinElmer Pyris 1 TGA (or similar). The instrument was calibrated using a certified weight and certified Alumel and Perkalloy for temperature. A predefined amount of sample (typically ca. 5 mg) was loaded into an aluminium crucible, and was heated at 20° C./min from ambient temperature to 400° C. A nitrogen purge at 20 mL/min was maintained over the sample.

7.10 Loss on Drying

Determine in duplicate the loss on drying of the sample using a 1 g portion, accurately weighed, dried at 70° C., under vacuum to constant weight.

Calculation:

$$\% \text{ Loss on Drying} = \frac{(W_{INITIAL} - W_{FINAL})}{W_{SAMPLE}} \times 100$$

Where:

$W_{INITIAL}$=Initial weight of dish and sample prior to drying (g)

$W_{FINAL}$=Final weight of dish and dried sample (g)

$W_{SAMPLE}$=Weight of sample (g)

Example 8

Forced Degradation Studies

Psilocybin drug substance was stressed under various conditions in solution and in the solid state to provide samples to evaluate analytical method selectivity.

The forced degradation study was performed on Psilocybin; based on the requirements of ICH Q1A(R2). Testing under stressed conditions has provided information on potential degradation pathways and the intrinsic stability of Psilocybin. The optimised analytical method employed demonstrated specificity to Psilocybin; it was shown to be suitable and changes to identity, purity and potency of the product can be detected using this method. The method used has also been shown to be free from interferences from likely impurities and degradation products in accordance with ICH Q2(R1) (Validation of Analytical Procedures) with reference to specificity. Therefore, the HPLC method is deemed suitable for determining purity of Psilocybin and related impurities.

The control sample of Psilocybin was stable in solution over the study period (study period was 7 days for non-photostability samples). Psilocybin degraded slowly when heated in solution producing psilocin as the major impurity. Psilocybin was also stable under acid conditions at room temperature. However, at 60° C. a slow and steady degradation was observed producing psilocin as the main impurity. Psilocybin was slightly unstable at room temperature in the presence of base with slow degradation to a range of impurities over the study period. Only very low levels of impurities were formed under the peroxide conditions with the overall purity dropping by ~0.5%. In the solid state, slow chemical degradation was noted (3 days at 150° C.) predominantly producing psilocin (stage 3) as an impurity. Psilocybin was stable under photostability conditions both as a solid and when in solution.

Stability Studies

Stability studies were undertaken with two batches of Psilocybin as shown in Table 24.

TABLE 24

| Study number/ Study start | Drug Substance Lot No. | Packaging | Site of Manufacture | Lot Use | Storage Condition | Intended time points/Study Status |
|---|---|---|---|---|---|---|
| ON-YXSTAB0138 | GM764B | Double food grade Polythene bags. Outer Polythene container | Onyx Scientific | Ref. Std. | 2-8° C. | 1, 3, 6 months ongoing |
| | | | | | 25° C./60% RH | 1, 3, 6 months ongoing |
| | | | | | 40° C./75% RH | 1, 3, 6 months ongoing |
| ON-YXSTAB0139 | 170231 | Double food grade Polythene bags. Outer Polythene container | Onyx Scientific | Clinical | 2-8° C. | 1, 3, 6, 9, 12, 18, 24, 36 months ongoing |
| | | | | | 25° C./60% RH | 1, 3, 6, 9, 12, 18, 24, 36 months ongoing |
| | | | | | 40° C./75% RH | 1, 3, 6 months ongoing |

Samples were double bagged in food grade polythene bags and sealed in an outer polythene container and placed on storage at 2-8° C., 25° C./60% RH and 45° C./75% RH, a desiccant bag is included between the inner polythene bags to prevent moisture uptake. Tests for appearance, water content, purity and assay were carried out.

The protocols for the two studies are shown in Table 25 and Table 26.

The one month and three months stability data for batch GM764B are detailed in Table 27 and Table 28 below. The one, three, six, nine and twelve month stability data for GMP batch 170231 are provided in Table 29, Table 30, Table 31, Table 32 and Table 33 respectively below.

TABLE 25

Onyx Stability Trial Protocol Sheet

| Product: | Psilocybin | Onyx trial number: | ONYXSTAB0138 |
|---|---|---|---|
| Batch number: | GM764B | Trial due start date: | 10 MAR. 2017 |
| Test method: | N/A | Date of manufacture: | 6 FEB. 2017 |
| Additional information: | | 1200 mg of material required in each container. | |
| Packaging components: | | Double polythene bagged lined contained within 300 ml HDPE container (food grade). Insert a desiccant bag between the two polythene bags. | |
| Test parameters Routine tests | | Appearance Assay (Anhydrous basis) by $^1$H-NMR Water Content by loss on drying Chemical Purity/Impurities by HPLC | |

| Months | 1 | 3 | 6 | Spares | Total |
|---|---|---|---|---|---|
| 2° C.-8° C. | X | X | X | 2 | 5 |
| 25° C./60% RH | X | X | X | 2 | 5 |
| 40° C./75% RH | X | X | X | 0 | 3 |
| Date due off | 10 APR. 2017 | 10 JUN. 2017 | 10 SEP. 2017 | | 13 |

TABLE 26

Onyx Stability Trial Protocol Sheet

| Product: | Psilocybin | Onyx trial number: | ONYXSTAB0139 |
|---|---|---|---|
| Batch number: | 170231 | Trial due start date: | 31 MAR. 2017 |
| Test method: | SS/PSILOCYBIN/ | Date of manufacture: | 27 FEB. 2017 |
| Additional information: | | 2200 mg of material required in each container. | |
| Packaging components: | | Double polythene bagged lined contained within 300 ml HDPE container (food grade). Insert a desiccant bag between the two polythene bags. | |
| Test parameters Routine tests | | Appearance Assay (on a dry basis) by HPLC Water Content by loss on drying Chemical Purity/Impurities by HPLC | |

| Timepoint | 1 month | 3 months | 6 months | 9 months | 12 months |
|---|---|---|---|---|---|
| 2-8° C. | X | X | X | X | X |
| 25° C./60%RH | X | X | X | X | X |
| 40° C./75%RH | X | X | X | | |
| Date due off | 31 APR. 2017 | 30 JUN. 2017 | 30 SEP. 2017 | 31 DEC. 2017 | 31 MAR. 2018 |

TABLE 26-continued

Onyx Stability Trial Protocol Sheet

| Timepoint | 18 months | 24 months | 36 months | Spares | Total |
|---|---|---|---|---|---|
| 2-8° C. | X | X | X | 2 | 10 |
| 25° C./60% RH | X | X | X | 2 | 10 |
| 40° C./75% RH |  |  |  | 1 | 4 |
| Date due off | 30 SEP. 2018 | 31 MAR. 2019 | 31 MAR. 2020 |  | 24 |

TABLE 27

One Month Stability Data for Batch GM764B

| Test | Specification Limit | T = 0 | T = 1 month | T = 1 month | T = 1 month |
|---|---|---|---|---|---|
| Condition | N/A | N/A | 2° C.-8° C. | 25° C./60% RH | 40° C./75% RH |
| Appearance | For information only. | An off white solid. Free from visible contamination | An off white solid. Free from visible contamination | An off white solid. Free from visible contamination | An off white solid. Free from visible contamination |
| Assay by $^1$H-NMR | For information only. | 97% w/w | 99% w/w | 98% w/w | 96% w/w |
| Water content by loss on drying | For information only. | 0.86% w/w | 0.35% w/w | 0.20% w/w | 0.14% w/w |
| Chemical Purity By HPLC | For information only. | 99.24% | 99.24% | 99.22% | 99.23% |
| Impurities by HPLC: (Quote all GT 0.05%) | For Information only. |  |  |  |  |
| | RRT 0.86 | 0.05% | 0.05% | 0.05% | 0.05% |
| | RRT 1.46 | 0.05% | 0.09% | 0.10% | 0.10% |
| | RRT 1.59 (Psilocin) | 0.37% | 0.35% | 0.34% | 0.34% |
| | Total Impurities | 0.76% | 0.76% | 0.78% | 0.77% |

TABLE 28

Three Month Stability Data for Batch GM764B

| Test | Specification Limit | T = 0 | T = 3 month | T = 3 month | T = 3 month |
|---|---|---|---|---|---|
| Condition | N/A | N/A | 2° C.-8° C. | 25° C.-60% RH | 40° C.-75% RH |
| Appearance | For information only. | An off white solid. Free from visible contamination | An off white solid. Free from visible contamination | An off white solid. Free from visible contamination | An off white solid. Free from visible contamination |
| Assay by $^1$H-NMR | For information only. | 97% w/w | 97% w/w | 99% w/w | 97% w/w |
| Water content by loss on drying | For information only. | 0.86% w/w | 0.26% w/w | 0.08% w/w | 0.14% w/w |
| Chemical Purity By HPLC | For information only. | 99.24% | 99.31% | 99.27% | 99.26% |
| Impurities by HPLC: (Quote all GT 0.05%) | For Information only. |  |  |  |  |
| | RRT 0.86 | 0.05% | LT 0.05% | LT 0.05% | LT 0.05% |
| | RRT 1.46 | 0.05% | 0.10% | 0.09% | 0.10% |
| | RRT 1.59 (Psilocin) | 0.37% | 0.37% | 0.36% | 0.37% |
| | Total Impurities | 0.76% | 0.69% | 0.73% | 0.74% |

TABLE 29

One Month Stability Data for Batch 170231

| Test | Specification Limit | T = 0 | T = 1 month | T = 1 month | T = 1 month |
|---|---|---|---|---|---|
| Condition | N/A | N/A | 2° C.-8° C. | 25° C./60% RH | 40° C./75% RH |
| Appearance | For information only. | An off white solid. Free from visible contamination | An off white solid. Free from visible contamination | An off white solid. Free from visible contamination | An off white solid. Free from visible contamination |

TABLE 29-continued

One Month Stability Data for Batch 170231

| Test | Specification Limit | T = 0 | T = 1 month | T = 1 month | T = 1 month |
|---|---|---|---|---|---|
| Chemical Purity By HPLC | For information only. | 99.28% | 99.20% | 99.16% | 99.17% |
| Impurities by HPLC: (Quote all GT 0.05%) | For Information only. | | | | |
| RRT 1.49 | | 0.06% | 0.05% | 0.05% | 0.06% |
| RRT 1.62 (Psilocin) | | 0.39% | 0.36% | 0.37% | 0.36% |
| RRT 1.70 | | 0.05% | LT 0.05% | LT 0.05% | LT 0.05% |
| Impurity at RRT 1.89 | | LT 0.05% | LT 0.05% | LT 0.05% | LT 0.05% |
| Impurity at RRT 2.45 | | LT 0.05% | LT 0.05% | LT 0.05% | LT 0.05% |
| Impurities LT 0.05% | | 0.22% | 0.39% | 0.42% | 0.41% |
| Total Impurities | | 0.72% | 0.80% | 0.84% | 0.83% |
| Assay by HPLC (on a dry basis) | For information only | 98.65% w/w | 98.76% w/w | 97.98% w/w | 98.52% w/w |
| Water content by loss on drying | For information only. | 0.32% w/w | 0.27% w/w | 0.17% w/w | 0.19% w/w |

TABLE 30

Three Month Stability Data for Batch 170231

| Test | Specification Limit | T = 0 | T = 3 months | T = 3 month | T = 3 month |
|---|---|---|---|---|---|
| Condition | N/A | N/A | 2° C.-8° C. | 25° C./60% RH | 40° C./75% RH |
| Appearance | For information only. | An off white solid. Free from visible contamination | An off white solid. Free from visible contamination | An off white solid. Free from visible contamination | An off white solid. Free from visible contamination |
| Chemical Purity By HPLC | For information only. | 99.28% | 99.30% | 99.31% | 99.17% |
| Impurities by HPLC: (Quote all GT 0.05%) | For Information only. | | | | |
| RRT 0.69 | | LT 0.05% | 0.05% | LT 0.05% | LT 0.05% |
| RRT 1.49 | | 0.06% | 0.05% | 0.05% | 0.06% |
| RRT 1.62 (Psilocin) | | 0.39% | 0.37% | 0.36% | 0.39% |
| RRT 1.70 | | 0.05% | LT 0.05% | LT 0.05% | LT 0.05% |
| Impurity at RRT 1.89 | | LT 0.05% | LT 0.05% | LT 0.05% | LT 0.05% |
| Impurity at RRT 2.45 | | LT 0.05% | LT 0.05% | LT 0.05% | LT 0.05% |
| Impurities LT 0.05% | | 0.22% | 0.22% | 0.27% | 0.34% |
| Total Impurities | | 0.72% | 0.70% | 0.69% | 0.79% |
| Assay by HPLC (on a dry basis) | For information only | 98.65% w/w | 98.45% w/w | 99.46% w/w | 98.64% w/w |
| Water content by loss on drying | For information only. | 0.32% w/w | 0.17% w/w | 0.01% w/w | 0.19% w/w |

TABLE 31

Six Month Stability Data for Batch 170231

| Test | Specification Limit | T = 0 | T = 6 months | T = 6 months | T = 6 months |
|---|---|---|---|---|---|
| Condition | N/A | N/A | 2° C.-8° C. | 25° C.-60% RH | 40° C.-75% RH |
| Appearance | For information only. | An off white solid. Free from visible contamination | An off white solid. Free from visible contamination | An off white solid. Free from visible contamination | An off white solid. Free from visible contamination |
| Chemical Purity By HPLC | For information only. | 99.28% | 99.20% | 99.19% | 99.12% |
| Impurities by HPLC: (Quote all GT 0.05%) | For Information only. | | | | |
| RRT 0.69 | | LT 0.05% | 0.06% | 0.06% | 0.06% |
| RRT 1.49 | | 0.06% | 0.07% | 0.07% | 0.08% |
| RRT 1.62 | | 0.39% | LT 0.05% | LT 0.05% | LT 0.05% |
| (Psilocin) | | | 0.35% | 0.34% | 0.38% |
| RRT 1.70 | | 0.05% | LT 0.05% | LT 0.05% | LT 0.05% |

TABLE 31-continued

Six Month Stability Data for Batch 170231

| Test | Specification Limit | T = 0 | T = 6 months | T = 6 months | T = 6 months |
|---|---|---|---|---|---|
| Impurity at RRT 1.89 | | LT 0.05% | LT 0.05% | LT 0.05% | LT 0.05% |
| Impurity at RRT 2.45 | | LT 0.05% | LT 0.05% | LT 0.05% | LT 0.05% |
| Impurities LT 0.05% | | 0.22% | 0.32% | 0.34% | 0.36% |
| Total Impurities | | 0.72% | 0.80% | 0.81% | 0.88% |
| Assay by HPLC (on a dry basis) | For information only | 98.65% w/w | 97.97% w/w | 98.04% w/w | 100.10% w/w |
| Water content by loss on drying | For information only. | 0.32% w/w | 0.06% w/w | 0.32% w/w | 2.26% w/w |

TABLE 32

Nine Month Stability Data for Batch 170231

| Test | Specification Limit | T = 0 | T = 9 months | T = 9 months |
|---|---|---|---|---|
| Condition | N/A | N/A | 2° C.-8° C. | 25° C.-60% RH |
| Appearance | For information only. | An off white solid. Free from visible contamination | An off white solid. Free from visible contamination | An off white solid. Free from visible contamination |
| Chemical Purity By HPLC | For information only. | 99.28% | 99.16% | 99.16% |
| Impurities by HPLC: (Quote all GT 0.05%) | For Information only. | | | |
| RRT 0.69 | | LT 0.05% | LT 0.05% | LT 0.05% |
| RRT 1.49 | | 0.06% | LT 0.05% | LT 0.05% |
| RRT 1.62 (Psilocin) | | 0.39% | 0.07% 0.06% | 0.05% 0.06% |
| RRT 1.70 | | 0.05% | 0.37% | 0.37% |
| Impurity at RRT 1.89 | | LT 0.05% | LT 0.05% | LT 0.05% |
| Impurity at RRT 2.45 | | LT 0.05% | LT 0.05% | LT 0.05% |
| Impurities LT 0.05% | | 0.22% | LT 0.05% 0.34% | LT 0.05% 0.35% |
| Total Impurities | | 0.72% | 0.84% | 0.84% |
| Assay by HPLC (on a dry basis) | For information only | 98.65% w/w | 97.53% w/w | 98.12% w/w |
| Water content by loss on drying | For information only. | 0.32% w/w | 0.21% w/w | 0.10% w/w |

TABLE 33

Twelve Month Stability Data for Batch 170231

| Test | Specification Limit | T = 0 | T = 12 months | T = 12 months |
|---|---|---|---|---|
| Condition | N/A | N/A | 2° C.-8° C. | 25° C./60% RH |
| Appearance | For information only. | An off white solid. Free from visible contamination | An off white solid. Free from visible contamination | An off white solid. Free from visible contamination |
| Chemical Purity By HPLC | For information only. | 99.28% | 99.25% | 99.25% |
| Impurities by HPLC: (Quote all GT 0.05%) | For Information only. | | | |
| RRT 0.69 | | LT 0.05% | LT 0.05% | LT 0.05% |
| RRT 1.49 | | 0.06% | LT 0.05% | LT 0.05% |
| RRT 1.62 (Psilocin) | | 0.39% | 0.37% | 0.37% |
| RRT 1.70 | | 0.05% | LT 0.05% | LT 0.05% |
| Impurity at RRT 1.89 | | LT 0.05% | LT 0.05% | ND |
| Impurity at RRT 2.45 | | LT 0.05% | LT 0.05% | LT 0.05% |
| Impurities LT 0.05% | | 0.22% | 0.38% | 0.38% |
| Total Impurities | | 0.72% | 0.75% | 0.75% |
| Assay by HPLC (on a dry basis) | For information only | 98.65% w/w | 99.63% w/w | 98.97% w/w |
| Water content by loss on drying | For information only. | 0.32% w/w | 0.49% w/w | 0.61% w/w |

Over the first 12 months of the ICH stability study Psilocybin has proven to be chemically stable under low temperature (2-8° C.), ambient (25° C./60% RH) and accelerated (40° C./75% RH) conditions. There has been no change in the appearance and HPLC analysis has also remained consistent. The water content has varied in all samples, due to the initial impact and then aging of the desiccant bags used in the study.

Example 9—Experimental to Form Hydrate A

Psilocybin (200 mg) was charged to a crystallisation tube followed by deionised water (4 ml). The mixture was equilibrated at 25° C. for 2 hours before the solid was isolated by vacuum filtration. The material was split into two equal portions. One portion was not subjected to further drying to give Hydrate A, lot GK2, by XRPD and DSC (diffractogram and thermogram consistent with FIG. 7d and FIG. 8d respectively).

Example 10—Experimental to Form Polymorph B

Figure 7C:
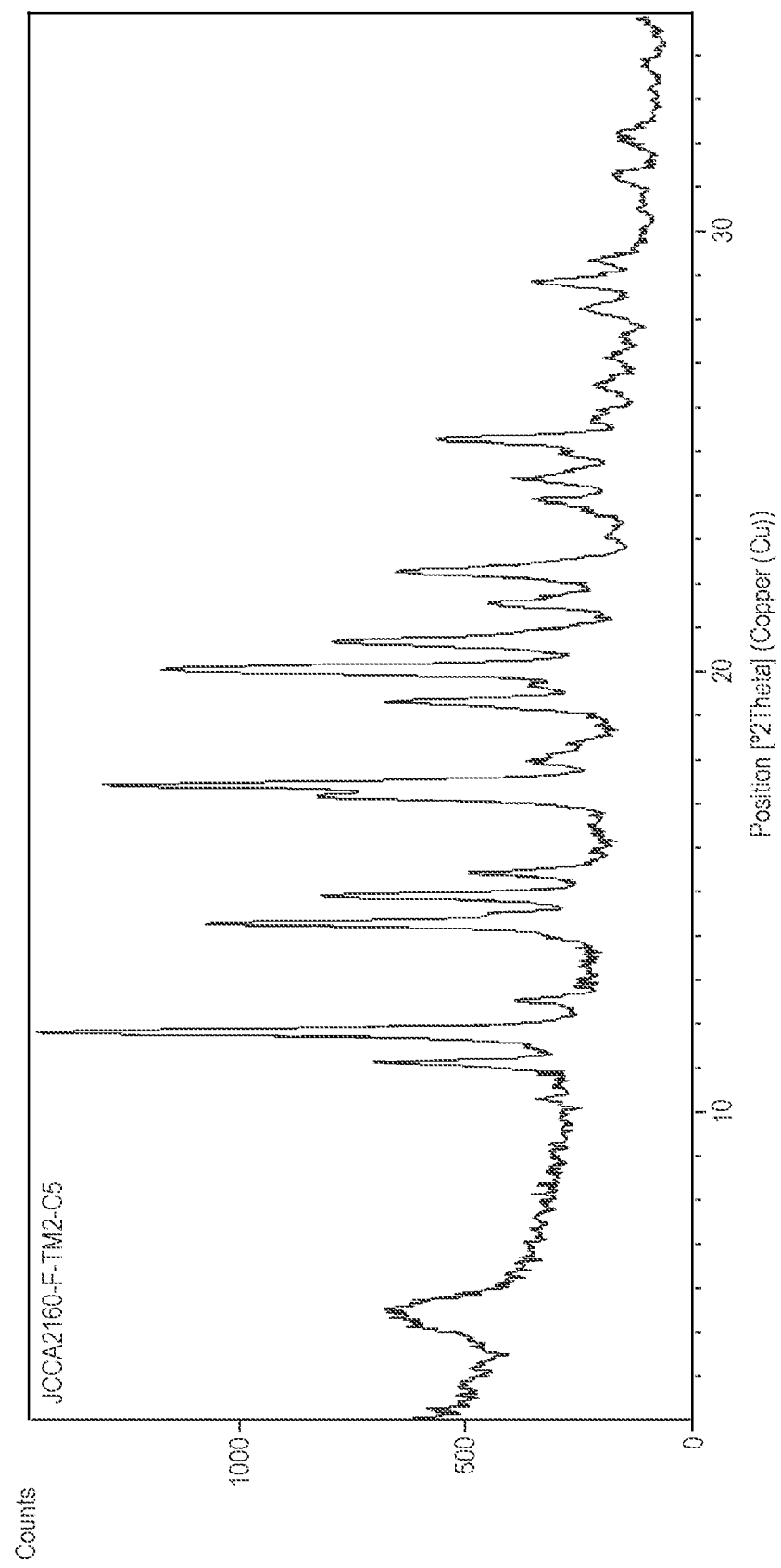
FIG. 7c is a XRPD diffractogram of Polymorph B (JCCA2160-F-TM2)
Figure 8C:
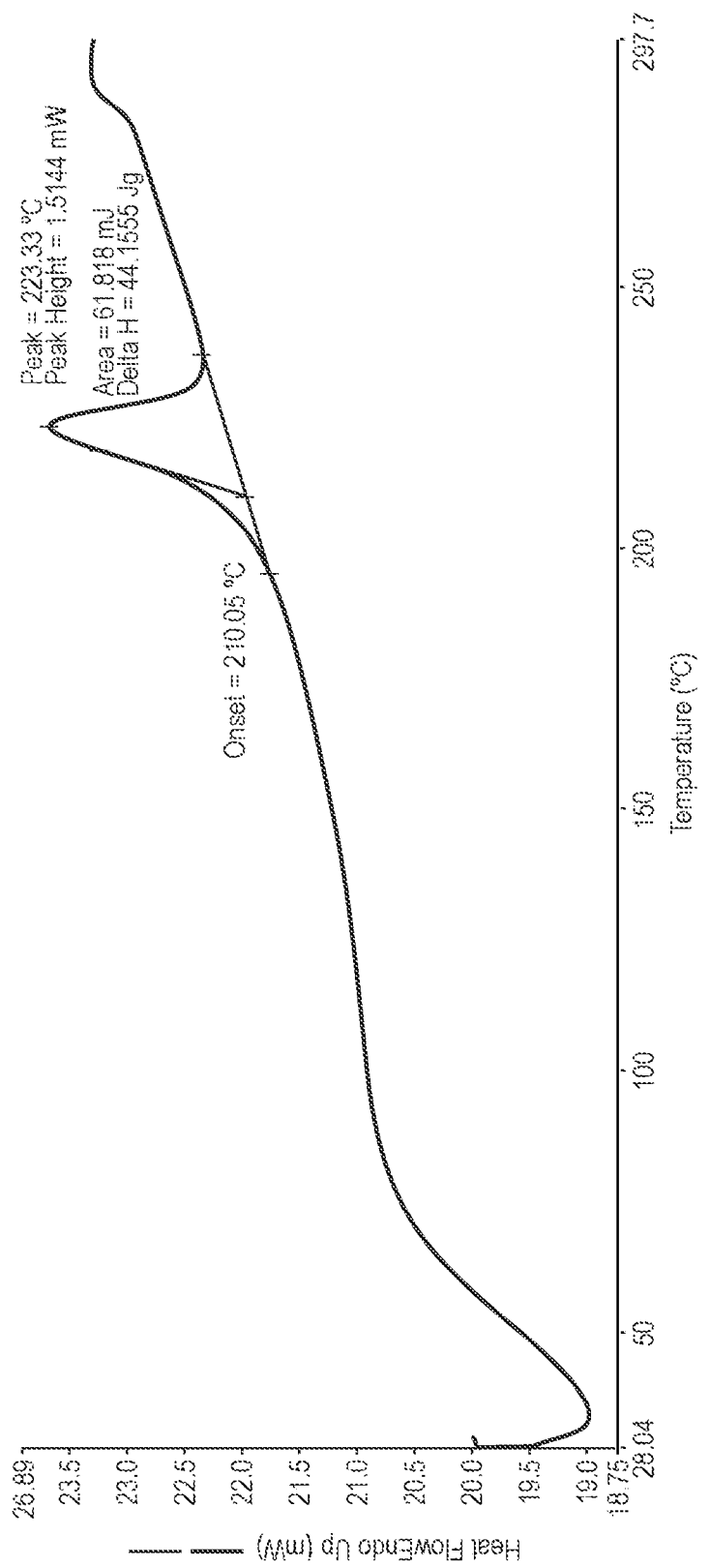
FIG. 8c is a DSC thermograph of Polymorph B (GM748A)

Psilocybin Polymorph A (250 mg) was charged to a round bottom flask, heated to 173° C. using an oil bath and held at temperature for 5 minutes. The solid was cooled to ambient temperature and isolated to give lot GK3 with a recovery of 93%. Analysis by XRPD and DSC revealed lot GK3 to be Polymorph B (diffractogram and thermogram consistent with FIG. 7c and FIG. 8c respectively).

Example 11—Solid State Investigations

Figure 17:
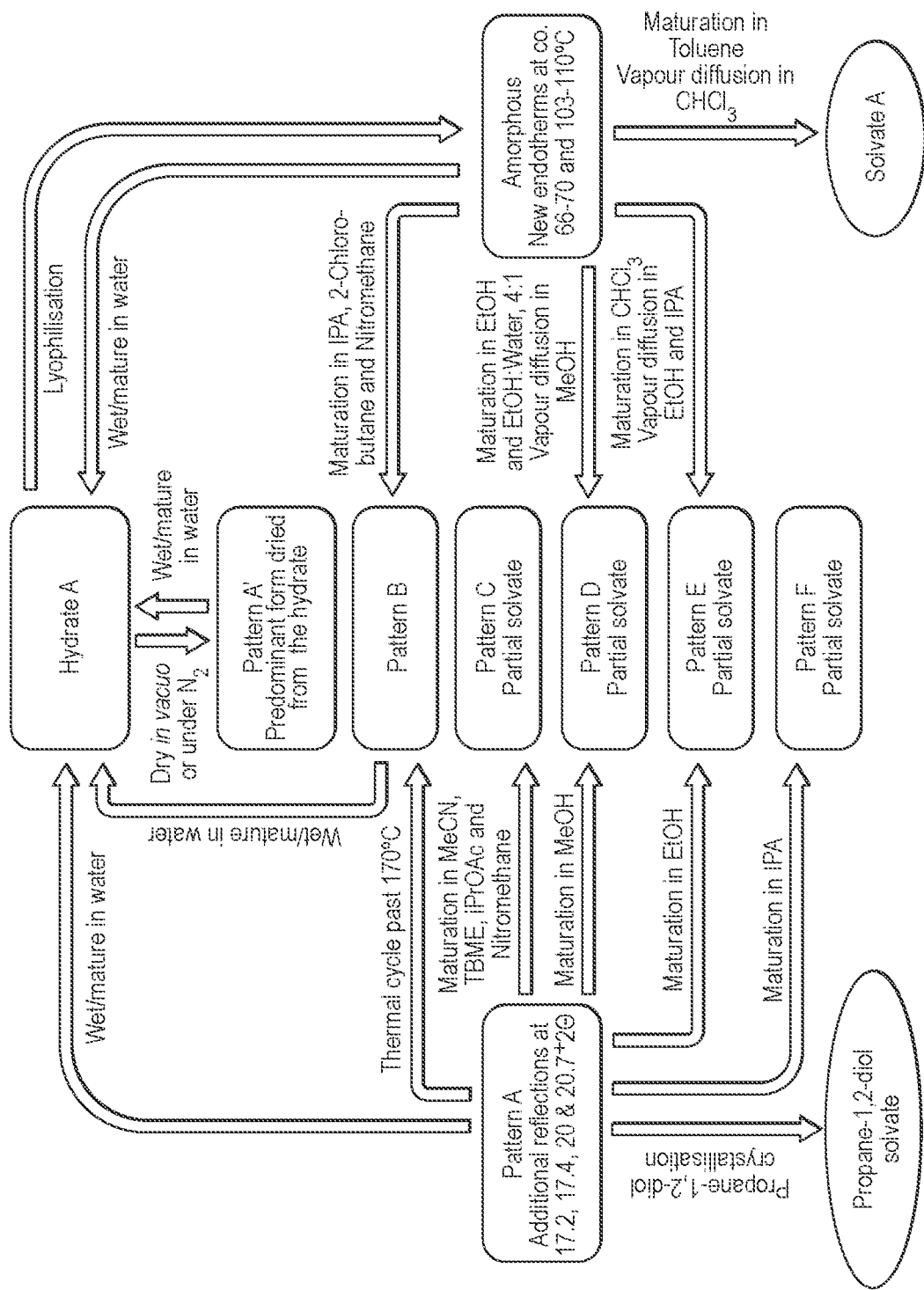
FIG. 17 is a form phase diagram showing the interrelationship of forms in different solvent systems.

A number of polymorphism investigations were completed. A summary of the solid forms found is shown in FIG. 17. The majority of the forms found were derived from solvent perturbation; in some cases stoichiometric solvates were isolated and in other cases non-stoichiometric solvates.
Slurries of Polymorph A Solvent mediated equilibrations of Psilocybin Pattern A were conducted as a primary route into modification of the solid form and to visually assess the solubility of the material in a range of 24 solvents between 25 and 50° C.

Psilocybin Pattern A (40 mg) was dosed into tubes at room temperature and solvents as listed in Table 34 were added in aliquots of 0.4 ml (10 vol.) to a total volume of 1.2 ml (30 vol.) and observations noted. The mixtures were agitated constantly. Heat cycling was conducted as follows: 50° C. for 18 hours, cool over 2 hours to 20° C., mature for 4 hours, heat to 50° C. for 4 hours, cool to 20° C. over 2 hours, mature for 18 hours. A repeat 50° C.-20° C. cycle over 24 hours was conducted and the following applied:

Isolation post heating to 50° C. where solids were sufficient=A series
Isolation post cooling to 20° C. where solids were sufficient=B series
All isolated solids were dried in vacuo at 50° C. for 24 hours and analysed by XRPD. The observations are provided in Table 34.

The API was largely insoluble in the solvents and solvent mixtures tested in 30 volumes at 50° C. resulting in heavy suspensions. Water did solubilise Psilocybin at 50° C.

TABLE 34

Tabulated observations for heat cycling slurry maturations and using Pattern A blend as input

| Entry | Solvent | Obs. 20° C., 0.4 ml | Obs. 20° C., 0.8 ml | Obs. 20° C., 1.2 ml | Obs. 50° C. | XRPD A series | XRPD B series |
|---|---|---|---|---|---|---|---|
| 1 | Cyclohexane | Susp. | Susp. | Susp. | Susp. | A | A |
| 2 | Chlorobenzene | Susp. | Susp. | Susp. | Susp. | A | A |
| 3 | 2-Chlorobutane | Susp. | Susp. | Susp. | Susp. | A | A |
| 4 | Benzotrifluoride | Susp. | Susp. | Susp. | Susp. | A | A |
| 5 | Anisole | Susp. | Susp. | Susp. | Susp. | A | A |
| 6 | Nitromethane | Susp. | Susp. | Susp. | Susp. | C | C |
| 7 | CPME | Susp. | Susp. | Susp. | Susp. | A | A |
| 8 | Heptane | Susp. | Susp. | Susp. | Susp. | A | A |
| 9 | TBME | Susp. | Susp. | Susp. | Susp. | C | A |
| 10 | MIBK | Susp. | Susp. | Susp. | Susp. | A | A |
| 11 | MEK | Susp. | Susp. | Susp. | Susp. | A | A |
| 12 | iPrOAc | Susp. | Susp. | Susp. | Susp. | C | C |
| 13 | EtOAc | Susp. | Susp. | Susp. | Susp. | A | A |
| 14 | Toluene | Susp. | Susp. | Susp. | Susp. | A | A |
| 15 | THF | Susp. | Susp. | Susp. | Susp. | A | A |
| 16 | $CHCl_3$ | Susp. | Susp. | Susp. | Susp. | A | A |
| 17 | MeOH | Susp. | Susp. | Susp. | Susp. | D | D |
| 18 | EtOH | Susp. | Susp. | Susp. | Susp. | E | E |
| 19 | IPA | Susp. | Susp. | Susp. | Susp. | F | F |
| 20 | MeCN | Susp. | Susp. | Susp. | Susp. | C | A |
| 21 | Water | Susp. | Susp. | Susp. | Solution | n/a | A |
| 22 | 4:1 EtOH/water | Susp. | Susp. | Susp. | Susp. | A | A |
| 23 | 4:1 THF/water | Susp. | Susp. | Susp. | Susp. | A | Hydrate A |
| 24 | 4:1 IPA/water | Susp. | Susp. | Susp. | Susp. | A | C |

Figure 18:
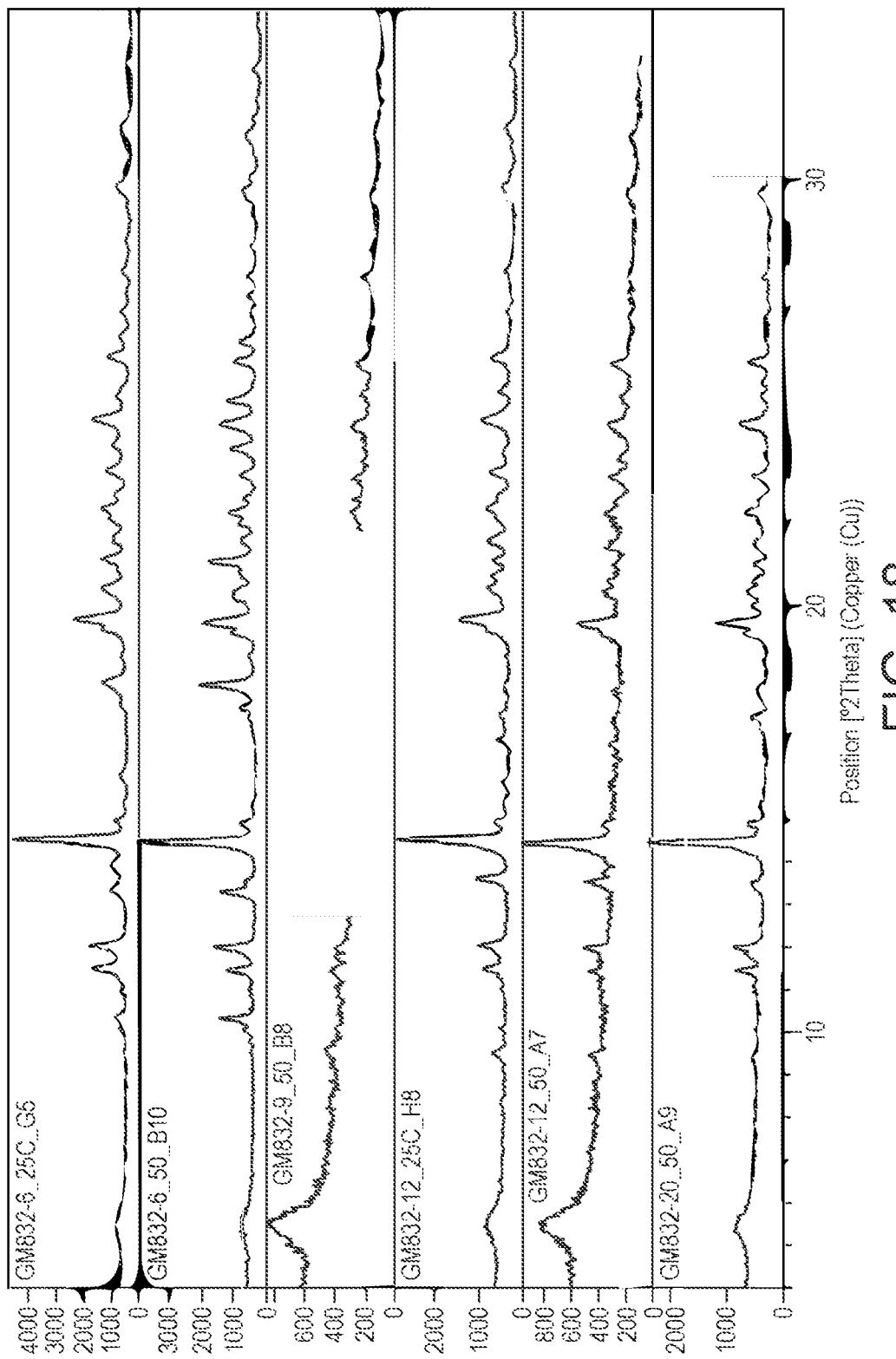
FIG. 18 is XRPD diffractogram—Pattern C for solids isolated at 25 and 50° C.

Results:

In the figures (FIG. 18 and FIG. 19), "250" denotes isolation of the solid at 25° C. and "50° C." denotes isolation of the solid at 50° C. For example, GM832-20_50_A9 represents GM832 entry 20 (MeCN) isolated at 5000.

50° C. Slurries

Entries 1, 2, 3, 4, 5, 7, 8, 10, 11, 13, 14, 15, 16, 22, 23, 24: XRPD diffractogram broadly consistent with Polymorph A, but with an additional peak of varying intensity at 18 °2θ.

Entries 6, 9, 12, 20: XRPD diffractogram acquired for the isolated solids were broadly consistent (see FIG. 18) with additional peaks at 10 °2θ and 13.2 °2θ observed for some samples. This XRPD diffractogram was designated Pattern C. There is no chemotype correlation between the solvents ($CH_3NO_2$, TBME, iPrOAc and $CH_3CN$).

Figure 19:
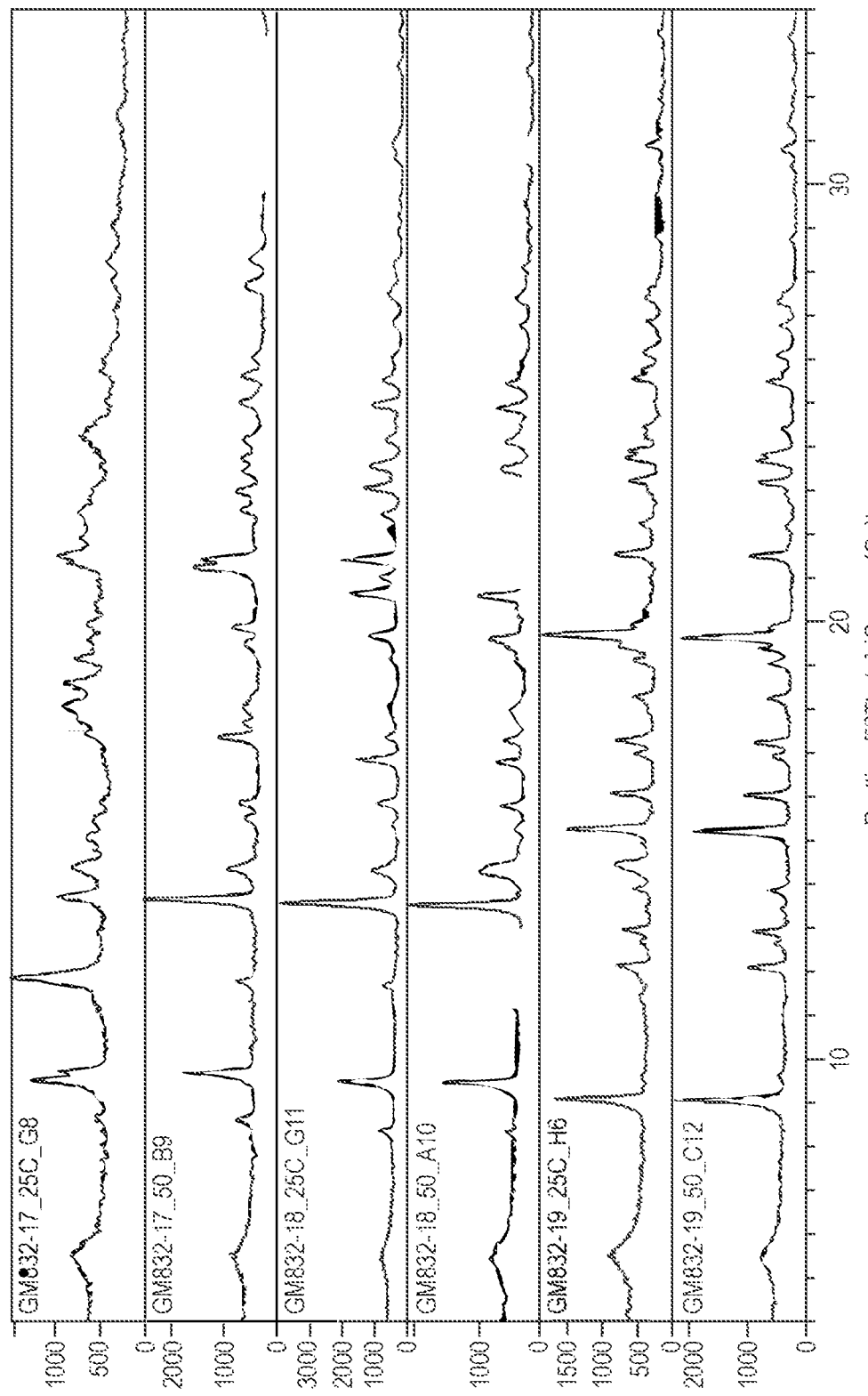
FIG. 19 is XRPD diffractograms—Patterns D, E and F for solids isolated at 25 and 50° C.

Entry 17: XRPD diffractogram acquired had multiple diffraction peaks (FIG. 19). The XRPD diffractogram was designated Pattern D.

Entry 18: XRPD diffractogram acquired had multiple diffraction peaks (FIG. 19). The XRPD diffractogram was designated Pattern E.

Entry 19: XRPD diffractogram acquired had multiple diffraction peaks (FIG. 19). The XRPD diffractogram was designated Pattern F.

25° C. Slurries:

Entries 1, 2, 3, 4, 5, 7, 8, 9, 10, 11, 13, 14, 15, 16, 20, 21, 22: XRPD diffractograms are all similar to that acquired for Polymorph A.

Entries 6, 12, 24: XRPD diffractograms acquired for the isolated solids were broadly consistent (see FIG. 18) with Pattern C.

Entry 23: XRPD analysis showed Hydrate A had formed.

Entry 17: XRPD diffractogram acquired had multiple diffraction peaks (FIG. 19). The XRPD diffractogram was designated Pattern D.

Entry 18: XRPD diffractogram acquired had multiple diffraction peaks (FIG. 19). The XRPD diffractogram was designated Pattern E.

Entry 19: XRPD diffractogram acquired had multiple diffraction peaks (FIG. 19). The XRPD diffractogram was designated Pattern F.

Analysis of Results:

The XRPD diffractograms for the solids isolated at 25° C. are broadly the same as for the XRPD diffractograms acquired for the solids isolated at 50° C.

Patterns D, E and F were derived from alcohols (MeOH, EtOH and IPA). Solvated states were postulated considering an Ethanol Solvate was previously isolated during development. The XRPD diffractograms for the Ethanol Solvate are not identical, however, given that exact solvent level variation may deliver varying states of order within the lattice, the comparison between these XRPD diffractograms provides a strong hypothesis that these more significant phase variations are invoked by solvent entrainment.

Figure 7D:
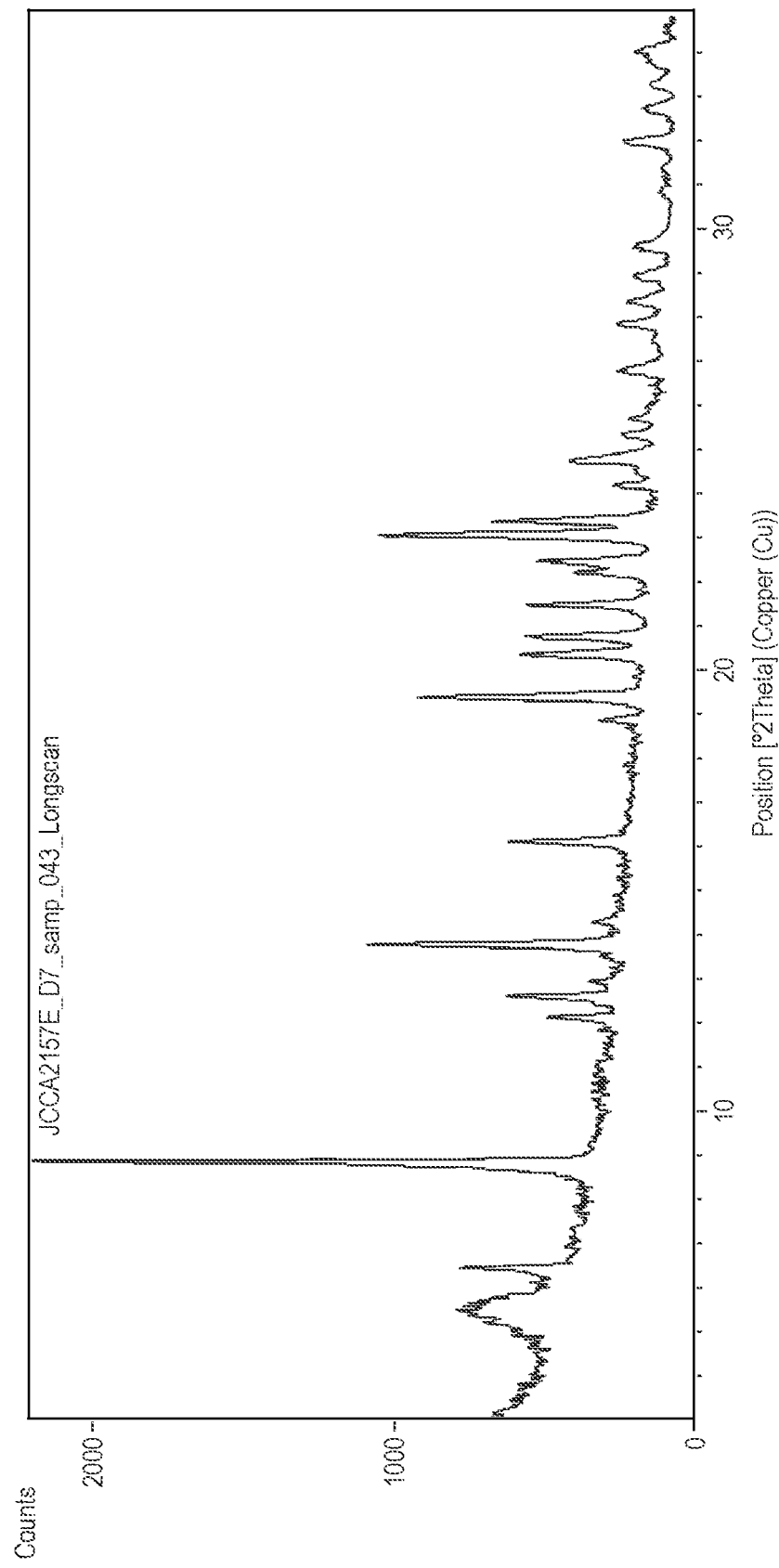
FIG. 7d is a XRPD diffractogram of a Hydrate A (JCCA2157E)
Figure 7E:
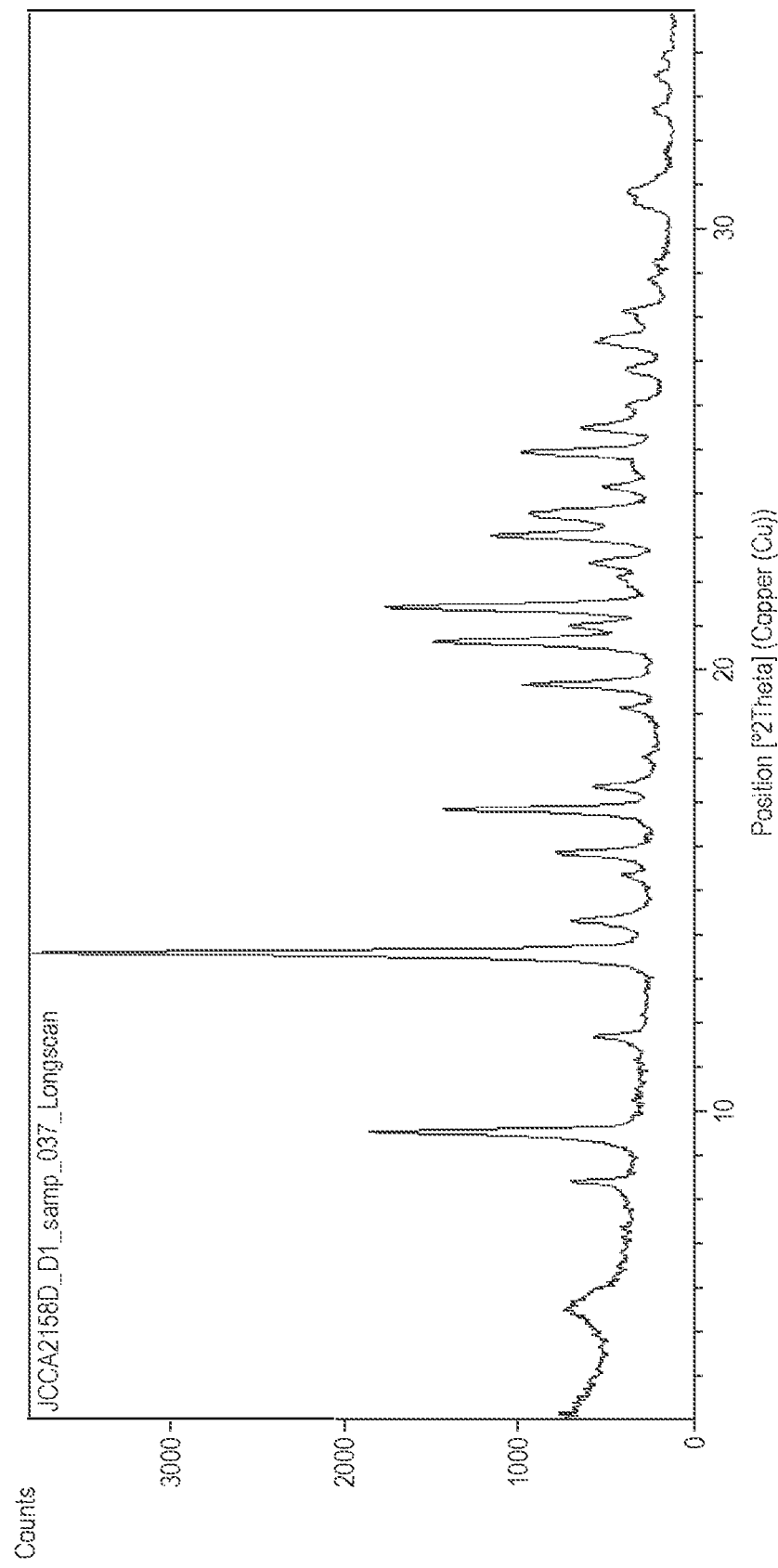
FIG. 7e is a XRPD diffractogram of an ethanol solvate (JCCA2158D)
Figure 7F:
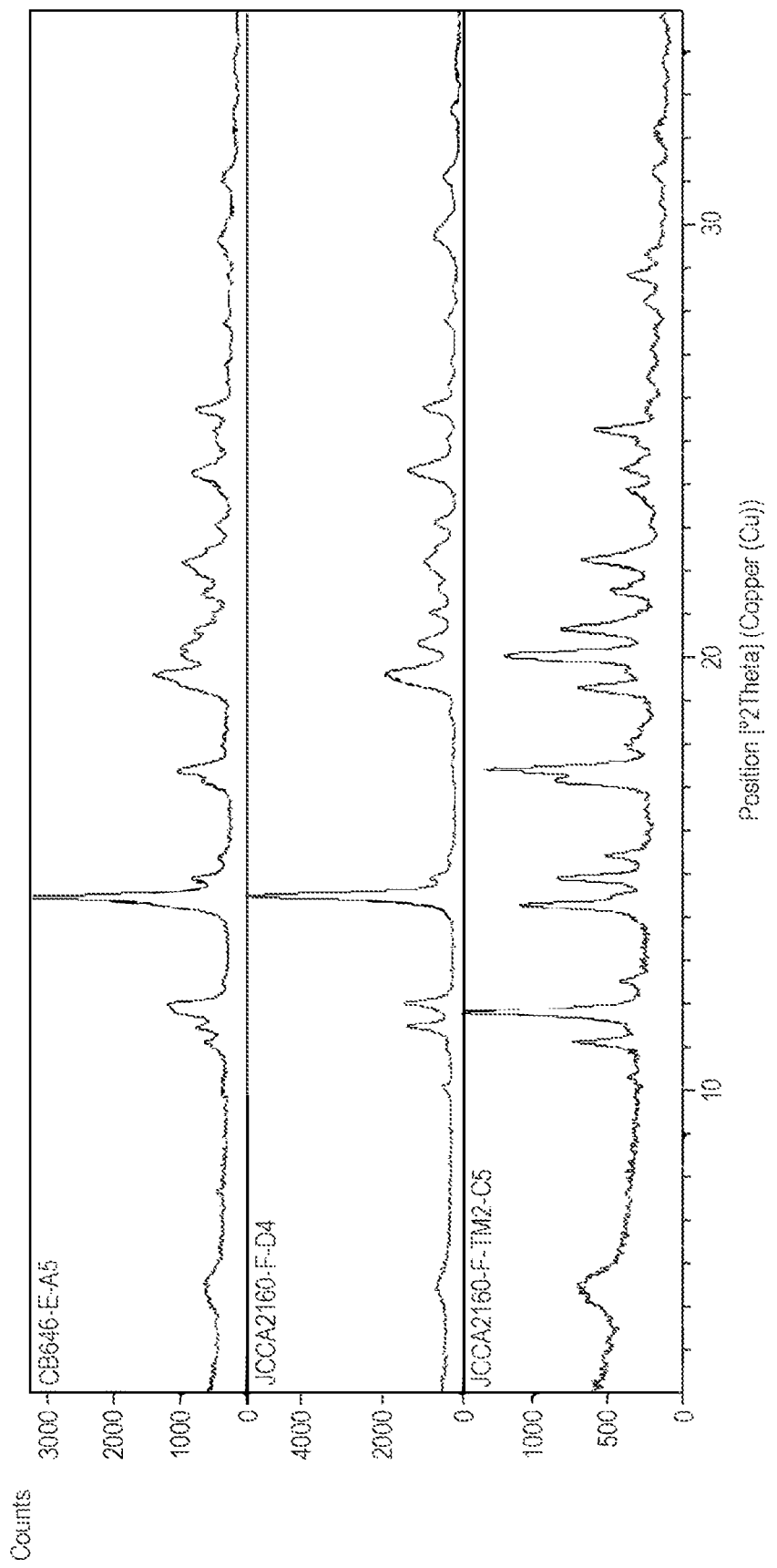
FIG. 7f is a XRPD diffractogram of product obtained during development of the process (CB646-E) (top)—compared to the diffractograms Polymorph A' (JCCA2160F) (middle) and Polymorph B (JCCA2160-TM2) (bottom)
Figure 8D:
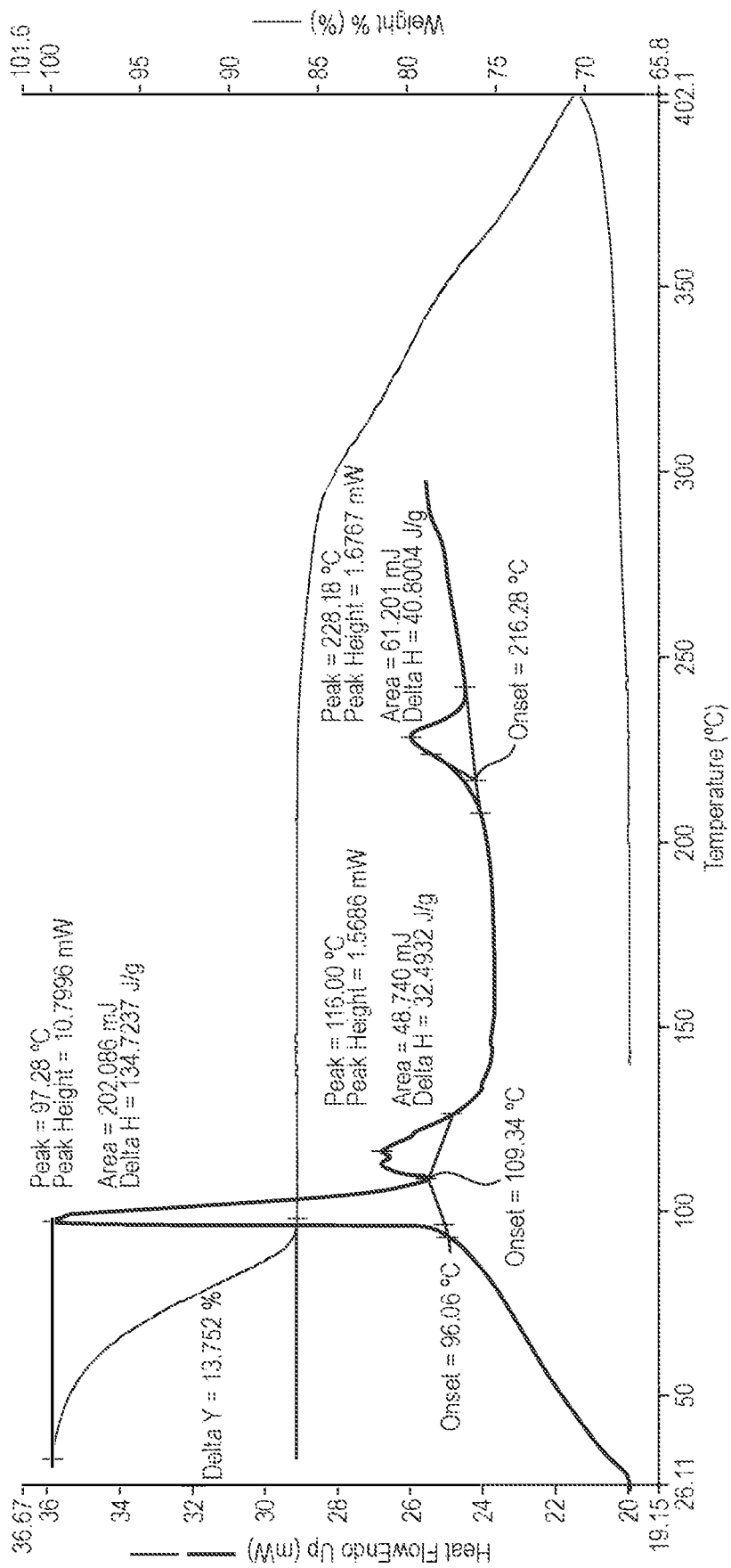
FIG. 8d is a DSC and TGA thermograph of Hydrate A (JCCA2157E)
Figure 8E:
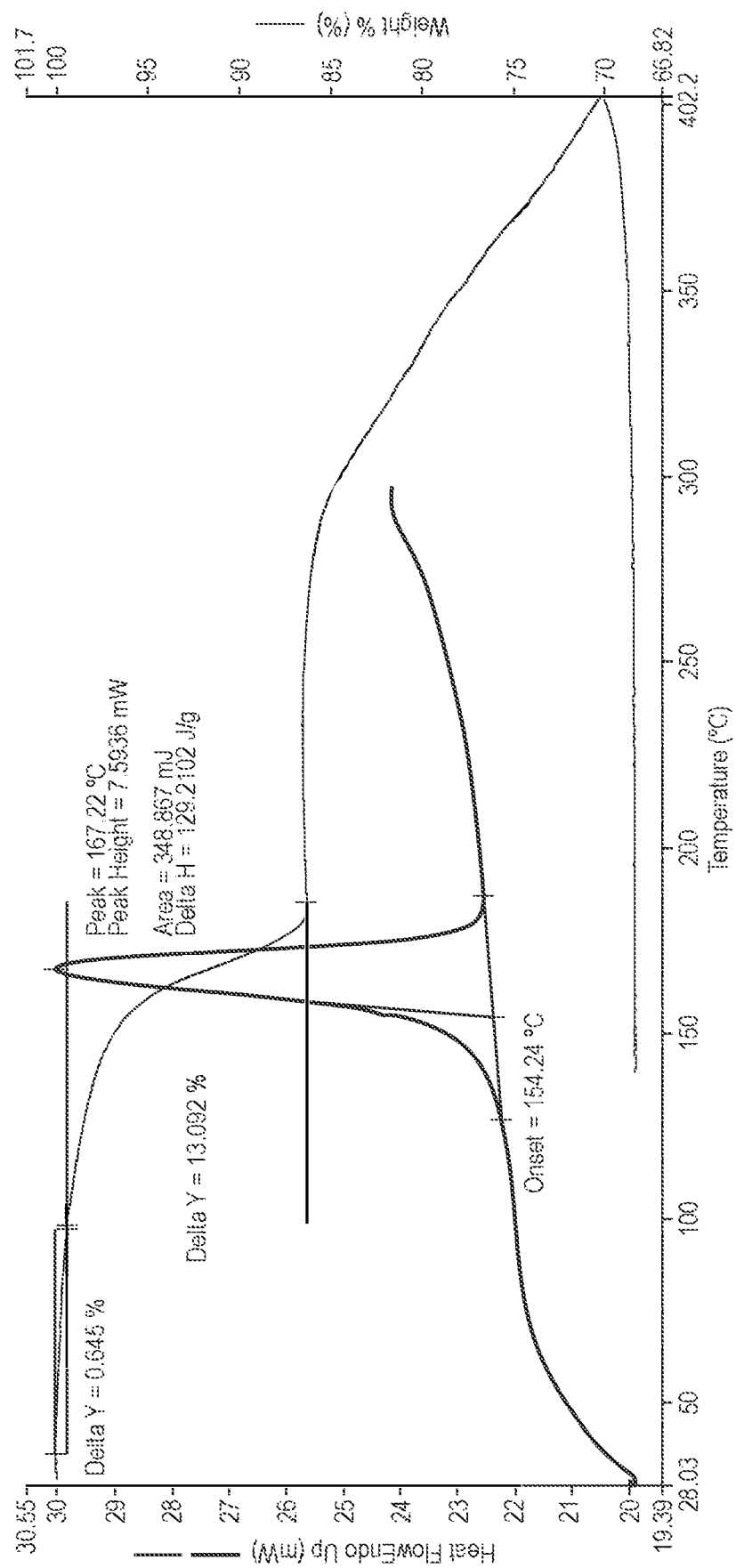
FIG. 8e is a DSC and TGA thermograph of ethanol solvate (JCCA2158D)
Figure 9:
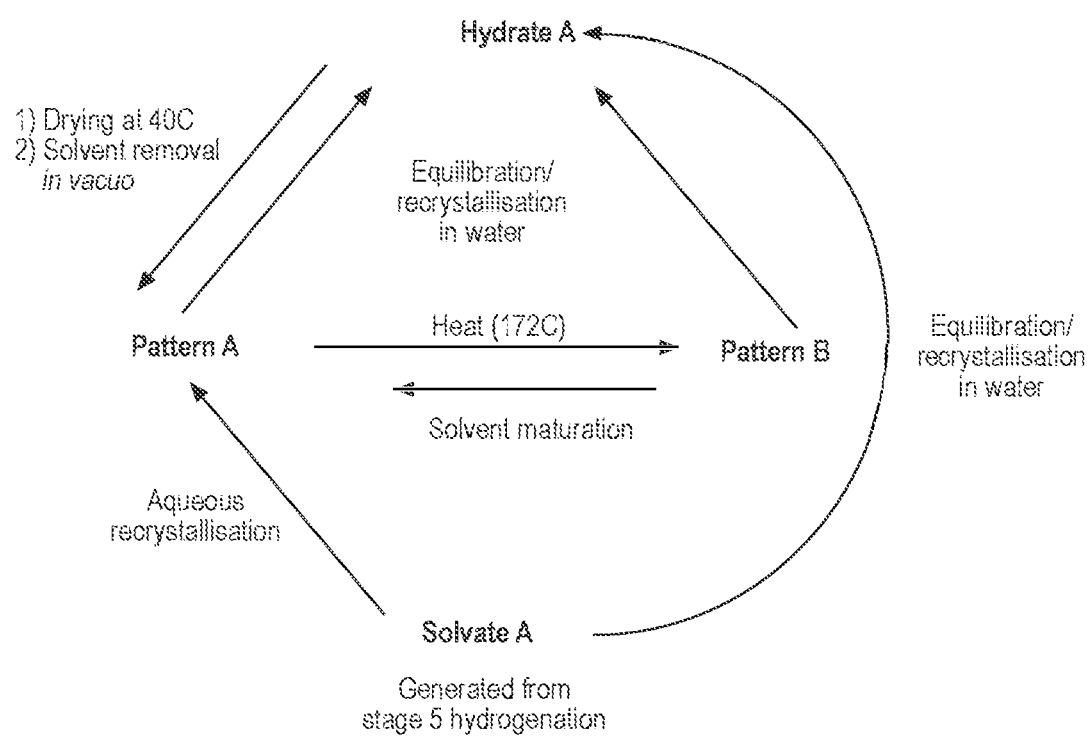
FIG. 9 is a form phase diagram showing the interrelationship of form in water-based systems.

XRPD patterns D, E and F (FIG. 19) are all dissimilar to the XRPD diffractogram for Hydrate (FIG. 7d).

Direct comparison of the XRPD diffractograms acquired for the MeOH, EtOH and IPA derived solids (Patterns D, E and F—FIG. 19) isolated at the two temperatures shows conforming diffractograms; the two MeOH diffractograms are similar while the EtOH and IPA are directly comparable.

DSC analysis was performed on the isolated solids, and where sufficient sample was available, TGA. The solids that delivered Patterns D, E and F all features endotherms at ca. 170-180° C. but otherwise proffered distinct thermal profiles. TGA analysis for the MeOH slurry isolated solid showed one protracted mass loss from ca. 25-190° C. (3.1%). A stochiometric methanol solvate would require 10.3% weight solvent. TGA analysis of the EtOH slurry isolated solid showed two distinct mass loss steps. The first one occurred before 100° C. (0.3% weight) is considered to be due to water, and the second larger loss (11.5% weight) due to solvent. A stoichiometric ethanol solvate requires 13.9% weight solvent. TGA analysis of the IPA slurry isolated solid featured two distinct mass loss steps. The first mass loss before 100° C. (0.4% weight) is considered to be due to water, while the second larger mass loss (13.9% weight) is considered to be due to residual solvent. A stoichiometric IPA solvate requires 17.5% weight solvent.

Slurries of Amorphous Psilocybin

In order to generate amorphous material a small sample of Psilocybin (0.5 g) was dissolved in water (0.5 L, 1000 vol.), polish filtered and lyophilised. Psilocybin was recovered as an off white fibrous material (lot MC1368A; 412 mg, 82%, XRPD amorphous).

To assess visually solubility of the amorphous API and to induce form modification, a series of slurry maturations were performed as follows:

Psilocybin (15 mg) was charged to tubes. Solvent was then added at ambient temperature (20° C., 0.3 ml, 20 vol.) and the suspensions agitated. Observations were made. After 1 hour of stirring, samples were heated to 45° C. for 18 hours and observations made. Samples were heated to 50° C. for 8 hours and observations were made. The samples were agitated for 72 hours at 25° C. and subject to a final heat cycle, prior to isolation. Observations are shown in Table 35.

TABLE 35

Observations of amorphous Psilocybin during heat cycling slurry maturation and form fate

| Entry | Solvent | Obs. at 20° C. | Obs. at 45° C. | Obs. at 50° C. | XRPD Data |
|---|---|---|---|---|---|
| A | Cyclohexane | Susp. | Susp. | Susp. | Semi-crystalline |
| B | Chlorobenzene | Susp. | Susp. | Susp. | Semi-crystalline |
| C | Chlorobutane | Susp. | Susp. | Susp. | Pattern B |
| D | Benzotrifluoride | Susp. | Susp. | Susp. | Semi-crystalline |
| E | Anisole | Susp. | Susp. | Susp. | Semi-crystalline |
| F | Nitromethane | Susp. | Susp. | Susp. | Pattern B |
| G | CPME | Susp. | Susp. | Susp. | Semi-crystalline |
| H | Heptane | Susp. | Susp. | Susp. | Semi-crystalline |
| I | TBME | Susp | Susp. | Susp. | Semi-crystalline |
| J | MIBK | Susp. | Susp. | Susp. | Semi-crystalline |
| K | MEK | Susp. | Susp. | Susp. | Semi-crystalline |
| L | iPrOAc | Susp. | Susp. | Susp. | Semi-crystalline |
| M | EtOAc | Susp. | Susp. | Susp. | Semi-crystalline |
| N | Toluene | Susp. | Susp. | Susp. | Similar to Solvate A |
| O | THF | Susp. | Susp. | Susp. | Semi-crystalline |
| P | Chloroform | Susp. | Susp. | Susp. | Similar to Pattern E |
| R | MeOH | Susp. | Susp. | Susp. | Semi-crystalline |
| S | EtOH | Susp. | Susp. | Susp. | Pattern D |
| T | IPA | Susp. | Susp. | Susp. | Pattern B |
| U | Acetonitrile | Susp. | Susp. | Susp. | Amorphous |
| V | Water | Susp. | Susp. | Susp. | Similar to Pattern A |
| W | 4:1 EtOH/water | Susp. | Susp. | Susp. | Similar to Pattern D |
| X | 4:1 THF/water | Susp. | Susp. | Susp. | Similar to Pattern A |
| Y | 4:1 IPA/water | Susp. | Susp. | Susp. | Similar to Pattern A |

Results

The majority of solvents returned a solid that was considered to be semi-crystalline (predominantly amorphous with a notable reflection at ca. 18 °2θ).

Truly amorphous was returned from equilibration in MeCN.

Figure 20:
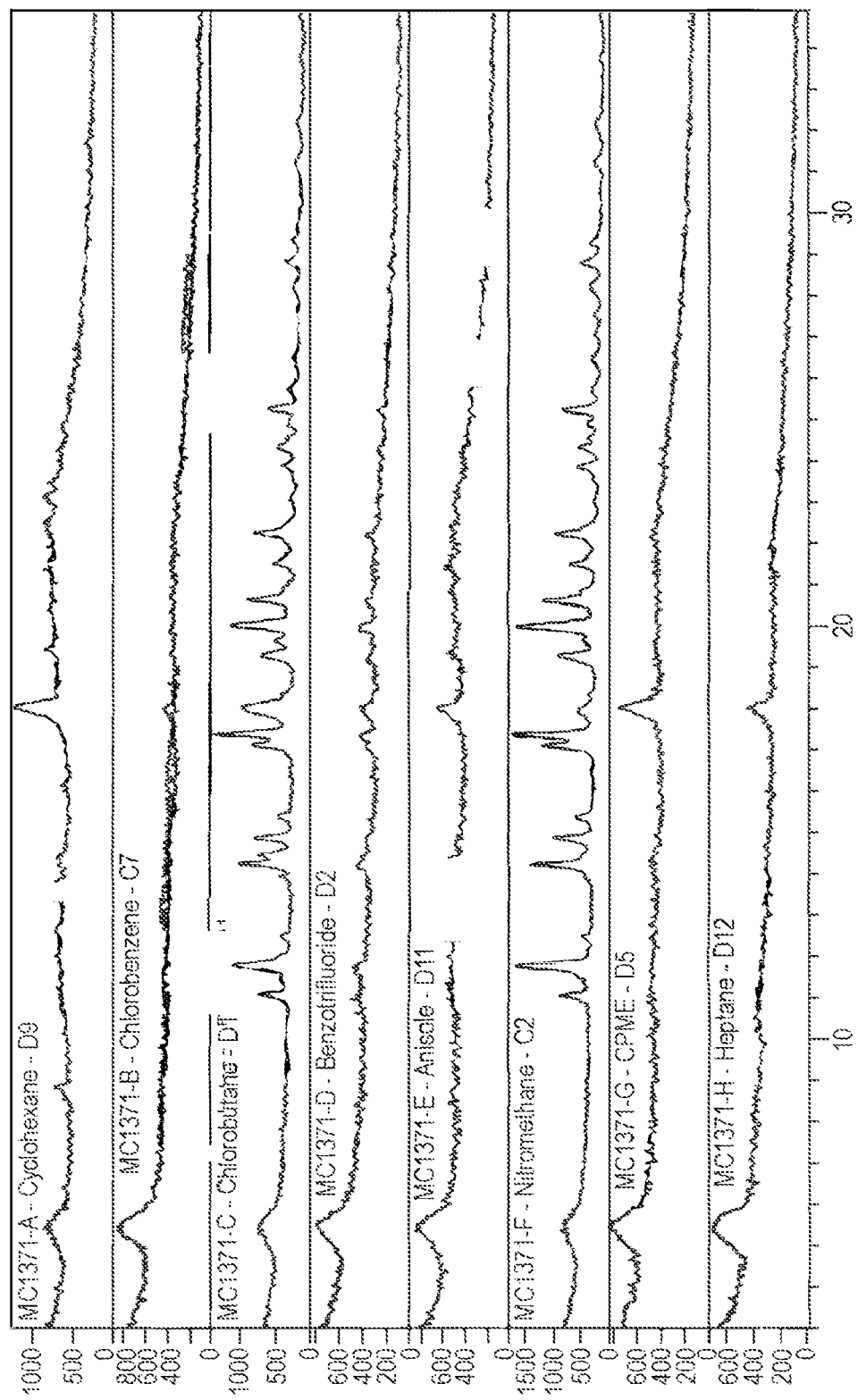
FIG. 20 is a comparison of the XRPD diffractograms acquired for the solids isolated from the equilibration of amorphous Psilocybin in solvents A to H.
Figure 21:
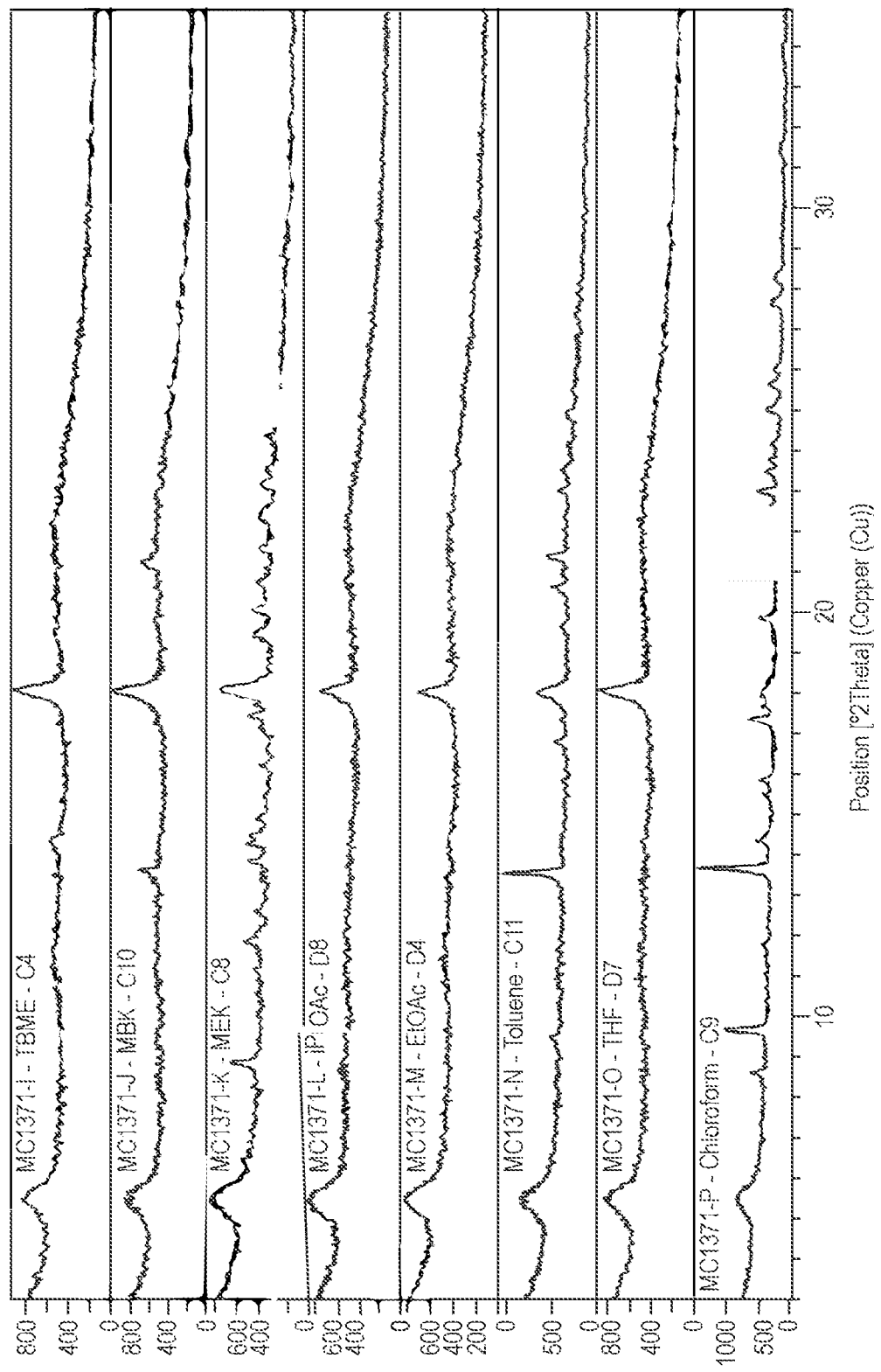
FIG. 21 is a comparison of the XRPD diffractograms acquired for the solids isolated from the equilibration of amorphous Psilocybin in solvents I to P.
Figure 22:
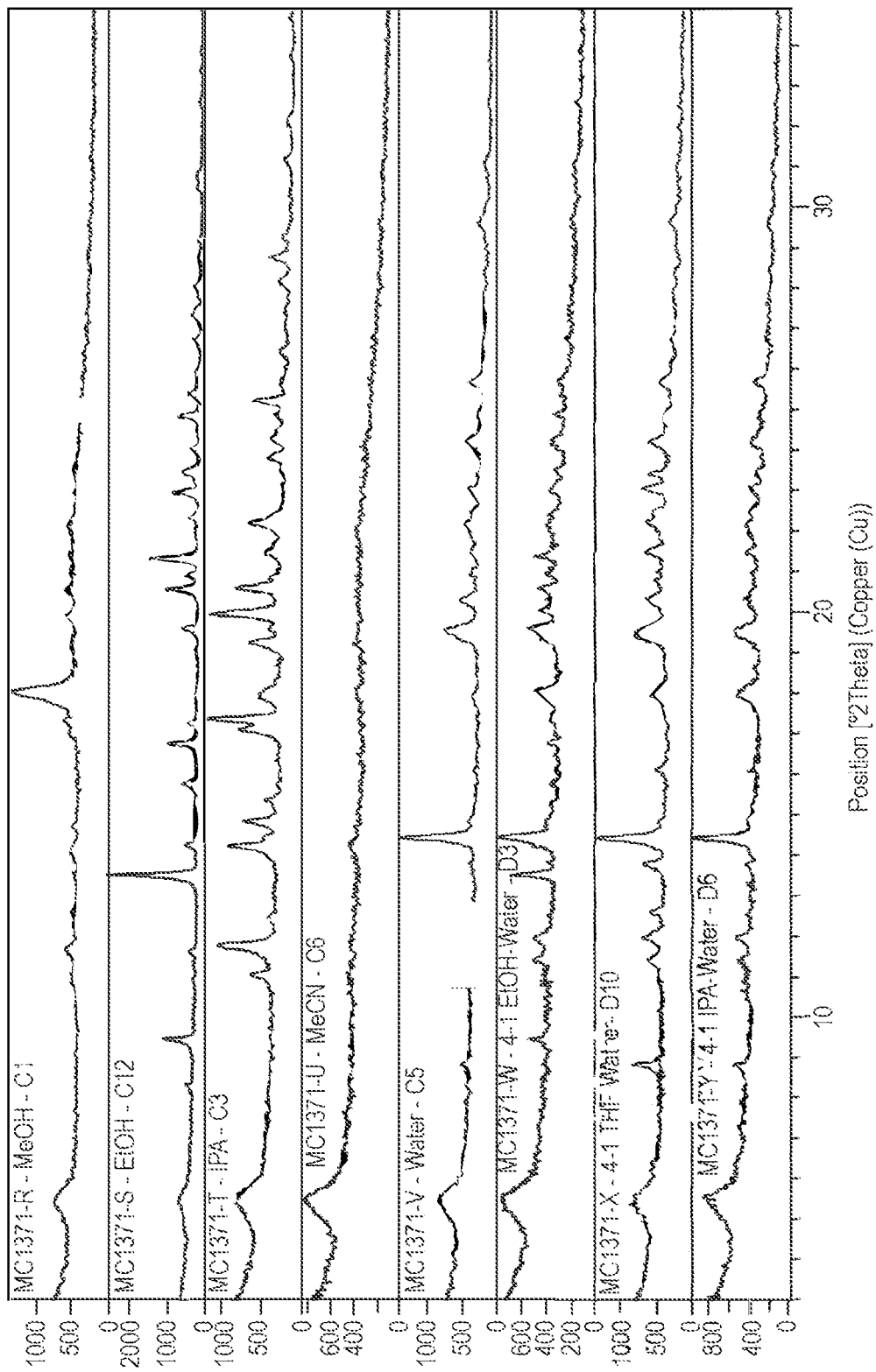
FIG. 22 is a comparison of the XRPD diffractograms acquired for the solids isolated from the equilibration of amorphous Psilocybin in solvents R to Y.

Polymorph B was returned from chlorobutane, nitromethane and IPA (FIGS. 20 and 22).

Pattern D, which was isolated from MeOH in the Polymorph A slurry experiments discussed above, was returned from the EtOH equilibration whereas MeOH in this study returned a semi-crystalline solid.

Solids similar to Pattern A were recovered from water, THF:Water and IPA:Water (4:1).

A solid similar to Pattern D was recovered from EtOH: Water (4:1), supporting the finding of the isolation of Pattern D from EtOH alone.

A solid similar to Pattern E was recovered from Chloroform.

From none of the solvents investigated was true Polymorph A or A' isolated following extended equilibration and thermal maturation of amorphous Psilocybin.

Example 12—Formulation Development

An initial series of experiments were conducted using formulations as set out in Table 36 below. The objective was to identify suitable single filler or combination fillers for large scale formulation.

TABLE 36

| | Batch No (% w/w) | | |
|---|---|---|---|
| Material Name | APL-117-6085-01 | APL-117-6085-02 | APL-117-6085-03 |
| Psilocybin | 1.0 | 1.0 | 1.0 |
| Microcrystalline cellulose Ph 102 | 91.5 | 49.5 | 81.5 |
| Pregelatinised Starch (Starch 1500) | — | 45.0 | — |
| Compact Cel MAB | — | — | 10 |
| Hydroxypropyl Cellulose (Klucel EXF) | 3.0 | 3.0 | 3.0 |
| Sodium Starch Glycolate | 3.0 | 3.0 | 3.0 |
| Colloidal silicon Dioxide | 0.5 | 0.5 | 0.5 |
| Magnesium Stearate (Vegetable Derived) | 1.0 | 1.0 | 1.0 |
| Sodium Stearyl Fumarate | — | — | — |
| TOTAL | 100.0 | 100.0 | 100.0 |

The outcome, in terms of key physiochemical properties—Material flow, Blend Uniformity, and Content Uniformity are set out in Table 37 below:

TABLE 37

| Batch No | Strength (mg) | Material flow (Carrs Index) | Blend Uniformity | Content uniformity |
|---|---|---|---|---|
| APL-117-6085-01 | 1.0 | 19.1 | TOP = 127.9<br>Middle = 106.4<br>Bottom = 104.5<br>Mean = 112.9<br>% RSD = 10.9 | % Label claim = 92.4<br>AV = 7.9 |
| APL-117-6085-02 | 1.0 | 19.1 | TOP = 115.9<br>Middle = 106.6<br>Bottom = 106.1<br>Mean = 109.6<br>% RSD = 4.9 | % Label claim = 95.2<br>AV = 5.9 |
| APL-117-6085-03 | 1.0 | 22.4 | TOP = 105.0<br>Middle = 101.4<br>Bottom = 98.7<br>Mean = 101.7<br>% RSD = 3.8 | % Label claim = 96.3<br>AV = 4.6 |

Whilst batch (APL-117-6085-03) showed good blend uniformity across different sample analysed (TOP, MIDDLE and BOTTOM) and very good content uniformity its flow property (based on Carr's index) were towards the high end and it was predicted that the formulation would not accommodate higher drug loads.

For this reason, a number of alternative formulations were trialed. The objective was to consider other filler combinations with the aim of improving the powder flow as well as achieving good blend uniformity and content uniformity.

Formulations containing less Compactcel MAB and higher amount of glidant compared to Batch 3 (APL-117-6085-03) were also trialed These further formulations are set out in Table 38 below.

TABLE 38

| | Batch No (% w/w) | | |
|---|---|---|---|
| Material Name | APL-117-6085-05 | APL-117-6085-06 | APL-117-6085-07 |
| Psilocybin | 1.0 | 1.0 | 5.0 |
| Microcrystalline cellulose Ph 102 | — | 89.0 | 85.0 |
| Pregelatinised Starch (Starch 1500) | 45.0 | — | — |
| Compact Cel MAB | — | 5.0 | 5.0 |
| Microcrystaline Cellulose CEOLUS UF 702 | 49.5 | — | — |
| Sodium Starch Glycolate | 3.0 | 3.0 | 3.0 |
| Colloidal silicon Dioxide | 0.5 | 1.0 | 1.0 |
| Sodium Stearyl Fumarate | 1.0 | 1.0 | 1.0 |
| TOTAL | 100.0 | 100.0 | 100.0 |

The results for these Batches are shown in Table 39 below:

TABLE 39

| Batch No | Strength (mg) | Material flow (Carrs Index) | Blend Uniformity | Content uniformity |
|---|---|---|---|---|
| APL-117-6085-05 | 1.0 | 20.9 | TOP = 130.0<br>Middle = 105.4<br>Bottom = 107.2<br>Mean = 114.2<br>% RSD = 12.6% | % Label claim = 88.3<br>AV = 16.5 |
| APL-117-6085-06 | 1.0 | 20.0 | TOP = 107.0<br>Middle = 96.2<br>Bottom = 95.5<br>Mean = 99.6<br>% RSD = 6.5 | % Label claim = 96.2<br>AV = 10.5 |
| APL-117-6085-07 | 5.0 | 24.3 | TOP = 91.5<br>Middle = 94.2<br>Bottom = 94.8<br>Mean = 93.5<br>% RSD = 7.0 | % Label claim = 96.0<br>AV = 11.9 |

APL-117-6085-05 failed to achieve good blend uniformity, and also failed on content uniformity criteria.

APL-117-6085-06 and APL-117-6085-07 both exhibited improved powder flow, but the blend uniformity for both formulations was poorer than APL-117-6085-03.

As a consequence, Applicant looked at modified excipients and more particularly silicified fillers with different particle sizes. These formulations are set out in Table 40 below:

TABLE 40

| | Batch No (% w/w) | |
|---|---|---|
| Material Name | APL-117-6085-11 | APL-117-6085-12 |
| Psilocybin | 5.0 | 1.0 |
| Prosolv 50 | 10.5 | 15.5 |
| Prosolv 90 | 80.0 | 79.0 |
| Sodium Starch Glycolate | 3.0 | 3.0 |

TABLE 40-continued

| Material Name | Batch No (% w/w) | |
|---|---|---|
| | APL-117-6085-11 | APL-117-6085-12 |
| Colloidal silicon Dioxide | 0.5 | 0.5 |
| Sodium Stearyl Fumarate | 1.0 | 1.0 |
| TOTAL | 100.0 | 100.0 |

Prosolv is a silicified microcrystalline cellulose, and the two variants were selected to determine if particle size affected outcome. Compared to standard microcrystalline cellulose (typical size range, depending on sieving, is 80-350 microns) the Prosolv has a finer particle size distribution, and that gives an increased surface area. The increased surface area it was hypothesised might provide superior flow and increased compaction together with improved content uniformity and stability in the formulation. The ratio of Prosolv 50 and Prosolv 90 was to produce a particle size distribution across both finer and coarser particles.

The results are set out in Table 41 below

TABLE 41

| Batch No | Strength (mg) | Material flow (Carrs Index) | Blend Uniformity | Content uniformity |
|---|---|---|---|---|
| APL-117-6085-11 | 5.0 | 24.3 | TOP = 103.4 Middle = 100.4 Bottom = 100.2 Mean = 101.5 % RSD = 2.0 | % Label claim = 94.1 AV = 6.0 |
| APL-117-6085-12 | 1.0 | 21.1 | TOP = 101.9 Middle = 98.4 Bottom = 99.9 Mean = 100.1 % RSD = 3.8% | % Label claim = 100.5 AV = 5.8 |

It can be seen that the key parameters of content uniformity (greater than 90%, and infact greater than 94%) and AV (less than 10, and infact less than 7) are excellent as is the consistency in blend uniformity (greater than 95% allowing for error).

The invention claimed is:

1. Crystalline psilocybin characterized by X-ray powder diffraction (XRPD) peaks at 11.5±0.1, 12.0±0.1, 14.5±0.1, 17.5±0.1 and 19.7±0.1 °2θ, wherein the crystalline psilocybin has a chemical purity of greater than 97% as determined by high-performance liquid chromatography (HPLC) analysis.

2. The crystalline psilocybin of claim 1, further characterized by XRPD peaks at least one of 20.4±0.1, 22.2±0.1, 24.3±0.1, or 25.7±0.1 °2θ.

3. The crystalline psilocybin of claim 1, further characterized by a XRPD diffraction pattern that is substantially the same as shown in FIG. 7a.

4. The crystalline psilocybin of claim 1, having a chemical purity of greater than 98%.

5. The crystalline psilocybin of claim 1, further characterized by a water content of <0.5% w/w as determined by Karl Fisher Titration.

6. The crystalline psilocybin of claim 1, having less than 1% psilocin as determined by HPLC analysis.

7. The crystalline psilocybin of claim 1, having less than 0.5% psilocin as determined by HPLC analysis.

8. The crystalline psilocybin of claim 1, having less than 1% phosphoric acid as determined by $^{31}$P nuclear magnetic resonance (NMR).

9. The crystalline psilocybin of claim 1, having less than 0.5% phosphoric acid as determined by $^{31}$P NMR.

10. The crystalline psilocybin of claim 1, further characterized by a <0.5% w/w loss in the TGA thermogram between 25° C. and 200° C.

11. The crystalline psilocybin of claim 1, further characterized by an endothermic event in a differential scanning calorimetry (DSC) thermogram having an onset temperature of between 205° C. and 220° C.

12. The crystalline psilocybin of claim 1, further characterized by an endothermic event in a DSC thermogram having an onset temperature of between 145° C. and 155° C.

13. The crystalline psilocybin of claim 1, comprising crystals with a size ranging from 50 to 200 microns.

14. The crystalline psilocybin of claim 1, comprising less than 1% of:

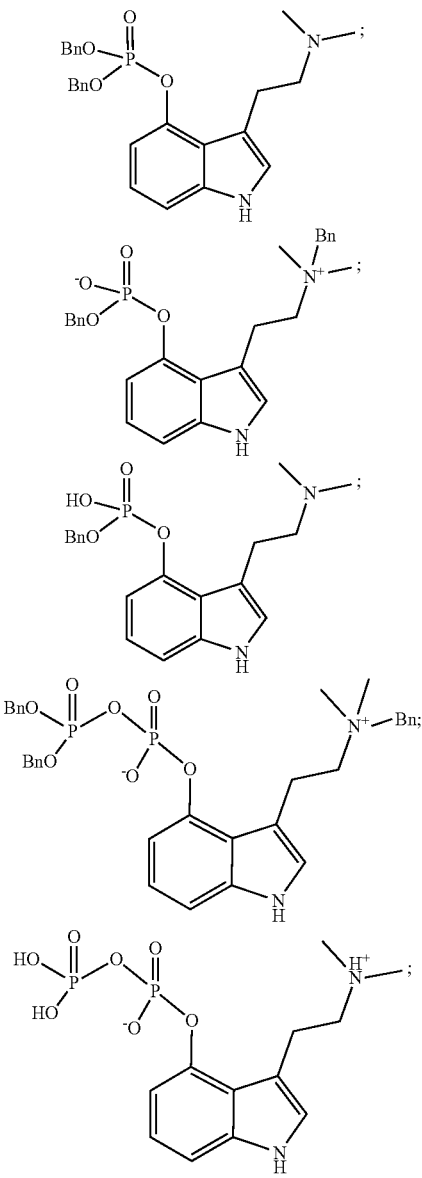

-continued

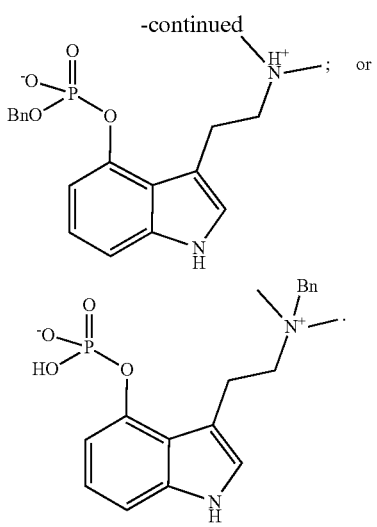

15. A pharmaceutical composition comprising a therapeutically effective amount of the crystalline psilocybin of claim 1 and a pharmaceutically acceptable excipient.

16. The pharmaceutical composition of claim 15, wherein the pharmaceutical composition is a capsule.

17. The pharmaceutical composition of claim 15, wherein the pharmaceutical composition is a tablet.

18. The pharmaceutical composition of claim 15, comprising about 1 mg to about 40 mg of the crystalline psilocybin.

19. The pharmaceutical composition of claim 15, comprising about 1 mg of the crystalline psilocybin.

20. The pharmaceutical composition of claim 15, comprising about 25 mg of the crystalline psilocybin.

21. The pharmaceutical composition of claim 15, wherein the crystalline psilocybin has a chemical purity of greater than 98%.

22. The pharmaceutical composition of claim 15, wherein the crystalline psilocybin has content of <0.5% w/w as determined by Karl Fisher Titration.

23. The pharmaceutical composition of claim 15, having less than 1% psilocin as determined by HPLC analysis.

24. The pharmaceutical composition of claim 15, having less than 1% phosphoric acid as determined by $^{31}$P NMR.

25. The pharmaceutical composition of claim 18, having less than 1% psilocin as determined by HPLC analysis.

26. The pharmaceutical composition of claim 18, having less than 0.5% psilocin as determined by HPLC analysis.

27. The pharmaceutical composition of claim 19, having less than 1% psilocin as determined by HPLC analysis.

28. The pharmaceutical composition of claim 19, having less than 0.5% psilocin as determined by HPLC analysis.

29. The pharmaceutical composition of claim 20, having less than 1% psilocin as determined by HPLC analysis.

30. The pharmaceutical composition of claim 20, having less than 0.5% psilocin as determined by HPLC analysis.

* * * * *